US012569173B2

(12) United States Patent     (10) Patent No.:   US 12,569,173 B2

Yee et al.                    (45) Date of Patent:   *Mar. 10, 2026

(54) ANALYTE SENSOR AND APPARATUS FOR INSERTION OF THE SENSOR

(71) Applicant: ABBOTT DIABETES CARE INC., Alameda, CA (US)

(72) Inventors: Phillip Yee, San Francisco, CA (US); Christopher A. Thomas, San Leandro, CA (US); Udo Hoss, Castro Valley, CA (US); Lei He, Moraga, CA (US); Michael R. Love, Pleasanton, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/561,414

(22) Filed: Dec. 23, 2021

(65) Prior Publication Data

US 2022/0110560 A1     Apr. 14, 2022

Related U.S. Application Data

(63) Continuation of application No. 17/221,169, filed on Apr. 2, 2021, now Pat. No. 11,213,229, which is a
(Continued)

(51) Int. Cl.
    *A61B 5/00*        (2006.01)
    *A61B 5/0205*     (2006.01)
(Continued)

(52) U.S. Cl.
    CPC ........ *A61B 5/14865* (2013.01); *A61B 5/0004* (2013.01); *A61B 5/002* (2013.01); *A61B 5/0022* (2013.01); *A61B 5/0024* (2013.01); *A61B 5/02055* (2013.01); *A61B 5/14503* (2013.01); *A61B 5/14532* (2013.01); *A61B 5/6849* (2013.01); *A61B 5/6898* (2013.01);
(Continued)

(58) Field of Classification Search
    CPC ............ A61B 5/14865; A61B 5/14503; A61B 5/14532; A61B 5/6849
    See application file for complete search history.

(56) References Cited

U.S. PATENT DOCUMENTS

| | | | |
|---|---|---|---|
| 2,402,306 | A | 6/1946 | Turkel |
| 2,752,918 | A | 7/1956 | Uytenbogaart |

(Continued)

FOREIGN PATENT DOCUMENTS

| | | |
|---|---|---|
| AU | 2003259741 | 2/2004 |
| CA | 2291105 | 12/1998 |

(Continued)

OTHER PUBLICATIONS

Aussedat, B., et al., "A User-Friendly Method for Calibrating a Subcutaneous Glucose Sensor-Based Hypoglycemic Alarm", Biosensors & Bioelectronics, vol. 12, No. 11, 1997, pp. 1061-1071.

(Continued)

*Primary Examiner* — Christian Jang
(74) *Attorney, Agent, or Firm* — ONE LLP

(57) ABSTRACT

An apparatus for insertion of a medical device in the skin of a subject is provided.

30 Claims, 29 Drawing Sheets

Related U.S. Application Data continuation of application No. 17/009,647, filed on Sep. 1, 2020, now Pat. No. 11,006,870, which is a continuation of application No. 16/736,728, filed on Jan. 7, 2020, now Pat. No. 10,786,190, which is a continuation of application No. 15/994,129, filed on May 31, 2018, now abandoned, which is a continuation of application No. 15/475,647, filed on Mar. 31, 2017, now Pat. No. 9,993,188, which is a continuation of application No. 15/192,531, filed on Jun. 24, 2016, now Pat. No. 9,636,068, which is a continuation of application No. 12/698,129, filed on Feb. 1, 2010, now Pat. No. 9,402,544.

(60) Provisional application No. 61/149,639, filed on Feb. 3, 2009.

(51) Int. Cl.
| | |
|---|---|
| *A61B 5/145* | (2006.01) |
| *A61B 5/1486* | (2006.01) |
| *A61M 5/158* | (2006.01) |
| *A61M 5/172* | (2006.01) |
| *A61M 5/32* | (2006.01) |
| *C12Q 1/00* | (2006.01) |
| *G06K 7/10* | (2006.01) |
| *H04L 67/12* | (2022.01) |

(52) U.S. Cl.
CPC ............. *A61B 5/72* (2013.01); *A61B 5/7405* (2013.01); *A61B 5/742* (2013.01); *A61B 5/7425* (2013.01); *A61B 5/7455* (2013.01); *A61M 5/158* (2013.01); *A61M 5/1723* (2013.01); *C12Q 1/001* (2013.01); *C12Q 1/006* (2013.01); *G06K 7/10366* (2013.01); *H04L 67/12* (2013.01); *A61B 2560/0214* (2013.01); *A61B 2560/0412* (2013.01); *A61B 2560/0475* (2013.01); *A61B 2560/0487* (2013.01); *A61B 2562/0295* (2013.01); *A61M 2005/1726* (2013.01); *A61M 5/3286* (2013.01); *A61M 2205/33* (2013.01); *A61M 2205/3584* (2013.01); *A61M 2205/502* (2013.01); *A61M 2230/201* (2013.01)

(56) References Cited

U.S. PATENT DOCUMENTS

| | | | |
|---|---|---|---|
| 3,123,790 A | 3/1964 | Tyler |
| 3,132,123 A | 5/1964 | Harris, Jr. et al. |
| 3,173,200 A | 3/1965 | Dunmire et al. |
| 3,211,001 A | 10/1965 | Petit |
| 3,260,656 A | 7/1966 | Ross, Jr. |
| 3,517,670 A | 6/1970 | Speelman |
| 3,522,807 A | 8/1970 | Millenbach |
| 3,581,062 A | 5/1971 | Aston |
| 3,653,841 A | 4/1972 | Klein |
| 3,670,727 A | 6/1972 | Reiterman |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,926,760 A | 12/1975 | Allen |
| 3,949,388 A | 4/1976 | Fuller |
| 3,960,497 A | 6/1976 | Acord et al. |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,033,330 A | 7/1977 | Willis et al. |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,120,292 A | 10/1978 | LeBlanc, Jr. et al. |
| 4,129,128 A | 12/1978 | McFarlane |
| 4,151,845 A | 5/1979 | Clemens |
| 4,168,205 A | 9/1979 | Danninger et al. |
| 4,172,770 A | 10/1979 | Semersky et al. |
| 4,178,916 A | 12/1979 | McNamara |
| 4,203,446 A | 5/1980 | Hofert et al. |
| 4,206,755 A | 6/1980 | Klein |
| 4,224,125 A | 9/1980 | Nakamura et al. |
| 4,240,438 A | 12/1980 | Updike et al. |
| 4,240,889 A | 12/1980 | Yoda et al. |
| 4,245,634 A | 1/1981 | Albisser et al. |
| 4,247,297 A | 1/1981 | Berti et al. |
| 4,294,258 A | 10/1981 | Bernard |
| 4,305,401 A | 12/1981 | Reissmueller et al. |
| 4,308,981 A | 1/1982 | Miura |
| 4,327,725 A | 5/1982 | Cortese et al. |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,353,888 A | 10/1982 | Sefton |
| 4,356,074 A | 10/1982 | Johnson |
| 4,365,637 A | 12/1982 | Johnson |
| 4,366,033 A | 12/1982 | Richter et al. |
| 4,373,527 A | 2/1983 | Fischell |
| 4,375,399 A | 3/1983 | Havas et al. |
| 4,384,586 A | 5/1983 | Christiansen |
| 4,390,621 A | 6/1983 | Bauer |
| 4,392,849 A | 7/1983 | Petre et al. |
| 4,401,122 A | 8/1983 | Clark, Jr. |
| 4,404,066 A | 9/1983 | Johnson |
| 4,418,148 A | 11/1983 | Oberhardt |
| 4,425,920 A | 1/1984 | Bourland et al. |
| 4,427,004 A | 1/1984 | Miller et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,441,968 A | 4/1984 | Emmer et al. |
| 4,450,842 A | 5/1984 | Zick et al. |
| 4,458,686 A | 7/1984 | Clark, Jr. |
| 4,461,691 A | 7/1984 | Frank |
| 4,464,170 A | 8/1984 | Clemens et al. |
| 4,469,110 A | 9/1984 | Slama |
| 4,477,314 A | 10/1984 | Richter et al. |
| 4,478,976 A | 10/1984 | Goertz et al. |
| 4,484,987 A | 11/1984 | Gough |
| 4,494,950 A | 1/1985 | Fischell |
| 4,509,531 A | 4/1985 | Ward |
| 4,522,690 A | 6/1985 | Venkatasetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,553,541 A | 11/1985 | Burns |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,592,745 A | 6/1986 | Rex et al. |
| 4,595,011 A | 6/1986 | Phillips |
| 4,619,754 A | 10/1986 | Niki et al. |
| 4,619,793 A | 10/1986 | Lee |
| 4,622,966 A | 11/1986 | Beard |
| 4,627,445 A | 12/1986 | Garcia et al. |
| 4,627,842 A | 12/1986 | Katz |
| 4,627,908 A | 12/1986 | Miller |
| 4,633,878 A | 1/1987 | Bombardieri |
| 4,637,403 A | 1/1987 | Garcia et al. |
| 4,639,062 A | 1/1987 | Taniguchi et al. |
| 4,650,547 A | 3/1987 | Gough |

(56)  References Cited

U.S. PATENT DOCUMENTS

| | | |
|---|---|---|
| 4,654,197 A | 3/1987 | Lilja et al. |
| 4,655,880 A | 4/1987 | Liu |
| 4,655,885 A | 4/1987 | Hill et al. |
| 4,663,824 A | 5/1987 | Kenmochi |
| 4,665,906 A | 5/1987 | Jervis |
| 4,671,288 A | 6/1987 | Gough |
| 4,675,346 A | 6/1987 | Lin et al. |
| 4,679,562 A | 7/1987 | Luksha |
| 4,680,268 A | 7/1987 | Clark, Jr. |
| 4,682,602 A | 7/1987 | Prohaska |
| 4,684,245 A | 8/1987 | Goldring |
| 4,684,537 A | 8/1987 | Graetzel et al. |
| 4,685,463 A | 8/1987 | Williams |
| 4,685,466 A | 8/1987 | Ran |
| 4,690,675 A | 9/1987 | Katz |
| 4,698,057 A | 10/1987 | Joishy |
| 4,703,324 A | 10/1987 | White |
| 4,703,756 A | 11/1987 | Gough et al. |
| 4,711,245 A | 12/1987 | Higgins et al. |
| 4,711,247 A | 12/1987 | Fishman |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,729,672 A | 3/1988 | Takagi |
| 4,731,726 A | 3/1988 | Allen, III |
| 4,749,985 A | 6/1988 | Corsberg |
| 4,755,173 A | 7/1988 | Konopka |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,683 A | 11/1988 | Wozniak et al. |
| 4,781,798 A | 11/1988 | Gough |
| 4,784,736 A | 11/1988 | Lonsdale et al. |
| 4,785,868 A | 11/1988 | Koenig, Jr. |
| 4,795,707 A | 1/1989 | Niiyama et al. |
| 4,796,634 A | 1/1989 | Huntsman et al. |
| 4,805,624 A | 2/1989 | Yao et al. |
| 4,813,424 A | 3/1989 | Wilkins |
| 4,815,469 A | 3/1989 | Cohen et al. |
| 4,817,603 A | 4/1989 | Turner et al. |
| 4,818,994 A | 4/1989 | Orth et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| RE32,947 E | 6/1989 | Dormer et al. |
| 4,840,893 A | 6/1989 | Hill et al. |
| 4,847,785 A | 7/1989 | Stephens |
| 4,848,351 A | 7/1989 | Finch |
| 4,852,025 A | 7/1989 | Herpichböhm |
| 4,854,322 A | 8/1989 | Ash et al. |
| 4,856,648 A | 8/1989 | Krueger |
| 4,865,038 A | 9/1989 | Rich et al. |
| 4,871,351 A | 10/1989 | Feingold |
| 4,871,440 A | 10/1989 | Nagata et al. |
| 4,874,500 A | 10/1989 | Madou et al. |
| 4,890,620 A | 1/1990 | Gough |
| 4,894,137 A | 1/1990 | Takizawa et al. |
| 4,895,147 A | 1/1990 | Bodicky et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,921,199 A | 5/1990 | Villaveces |
| 4,923,586 A | 5/1990 | Katayama et al. |
| 4,924,879 A | 5/1990 | O'Brien |
| 4,925,268 A | 5/1990 | Iyer et al. |
| 4,927,516 A | 5/1990 | Yamaguchi et al. |
| 4,934,369 A | 6/1990 | Maxwell |
| 4,935,105 A | 6/1990 | Churchouse |
| 4,935,345 A | 6/1990 | Guibeau et al. |
| 4,938,860 A | 7/1990 | Wogoman |
| 4,944,299 A | 7/1990 | Silvian |
| 4,950,378 A | 8/1990 | Nagara |
| 4,953,552 A | 9/1990 | DeMarzo |
| 4,954,129 A | 9/1990 | Giuliani et al. |
| 4,969,468 A | 11/1990 | Byers et al. |
| 4,970,145 A | 11/1990 | Bennetto et al. |
| 4,974,929 A | 12/1990 | Curry |
| 4,985,142 A | 1/1991 | Laycock et al. |
| 4,986,271 A | 1/1991 | Wilkins |
| 4,988,341 A | 1/1991 | Columbus et al. |
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |
| 5,002,054 A | 3/1991 | Ash et al. |
| 5,006,110 A | 4/1991 | Garrison et al. |
| 5,013,161 A | 5/1991 | Zaragoza et al. |
| 5,019,974 A | 5/1991 | Beckers |
| 5,035,860 A | 7/1991 | Kleingeld et al. |
| 5,036,860 A | 8/1991 | Leigh et al. |
| 5,047,044 A | 9/1991 | Smith et al. |
| 5,050,612 A | 9/1991 | Matsumura |
| 5,051,688 A | 9/1991 | Murase et al. |
| 5,055,171 A | 10/1991 | Peck |
| 5,058,592 A | 10/1991 | Whisler |
| 5,067,957 A | 11/1991 | Jervis |
| 5,068,536 A | 11/1991 | Rosenthal |
| 5,070,535 A | 12/1991 | Hochmair et al. |
| 5,082,550 A | 1/1992 | Rishpon et al. |
| 5,082,786 A | 1/1992 | Nakamoto |
| 5,086,246 A | 2/1992 | Dymond et al. |
| 5,089,112 A | 2/1992 | Skotheim et al. |
| 5,095,904 A | 3/1992 | Seligman et al. |
| 5,101,814 A | 4/1992 | Palti |
| 5,106,365 A | 4/1992 | Hernandez |
| 5,108,564 A | 4/1992 | Szuminsky et al. |
| 5,108,889 A | 4/1992 | Smith et al. |
| 5,109,850 A | 5/1992 | Blanco et al. |
| 5,120,420 A | 6/1992 | Nankai et al. |
| 5,122,925 A | 6/1992 | Inpyn |
| 5,124,661 A | 6/1992 | Zellin et al. |
| 5,126,034 A | 6/1992 | Carter et al. |
| 5,133,856 A | 7/1992 | Yamaguchi et al. |
| 5,135,003 A | 8/1992 | Souma |
| 5,135,004 A | 8/1992 | Adams et al. |
| 5,140,985 A | 8/1992 | Schroeder et al. |
| 5,141,868 A | 8/1992 | Shanks et al. |
| 5,161,532 A | 11/1992 | Joseph |
| 5,162,407 A | 11/1992 | Turner |
| 5,165,407 A | 11/1992 | Wilson et al. |
| 5,173,165 A | 12/1992 | Schmid et al. |
| 5,174,291 A | 12/1992 | Schoonen et al. |
| 5,190,041 A | 3/1993 | Palti |
| 5,190,546 A | 3/1993 | Jervis |
| 5,192,416 A | 3/1993 | Wang et al. |
| 5,193,545 A | 3/1993 | Marsoner et al. |
| 5,198,367 A | 3/1993 | Aizawa et al. |
| 5,202,261 A | 4/1993 | Musho et al. |
| 5,204,264 A | 4/1993 | Kaminer et al. |
| 5,205,297 A | 4/1993 | Montecalvo et al. |
| 5,205,920 A | 4/1993 | Oyama et al. |
| 5,208,154 A | 5/1993 | Weaver et al. |
| 5,209,229 A | 5/1993 | Gilli |
| 5,217,595 A | 6/1993 | Smith et al. |
| 5,228,449 A | 7/1993 | Christ et al. |
| 5,229,282 A | 7/1993 | Yoshioka et al. |
| 5,231,988 A | 8/1993 | Wernicke et al. |
| 5,234,835 A | 8/1993 | Nestor et al. |
| 5,238,729 A | 8/1993 | Debe |
| 5,243,696 A | 9/1993 | Carr et al. |
| 5,245,314 A | 9/1993 | Kah et al. |
| 5,246,867 A | 9/1993 | Lakowicz et al. |

(56)  References Cited

U.S. PATENT DOCUMENTS

| | | | |
|---|---|---|---|
| 5,250,439 A | 10/1993 | Musho et al. |
| 5,251,126 A | 10/1993 | Kahn et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,267,963 A | 12/1993 | Bachynsky |
| 5,271,815 A | 12/1993 | Wong |
| 5,279,294 A | 1/1994 | Anderson |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,289,497 A | 2/1994 | Jackobson et al. |
| 5,293,546 A | 3/1994 | Tadros et al. |
| 5,293,877 A | 3/1994 | O'Hara et al. |
| 5,299,571 A | 4/1994 | Mastrototaro |
| 5,305,008 A | 4/1994 | Turner et al. |
| 5,318,583 A | 6/1994 | Rabenau et al. |
| 5,320,098 A | 6/1994 | Davidson |
| 5,320,715 A | 6/1994 | Berg |
| 5,320,725 A | 6/1994 | Gregg et al. |
| 5,322,063 A | 6/1994 | Allen et al. |
| 5,333,615 A | 8/1994 | Craelius et al. |
| 5,337,747 A | 8/1994 | Neftel |
| 5,340,722 A | 8/1994 | Wolfbeis et al. |
| 5,342,789 A | 8/1994 | Chick et al. |
| 5,352,348 A | 10/1994 | Young et al. |
| 5,356,420 A | 10/1994 | Czernecki et al. |
| 5,356,786 A | 10/1994 | Heller et al. |
| 5,360,404 A | 11/1994 | Novacek et al. |
| 5,368,028 A | 11/1994 | Palti |
| 5,372,133 A | 12/1994 | Hogen Esch |
| 5,372,427 A | 12/1994 | Padovani et al. |
| 5,376,251 A | 12/1994 | Kaneko et al. |
| 5,378,628 A | 1/1995 | Gratzel et al. |
| 5,379,238 A | 1/1995 | Stark |
| 5,384,547 A | 1/1995 | Lynk et al. |
| 5,387,327 A | 2/1995 | Khan |
| 5,390,670 A | 2/1995 | Centa et al. |
| 5,390,671 A | 2/1995 | Lord et al. |
| 5,391,250 A | 2/1995 | Cheney, II et al. |
| 5,394,877 A | 3/1995 | Orr et al. |
| 5,395,504 A | 3/1995 | Saurer et al. |
| 5,400,782 A | 3/1995 | Beaubiah |
| 5,400,794 A | 3/1995 | Gorman |
| 5,402,780 A | 4/1995 | Faasse, Jr. |
| 5,407,431 A | 4/1995 | Botich et al. |
| 5,408,999 A | 4/1995 | Singh et al. |
| 5,410,326 A | 4/1995 | Goldstein |
| 5,411,647 A | 5/1995 | Johnson et al. |
| 5,425,361 A | 6/1995 | Fenzlein et al. |
| 5,425,868 A | 6/1995 | Pedersen |
| 5,431,160 A | 7/1995 | Wilkins |
| 5,431,921 A | 7/1995 | Thombre |
| 5,437,999 A | 8/1995 | Diebold et al. |
| 5,438,983 A | 8/1995 | Falcone |
| 5,462,051 A | 10/1995 | Oka et al. |
| 5,462,645 A | 10/1995 | Albery et al. |
| 5,469,846 A | 11/1995 | Khan |
| 5,472,317 A | 12/1995 | Field et al. |
| 5,482,473 A | 1/1996 | Lord et al. |
| 5,484,403 A | 1/1996 | Yoakum et al. |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,499,243 A | 3/1996 | Hall |
| 5,507,288 A | 4/1996 | Bocker et al. |
| 5,509,410 A | 4/1996 | Hill et al. |
| 5,514,718 A | 5/1996 | Lewis et al. |
| 5,516,832 A | 5/1996 | Kennan et al. |
| 5,527,288 A | 6/1996 | Gross et al. |
| 5,531,878 A | 7/1996 | Vadgama et al. |
| 5,532,686 A | 7/1996 | Urbas et al. |
| 5,533,977 A | 7/1996 | Metcalf et al. |
| 5,536,259 A | 7/1996 | Utterberg |
| 5,543,326 A | 8/1996 | Heller et al. |
| 5,544,196 A | 8/1996 | Tiedmann, Jr. et al. |
| 5,545,191 A | 8/1996 | Mann et al. |
| 5,549,568 A | 8/1996 | Sheilds |
| 5,551,427 A | 9/1996 | Altman |
| 5,555,190 A | 9/1996 | Derby et al. |
| 5,558,638 A | 9/1996 | Evers et al. |
| 5,560,357 A | 10/1996 | Faupei et al. |
| 5,562,713 A | 10/1996 | Silvian |
| 5,564,434 A | 10/1996 | Halperin et al. |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,571,022 A | 11/1996 | Schaarschmidt |
| 5,575,563 A | 11/1996 | Chiu et al. |
| 5,581,206 A | 12/1996 | Chevallier et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halli et al. |
| 5,589,326 A | 12/1996 | Deng et al. |
| 5,593,852 A | 1/1997 | Heller et al. |
| 5,596,150 A | 1/1997 | Arndt et al. |
| 5,597,378 A | 1/1997 | Jervis |
| 5,600,301 A | 2/1997 | Robinson, III |
| 5,601,435 A | 2/1997 | Quy |
| 5,609,575 A | 3/1997 | Larson et al. |
| 5,613,978 A | 3/1997 | Harding |
| 5,617,851 A | 4/1997 | Lipkovker |
| 5,623,933 A | 4/1997 | Amano et al. |
| 5,626,566 A | 5/1997 | Petersen et al. |
| 5,628,310 A | 5/1997 | Rao et al. |
| 5,628,324 A | 5/1997 | Sarbach |
| 5,628,890 A | 5/1997 | Carter et al. |
| 5,632,557 A | 5/1997 | Simons |
| 5,634,468 A | 6/1997 | Platt et al. |
| 5,636,640 A | 6/1997 | Staehlin |
| 5,638,832 A | 6/1997 | Singer et al. |
| 5,640,954 A | 6/1997 | Pfeiffer et al. |
| 5,651,869 A | 7/1997 | Yoshioka et al. |
| 5,653,239 A | 8/1997 | Pompei et al. |
| 5,659,454 A | 8/1997 | Vermesse |
| 5,660,163 A | 8/1997 | Schulman et al. |
| 5,665,071 A | 9/1997 | Wyrick |
| 5,665,222 A | 9/1997 | Heller et al. |
| 5,669,543 A | 9/1997 | Ueno |
| 5,669,890 A | 9/1997 | Grimm |
| 5,670,031 A | 9/1997 | Hintsche et al. |
| 5,673,322 A | 9/1997 | Pepe et al. |
| 5,680,858 A | 10/1997 | Hansen et al. |
| 5,682,233 A | 10/1997 | Brinda |
| 5,695,623 A | 12/1997 | Michel et al. |
| 5,707,502 A | 1/1998 | McCaffrey et al. |
| 5,708,247 A | 1/1998 | McAleer et al. |
| 5,711,001 A | 1/1998 | Bussan et al. |
| 5,711,297 A | 1/1998 | Iliff et al. |
| 5,711,861 A | 1/1998 | Ward et al. |
| 5,711,862 A | 1/1998 | Sakoda et al. |
| 5,724,030 A | 3/1998 | Urbas et al. |
| 5,726,646 A | 3/1998 | Bane et al. |
| 5,733,044 A | 3/1998 | Rose et al. |
| 5,733,259 A | 3/1998 | Valcke et al. |
| 5,733,262 A | 3/1998 | Paul |
| 5,733,313 A | 3/1998 | Barreras, Sr. et al. |
| 5,735,285 A | 4/1998 | Albert et al. |
| 5,738,220 A | 4/1998 | Geszler |
| 5,741,211 A | 4/1998 | Renirie et al. |
| 5,743,262 A | 4/1998 | Lepper, Jr. et al. |
| 5,746,217 A | 5/1998 | Erickson et al. |
| 5,746,697 A | 5/1998 | Swedlow et al. |
| 5,748,103 A | 5/1998 | Flach et al. |

(56) References Cited

U.S. PATENT DOCUMENTS

| | | | |
|---|---|---|---|
| 5,749,656 A | 5/1998 | Boehm et al. |
| 5,749,907 A | 5/1998 | Mann |
| 5,758,290 A | 5/1998 | Nealon et al. |
| 5,766,131 A | 6/1998 | Kondo et al. |
| 5,770,028 A | 6/1998 | Maley et al. |
| 5,771,001 A | 6/1998 | Cobb |
| 5,771,891 A | 6/1998 | Gozani |
| 5,772,586 A | 6/1998 | Heinonen et al. |
| 5,778,879 A | 7/1998 | Ota et al. |
| 5,779,665 A | 7/1998 | Mastrototaro et al. |
| 5,786,439 A | 7/1998 | Van Antwerp et al. |
| 5,791,344 A | 8/1998 | Schulman et al. |
| 5,798,961 A | 8/1998 | Heyden et al. |
| 5,800,420 A | 9/1998 | Gross et al. |
| 5,804,047 A | 9/1998 | Kambe et al. |
| 5,807,375 A | 9/1998 | Gross et al. |
| 5,814,020 A | 9/1998 | Gross |
| 5,820,551 A | 10/1998 | Hill et al. |
| 5,820,570 A | 10/1998 | Erickson et al. |
| 5,820,622 A | 10/1998 | Gross et al. |
| 5,822,715 A | 10/1998 | Worthington et al. |
| 5,823,802 A | 10/1998 | Bartley |
| 5,827,184 A | 10/1998 | Netherly et al. |
| 5,830,064 A | 11/1998 | Bradish et al. |
| 5,833,603 A | 11/1998 | Kovacs et al. |
| 5,840,020 A | 11/1998 | Heinonen et al. |
| 5,842,983 A | 12/1998 | Abel et al. |
| 5,851,197 A | 12/1998 | Marano et al. |
| 5,856,758 A | 1/1999 | Joffe et al. |
| 5,858,001 A | 1/1999 | Tsals et al. |
| 5,865,804 A | 2/1999 | Bachynsky |
| 5,871,494 A | 2/1999 | Simons et al. |
| 5,875,186 A | 2/1999 | Belanger et al. |
| 5,879,311 A | 3/1999 | Duchon et al. |
| 5,885,211 A | 3/1999 | Eppstein et al. |
| 5,891,049 A | 4/1999 | Cyrus et al. |
| 5,899,855 A | 5/1999 | Brown |
| 5,899,856 A | 5/1999 | Schoendorfer et al. |
| 5,914,026 A | 6/1999 | Blubaugh, Jr. et al. |
| 5,918,603 A | 7/1999 | Brown |
| 5,919,141 A | 7/1999 | Money et al. |
| 5,921,963 A | 7/1999 | Erez et al. |
| 5,924,979 A | 7/1999 | Sedlow et al. |
| 5,925,021 A | 7/1999 | Castellano et al. |
| 5,931,814 A | 8/1999 | Gross et al. |
| 5,931,868 A | 8/1999 | Gross |
| 5,935,224 A | 8/1999 | Svancarek et al. |
| 5,938,679 A | 8/1999 | Freeman et al. |
| 5,942,979 A | 8/1999 | Luppino |
| 5,948,006 A | 9/1999 | Mann |
| 5,951,485 A | 9/1999 | Cyrus et al. |
| 5,951,492 A | 9/1999 | Douglas et al. |
| 5,951,521 A | 9/1999 | Mastrototaro et al. |
| 5,951,582 A | 9/1999 | Thorne et al. |
| 5,954,643 A | 9/1999 | Van Antwerp |
| 5,954,685 A | 9/1999 | Tierny |
| 5,957,854 A | 9/1999 | Besson et al. |
| 5,961,451 A | 10/1999 | Reber et al. |
| 5,964,718 A | 10/1999 | Duchon et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,971,941 A | 10/1999 | Simons et al. |
| 5,972,199 A | 10/1999 | Heller et al. |
| 5,987,353 A | 11/1999 | Khatchatrian et al. |
| 5,993,411 A | 11/1999 | Choi |
| 5,995,860 A | 11/1999 | Sun et al. |
| 5,997,501 A | 12/1999 | Gross et al. |
| 6,001,067 A | 12/1999 | Shults et al. |
| 6,004,278 A | 12/1999 | Botich et al. |
| 6,017,335 A | 1/2000 | Burnham |
| 6,022,315 A | 2/2000 | Iliff |
| 6,022,368 A | 2/2000 | Gavronsky et al. |
| 6,024,699 A | 2/2000 | Surwit et al. |
| 6,026,321 A | 2/2000 | Miyata et al. |
| 6,027,459 A | 2/2000 | Shain et al. |
| 6,028,413 A | 2/2000 | Brockmann |
| 6,032,064 A | 2/2000 | Devlin et al. |
| 6,036,924 A | 3/2000 | Simons et al. |
| 6,048,352 A | 4/2000 | Douglas et al. |
| 6,049,727 A | 4/2000 | Crothall |
| 6,052,565 A | 4/2000 | Ishikura et al. |
| 6,054,194 A | 4/2000 | Kane |
| 6,056,718 A | 5/2000 | Funderburk et al. |
| 6,059,946 A | 5/2000 | Yukawa et al. |
| 6,066,243 A | 5/2000 | Anderson et al. |
| 6,068,399 A | 5/2000 | Tseng |
| 6,071,294 A | 6/2000 | Simons et al. |
| 6,071,391 A | 6/2000 | Gotoh et al. |
| 6,083,710 A | 7/2000 | Heller et al. |
| 6,085,342 A | 7/2000 | Marholev et al. |
| 6,088,605 A | 7/2000 | Griffith et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,091,987 A | 7/2000 | Thompson |
| 6,093,172 A | 7/2000 | Funderburk et al. |
| 6,096,364 A | 8/2000 | Bok et al. |
| 6,097,480 A | 8/2000 | Kaplan |
| 6,099,484 A | 8/2000 | Douglas et al. |
| 6,102,896 A | 8/2000 | Roser |
| 6,103,033 A | 8/2000 | Say et al. |
| 6,106,484 A | 8/2000 | Terwilliger |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,129,666 A | 10/2000 | DeLuca et al. |
| 6,130,623 A | 10/2000 | MacLellan et al. |
| 6,132,449 A | 10/2000 | Lum et al. |
| 6,134,461 A | 10/2000 | Say et al. |
| 6,141,573 A | 10/2000 | Kurnik et al. |
| 6,143,164 A | 11/2000 | Heller et al. |
| 6,144,837 A | 11/2000 | Quy |
| 6,144,871 A | 11/2000 | Saito et al. |
| 6,144,922 A | 11/2000 | Douglas et al. |
| 6,149,626 A | 11/2000 | Bachynsky et al. |
| 6,157,850 A | 12/2000 | Diab et al. |
| 6,159,147 A | 12/2000 | Lichter et al. |
| 6,159,181 A | 12/2000 | Crossman et al. |
| 6,161,095 A | 12/2000 | Brown |
| 6,162,611 A | 12/2000 | Heller et al. |
| 6,168,606 B1 | 1/2001 | Levin et al. |
| 6,175,752 B1 | 1/2001 | Say et al. |
| 6,186,982 B1 | 2/2001 | Gross et al. |
| 6,192,891 B1 | 2/2001 | Gravel et al. |
| 6,197,040 B1 | 3/2001 | LeVaughn et al. |
| 6,198,946 B1 | 3/2001 | Shin et al. |
| 6,200,265 B1 | 3/2001 | Walsh et al. |
| 6,203,495 B1 | 3/2001 | Bardy et al. |
| 6,212,416 B1 | 4/2001 | Ward et al. |
| 6,213,972 B1 | 4/2001 | Butterfield et al. |
| 6,219,574 B1 | 4/2001 | Cormier et al. |
| 6,223,283 B1 | 4/2001 | Chaiken et al. |
| 6,231,531 B1 | 5/2001 | Lum et al. |
| 6,233,471 B1 | 5/2001 | Berner et al. |
| 6,237,394 B1 | 5/2001 | Harris et al. |
| 6,248,067 B1 | 6/2001 | Causey, III et al. |
| 6,254,536 B1 | 7/2001 | DeVito |
| 6,254,586 B1 | 7/2001 | Mann et al. |
| 6,264,810 B1 | 7/2001 | Stol et al. |
| 6,270,455 B1 | 8/2001 | Brown |
| 6,275,717 B1 | 8/2001 | Gross et al. |
| 6,283,761 B1 | 9/2001 | Joao |
| 6,283,982 B1 | 9/2001 | Levaughn et al. |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,298,255 B1 | 10/2001 | Cordero et al. |
| 6,299,347 B1 | 10/2001 | Pompei |

(56)　　　　　References Cited

U.S. PATENT DOCUMENTS

| | | | |
|---|---|---|---|
| 6,299,757 B1 | 10/2001 | Feldman et al. |
| 6,302,866 B1 | 10/2001 | Marggi |
| 6,304,766 B1 | 10/2001 | Colvin, Jr. |
| 6,306,104 B1 | 10/2001 | Cunningham et al. |
| 6,306,141 B1 | 10/2001 | Jervis |
| 6,309,884 B1 | 10/2001 | Cooper et al. |
| 6,314,317 B1 | 11/2001 | Willis |
| 6,329,161 B1 | 12/2001 | Heller et al. |
| 6,331,244 B1 | 12/2001 | Lewis et al. |
| 6,336,269 B1 | 1/2002 | Eldridge et al. |
| 6,338,790 B1 | 1/2002 | Feldman et al. |
| 6,341,232 B1 | 1/2002 | Conn et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,364,890 B1 | 4/2002 | Lum et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,368,339 B1 | 4/2002 | Amplatz |
| 6,377,828 B1 | 4/2002 | Chaiken et al. |
| 6,377,829 B1 | 4/2002 | Ai-Ali |
| 6,377,894 B1 | 4/2002 | Deweese et al. |
| 6,379,301 B1 | 4/2002 | Worthington et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,409,740 B1 | 6/2002 | Kuhr et al. |
| 6,413,393 B1 | 7/2002 | Van Antwerp et al. |
| 6,416,471 B1 | 7/2002 | Kumar et al. |
| 6,418,332 B1 | 7/2002 | Mastrototaro et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,433,743 B1 | 8/2002 | Massy et al. |
| 6,435,017 B1 | 8/2002 | Nowicki, Jr. et al. |
| 6,437,679 B1 | 8/2002 | Roques |
| 6,438,414 B1 | 8/2002 | Conn et al. |
| 6,440,068 B1 | 8/2002 | Brown et al. |
| 6,442,413 B1 | 8/2002 | Silver |
| 6,445,374 B2 | 9/2002 | Albert et al. |
| 6,451,025 B1 | 9/2002 | Jervis |
| 6,458,109 B1 | 10/2002 | Henley et al. |
| 6,461,496 B1 | 10/2002 | Feldman et al. |
| 6,471,689 B1 | 10/2002 | Joseph et al. |
| 6,472,220 B1 | 10/2002 | Simons et al. |
| 6,478,736 B1 | 11/2002 | Mault |
| 6,482,176 B1 | 11/2002 | Wich |
| 6,484,045 B1 | 11/2002 | Holker et al. |
| 6,484,046 B1 | 11/2002 | Say et al. |
| 6,493,069 B1 | 12/2002 | Nagashimada et al. |
| 6,494,830 B1 | 12/2002 | Wessel |
| 6,496,729 B2 | 12/2002 | Thompson |
| 6,497,655 B1 | 12/2002 | Linberg et al. |
| 6,503,381 B1 | 1/2003 | Gotoh et al. |
| 6,510,344 B1 | 1/2003 | Halpern |
| 6,514,460 B1 | 2/2003 | Fendrock |
| 6,514,689 B2 | 2/2003 | Han et al. |
| 6,514,718 B2 | 2/2003 | Heller et al. |
| 6,520,326 B2 | 2/2003 | McIvor et al. |
| 6,522,927 B1 | 2/2003 | Bishay et al. |
| 6,533,805 B1 | 3/2003 | Jervis |
| 6,537,242 B1 | 3/2003 | Palmer |
| 6,540,891 B1 | 4/2003 | Stewart et al. |
| 6,544,212 B2 | 4/2003 | Galley et al. |
| 6,546,268 B1 | 4/2003 | Ishikawa et al. |
| 6,549,796 B2 | 4/2003 | Sohrab |
| 6,551,494 B1 | 4/2003 | Heller et al. |
| 6,551,496 B1 | 4/2003 | Moles et al. |
| 6,554,795 B2 | 4/2003 | Bagaoisan et al. |
| 6,554,798 B1 | 4/2003 | Lam et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,572,566 B2 | 6/2003 | Effenhauser |
| 6,574,490 B2 | 6/2003 | Abbink et al. |
| 6,574,510 B2 | 6/2003 | Von Arx et al. |
| 6,575,895 B1 | 6/2003 | Blair |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,584,335 B1 | 6/2003 | Haar et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,602,268 B2 | 8/2003 | Kuhr et al. |
| 6,603,995 B1 | 8/2003 | Carter |
| 6,604,050 B2 | 8/2003 | Trippel et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,607,543 B2 | 8/2003 | Purcell et al. |
| 6,608,562 B1 | 8/2003 | Kimura et al. |
| 6,610,012 B2 | 8/2003 | Mault |
| 6,611,206 B2 | 8/2003 | Eshelman et al. |
| 6,613,015 B2 | 9/2003 | Sandstrom et al. |
| 6,616,819 B1 | 9/2003 | Liamos et al. |
| 6,618,934 B1 | 9/2003 | Feldman et al. |
| 6,627,154 B1 | 9/2003 | Goodman et al. |
| 6,631,281 B1 | 10/2003 | Kastle |
| 6,633,772 B2 | 10/2003 | Ford et al. |
| 6,635,014 B2 | 10/2003 | Starkweather et al. |
| 6,635,167 B1 | 10/2003 | Batman et al. |
| 6,637,611 B2 | 10/2003 | Luch |
| 6,641,533 B2 | 11/2003 | Causey, III et al. |
| 6,645,359 B1 | 11/2003 | Bhullar et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,662,439 B1 | 12/2003 | Bhullar |
| 6,666,849 B1 | 12/2003 | Marshall et al. |
| 6,668,196 B1 | 12/2003 | Villegas et al. |
| 6,671,534 B2 | 12/2003 | Putz |
| 6,675,030 B2 | 1/2004 | Ciurczak et al. |
| 6,676,290 B1 | 1/2004 | Lu |
| 6,676,816 B2 | 1/2004 | Mao et al. |
| 6,682,546 B2 | 1/2004 | Amplatz |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,699,188 B2 | 3/2004 | Wessel |
| 6,702,857 B2 | 3/2004 | Brauker et al. |
| 6,706,159 B2 | 3/2004 | Moerman et al. |
| 6,721,582 B2 | 4/2004 | Trepagnier et al. |
| 6,730,025 B1 | 5/2004 | Platt |
| 6,730,072 B2 | 5/2004 | Shawgo et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,735,183 B2 | 5/2004 | O'Toole et al. |
| 6,735,479 B2 | 5/2004 | Fabian et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,743,635 B2 | 6/2004 | Neel et al. |
| 6,746,582 B2 | 6/2004 | Heller et al. |

(56) References Cited

U.S. PATENT DOCUMENTS

| | | | |
|---|---|---|---|
| 6,748,445 B1 | 6/2004 | Darcey et al. |
| 6,749,740 B2 | 6/2004 | Liamos et al. |
| 6,758,810 B2 | 7/2004 | Lebel et al. |
| 6,758,835 B2 | 7/2004 | Close et al. |
| 6,764,581 B1 | 7/2004 | Forrow et al. |
| 6,767,440 B1 | 7/2004 | Bhullar et al. |
| 6,770,030 B1 | 8/2004 | Schaupp et al. |
| 6,773,671 B1 | 8/2004 | Lewis et al. |
| 6,781,522 B2 | 8/2004 | Sleva et al. |
| 6,790,178 B1 | 9/2004 | Mault et al. |
| 6,804,558 B2 | 10/2004 | Haller et al. |
| 6,804,561 B2 | 10/2004 | Stover |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,814,844 B2 | 11/2004 | Bhullar et al. |
| 6,830,551 B1 | 12/2004 | Uchigaki et al. |
| 6,837,858 B2 | 1/2005 | Cunningham et al. |
| 6,837,885 B2 | 1/2005 | Koblish et al. |
| 6,837,988 B2 | 1/2005 | Leong et al. |
| 6,849,052 B2 | 2/2005 | Ughigaki et al. |
| 6,850,790 B2 | 2/2005 | Berner et al. |
| 6,850,859 B1 | 2/2005 | Schuh |
| 6,854,882 B2 | 2/2005 | Chen |
| 6,862,465 B2 | 3/2005 | Shults et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,923,764 B2 | 8/2005 | Aceti et al. |
| 6,925,393 B1 | 8/2005 | Kalatz et al. |
| 6,931,327 B2 | 8/2005 | Goode, Jr. et al. |
| 6,932,892 B2 | 8/2005 | Chen |
| 6,932,894 B2 | 8/2005 | Mao et al. |
| 6,936,006 B2 | 8/2005 | Sabra |
| 6,937,222 B2 | 8/2005 | Numao |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman IV et al. |
| 6,954,662 B2 | 10/2005 | Freger et al. |
| 6,958,705 B2 | 10/2005 | Lebel et al. |
| 6,959,211 B2 | 10/2005 | Rule et al. |
| 6,960,192 B1 | 11/2005 | Flaherty et al. |
| 6,968,294 B2 | 11/2005 | Gutta et al. |
| 6,971,274 B2 | 12/2005 | Olin |
| 6,971,999 B2 | 12/2005 | Py et al. |
| 6,973,706 B2 | 12/2005 | Say et al. |
| 6,974,437 B2 | 12/2005 | Lebel et al. |
| 6,975,893 B2 | 12/2005 | Say et al. |
| 6,983,867 B1 | 1/2006 | Fugere |
| 6,990,366 B2 | 1/2006 | Say et al. |
| 6,997,907 B2 | 2/2006 | Safabash et al. |
| 6,998,247 B2 | 2/2006 | Monfre et al. |
| 6,999,854 B2 | 2/2006 | Roth |
| 7,003,336 B2 | 2/2006 | Holker et al. |
| 7,003,340 B2 | 2/2006 | Say et al. |
| 7,003,341 B2 | 2/2006 | Say et al. |
| 7,005,857 B2 | 2/2006 | Stiene et al. |
| 7,009,511 B2 | 3/2006 | Mazar et al. |
| 7,010,356 B2 | 3/2006 | Jog et al. |
| 7,015,817 B2 | 3/2006 | Copley et al. |
| 7,016,713 B2 | 3/2006 | Gardner et al. |
| 7,020,508 B2 | 3/2006 | Stivoric et al. |
| 7,022,072 B2 | 4/2006 | Fox et al. |
| 7,022,219 B2 | 4/2006 | Mansouri et al. |
| 7,024,236 B2 | 4/2006 | Ford et al. |
| 7,024,245 B2 | 4/2006 | Lebel et al. |
| 7,025,743 B2 | 4/2006 | Mann et al. |
| 7,025,774 B2 | 4/2006 | Freeman et al. |
| 7,027,848 B2 | 4/2006 | Robinson et al. |
| 7,027,859 B1 | 4/2006 | McNichols et al. |
| 7,027,931 B1 | 4/2006 | Jones et al. |
| 7,029,444 B2 | 4/2006 | Shin et al. |
| 7,041,057 B1 | 5/2006 | Faupel et al. |
| 7,041,068 B2 | 5/2006 | Freeman et al. |
| 7,041,468 B2 | 5/2006 | Drucker et al. |
| 7,043,305 B2 | 5/2006 | KenKnight et al. |
| 7,046,153 B2 | 5/2006 | Oja et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,073,246 B2 | 7/2006 | Bhullar et al. |
| 7,074,307 B2 | 7/2006 | Simpson et al. |
| 7,081,195 B2 | 7/2006 | Simpson et al. |
| 7,082,334 B2 | 7/2006 | Boute et al. |
| 7,097,637 B2 | 8/2006 | Triplett et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,120,483 B2 | 10/2006 | Russel et al. |
| 7,123,950 B2 | 10/2006 | Mannheimer |
| 7,124,027 B1 | 10/2006 | Ernst et al. |
| 7,125,382 B2 | 10/2006 | Zhou et al. |
| 7,131,984 B2 | 11/2006 | Sato et al. |
| 7,134,999 B2 | 11/2006 | Brauker et al. |
| 7,136,689 B2 | 11/2006 | Shults et al. |
| 7,144,384 B2 | 12/2006 | Gorman et al. |
| 7,146,202 B2 | 12/2006 | Ward et al. |
| 7,154,398 B2 | 12/2006 | Chen et al. |
| 7,155,290 B2 | 12/2006 | Von Arx et al. |
| 7,167,818 B2 | 1/2007 | Brown |
| 7,169,600 B2 | 1/2007 | Hoss et al. |
| 7,171,274 B2 | 1/2007 | Starkweather et al. |
| 7,174,199 B2 | 2/2007 | Berner et al. |
| 7,179,226 B2 | 2/2007 | Crothall et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,207,974 B2 | 4/2007 | Safabash et al. |
| 7,220,387 B2 | 5/2007 | Flaherty et al. |
| 7,223,276 B2 | 5/2007 | List et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,228,162 B2 | 6/2007 | Ward et al. |
| 7,228,182 B2 | 6/2007 | Healy et al. |
| 7,237,712 B2 | 7/2007 | DeRocco et al. |
| 7,267,665 B2 | 9/2007 | Steil et al. |
| 7,276,029 B2 | 10/2007 | Goode, Jr. et al. |
| 7,276,146 B2 | 10/2007 | Wilsey |
| 7,276,147 B2 | 10/2007 | Wilsey |
| 7,278,983 B2 | 10/2007 | Ireland et al. |
| 7,286,894 B1 | 10/2007 | Grant et al. |
| 7,287,318 B2 | 10/2007 | Bhullar et al. |
| 7,291,497 B2 | 11/2007 | Holmes et al. |
| 7,295,867 B2 | 11/2007 | Berner et al. |
| 7,297,151 B2 | 11/2007 | Boecker et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,324,850 B2 | 1/2008 | Persen et al. |
| 7,329,239 B2 | 2/2008 | Safabash et al. |
| 7,335,294 B2 | 2/2008 | Heller et al. |
| 7,340,287 B2 | 3/2008 | Mason et al. |
| 7,340,309 B2 | 3/2008 | Miazga et al. |
| 7,344,500 B2 | 3/2008 | Talbot et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |

(56)                    References Cited

U.S. PATENT DOCUMENTS

| | | | |
|---|---|---|---|
| 7,381,184 | B2 | 6/2008 | Funderburk et al. |
| 7,384,397 | B2 | 6/2008 | Zhang et al. |
| 7,386,937 | B2 | 6/2008 | Bhullar et al. |
| 7,387,010 | B2 | 6/2008 | Sunshine et al. |
| 7,399,277 | B2 | 7/2008 | Saidara et al. |
| 7,400,111 | B2 | 7/2008 | Batman et al. |
| 7,401,111 | B1 | 7/2008 | Batman et al. |
| 7,402,153 | B2 | 7/2008 | Steil et al. |
| 7,404,796 | B2 | 7/2008 | Ginsberg |
| 7,407,493 | B2 | 8/2008 | Cane |
| 7,408,132 | B2 | 8/2008 | Wambsganss et al. |
| 7,416,541 | B2 | 8/2008 | Yuzhakov et al. |
| 7,419,573 | B2 | 9/2008 | Gundel |
| 7,424,318 | B2 | 9/2008 | Brister et al. |
| 7,429,255 | B2 | 9/2008 | Thompson |
| 7,433,727 | B2 | 10/2008 | Ward |
| 7,448,996 | B2 | 11/2008 | Khanuja et al. |
| 7,455,663 | B2 | 11/2008 | Bikovsky |
| 7,460,898 | B2 | 12/2008 | Brister et al. |
| 7,462,264 | B2 | 12/2008 | Heller et al. |
| 7,467,003 | B2 | 12/2008 | Brister et al. |
| 7,468,125 | B2 | 12/2008 | Kraft et al. |
| 7,471,972 | B2 | 12/2008 | Rhodes et al. |
| 7,476,827 | B1 | 1/2009 | Bhullar et al. |
| 7,481,819 | B2 | 1/2009 | Koeppel et al. |
| 7,492,254 | B2 | 2/2009 | Bandy et al. |
| 7,494,465 | B2 | 2/2009 | Brister et al. |
| 7,497,827 | B2 | 3/2009 | Brister et al. |
| 7,499,002 | B2 | 3/2009 | Blasko et al. |
| 7,519,408 | B2 | 4/2009 | Rasdal et al. |
| 7,545,272 | B2 | 6/2009 | Goodnow et al. |
| 7,547,281 | B2 | 6/2009 | Hayes et al. |
| 7,565,197 | B2 | 7/2009 | Haubrich et al. |
| 7,568,619 | B2 | 8/2009 | Todd et al. |
| 7,569,030 | B2 | 8/2009 | Lebel et al. |
| 7,574,266 | B2 | 8/2009 | Pudding et al. |
| 7,582,059 | B2 | 9/2009 | Funderburk et al. |
| 7,583,990 | B2 | 9/2009 | Goode, Jr. et al. |
| 7,585,287 | B2 | 9/2009 | Bresina et al. |
| 7,591,801 | B2 | 9/2009 | Brauker et al. |
| 7,599,726 | B2 | 10/2009 | Goode, Jr. et al. |
| 7,602,310 | B2 | 10/2009 | Mann et al. |
| 7,604,178 | B2 | 10/2009 | Stewart |
| 7,604,592 | B2 | 10/2009 | Freeman et al. |
| 7,613,491 | B2 | 11/2009 | Boock et al. |
| 7,615,007 | B2 | 11/2009 | Shults et al. |
| 7,618,369 | B2 | 11/2009 | Hayter et al. |
| 7,632,228 | B2 | 12/2009 | Brauker et al. |
| 7,635,594 | B2 | 12/2009 | Holmes et al. |
| 7,637,868 | B2 | 12/2009 | Saint et al. |
| 7,640,048 | B2 | 12/2009 | Dobbles et al. |
| 7,643,798 | B2 | 1/2010 | Ljung |
| 7,651,596 | B2 | 1/2010 | Petisce et al. |
| 7,651,845 | B2 | 1/2010 | Doyle, III et al. |
| 7,653,425 | B2 | 1/2010 | Hayter et al. |
| 7,654,956 | B2 | 2/2010 | Brister et al. |
| 7,657,297 | B2 | 2/2010 | Simpson et al. |
| 7,659,823 | B1 | 2/2010 | Killian et al. |
| 7,660,615 | B2 | 2/2010 | VanAntwerp et al. |
| 7,666,149 | B2 | 2/2010 | Simons et al. |
| 7,668,596 | B2 | 2/2010 | Von Arx et al. |
| 7,682,338 | B2 | 3/2010 | Griffin |
| 7,697,967 | B2 | 4/2010 | Stafford |
| 7,699,775 | B2 | 4/2010 | Desai et al. |
| 7,699,807 | B2 | 4/2010 | Faust et al. |
| 7,701,052 | B2 | 4/2010 | Borland et al. |
| 7,711,402 | B2 | 5/2010 | Shults et al. |
| 7,713,574 | B2 | 5/2010 | Brister et al. |
| 7,715,893 | B2 | 5/2010 | Kamath et al. |
| 7,727,147 | B1 | 6/2010 | Osorio et al. |
| 7,729,737 | B2 | 6/2010 | Ward |
| 7,731,657 | B2 | 6/2010 | Stafford |
| 7,731,691 | B2 | 6/2010 | Cote et al. |
| 7,736,310 | B2 | 6/2010 | Taub et al. |
| 7,736,344 | B2 | 6/2010 | Moberg et al. |
| 7,741,734 | B2 | 6/2010 | Joannopoulos et al. |
| 7,763,042 | B2 | 7/2010 | Iio et al. |
| 7,766,829 | B2 | 8/2010 | Sloan et al. |
| 7,768,387 | B2 | 8/2010 | Fennell et al. |
| 7,771,352 | B2 | 8/2010 | Shults et al. |
| 7,774,145 | B2 | 8/2010 | Brauker et al. |
| 7,775,444 | B2 | 8/2010 | DeRocco et al. |
| 7,778,680 | B2 | 8/2010 | Goode, Jr. et al. |
| 7,779,332 | B2 | 8/2010 | Karr et al. |
| 7,780,827 | B1 | 8/2010 | Bhullar et al. |
| 7,782,192 | B2 | 8/2010 | Jeckelmann et al. |
| 7,783,333 | B2 | 8/2010 | Brister et al. |
| 7,791,467 | B2 | 9/2010 | Mazar et al. |
| 7,792,562 | B2 | 9/2010 | Shults et al. |
| 7,811,231 | B2 | 10/2010 | Jin et al. |
| 7,813,809 | B2 | 10/2010 | Strother et al. |
| 7,822,454 | B1 | 10/2010 | Alden et al. |
| 7,826,981 | B2 | 11/2010 | Goode, Jr. et al. |
| 7,831,310 | B2 | 11/2010 | Lebel et al. |
| 7,833,151 | B2 | 11/2010 | Khait et al. |
| 7,833,170 | B2 | 11/2010 | Matsumoto et al. |
| 7,837,633 | B2 | 11/2010 | Conway et al. |
| 7,842,046 | B1 | 11/2010 | Nakao |
| 7,846,132 | B2 | 12/2010 | Gravesen et al. |
| 7,850,652 | B2 | 12/2010 | Liniger et al. |
| 7,860,574 | B2 | 12/2010 | Von Arx et al. |
| 7,866,026 | B1 | 1/2011 | Wang et al. |
| 7,867,244 | B2 | 1/2011 | Lathrop et al. |
| 7,873,299 | B2 | 1/2011 | Berner et al. |
| 7,882,611 | B2 | 2/2011 | Shah et al. |
| 7,883,464 | B2 | 2/2011 | Stafford |
| 7,883,473 | B2 | 2/2011 | LeVaughn et al. |
| 7,885,697 | B2 | 2/2011 | Brister et al. |
| 7,889,069 | B2 | 2/2011 | Fifolt et al. |
| 7,896,844 | B2 | 3/2011 | Thalmann et al. |
| 7,899,511 | B2 | 3/2011 | Shults et al. |
| 7,899,545 | B2 | 3/2011 | John |
| 7,905,833 | B2 | 3/2011 | Brister et al. |
| 7,912,655 | B2 | 3/2011 | Power et al. |
| 7,912,674 | B2 | 3/2011 | Killoren Clark et al. |
| 7,914,450 | B2 | 3/2011 | Goode, Jr. et al. |
| 7,914,460 | B2 | 3/2011 | Melker et al. |
| 7,916,013 | B2 | 3/2011 | Stevenson |
| 7,920,906 | B2 | 4/2011 | Goode, Jr. et al. |
| 7,920,907 | B2 | 4/2011 | McGarraugh et al. |
| 7,938,797 | B2 | 5/2011 | Estes |
| 7,941,200 | B2 | 5/2011 | Weinart et al. |
| 7,946,984 | B2 | 5/2011 | Brister et al. |
| 7,946,985 | B2 | 5/2011 | Mastrototaro et al. |
| 7,955,258 | B2 | 6/2011 | Goscha et al. |
| 7,955,297 | B2 | 6/2011 | Radmer et al. |
| 7,970,448 | B2 | 6/2011 | Shults et al. |
| 7,970,449 | B2 | 6/2011 | Ward |
| 7,972,296 | B2 | 7/2011 | Braig et al. |
| 7,974,672 | B2 | 7/2011 | Shults et al. |
| 7,976,467 | B2 | 7/2011 | Young et al. |
| 7,978,063 | B2 | 7/2011 | Baldus et al. |
| 7,985,203 | B2 | 7/2011 | Haueter et al. |
| 7,985,222 | B2 | 7/2011 | Gall et al. |
| 7,996,158 | B2 | 8/2011 | Hayter et al. |
| 7,999,674 | B2 | 8/2011 | Kamen |
| 8,000,918 | B2 | 8/2011 | Fjield et al. |
| 8,005,524 | B2 | 8/2011 | Brauker et al. |
| 8,010,174 | B2 | 8/2011 | Goode, Jr. et al. |
| 8,010,256 | B2 | 8/2011 | Oowada |
| 8,016,774 | B2 | 9/2011 | Freeman et al. |
| 8,028,837 | B2 | 10/2011 | Gerstle et al. |
| 8,029,441 | B2 | 10/2011 | Mazza et al. |
| 8,029,442 | B2 | 10/2011 | Funderburk et al. |
| 8,072,310 | B1 | 12/2011 | Everhart |
| 8,090,445 | B2 | 1/2012 | Ginggen |
| 8,093,991 | B2 | 1/2012 | Stevenson et al. |
| 8,094,009 | B2 | 1/2012 | Allen et al. |
| 8,098,159 | B2 | 1/2012 | Batra et al. |
| 8,098,160 | B2 | 1/2012 | Howarth et al. |
| 8,098,161 | B2 | 1/2012 | Lavedas |
| 8,098,201 | B2 | 1/2012 | Choi et al. |
| 8,098,208 | B2 | 1/2012 | Ficker et al. |
| 8,102,021 | B2 | 1/2012 | Degani |

(56)        References Cited

U.S. PATENT DOCUMENTS

| | | | |
|---|---|---|---|
| 8,102,154 | B2 | 1/2012 | Bishop et al. |
| 8,102,263 | B2 | 1/2012 | Yeo et al. |
| 8,102,789 | B2 | 1/2012 | Rosar et al. |
| 8,103,241 | B2 | 1/2012 | Young et al. |
| 8,103,325 | B2 | 1/2012 | Swedlow et al. |
| 8,103,471 | B2 | 1/2012 | Hayter |
| 8,111,042 | B2 | 2/2012 | Bennett |
| 8,112,240 | B2 | 2/2012 | Fennell |
| 8,115,488 | B2 | 2/2012 | McDowell |
| 8,116,681 | B2 | 2/2012 | Baarman |
| 8,116,683 | B2 | 2/2012 | Baarman |
| 8,117,481 | B2 | 2/2012 | Anselmi et al. |
| 8,120,493 | B2 | 2/2012 | Burr |
| 8,124,452 | B2 | 2/2012 | Sheats |
| 8,130,093 | B2 | 3/2012 | Mazar et al. |
| 8,131,351 | B2 | 3/2012 | Kalgren et al. |
| 8,131,365 | B2 | 3/2012 | Zhang et al. |
| 8,131,565 | B2 | 3/2012 | Dicks et al. |
| 8,132,037 | B2 | 3/2012 | Fehr et al. |
| 8,135,352 | B2 | 3/2012 | Langsweirdt et al. |
| 8,136,735 | B2 | 3/2012 | Arai et al. |
| 8,138,925 | B2 | 3/2012 | Downie et al. |
| 8,140,160 | B2 | 3/2012 | Pless et al. |
| 8,140,168 | B2 | 3/2012 | Olson et al. |
| 8,140,299 | B2 | 3/2012 | Siess |
| 8,140,312 | B2 | 3/2012 | Hayter et al. |
| 8,150,321 | B2 | 4/2012 | Winter et al. |
| 8,150,516 | B2 | 4/2012 | Levine et al. |
| 8,160,670 | B2 | 4/2012 | Quyang et al. |
| 8,160,900 | B2 | 4/2012 | Taub et al. |
| 8,172,805 | B2 | 5/2012 | Mogensen et al. |
| 8,175,673 | B2 | 5/2012 | Say et al. |
| 8,179,266 | B2 | 5/2012 | Hermle |
| 8,180,423 | B2 | 5/2012 | Mang et al. |
| 8,192,394 | B2 | 6/2012 | Estes et al. |
| 8,216,138 | B1 | 7/2012 | McGaraugh et al. |
| 8,221,332 | B2 | 7/2012 | Robbins et al. |
| 8,224,410 | B2 | 7/2012 | Hadvary et al. |
| 8,239,166 | B2 | 8/2012 | Hayter et al. |
| 8,255,026 | B1 | 8/2012 | Al-Ali |
| 8,260,558 | B2 | 9/2012 | Hayter et al. |
| 8,262,618 | B2 | 9/2012 | Scheurer |
| 8,282,549 | B2 | 10/2012 | Brauker et al. |
| 8,333,714 | B2 | 12/2012 | Stafford |
| 8,346,335 | B2 | 1/2013 | Harper et al. |
| 8,346,337 | B2 | 1/2013 | Heller et al. |
| 8,373,544 | B2 | 2/2013 | Pitt-Plady |
| 8,374,668 | B1 | 2/2013 | Hayter et al. |
| 8,376,945 | B2 | 2/2013 | Hayter et al. |
| 8,377,271 | B2 | 2/2013 | Mao et al. |
| 8,382,671 | B2 | 2/2013 | Anthony et al. |
| 8,398,664 | B2 | 3/2013 | Lamps et al. |
| 8,409,093 | B2 | 4/2013 | Bugler |
| 8,409,145 | B2 | 4/2013 | Raymond et al. |
| 8,439,838 | B2 | 5/2013 | Mogensen et al. |
| 8,444,560 | B2 | 5/2013 | Hayter et al. |
| 8,461,985 | B2 | 6/2013 | Fennell et al. |
| 8,469,986 | B2 | 6/2013 | Schraga |
| 8,512,243 | B2 | 8/2013 | Stafford |
| 8,515,518 | B2 | 8/2013 | Ouyang et al. |
| 8,515,519 | B2 | 8/2013 | Brister et al. |
| 8,538,512 | B1 | 9/2013 | Bibian et al. |
| 8,545,403 | B2 | 10/2013 | Peyser et al. |
| 8,560,038 | B2 | 10/2013 | Hayter et al. |
| 8,562,567 | B2 | 10/2013 | Gundberg |
| 8,571,808 | B2 | 10/2013 | Hayter |
| 8,583,205 | B2 | 11/2013 | Budiman et al. |
| 8,585,591 | B2 | 11/2013 | Sloan et al. |
| 8,597,570 | B2 | 12/2013 | Terashima et al. |
| 8,600,681 | B2 | 12/2013 | Hayter et al. |
| 8,602,991 | B2 | 12/2013 | Stafford |
| 8,612,163 | B2 | 12/2013 | Hayter et al. |
| 8,615,282 | B2 | 12/2013 | Brister et al. |
| 8,617,069 | B2 | 12/2013 | Bernstein et al. |
| 8,617,071 | B2 | 12/2013 | Say et al. |
| 8,622,903 | B2 | 1/2014 | Jin et al. |
| 8,628,498 | B2 | 1/2014 | Safabach et al. |
| 8,641,674 | B2 | 2/2014 | Bobroff et al. |
| 8,652,043 | B2 | 2/2014 | Drucker et al. |
| 8,682,408 | B2 | 3/2014 | Boock et al. |
| 8,682,615 | B2 | 3/2014 | Hayter et al. |
| 8,684,930 | B2 | 4/2014 | Feldman et al. |
| 8,692,655 | B2 | 4/2014 | Zimman et al. |
| 8,710,993 | B2 | 4/2014 | Hayter et al. |
| 8,747,363 | B2 | 6/2014 | Nielsen et al. |
| 8,750,955 | B2 | 6/2014 | Brister et al. |
| 8,771,183 | B2 | 7/2014 | Sloan |
| 8,797,163 | B2 | 8/2014 | Finkenzeller |
| 8,808,515 | B2 | 8/2014 | Feldman et al. |
| 8,834,366 | B2 | 9/2014 | Hayter et al. |
| 8,845,536 | B2 | 9/2014 | Brauker et al. |
| 8,870,822 | B2 | 10/2014 | Thalmann et al. |
| 8,880,138 | B2 | 11/2014 | Cho |
| 8,945,056 | B2 | 2/2015 | Lio et al. |
| 8,961,413 | B2 | 2/2015 | Teller et al. |
| 9,007,781 | B2 | 4/2015 | Moein et al. |
| 9,014,774 | B2 | 4/2015 | Mao et al. |
| 9,031,630 | B2 | 5/2015 | Hoss et al. |
| 9,060,719 | B2 | 6/2015 | Hayter et al. |
| 9,060,805 | B2 | 6/2015 | Goodnow et al. |
| 9,066,697 | B2 | 6/2015 | Peyser et al. |
| 9,101,302 | B2 | 8/2015 | Mace et al. |
| 9,186,098 | B2 | 11/2015 | Lee et al. |
| 9,215,992 | B2 | 12/2015 | Donnay et al. |
| 9,241,631 | B2 | 1/2016 | Valdes et al. |
| 9,259,175 | B2 | 2/2016 | Stafford |
| 9,265,453 | B2 | 2/2016 | Curry et al. |
| 9,289,179 | B2 | 3/2016 | Hayter et al. |
| 9,295,786 | B2 | 3/2016 | Gottlieb et al. |
| 9,357,951 | B2 | 6/2016 | Simpson et al. |
| 9,398,872 | B2 | 7/2016 | Hayter et al. |
| 9,402,544 | B2 | 8/2016 | Yee et al. |
| 9,402,570 | B2 | 8/2016 | Pace et al. |
| 9,439,586 | B2 | 9/2016 | Bugler |
| 9,451,910 | B2 | 9/2016 | Brister et al. |
| 9,474,479 | B2 | 10/2016 | Pusey et al. |
| 9,480,421 | B2 | 11/2016 | Stafford |
| 9,483,608 | B2 | 11/2016 | Hayter et al. |
| 9,504,471 | B2 | 11/2016 | Vaitekunas et al. |
| 9,558,325 | B2 | 1/2017 | Hayter et al. |
| 9,566,384 | B2 | 2/2017 | Gyrn et al. |
| 9,636,068 | B2 | 5/2017 | Yee et al. |
| 9,668,682 | B2 | 6/2017 | Brister et al. |
| 9,743,876 | B2 | 8/2017 | Gelfand et al. |
| 9,808,574 | B2 | 11/2017 | Yodfat et al. |
| 9,814,414 | B2 | 11/2017 | Brister et al. |
| 10,213,139 | B2 | 2/2019 | Rao et al. |
| 10,292,632 | B2 | 5/2019 | Lee et al. |
| 10,342,489 | B2 | 7/2019 | Stafford |
| 10,772,547 | B1 | 9/2020 | Lee et al. |
| 10,820,842 | B2 | 11/2020 | Harper |
| 10,827,954 | B2 | 11/2020 | Hoss et al. |
| 10,874,338 | B2 | 12/2020 | Stafford |
| 10,881,340 | B2 | 1/2021 | Curry et al. |
| 10,881,341 | B1 | 1/2021 | Curry et al. |
| 10,945,647 | B2 | 3/2021 | Mazza et al. |
| 10,945,649 | B2 | 3/2021 | Lee et al. |
| 10,952,653 | B2 | 3/2021 | Harper |
| 10,959,654 | B2 | 3/2021 | Curry et al. |
| 10,966,644 | B2 | 4/2021 | Stafford |
| 10,973,443 | B2 | 4/2021 | Funderburk et al. |
| 10,980,461 | B2 | 4/2021 | Bohm et al. |
| 11,000,213 | B2 | 5/2021 | Kamath et al. |
| 11,000,216 | B2 | 5/2021 | Curry et al. |
| 11,006,870 | B2 * | 5/2021 | Yee .......................... A61B 5/72 |
| 11,006,871 | B2 * | 5/2021 | Yee .................... A61M 5/1723 |
| 11,013,440 | B2 | 5/2021 | Lee et al. |
| 11,051,724 | B2 | 7/2021 | Pace et al. |
| 11,064,917 | B2 | 7/2021 | Simpson et al. |
| 11,116,430 | B2 | 9/2021 | Funderburk et al. |
| 11,141,084 | B2 | 10/2021 | Funderburk et al. |
| 11,166,656 | B2 | 11/2021 | Yee et al. |
| 11,179,068 | B2 | 11/2021 | Pace et al. |
| 11,197,625 | B1 | 12/2021 | Schleicher et al. |

(56) References Cited

U.S. PATENT DOCUMENTS

| | | | |
|---|---|---|---|
| 11,202,591 B2 * | 12/2021 | Yee | G06K 7/10366 |
| 11,213,229 B2 * | 1/2022 | Yee | A61M 5/1723 |
| 11,246,519 B2 | 2/2022 | Donnay et al. | |
| 11,266,335 B2 | 3/2022 | Donnay et al. | |
| 11,298,056 B2 | 4/2022 | Harper | |
| 11,298,058 B2 | 4/2022 | Stafford | |
| 11,510,625 B2 | 11/2022 | Gray et al. | |
| 2001/0016682 A1 | 8/2001 | Berner et al. | |
| 2001/0034479 A1 | 10/2001 | Ring et al. | |
| 2001/0037060 A1 | 11/2001 | Thompson et al. | |
| 2001/0037366 A1 | 11/2001 | Webb et al. | |
| 2001/0039387 A1 | 11/2001 | Rutynowski et al. | |
| 2001/0044608 A1 | 11/2001 | Odell et al. | |
| 2001/0047127 A1 | 11/2001 | New et al. | |
| 2001/0056262 A1 | 12/2001 | Cabin et al. | |
| 2002/0002344 A1 | 1/2002 | Douglas et al. | |
| 2002/0010390 A1 | 1/2002 | Guice et al. | |
| 2002/0013522 A1 | 1/2002 | Lav et al. | |
| 2002/0013538 A1 | 1/2002 | Teller | |
| 2002/0016534 A1 | 2/2002 | Trepagnier et al. | |
| 2002/0016568 A1 | 2/2002 | Lebel et al. | |
| 2002/0019022 A1 | 2/2002 | Dunn et al. | |
| 2002/0019584 A1 | 2/2002 | Schulze et al. | |
| 2002/0019586 A1 | 2/2002 | Teller et al. | |
| 2002/0019606 A1 | 2/2002 | Lebel et al. | |
| 2002/0022855 A1 | 2/2002 | Bobroff et al. | |
| 2002/0023852 A1 | 2/2002 | McIvor et al. | |
| 2002/0029058 A1 | 3/2002 | Vaughn et al. | |
| 2002/0032386 A1 | 3/2002 | Sackner et al. | |
| 2002/0039026 A1 | 4/2002 | Stroth et al. | |
| 2002/0042090 A1 | 4/2002 | Heller et al. | |
| 2002/0045808 A1 | 4/2002 | Ford et al. | |
| 2002/0049482 A1 | 4/2002 | Fabian et al. | |
| 2002/0050250 A1 | 5/2002 | Peterson et al. | |
| 2002/0055711 A1 | 5/2002 | Lavi et al. | |
| 2002/0057993 A1 | 5/2002 | Maisey et al. | |
| 2002/0065454 A1 | 5/2002 | Lebel et al. | |
| 2002/0066764 A1 | 6/2002 | Perry et al. | |
| 2002/0072720 A1 | 6/2002 | Hague et al. | |
| 2002/0072784 A1 | 6/2002 | Sheppard et al. | |
| 2002/0074162 A1 | 6/2002 | Su et al. | |
| 2002/0076966 A1 | 6/2002 | Carron et al. | |
| 2002/0077599 A1 | 6/2002 | Wojcik | |
| 2002/0082487 A1 | 6/2002 | Kollias et al. | |
| 2002/0084196 A1 | 7/2002 | Liamos et al. | |
| 2002/0091796 A1 | 7/2002 | Higginson et al. | |
| 2002/0093969 A1 | 7/2002 | Lin et al. | |
| 2002/0095076 A1 | 7/2002 | Krausman et al. | |
| 2002/0103499 A1 | 8/2002 | Perez et al. | |
| 2002/0106709 A1 | 8/2002 | Potts et al. | |
| 2002/0111832 A1 | 8/2002 | Judge | |
| 2002/0117639 A1 | 8/2002 | Paolini et al. | |
| 2002/0118528 A1 | 8/2002 | Su et al. | |
| 2002/0119711 A1 | 8/2002 | VanAntwerp et al. | |
| 2002/0120186 A1 | 8/2002 | Keimel | |
| 2002/0124017 A1 | 9/2002 | Mault | |
| 2002/0128594 A1 | 9/2002 | Das et al. | |
| 2002/0130042 A1 | 9/2002 | Moerman et al. | |
| 2002/0133066 A1 | 9/2002 | Miller et al. | |
| 2002/0147135 A1 | 10/2002 | Schnell | |
| 2002/0150959 A1 | 10/2002 | Lejeune et al. | |
| 2002/0151770 A1 | 10/2002 | Noll et al. | |
| 2002/0151796 A1 | 10/2002 | Koulik | |
| 2002/0151816 A1 | 10/2002 | Rich et al. | |
| 2002/0154050 A1 | 10/2002 | Krupp et al. | |
| 2002/0161288 A1 | 10/2002 | Shin et al. | |
| 2002/0161290 A1 | 10/2002 | Chance | |
| 2002/0161338 A1 | 10/2002 | Peterson | |
| 2002/0164836 A1 | 11/2002 | Ho | |
| 2002/0165462 A1 | 11/2002 | Westbrook et al. | |
| 2002/0169369 A1 | 11/2002 | Ward et al. | |
| 2002/0169439 A1 | 11/2002 | Flaherty et al. | |
| 2002/0169635 A1 | 11/2002 | Shillingburg | |
| 2002/0183604 A1 | 12/2002 | Gowda et al. | |
| 2002/0185128 A1 | 12/2002 | Theobald | |
| 2002/0185130 A1 | 12/2002 | Wright et al. | |
| 2002/0188748 A1 | 12/2002 | Blackwell et al. | |
| 2002/0197522 A1 | 12/2002 | Lawrence et al. | |
| 2002/0198444 A1 | 12/2002 | Ughigaki et al. | |
| 2002/0198543 A1 | 12/2002 | Burdulis et al. | |
| 2003/0004403 A1 | 1/2003 | Drinan et al. | |
| 2003/0020477 A1 | 1/2003 | Goldstein | |
| 2003/0023189 A1 | 1/2003 | Kuo | |
| 2003/0023317 A1 | 1/2003 | Brauker et al. | |
| 2003/0023461 A1 | 1/2003 | Quintanilla et al. | |
| 2003/0028089 A1 | 2/2003 | Galley et al. | |
| 2003/0028184 A1 | 2/2003 | Lebel et al. | |
| 2003/0032077 A1 | 2/2003 | Itoh et al. | |
| 2003/0032867 A1 | 2/2003 | Crothall et al. | |
| 2003/0032874 A1 | 2/2003 | Rhodes et al. | |
| 2003/0042137 A1 | 3/2003 | Mao et al. | |
| 2003/0050546 A1 | 3/2003 | Desai et al. | |
| 2003/0054428 A1 | 3/2003 | Monfre et al. | |
| 2003/0055380 A1 | 3/2003 | Flaherty | |
| 2003/0060692 A1 | 3/2003 | Ruchti et al. | |
| 2003/0060753 A1 | 3/2003 | Starkweather et al. | |
| 2003/0065308 A1 | 4/2003 | Lebel et al. | |
| 2003/0069509 A1 | 4/2003 | Matzinger et al. | |
| 2003/0069510 A1 | 4/2003 | Semler | |
| 2003/0076792 A1 | 4/2003 | Theimer | |
| 2003/0077642 A1 | 4/2003 | Fritsch et al. | |
| 2003/0078481 A1 | 4/2003 | McIvor et al. | |
| 2003/0078560 A1 | 4/2003 | Miller et al. | |
| 2003/0083686 A1 | 5/2003 | Freeman et al. | |
| 2003/0088166 A1 | 5/2003 | Say et al. | |
| 2003/0097092 A1 | 5/2003 | Flaherty | |
| 2003/0100040 A1 | 5/2003 | Bonnecaze et al. | |
| 2003/0100821 A1 | 5/2003 | Heller et al. | |
| 2003/0109775 A1 | 6/2003 | O'Neil et al. | |
| 2003/0114897 A1 | 6/2003 | Von Arx et al. | |
| 2003/0114898 A1 | 6/2003 | Von Arx et al. | |
| 2003/0119457 A1 | 6/2003 | Standke | |
| 2003/0125612 A1 | 7/2003 | Fox et al. | |
| 2003/0130616 A1 | 7/2003 | Steil et al. | |
| 2003/0134347 A1 | 7/2003 | Heller et al. | |
| 2003/0135127 A1 | 7/2003 | Sackner et al. | |
| 2003/0135333 A1 | 7/2003 | Aceti et al. | |
| 2003/0144579 A1 | 7/2003 | Buss | |
| 2003/0144581 A1 | 7/2003 | Conn et al. | |
| 2003/0144608 A1 | 7/2003 | Kojima et al. | |
| 2003/0153900 A1 | 8/2003 | Aceti et al. | |
| 2003/0155656 A1 | 8/2003 | Chiu et al. | |
| 2003/0168338 A1 | 9/2003 | Gao et al. | |
| 2003/0176933 A1 | 9/2003 | Lebel et al. | |
| 2003/0187338 A1 | 10/2003 | Say et al. | |
| 2003/0188427 A1 | 10/2003 | Say et al. | |
| 2003/0199744 A1 | 10/2003 | Buse et al. | |
| 2003/0199790 A1 | 10/2003 | Boecker et al. | |
| 2003/0199910 A1 | 10/2003 | Boecker et al. | |
| 2003/0204290 A1 | 10/2003 | Sadler et al. | |
| 2003/0208113 A1 | 11/2003 | Mault et al. | |
| 2003/0208114 A1 | 11/2003 | Ackerman | |
| 2003/0212317 A1 | 11/2003 | Kovatchev et al. | |
| 2003/0212379 A1 | 11/2003 | Bylund et al. | |
| 2003/0212579 A1 | 11/2003 | Brown et al. | |
| 2003/0216621 A1 | 11/2003 | Alpert et al. | |
| 2003/0216630 A1 | 11/2003 | Jersey-Willuhn et al. | |
| 2003/0217966 A1 | 11/2003 | Tapsak et al. | |
| 2003/0225361 A1 | 12/2003 | Sabra | |
| 2003/0225373 A1 | 12/2003 | Bobroff et al. | |
| 2003/0236489 A1 | 12/2003 | Jacobson et al. | |
| 2004/0002682 A1 | 1/2004 | Kovelman et al. | |
| 2004/0010207 A1 | 1/2004 | Flaherty et al. | |
| 2004/0011671 A1 | 1/2004 | Shults et al. | |
| 2004/0015131 A1 | 1/2004 | Flaherty et al. | |
| 2004/0017300 A1 | 1/2004 | Kotzin et al. | |
| 2004/0030226 A1 | 2/2004 | Quy | |
| 2004/0030531 A1 | 2/2004 | Miller et al. | |
| 2004/0030581 A1 | 2/2004 | Levin et al. | |
| 2004/0034289 A1 | 2/2004 | Teller et al. | |
| 2004/0039255 A1 | 2/2004 | Simonsen et al. | |
| 2004/0039298 A1 | 2/2004 | Abreu | |
| 2004/0040840 A1 | 3/2004 | Mao et al. | |
| 2004/0045879 A1 | 3/2004 | Shults et al. | |

(56) References Cited

U.S. PATENT DOCUMENTS

| | | |
|---|---|---|
| 2004/0054263 A1 | 3/2004 | Moerman et al. |
| 2004/0060818 A1 | 4/2004 | Feldman et al. |
| 2004/0061232 A1 | 4/2004 | Shah et al. |
| 2004/0063435 A1 | 4/2004 | Sakamoto et al. |
| 2004/0064068 A1 | 4/2004 | DeNuzzio et al. |
| 2004/0064133 A1 | 4/2004 | Miller et al. |
| 2004/0072357 A1 | 4/2004 | Steine et al. |
| 2004/0073266 A1 | 4/2004 | Haefner et al. |
| 2004/0078215 A1 | 4/2004 | Dahlin et al. |
| 2004/0096959 A1 | 5/2004 | Steine et al. |
| 2004/0100376 A1 | 5/2004 | Lye et al. |
| 2004/0105411 A1 | 6/2004 | Boatwright et al. |
| 2004/0106858 A1 | 6/2004 | Say et al. |
| 2004/0106859 A1 | 6/2004 | Say et al. |
| 2004/0106860 A1 | 6/2004 | Say et al. |
| 2004/0111017 A1 | 6/2004 | Say et al. |
| 2004/0116847 A1 | 6/2004 | Wall |
| 2004/0116865 A1 | 6/2004 | Bengtsson |
| 2004/0116866 A1 | 6/2004 | Gorman et al. |
| 2004/0117204 A1 | 6/2004 | Mazar et al. |
| 2004/0119169 A1 | 6/2004 | Hanawa |
| 2004/0122353 A1 | 6/2004 | Shahmirian et al. |
| 2004/0122489 A1 | 6/2004 | Mazar et al. |
| 2004/0133089 A1 | 7/2004 | Kilcoyne et al. |
| 2004/0133164 A1 | 7/2004 | Funderburk et al. |
| 2004/0133390 A1 | 7/2004 | Osorio et al. |
| 2004/0135571 A1 | 7/2004 | Uutela et al. |
| 2004/0135684 A1 | 7/2004 | Steinthal et al. |
| 2004/0138544 A1 | 7/2004 | Ward et al. |
| 2004/0138588 A1 | 7/2004 | Saikley et al. |
| 2004/0138688 A1 | 7/2004 | Giraud |
| 2004/0140211 A1 | 7/2004 | Broy et al. |
| 2004/0142403 A1 | 7/2004 | Hetzel et al. |
| 2004/0146909 A1 | 7/2004 | Duong et al. |
| 2004/0147872 A1 | 7/2004 | Thompson |
| 2004/0147996 A1 | 7/2004 | Miazga et al. |
| 2004/0152366 A1 | 8/2004 | Schultz et al. |
| 2004/0152622 A1 | 8/2004 | Keith et al. |
| 2004/0158207 A1 | 8/2004 | Hunn et al. |
| 2004/0162521 A1 | 8/2004 | Bengtsson et al. |
| 2004/0162678 A1 | 8/2004 | Hetzel et al. |
| 2004/0167801 A1 | 8/2004 | Say et al. |
| 2004/0171910 A1 | 9/2004 | Moore-Steele |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204673 A1 | 10/2004 | Flaherty |
| 2004/0204687 A1 | 10/2004 | Mogensen et al. |
| 2004/0204744 A1 | 10/2004 | Penner et al. |
| 2004/0204868 A1 | 10/2004 | Maynard et al. |
| 2004/0206625 A1 | 10/2004 | Bhullar et al. |
| 2004/0206916 A1 | 10/2004 | Colvin, Jr. et al. |
| 2004/0210122 A1 | 10/2004 | Sleburg |
| 2004/0221057 A1 | 11/2004 | Darcey et al. |
| 2004/0223876 A1 | 11/2004 | Kirollos et al. |
| 2004/0223985 A1 | 11/2004 | Dunfield et al. |
| 2004/0225199 A1 | 11/2004 | Evanyk et al. |
| 2004/0225262 A1 | 11/2004 | Fathallah et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0240426 A1 | 12/2004 | Wu et al. |
| 2004/0249253 A1 | 12/2004 | Racchini et al. |
| 2004/0249999 A1 | 12/2004 | Connolly et al. |
| 2004/0254433 A1 | 12/2004 | Bandis et al. |
| 2004/0254434 A1 | 12/2004 | Goodnow et al. |
| 2004/0258564 A1 | 12/2004 | Charlton |
| 2004/0260224 A1 | 12/2004 | Binder et al. |
| 2004/0267300 A1 | 12/2004 | Mace |
| 2005/0001024 A1 | 1/2005 | Kusaka et al. |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0006122 A1 | 1/2005 | Burnette |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0038465 A1 | 2/2005 | Shraga |
| 2005/0038680 A1 | 2/2005 | McMahon |
| 2005/0043598 A1 | 2/2005 | Goode, Jr. et al. |
| 2005/0049179 A1 | 3/2005 | Davidson et al. |
| 2005/0051427 A1 | 3/2005 | Brauker et al. |
| 2005/0051440 A1 | 3/2005 | Simpson et al. |
| 2005/0056552 A1 | 3/2005 | Simpson et al. |
| 2005/0065464 A1 | 3/2005 | Talbot et al. |
| 2005/0070774 A1 | 3/2005 | Addison et al. |
| 2005/0070819 A1 | 3/2005 | Poux et al. |
| 2005/0085872 A1 | 4/2005 | Yanagihara et al. |
| 2005/0090607 A1 | 4/2005 | Tapsak et al. |
| 2005/0090850 A1 | 4/2005 | Thoes et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0096520 A1 | 5/2005 | Maekawa et al. |
| 2005/0096587 A1 | 5/2005 | Santini, Jr. et al. |
| 2005/0101912 A1 | 5/2005 | Faust et al. |
| 2005/0101932 A1 | 5/2005 | Cote et al. |
| 2005/0103624 A1 | 5/2005 | Bhullar et al. |
| 2005/0104457 A1 | 5/2005 | Jordan et al. |
| 2005/0106713 A1 | 5/2005 | Phan et al. |
| 2005/0112169 A1 | 5/2005 | Brauker et al. |
| 2005/0112544 A1 | 5/2005 | Xu et al. |
| 2005/0113648 A1 | 5/2005 | Yang et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0115832 A1 | 6/2005 | Simpson et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0131347 A1 | 6/2005 | Marano-Ford et al. |
| 2005/0134731 A1 | 6/2005 | Lee et al. |
| 2005/0137488 A1 | 6/2005 | Henry et al. |
| 2005/0137530 A1 | 6/2005 | Campbell et al. |
| 2005/0143635 A1 | 6/2005 | Kamath et al. |
| 2005/0149066 A1 | 7/2005 | Stafford |
| 2005/0151976 A1 | 7/2005 | Toma |
| 2005/0154271 A1 | 7/2005 | Rasdal et al. |
| 2005/0154410 A1 | 7/2005 | Conway et al. |
| 2005/0159678 A1 | 7/2005 | Taniike et al. |
| 2005/0161346 A1 | 7/2005 | Simpson et al. |
| 2005/0165404 A1 | 7/2005 | Miller |
| 2005/0171442 A1 | 8/2005 | Shirasaki et al. |
| 2005/0173245 A1 | 8/2005 | Feldman et al. |
| 2005/0176136 A1 | 8/2005 | Burd et al. |
| 2005/0177398 A1 | 8/2005 | Watanabe et al. |
| 2005/0181010 A1 | 8/2005 | Hunter et al. |
| 2005/0182306 A1 | 8/2005 | Sloan |
| 2005/0182358 A1 | 8/2005 | Veit et al. |
| 2005/0187442 A1 | 8/2005 | Cho et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0197554 A1 | 9/2005 | Polcha |
| 2005/0197793 A1 | 9/2005 | Baker |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |

(56) References Cited

U.S. PATENT DOCUMENTS

| | | |
|---|---|---|
| 2005/0215871 A1 | 9/2005 | Feldman et al. |
| 2005/0221504 A1 | 10/2005 | Petruno et al. |
| 2005/0222518 A1 | 10/2005 | Dib |
| 2005/0222599 A1 | 10/2005 | Czemecki et al. |
| 2005/0236277 A9 | 10/2005 | Imran et al. |
| 2005/0236361 A1 | 10/2005 | Ufer et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245844 A1 | 11/2005 | Mace et al. |
| 2005/0245904 A1 | 11/2005 | Estes et al. |
| 2005/0247319 A1 | 11/2005 | Berger |
| 2005/0251033 A1 | 11/2005 | Scarantino et al. |
| 2005/0261563 A1 | 11/2005 | Zhou et al. |
| 2005/0267325 A1 | 12/2005 | Bouchier et al. |
| 2005/0267327 A1 | 12/2005 | Iizuka et al. |
| 2005/0269214 A1 | 12/2005 | Lee |
| 2005/0277164 A1 | 12/2005 | Drucker et al. |
| 2005/0277912 A1 | 12/2005 | John |
| 2005/0281234 A1 | 12/2005 | Kawamura et al. |
| 2005/0283114 A1 | 12/2005 | Bresina et al. |
| 2005/0283208 A1 | 12/2005 | Von Arx et al. |
| 2005/0283209 A1 | 12/2005 | Katoozi et al. |
| 2005/0284758 A1 | 12/2005 | Funke et al. |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0004270 A1 | 1/2006 | Bedard et al. |
| 2006/0004272 A1 | 1/2006 | Shah et al. |
| 2006/0004303 A1 | 1/2006 | Weidenhaupt et al. |
| 2006/0006141 A1 | 1/2006 | Ufer et al. |
| 2006/0009727 A1 | 1/2006 | O'Mahony et al. |
| 2006/0010098 A1 | 1/2006 | Goodnow et al. |
| 2006/0012464 A1 | 1/2006 | Nitzan et al. |
| 2006/0015020 A1 | 1/2006 | Neale et al. |
| 2006/0015024 A1 | 1/2006 | Brister et al. |
| 2006/0016700 A1* | 1/2006 | Brister ............ A61B 5/6849 |
| | | 205/792 |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025662 A1 | 2/2006 | Buse et al. |
| 2006/0025663 A1 | 2/2006 | Talbot et al. |
| 2006/0029177 A1 | 2/2006 | Cranford, Jr. et al. |
| 2006/0030789 A1 | 2/2006 | Allen |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040402 A1 | 2/2006 | Brauker et al. |
| 2006/0040793 A1 | 2/2006 | Martens et al. |
| 2006/0041276 A1 | 2/2006 | Chan |
| 2006/0042080 A1 | 3/2006 | Say et al. |
| 2006/0047220 A1 | 3/2006 | Sakata et al. |
| 2006/0049359 A1 | 3/2006 | Busta et al. |
| 2006/0058588 A1 | 3/2006 | Zdeblick |
| 2006/0064035 A1 | 3/2006 | Wang et al. |
| 2006/0068208 A1 | 3/2006 | Tapsak et al. |
| 2006/0079740 A1 | 4/2006 | Silver et al. |
| 2006/0081469 A1 | 4/2006 | Lee |
| 2006/0086624 A1 | 4/2006 | Tapsak et al. |
| 2006/0091006 A1 | 5/2006 | Wang et al. |
| 2006/0094944 A1 | 5/2006 | Chuang |
| 2006/0095014 A1 | 5/2006 | Ethelfeld |
| 2006/0116607 A1 | 6/2006 | Nakamura et al. |
| 2006/0129173 A1 | 6/2006 | Wilkinson |
| 2006/0129733 A1 | 6/2006 | Solbelman |
| 2006/0135908 A1 | 6/2006 | Liniger et al. |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0155210 A1 | 7/2006 | Beckman et al. |
| 2006/0155317 A1 | 7/2006 | List |
| 2006/0161194 A1 | 7/2006 | Freeman et al. |
| 2006/0161664 A1 | 7/2006 | Mastrototaro et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0181695 A1 | 8/2006 | Sage |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0189939 A1 | 8/2006 | Gonnelli et al. |
| 2006/0193375 A1 | 8/2006 | Lee et al. |
| 2006/0195029 A1 | 8/2006 | Shults et al. |
| 2006/0195133 A1 | 8/2006 | Freeman et al. |
| 2006/0200020 A1 | 9/2006 | Brister et al. |
| 2006/0200022 A1 | 9/2006 | Brauker et al. |
| 2006/0200181 A1 | 9/2006 | Fukuzawa et al. |
| 2006/0200970 A1 | 9/2006 | Brister et al. |
| 2006/0200981 A1 | 9/2006 | Bhullar et al. |
| 2006/0200982 A1 | 9/2006 | Bhullar et al. |
| 2006/0202805 A1 | 9/2006 | Schulman et al. |
| 2006/0202859 A1 | 9/2006 | Mastrototaro et al. |
| 2006/0211921 A1 | 9/2006 | Brauker et al. |
| 2006/0220839 A1 | 10/2006 | Fifolt et al. |
| 2006/0222566 A1 | 10/2006 | Brauker et al. |
| 2006/0222866 A1 | 10/2006 | Nakamura et al. |
| 2006/0224108 A1 | 10/2006 | Brauker et al. |
| 2006/0224109 A1 | 10/2006 | Steil et al. |
| 2006/0224141 A1 | 10/2006 | Rush et al. |
| 2006/0224171 A1 | 10/2006 | Sakata et al. |
| 2006/0226985 A1 | 10/2006 | Goodnow et al. |
| 2006/0229512 A1 | 10/2006 | Petisce et al. |
| 2006/0233839 A1 | 10/2006 | Jacquet |
| 2006/0247508 A1 | 11/2006 | Fennell |
| 2006/0247710 A1 | 11/2006 | Goetz et al. |
| 2006/0247895 A1 | 11/2006 | Liamos et al. |
| 2006/0248398 A1 | 11/2006 | Neel et al. |
| 2006/0253085 A1 | 11/2006 | Geismar et al. |
| 2006/0253086 A1 | 11/2006 | Moberg et al. |
| 2006/0258929 A1 | 11/2006 | Goode, Jr. et al. |
| 2006/0258939 A1 | 11/2006 | Pesach et al. |
| 2006/0258959 A1 | 11/2006 | Sode |
| 2006/0264785 A1 | 11/2006 | Dring et al. |
| 2006/0264888 A1 | 11/2006 | Moberg et al. |
| 2006/0270922 A1 | 11/2006 | Brauker et al. |
| 2006/0270923 A1 | 11/2006 | Brauker et al. |
| 2006/0271013 A1 | 11/2006 | Triplett et al. |
| 2006/0272652 A1 | 12/2006 | Stocker et al. |
| 2006/0273759 A1 | 12/2006 | Reggiardo |
| 2006/0276714 A1 | 12/2006 | Holt et al. |
| 2006/0276724 A1 | 12/2006 | Freeman et al. |
| 2006/0276771 A1 | 12/2006 | Galley et al. |
| 2006/0281985 A1 | 12/2006 | Ward et al. |
| 2006/0282042 A1 | 12/2006 | Walters et al. |
| 2006/0287591 A1 | 12/2006 | Ocvirk et al. |
| 2006/0287691 A1 | 12/2006 | Drew |
| 2006/0290496 A1 | 12/2006 | Peeters et al. |
| 2006/0293607 A1 | 12/2006 | Alt et al. |
| 2007/0007133 A1 | 1/2007 | Mang et al. |
| 2007/0010950 A1 | 1/2007 | Abensour et al. |
| 2007/0016129 A1 | 1/2007 | Liniger et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0027384 A1 | 2/2007 | Brister et al. |
| 2007/0027385 A1 | 2/2007 | Brister et al. |
| 2007/0027507 A1 | 2/2007 | Burdett et al. |

(56) References Cited

U.S. PATENT DOCUMENTS

| | | |
|---|---|---|
| 2007/0030154 A1 | 2/2007 | Aiki et al. |
| 2007/0032706 A1 | 2/2007 | Kamath et al. |
| 2007/0032717 A1 | 2/2007 | Brister et al. |
| 2007/0032718 A1 | 2/2007 | Shults et al. |
| 2007/0033074 A1 | 2/2007 | Nitzan et al. |
| 2007/0038044 A1 | 2/2007 | Dobbles et al. |
| 2007/0045902 A1 | 3/2007 | Brauker et al. |
| 2007/0049865 A1 | 3/2007 | Radmer et al. |
| 2007/0055799 A1 | 3/2007 | Koehler et al. |
| 2007/0056858 A1 | 3/2007 | Chen et al. |
| 2007/0059196 A1 | 3/2007 | Brister et al. |
| 2007/0060801 A1 | 3/2007 | Neinast |
| 2007/0060814 A1 | 3/2007 | Stafford |
| 2007/0060869 A1 | 3/2007 | Tolle et al. |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0088377 A1 | 4/2007 | Levaughn et al. |
| 2007/0090511 A1 | 4/2007 | Borland et al. |
| 2007/0093704 A1 | 4/2007 | Brister et al. |
| 2007/0093754 A1 | 4/2007 | Mogensen et al. |
| 2007/0093786 A1 | 4/2007 | Goldsmith et al. |
| 2007/0095661 A1 | 5/2007 | Wang et al. |
| 2007/0100218 A1 | 5/2007 | Sweitzer et al. |
| 2007/0100222 A1 | 5/2007 | Mastrototaro et al. |
| 2007/0106133 A1 | 5/2007 | Satchwell et al. |
| 2007/0106135 A1 | 5/2007 | Sloan et al. |
| 2007/0108048 A1 | 5/2007 | Wang et al. |
| 2007/0110124 A1 | 5/2007 | Shiraki et al. |
| 2007/0111196 A1 | 5/2007 | Alarcon et al. |
| 2007/0123819 A1 | 5/2007 | Memoe et al. |
| 2007/0124002 A1 | 5/2007 | Estes et al. |
| 2007/0129621 A1 | 6/2007 | Kellogg et al. |
| 2007/0135696 A1 | 6/2007 | Ward |
| 2007/0135774 A1 | 6/2007 | Turner et al. |
| 2007/0149873 A1 | 6/2007 | Say et al. |
| 2007/0149875 A1 | 6/2007 | Ouyang et al. |
| 2007/0153705 A1 | 7/2007 | Rosar et al. |
| 2007/0156033 A1 | 7/2007 | Causey, III et al. |
| 2007/0156094 A1 | 7/2007 | Safabash et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173741 A1 | 7/2007 | Deshmukh et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179406 A1 | 8/2007 | DeNuzzio et al. |
| 2007/0191701 A1 | 8/2007 | Feldman et al. |
| 2007/0191702 A1 | 8/2007 | Yodfat et al. |
| 2007/0197889 A1 | 8/2007 | Brister et al. |
| 2007/0199818 A1 | 8/2007 | Petyt et al. |
| 2007/0202562 A1 | 8/2007 | Curry et al. |
| 2007/0203407 A1 | 8/2007 | Hoss et al. |
| 2007/0203539 A1 | 8/2007 | Stone et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0213611 A1 | 9/2007 | Simpson et al. |
| 2007/0219480 A1 | 9/2007 | Kamen et al. |
| 2007/0219496 A1 | 9/2007 | Kamen et al. |
| 2007/0222609 A1 | 9/2007 | Duron et al. |
| 2007/0227911 A1 | 10/2007 | Wang et al. |
| 2007/0228071 A1 | 10/2007 | Kamen et al. |
| 2007/0231846 A1 | 10/2007 | Cosentino et al. |
| 2007/0232877 A1 | 10/2007 | He |
| 2007/0232878 A1 | 10/2007 | Kovatchev et al. |
| 2007/0232879 A1 | 10/2007 | Brister et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0244368 A1 | 10/2007 | Bayloff et al. |
| 2007/0244379 A1 | 10/2007 | Boock et al. |
| 2007/0244383 A1 | 10/2007 | Talbot et al. |
| 2007/0244398 A1 | 10/2007 | Lo et al. |
| 2007/0249922 A1 | 10/2007 | Peyser et al. |
| 2007/0253021 A1 | 11/2007 | Mehta et al. |
| 2007/0255116 A1 | 11/2007 | Mehta et al. |
| 2007/0255125 A1 | 11/2007 | Moberg et al. |
| 2007/0255302 A1 | 11/2007 | Koeppel et al. |
| 2007/0255321 A1 | 11/2007 | Gerber et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0282299 A1 | 12/2007 | Hellwig |
| 2007/0285238 A1 | 12/2007 | Batra |
| 2008/0004512 A1 | 1/2008 | Funderbunk et al. |
| 2008/0004515 A1 | 1/2008 | Jennewine et al. |
| 2008/0004573 A1 | 1/2008 | Kaufmann et al. |
| 2008/0004601 A1 | 1/2008 | Jennewine et al. |
| 2008/0004904 A1 | 1/2008 | Tran |
| 2008/0009304 A1 | 1/2008 | Fry |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0018433 A1 | 1/2008 | Pitt-Pladdy |
| 2008/0021543 A1 | 1/2008 | Shrivastava |
| 2008/0021666 A1 | 1/2008 | Goode, Jr. et al. |
| 2008/0027296 A1 | 1/2008 | Hadvary et al. |
| 2008/0027474 A1 | 1/2008 | Curry et al. |
| 2008/0029391 A1 | 2/2008 | Mao et al. |
| 2008/0030369 A1 | 2/2008 | Maim et al. |
| 2008/0031941 A1 | 2/2008 | Pettersson |
| 2008/0033254 A1 | 2/2008 | Kamath et al. |
| 2008/0033268 A1 | 2/2008 | Stafford |
| 2008/0033273 A1 | 2/2008 | Zhou et al. |
| 2008/0033318 A1 | 2/2008 | Mace et al. |
| 2008/0039702 A1 | 2/2008 | Hayter et al. |
| 2008/0045824 A1 | 2/2008 | Tapsak et al. |
| 2008/0046038 A1 | 2/2008 | Hill et al. |
| 2008/0055070 A1 | 3/2008 | Bange et al. |
| 2008/0057484 A1 | 3/2008 | Miyata et al. |
| 2008/0058625 A1 | 3/2008 | McGarraugh et al. |
| 2008/0058626 A1 | 3/2008 | Miyata et al. |
| 2008/0058678 A1 | 3/2008 | Miyata et al. |
| 2008/0058773 A1 | 3/2008 | John |
| 2008/0058830 A1 | 3/2008 | Cole et al. |
| 2008/0059227 A1 | 3/2008 | Clapp |
| 2008/0060955 A1 | 3/2008 | Goodnow |
| 2008/0061961 A1 | 3/2008 | John |
| 2008/0062055 A1 | 3/2008 | Cunningham et al. |
| 2008/0064437 A1 | 3/2008 | Chambers et al. |
| 2008/0064937 A1 | 3/2008 | McGarraugh et al. |
| 2008/0064941 A1 | 3/2008 | Funderbunk et al. |
| 2008/0064943 A1 | 3/2008 | Talbot et al. |
| 2008/0064944 A1 | 3/2008 | VanAntwerp et al. |
| 2008/0065646 A1 | 3/2008 | Zhang et al. |
| 2008/0066305 A1 | 3/2008 | Wang et al. |
| 2008/0067627 A1 | 3/2008 | Boeck et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0071580 A1 | 3/2008 | Marcus |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0092911 A1 | 4/2008 | Schulman et al. |
| 2008/0097246 A1 | 4/2008 | Stafford |
| 2008/0097289 A1 | 4/2008 | Steil et al. |
| 2008/0097908 A1 | 4/2008 | Dicks et al. |
| 2008/0099332 A1 | 5/2008 | Scott et al. |

(56)　References Cited

U.S. PATENT DOCUMENTS

| | | |
|---|---|---|
| 2008/0102441 A1 | 5/2008 | Chen et al. |
| 2008/0108942 A1 | 5/2008 | Brister et al. |
| 2008/0112848 A1 | 5/2008 | Huffstodt et al. |
| 2008/0114228 A1 | 5/2008 | McCluskey et al. |
| 2008/0114280 A1 | 5/2008 | Stafford |
| 2008/0119705 A1 | 5/2008 | Patel et al. |
| 2008/0119707 A1 | 5/2008 | Stafford |
| 2008/0119710 A1 | 5/2008 | Reggiardo et al. |
| 2008/0125636 A1 | 5/2008 | Ward et al. |
| 2008/0127052 A1 | 5/2008 | Rostoker |
| 2008/0129486 A1 | 6/2008 | Jeckelmann et al. |
| 2008/0133059 A1 | 6/2008 | Trippel et al. |
| 2008/0133702 A1 | 6/2008 | Sharma et al. |
| 2008/0139910 A1 | 6/2008 | Mastrototaro et al. |
| 2008/0146904 A1 | 6/2008 | Hunn |
| 2008/0148873 A1 | 6/2008 | Wang |
| 2008/0154205 A1 | 6/2008 | Wojcik |
| 2008/0154286 A1 | 6/2008 | Abbott et al. |
| 2008/0154513 A1 | 6/2008 | Kovatchev et al. |
| 2008/0161664 A1 | 7/2008 | Mastrototaro et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0167578 A1 | 7/2008 | Bryer et al. |
| 2008/0172205 A1 | 7/2008 | Breton et al. |
| 2008/0177149 A1 | 7/2008 | Weinart et al. |
| 2008/0177165 A1 | 7/2008 | Blomquist et al. |
| 2008/0179187 A1 | 7/2008 | Ouyang |
| 2008/0182537 A1 | 7/2008 | Manku et al. |
| 2008/0183060 A1 | 7/2008 | Steil et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0188796 A1 | 8/2008 | Steil et al. |
| 2008/0189051 A1 | 8/2008 | Goode, Jr. et al. |
| 2008/0194926 A1 | 8/2008 | Goh et al. |
| 2008/0194934 A1 | 8/2008 | Ray et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0201325 A1 | 8/2008 | Doniger et al. |
| 2008/0208025 A1 | 8/2008 | Shults et al. |
| 2008/0208026 A1 | 8/2008 | Noujaim et al. |
| 2008/0208113 A1 | 8/2008 | Damiano et al. |
| 2008/0214481 A1 | 9/2008 | Challoner et al. |
| 2008/0214900 A1 | 9/2008 | Fennell et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0215035 A1 | 9/2008 | Yodfat et al. |
| 2008/0228051 A1 | 9/2008 | Shults et al. |
| 2008/0228054 A1 | 9/2008 | Shults et al. |
| 2008/0234561 A1 | 9/2008 | Roesicke et al. |
| 2008/0234992 A1 | 9/2008 | Ray et al. |
| 2008/0235469 A1 | 9/2008 | Drew |
| 2008/0242961 A1 | 10/2008 | Brister et al. |
| 2008/0242962 A1 | 10/2008 | Roesicke et al. |
| 2008/0242963 A1 | 10/2008 | Essenpreis et al. |
| 2008/0243051 A1 | 10/2008 | DeStefano |
| 2008/0252459 A1 | 10/2008 | Butler et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255440 A1 | 10/2008 | Eilerson et al. |
| 2008/0255808 A1 | 10/2008 | Hayter |
| 2008/0256048 A1 | 10/2008 | Hayter |
| 2008/0262300 A1 | 10/2008 | Reynolds et al. |
| 2008/0262469 A1 | 10/2008 | Brister et al. |
| 2008/0267823 A1 | 10/2008 | Wang et al. |
| 2008/0269584 A1 | 10/2008 | Shekalim |
| 2008/0269673 A1 | 10/2008 | Butoi et al. |
| 2008/0269683 A1 | 10/2008 | Bikovsky |
| 2008/0269687 A1 | 10/2008 | Chong et al. |
| 2008/0269714 A1 | 10/2008 | Mastrototaro et al. |
| 2008/0275313 A1 | 11/2008 | Brister et al. |
| 2008/0275327 A1 | 11/2008 | Faarbaek et al. |
| 2008/0278333 A1 | 11/2008 | Fennell et al. |
| 2008/0281178 A1 | 11/2008 | Chuang et al. |
| 2008/0281179 A1 | 11/2008 | Fennell et al. |
| 2008/0283396 A1 | 11/2008 | Wang et al. |
| 2008/0287755 A1 | 11/2008 | Sass et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294024 A1 | 11/2008 | Cosentino et al. |
| 2008/0294096 A1 | 11/2008 | Uber et al. |
| 2008/0296155 A1 | 12/2008 | Shults et al. |
| 2008/0300476 A1 | 12/2008 | Stafford |
| 2008/0300572 A1 | 12/2008 | Rankers et al. |
| 2008/0306368 A1 | 12/2008 | Goode, Jr. et al. |
| 2008/0306434 A1 | 12/2008 | Dobbies et al. |
| 2008/0306435 A1 | 12/2008 | Kamath et al. |
| 2008/0306444 A1 | 12/2008 | Brister et al. |
| 2008/0308523 A1 | 12/2008 | Krulevitch et al. |
| 2008/0312518 A1 | 12/2008 | Jina et al. |
| 2008/0312601 A1 | 12/2008 | Cane |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0312859 A1 | 12/2008 | Skyggebjerg et al. |
| 2008/0319085 A1 | 12/2008 | Wright et al. |
| 2008/0319295 A1 | 12/2008 | Bernstein et al. |
| 2008/0319296 A1 | 12/2008 | Bernstein et al. |
| 2008/0319414 A1 | 12/2008 | Yodfat et al. |
| 2008/0319416 A1 | 12/2008 | Yodfat et al. |
| 2009/0005659 A1 | 1/2009 | Kollias et al. |
| 2009/0005665 A1 | 1/2009 | Hayter et al. |
| 2009/0005666 A1 | 1/2009 | Shin et al. |
| 2009/0005729 A1 | 1/2009 | Hendrixson et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0018425 A1 | 1/2009 | Ouyang et al. |
| 2009/0020502 A1 | 1/2009 | Bhullar et al. |
| 2009/0028824 A1 | 1/2009 | Chiang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0036915 A1 | 2/2009 | Karbowniczek et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048499 A1 | 2/2009 | Glejbol |
| 2009/0048503 A1 | 2/2009 | Dalal et al. |
| 2009/0048563 A1 | 2/2009 | Ethelfeld et al. |
| 2009/0054737 A1 | 2/2009 | Magar et al. |

(56) References Cited

U.S. PATENT DOCUMENTS

| | | |
|---|---|---|
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0054753 A1 | 2/2009 | Robinson et al. |
| 2009/0054866 A1 | 2/2009 | Teisen-Simony et al. |
| 2009/0055149 A1 | 2/2009 | Hayter et al. |
| 2009/0058635 A1 | 3/2009 | LaLonde et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063187 A1 | 3/2009 | Johnson et al. |
| 2009/0063402 A1 | 3/2009 | Hayter |
| 2009/0069658 A1 | 3/2009 | Say et al. |
| 2009/0069750 A1 | 3/2009 | Schraga |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088614 A1 | 4/2009 | Taub |
| 2009/0088787 A1 | 4/2009 | Koike et al. |
| 2009/0093687 A1 | 4/2009 | Telfort et al. |
| 2009/0099436 A1 | 4/2009 | Brister et al. |
| 2009/0099521 A1 | 4/2009 | Gravesen et al. |
| 2009/0102678 A1 | 4/2009 | Mazza et al. |
| 2009/0105554 A1 | 4/2009 | Stahmann et al. |
| 2009/0105560 A1 | 4/2009 | Solomon |
| 2009/0105568 A1 | 4/2009 | Bugler |
| 2009/0105569 A1 | 4/2009 | Stafford |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0108992 A1 | 4/2009 | Shafer |
| 2009/0112123 A1 | 4/2009 | Freeman et al. |
| 2009/0112478 A1 | 4/2009 | Mueller, Jr. et al. |
| 2009/0118592 A1 | 5/2009 | Klitgaard |
| 2009/0124877 A1 | 5/2009 | Shariati et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0124979 A1 | 5/2009 | Raymond et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0149728 A1 | 6/2009 | Van Antwerp et al. |
| 2009/0150186 A1 | 6/2009 | Cohen et al. |
| 2009/0150454 A1 | 6/2009 | Gejdos et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0171182 A1 | 7/2009 | Stafford |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0198186 A1 | 8/2009 | Mernoe et al. |
| 2009/0198215 A1 | 8/2009 | Chong et al. |
| 2009/0203981 A1 | 8/2009 | Brauker et al. |
| 2009/0204340 A1 | 8/2009 | Feldman et al. |
| 2009/0204341 A1 | 8/2009 | Brauker et al. |
| 2009/0210249 A1 | 8/2009 | Rasch-Menges et al. |
| 2009/0212766 A1 | 8/2009 | Olson et al. |
| 2009/0216100 A1 | 8/2009 | Ebner et al. |
| 2009/0216103 A1 | 8/2009 | Brister et al. |
| 2009/0216215 A1 | 8/2009 | Thalmann et al. |
| 2009/0234200 A1 | 9/2009 | Husheer |
| 2009/0240120 A1 | 9/2009 | Mensinger et al. |
| 2009/0240121 A1 | 9/2009 | Bickoff |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorensen |
| 2009/0253973 A1 | 10/2009 | Bashan et al. |
| 2009/0259118 A1 | 10/2009 | Feldman et al. |
| 2009/0259201 A1 | 10/2009 | Hwang et al. |
| 2009/0259202 A1 | 10/2009 | Leeflang et al. |
| 2009/0267765 A1 | 10/2009 | Greene et al. |
| 2009/0270765 A1 | 10/2009 | Ghesquire et al. |
| 2009/0277242 A1 | 11/2009 | Crane et al. |
| 2009/0281406 A1 | 11/2009 | McGarraugh et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0292184 A1 | 11/2009 | Funderburk et al. |
| 2009/0292185 A1 | 11/2009 | Funderburk et al. |
| 2009/0294277 A1 | 12/2009 | Thomas et al. |
| 2009/0298182 A1 | 12/2009 | Schulat et al. |
| 2009/0299152 A1 | 12/2009 | Taub et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299167 A1 | 12/2009 | Seymour |
| 2009/0299276 A1 | 12/2009 | Brauker et al. |
| 2009/0299301 A1 | 12/2009 | Gottleib et al. |
| 2010/0004597 A1 | 1/2010 | Gryn et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0014626 A1 | 1/2010 | Fennell et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022863 A1 | 1/2010 | Mogensen et al. |
| 2010/0022988 A1 | 1/2010 | Wochner et al. |
| 2010/0025238 A1 | 2/2010 | Gottlieb et al. |
| 2010/0030038 A1 | 2/2010 | Brauker et al. |
| 2010/0030053 A1 | 2/2010 | Goode, Jr. et al. |
| 2010/0030111 A1 | 2/2010 | Perriere |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0036281 A1 | 2/2010 | Doi |
| 2010/0041971 A1 | 2/2010 | Goode, Jr. et al. |
| 2010/0045465 A1 | 2/2010 | Brauker et al. |
| 2010/0049014 A1 | 2/2010 | Funderburk et al. |
| 2010/0049024 A1 | 2/2010 | Saint et al. |
| 2010/0049129 A1 | 2/2010 | Yokoi et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0069728 A1 | 3/2010 | Funderburk et al. |
| 2010/0076283 A1 | 3/2010 | Simpson et al. |

(56) References Cited

U.S. PATENT DOCUMENTS

| | | |
|---|---|---|
| 2010/0076379 A1 | 3/2010 | Matusch |
| 2010/0081905 A1 | 4/2010 | Bommakanti et al. |
| 2010/0081906 A1 | 4/2010 | Hayter et al. |
| 2010/0081908 A1 | 4/2010 | Dobbles et al. |
| 2010/0081910 A1 | 4/2010 | Brister et al. |
| 2010/0081953 A1 | 4/2010 | Syeda-Mahmood et al. |
| 2010/0087724 A1 | 4/2010 | Brauker et al. |
| 2010/0094251 A1 | 4/2010 | Estes et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0100113 A1 | 4/2010 | Iio et al. |
| 2010/0105999 A1 | 4/2010 | Dixon et al. |
| 2010/0106088 A1 | 4/2010 | Yodfat et al. |
| 2010/0113897 A1 | 5/2010 | Brenneman et al. |
| 2010/0119693 A1 | 5/2010 | Tapsak et al. |
| 2010/0119881 A1 | 5/2010 | Patel et al. |
| 2010/0121167 A1 | 5/2010 | McGarraugh et al. |
| 2010/0121169 A1 | 5/2010 | Petisce et al. |
| 2010/0137695 A1 | 6/2010 | Yodfat et al. |
| 2010/0141656 A1 | 6/2010 | Krieftewirth |
| 2010/0145229 A1 | 6/2010 | Perez et al. |
| 2010/0145377 A1 | 6/2010 | Lai et al. |
| 2010/0146300 A1 | 6/2010 | Brown |
| 2010/0152548 A1 | 6/2010 | Koski |
| 2010/0152554 A1 | 6/2010 | Steine et al. |
| 2010/0152674 A1 | 6/2010 | Kavazov et al. |
| 2010/0160757 A1 | 6/2010 | Weinert et al. |
| 2010/0160759 A1 | 6/2010 | Celentano et al. |
| 2010/0160760 A1 | 6/2010 | Shults et al. |
| 2010/0161269 A1 | 6/2010 | Kamath et al. |
| 2010/0168538 A1 | 7/2010 | Keenan et al. |
| 2010/0168540 A1 | 7/2010 | Kamath et al. |
| 2010/0168541 A1 | 7/2010 | Kamath et al. |
| 2010/0168542 A1 | 7/2010 | Kamath et al. |
| 2010/0168543 A1 | 7/2010 | Kamath et al. |
| 2010/0168544 A1 | 7/2010 | Kamath et al. |
| 2010/0168545 A1 | 7/2010 | Kamath et al. |
| 2010/0168546 A1 | 7/2010 | Kamath et al. |
| 2010/0168547 A1 | 7/2010 | Kamath et al. |
| 2010/0168660 A1 | 7/2010 | Galley et al. |
| 2010/0168677 A1 | 7/2010 | Gabriel et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode et al. |
| 2010/0174266 A1 | 7/2010 | Estes |
| 2010/0179399 A1 | 7/2010 | Goode, Jr. et al. |
| 2010/0179400 A1 | 7/2010 | Brauker et al. |
| 2010/0179401 A1 | 7/2010 | Rasdal et al. |
| 2010/0179402 A1 | 7/2010 | Goode, Jr. et al. |
| 2010/0179404 A1 | 7/2010 | Kamath et al. |
| 2010/0179405 A1 | 7/2010 | Goode, Jr. et al. |
| 2010/0179407 A1 | 7/2010 | Goode, Jr. et al. |
| 2010/0179408 A1 | 7/2010 | Kamath et al. |
| 2010/0179409 A1 | 7/2010 | Kamath et al. |
| 2010/0185065 A1 | 7/2010 | Goode, Jr. et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185072 A1 | 7/2010 | Goode, Jr. et al. |
| 2010/0185073 A1 | 7/2010 | Goode, Jr. et al. |
| 2010/0185074 A1 | 7/2010 | Goode, Jr. et al. |
| 2010/0185075 A1 | 7/2010 | Brister et al. |
| 2010/0185175 A1 | 7/2010 | Kamen et al. |
| 2010/0190435 A1 | 7/2010 | Cook et al. |
| 2010/0191082 A1 | 7/2010 | Brister et al. |
| 2010/0191087 A1 | 7/2010 | Talbot et al. |
| 2010/0191472 A1 | 7/2010 | Doniger et al. |
| 2010/0198033 A1 | 8/2010 | Krulevitch et al. |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0198042 A1 | 8/2010 | Sloan et al. |
| 2010/0198142 A1 | 8/2010 | Sloan et al. |
| 2010/0198314 A1 | 8/2010 | Wei |
| 2010/0204557 A1 | 8/2010 | Kiaie et al. |
| 2010/0204653 A1 | 8/2010 | Gryn et al. |
| 2010/0212583 A1 | 8/2010 | Brister et al. |
| 2010/0213057 A1 | 8/2010 | Feldman et al. |
| 2010/0213080 A1 | 8/2010 | Celentano et al. |
| 2010/0214104 A1 | 8/2010 | Goode, Jr. et al. |
| 2010/0217105 A1 | 8/2010 | Yodfat et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228111 A1 | 9/2010 | Friman et al. |
| 2010/0228497 A1 | 9/2010 | Kamath et al. |
| 2010/0230285 A1 | 9/2010 | Hoss et al. |
| 2010/0235439 A1 | 9/2010 | Goodnow et al. |
| 2010/0240975 A1 | 9/2010 | Goode, Jr. et al. |
| 2010/0240976 A1 | 9/2010 | Goode, Jr. et al. |
| 2010/0256471 A1 | 10/2010 | Say et al. |
| 2010/0259543 A1 | 10/2010 | Tarassenko et al. |
| 2010/0261987 A1 | 10/2010 | Kamath et al. |
| 2010/0262183 A1 | 10/2010 | Abbott et al. |
| 2010/0262201 A1 | 10/2010 | He et al. |
| 2010/0267161 A1 | 10/2010 | Wu et al. |
| 2010/0274107 A1 | 10/2010 | Boock et al. |
| 2010/0274111 A1 | 10/2010 | Say et al. |
| 2010/0274515 A1 | 10/2010 | Hoss et al. |
| 2010/0275108 A1 | 10/2010 | Sloan et al. |
| 2010/0280341 A1 | 11/2010 | Boock et al. |
| 2010/0286496 A1 | 11/2010 | Simpson et al. |
| 2010/0298684 A1 | 11/2010 | Leach et al. |
| 2010/0312176 A1 | 12/2010 | Lauer et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0324403 A1 | 12/2010 | Brister et al. |
| 2010/0325868 A1 | 12/2010 | Wang et al. |
| 2010/0326842 A1 | 12/2010 | Mazza et al. |
| 2010/0331642 A1 | 12/2010 | Bruce et al. |
| 2010/0331644 A1 | 12/2010 | Neale et al. |
| 2010/0331647 A1 | 12/2010 | Shah et al. |
| 2010/0331648 A1 | 12/2010 | Kamath et al. |
| 2010/0331651 A1 | 12/2010 | Groll |
| 2010/0331653 A1 | 12/2010 | Stafford |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0004276 A1 | 1/2011 | Blair et al. |
| 2011/0009727 A1 | 1/2011 | Mensinger et al. |
| 2011/0015509 A1 | 1/2011 | Peyser |
| 2011/0016691 A1 | 1/2011 | Alden et al. |
| 2011/0021889 A1 | 1/2011 | Hoss et al. |
| 2011/0022411 A1 | 1/2011 | Hjelm et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0040163 A1 | 2/2011 | Telson et al. |
| 2011/0040256 A1 | 2/2011 | Bobroff et al. |
| 2011/0040263 A1 | 2/2011 | Hordum et al. |
| 2011/0046456 A1 | 2/2011 | Hordum et al. |
| 2011/0046467 A1 | 2/2011 | Simpson et al. |
| 2011/0046977 A1 | 2/2011 | Goodnow et al. |
| 2011/0054275 A1 | 3/2011 | Stafford |
| 2011/0054282 A1 | 3/2011 | Nekoomaram et al. |
| 2011/0060196 A1 | 3/2011 | Stafford |
| 2011/0060530 A1 | 3/2011 | Fennell |
| 2011/0070633 A1 | 3/2011 | Matsumoto et al. |
| 2011/0073475 A1 | 3/2011 | Kastanos et al. |
| 2011/0077469 A1 | 3/2011 | Blocker et al. |

(56)

References Cited

U.S. PATENT DOCUMENTS

| | | |
|---|---|---|
| 2011/0077490 A1 | 3/2011 | Simpson et al. |
| 2011/0077494 A1 | 3/2011 | Doniger et al. |
| 2011/0077659 A1 | 3/2011 | Mandecki et al. |
| 2011/0081726 A1 | 4/2011 | Berman et al. |
| 2011/0082484 A1 | 4/2011 | Saravia et al. |
| 2011/0087196 A1 | 4/2011 | Hunn et al. |
| 2011/0097090 A1 | 4/2011 | Cao |
| 2011/0106126 A1 | 5/2011 | Love et al. |
| 2011/0112696 A1 | 5/2011 | Yodfat et al. |
| 2011/0118579 A1 | 5/2011 | Goode et al. |
| 2011/0118580 A1 | 5/2011 | Goode et al. |
| 2011/0123971 A1 | 5/2011 | Berkowitz et al. |
| 2011/0124992 A1 | 5/2011 | Brauker et al. |
| 2011/0124997 A1 | 5/2011 | Goode et al. |
| 2011/0125040 A1 | 5/2011 | Crawford et al. |
| 2011/0125410 A1 | 5/2011 | Goode et al. |
| 2011/0130970 A1 | 6/2011 | Goode et al. |
| 2011/0130971 A1 | 6/2011 | Goode et al. |
| 2011/0130998 A1 | 6/2011 | Goode et al. |
| 2011/0137257 A1 | 6/2011 | Gyrn et al. |
| 2011/0137571 A1 | 6/2011 | Power et al. |
| 2011/0144465 A1 | 6/2011 | Shults et al. |
| 2011/0148905 A1 | 6/2011 | Simmons et al. |
| 2011/0152637 A1 | 6/2011 | Kateraas et al. |
| 2011/0172510 A1 | 7/2011 | Chickering, III et al. |
| 2011/0178378 A1 | 7/2011 | Brister et al. |
| 2011/0178461 A1 | 7/2011 | Chong et al. |
| 2011/0184258 A1 | 7/2011 | Stafford |
| 2011/0184482 A1 | 7/2011 | Eberman et al. |
| 2011/0184752 A1 | 7/2011 | Ray et al. |
| 2011/0190603 A1 | 8/2011 | Stafford |
| 2011/0190614 A1 | 8/2011 | Brister et al. |
| 2011/0191044 A1 | 8/2011 | Stafford |
| 2011/0193704 A1 | 8/2011 | Harper et al. |
| 2011/0201910 A1 | 8/2011 | Rasdal et al. |
| 2011/0201911 A1 | 8/2011 | Johnson et al. |
| 2011/0208027 A1 | 8/2011 | Wagner et al. |
| 2011/0213225 A1 | 9/2011 | Bernstein et al. |
| 2011/0218414 A1 | 9/2011 | Kamath et al. |
| 2011/0218490 A1 | 9/2011 | Ocvirk et al. |
| 2011/0230741 A1 | 9/2011 | Liang et al. |
| 2011/0231107 A1 | 9/2011 | Brauker et al. |
| 2011/0231140 A1 | 9/2011 | Goode, Jr. et al. |
| 2011/0231141 A1 | 9/2011 | Goode, Jr. et al. |
| 2011/0231142 A1 | 9/2011 | Goode, Jr. et al. |
| 2011/0253533 A1 | 10/2011 | Shults et al. |
| 2011/0257495 A1 | 10/2011 | Hoss et al. |
| 2011/0257521 A1 | 10/2011 | Fraden |
| 2011/0257895 A1 | 10/2011 | Brauker et al. |
| 2011/0263958 A1 | 10/2011 | Brauker et al. |
| 2011/0263959 A1 | 10/2011 | Young et al. |
| 2011/0264378 A1 | 10/2011 | Breton et al. |
| 2011/0270062 A1 | 11/2011 | Goode, Jr. et al. |
| 2011/0270158 A1 | 11/2011 | Brauker et al. |
| 2011/0275919 A1 | 11/2011 | Petisce et al. |
| 2011/0282327 A1 | 11/2011 | Kellogg et al. |
| 2011/0287528 A1 | 11/2011 | Fern et al. |
| 2011/0288574 A1 | 11/2011 | Curry et al. |
| 2011/0289497 A1 | 11/2011 | Kiaie et al. |
| 2011/0290645 A1 | 12/2011 | Brister et al. |
| 2011/0313543 A1 | 12/2011 | Brauker et al. |
| 2011/0319729 A1 | 12/2011 | Donnay et al. |
| 2011/0319733 A1 | 12/2011 | Stafford |
| 2011/0319738 A1 | 12/2011 | Woodruff et al. |
| 2011/0319739 A1 | 12/2011 | Kamath et al. |
| 2011/0320130 A1 | 12/2011 | Valdes et al. |
| 2012/0010642 A1 | 1/2012 | Lee et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0088995 A1 | 4/2012 | Fennell et al. |
| 2012/0095406 A1 | 4/2012 | Gyrn et al. |
| 2012/0108934 A1 | 5/2012 | Valdes et al. |
| 2012/0108983 A1 | 5/2012 | Banet et al. |
| 2012/0116322 A1 | 5/2012 | Brink et al. |
| 2012/0123385 A1 | 5/2012 | Edwards et al. |
| 2012/0143135 A1 | 6/2012 | Cole et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0179113 A1 | 7/2012 | Yokota et al. |
| 2012/0184909 A1 | 7/2012 | Gyrn et al. |
| 2012/0190989 A1 | 7/2012 | Kaiser et al. |
| 2012/0197098 A1 | 8/2012 | Donnay et al. |
| 2012/0197222 A1 | 8/2012 | Donnay et al. |
| 2012/0245447 A1 | 9/2012 | Karan et al. |
| 2012/0265042 A1 | 10/2012 | Neinast et al. |
| 2012/0296327 A1 | 11/2012 | Hutchins et al. |
| 2012/0303043 A1 | 11/2012 | Donnay et al. |
| 2013/0035575 A1 | 2/2013 | Mayou et al. |
| 2013/0047981 A1 | 2/2013 | Bacon |
| 2013/0109940 A1 | 5/2013 | Yang et al. |
| 2013/0111248 A1 | 5/2013 | Ghesquiere et al. |
| 2013/0150691 A1 | 6/2013 | Pace et al. |
| 2013/0184547 A1 | 7/2013 | Taub et al. |
| 2013/0199312 A1 | 8/2013 | Wilmer et al. |
| 2013/0225959 A1 | 8/2013 | Bugler |
| 2013/0235166 A1 | 9/2013 | Jones et al. |
| 2013/0253289 A1 | 9/2013 | Hadvary et al. |
| 2013/0267811 A1 | 10/2013 | Pryor et al. |
| 2013/0317323 A1 | 11/2013 | Fujiwara et al. |
| 2014/0031655 A1 | 1/2014 | Stafford |
| 2014/0121480 A1 | 5/2014 | Budiman et al. |
| 2014/0148667 A1 | 5/2014 | Boock et al. |
| 2014/0171771 A1 | 6/2014 | Feldman et al. |
| 2014/0188053 A1 | 7/2014 | Lundquist |
| 2014/0228760 A1 | 8/2014 | Ethelfeld |
| 2014/0275907 A1 | 9/2014 | Feldman et al. |
| 2015/0005601 A1 | 1/2015 | Hoss et al. |
| 2015/0018643 A1 | 1/2015 | Cole et al. |
| 2015/0025338 A1 | 1/2015 | Lee et al. |
| 2015/0073238 A1 | 3/2015 | Matsumoto et al. |
| 2015/0105644 A1 | 4/2015 | Yang et al. |
| 2015/0141776 A1 | 5/2015 | Hadvary et al. |
| 2015/0164545 A1 | 6/2015 | Gyrn |
| 2015/0173661 A1 | 6/2015 | Myles |
| 2015/0241407 A1 | 8/2015 | Ou et al. |
| 2015/0326072 A1 | 11/2015 | Petras et al. |
| 2016/0058342 A1 | 3/2016 | Maiz-Aguinaga et al. |
| 2016/0058470 A1 | 3/2016 | Peterson et al. |
| 2016/0058474 A1 | 3/2016 | Peterson et al. |
| 2016/0128615 A1 | 5/2016 | Curry et al. |
| 2016/0157759 A1 | 6/2016 | Yang |
| 2016/0256106 A1 | 9/2016 | Krasnow et al. |
| 2016/0331283 A1 | 11/2016 | Rao et al. |
| 2016/0331284 A1 | 11/2016 | Pace |
| 2016/0338733 A1 | 11/2016 | Shah et al. |
| 2016/0338734 A1 | 11/2016 | Shah et al. |
| 2016/0354555 A1 | 12/2016 | Gibson et al. |
| 2017/0112531 A1 | 4/2017 | Schoonmaker et al. |
| 2017/0112533 A1 | 4/2017 | Schoonmaker et al. |
| 2017/0112534 A1 | 4/2017 | Schoonmaker et al. |
| 2017/0127985 A1 | 5/2017 | Thompson et al. |
| 2017/0128011 A1 | 5/2017 | Frey et al. |
| 2017/0165451 A1 | 6/2017 | Frey et al. |
| 2017/0188908 A1 | 7/2017 | Hoss et al. |
| 2017/0188910 A1 | 7/2017 | Halac et al. |
| 2017/0188912 A1 | 7/2017 | Halac et al. |
| 2017/0216536 A1 | 8/2017 | Scott |
| 2017/0265791 A1 | 9/2017 | Pace et al. |
| 2017/0290533 A1 | 10/2017 | Antonio et al. |
| 2017/0290534 A1 | 10/2017 | Antonio et al. |
| 2017/0290535 A1 | 10/2017 | Rao et al. |
| 2017/0290546 A1 | 10/2017 | Antonio et al. |
| 2017/0319137 A1 | 11/2017 | Tsubouchi et al. |
| 2017/0367630 A1 | 12/2017 | Arita et al. |
| 2017/0368268 A1 | 12/2017 | Chopra |
| 2018/0116572 A1 | 5/2018 | Simpson et al. |
| 2018/0125464 A1 | 5/2018 | Kolb et al. |
| 2018/0235520 A1 | 8/2018 | Rao et al. |
| 2018/0360493 A1 | 12/2018 | Baker et al. |
| 2018/0368771 A1 | 12/2018 | Gray et al. |
| 2019/0133501 A1 | 5/2019 | Rao et al. |

(56) References Cited

U.S. PATENT DOCUMENTS

| | | | |
|---|---|---|---|
| 2019/0133638 A1 | 5/2019 | Il et al. |
| 2019/0298240 A1 | 10/2019 | Lee et al. |
| 2020/0077928 A1 | 3/2020 | Brister et al. |
| 2020/0100712 A1 | 4/2020 | Stafford |
| 2020/0113494 A1 | 4/2020 | Akiyama |
| 2020/0178899 A1 | 6/2020 | Chae et al. |
| 2020/0196919 A1 | 6/2020 | Rao et al. |
| 2020/0397356 A1 | 12/2020 | Yee et al. |
| 2021/0030969 A1 | 2/2021 | Huang et al. |
| 2021/0113124 A1 | 4/2021 | Yee et al. |
| 2021/0161437 A1 | 6/2021 | Thomas et al. |
| 2021/0177315 A1 | 6/2021 | Thomas et al. |
| 2021/0204841 A1 | 7/2021 | Thomas et al. |
| 2021/0204843 A1 | 7/2021 | Mazza et al. |
| 2021/0378592 A1 | 12/2021 | Rodriguez et al. |
| 2022/0007973 A1 | 1/2022 | Rao et al. |
| 2022/0079475 A1 | 3/2022 | Cole et al. |
| 2022/0125480 A1 | 4/2022 | Rao et al. |
| 2023/0108476 A1 | 4/2023 | Rao |
| 2024/0293615 A1 | 9/2024 | Lanigan |

FOREIGN PATENT DOCUMENTS

| | | |
|---|---|---|
| CA | 2468577 | 6/2003 |
| CA | 2495648 | 2/2004 |
| CA | 2143172 | 7/2005 |
| CA | 2498682 | 9/2005 |
| CA | 2555749 | 9/2005 |
| CA | 2632709 | 6/2007 |
| CA | 2396613 | 3/2008 |
| CA | 2678336 | 5/2008 |
| CA | 2615575 | 6/2008 |
| CA | 2626349 | 9/2008 |
| CA | 2701374 | 4/2009 |
| CA | 2413148 | 8/2010 |
| CA | 2728831 | 7/2011 |
| CA | 2766693 A1 | 9/2011 |
| CA | 2617965 | 10/2011 |
| CA | 2766685 A1 | 12/2011 |
| CA | 3050721 | 7/2018 |
| CN | 1202872 | 5/2005 |
| CN | 101163440 | 4/2008 |
| CN | 101268932 | 9/2008 |
| CN | 101296650 | 10/2008 |
| CN | 201370857 | 12/2009 |
| DE | 4401400 | 7/1995 |
| DE | 201 10 059 | 8/2002 |
| DE | 101 17 285 | 11/2002 |
| DE | 10 2008 053 216 | 5/2010 |
| EP | 0 010 375 | 4/1980 |
| EP | 0 026 995 | 4/1981 |
| EP | 0 048 090 | 3/1982 |
| EP | 0 078 636 | 5/1983 |
| EP | 0 096 288 | 12/1983 |
| EP | 0098592 | 1/1984 |
| EP | 0 125 139 | 11/1984 |
| EP | 0127958 | 12/1984 |
| EP | 0 136 362 | 4/1985 |
| EP | 0 170 375 | 2/1986 |
| EP | 0 177 743 | 4/1986 |
| EP | 0 080 304 | 5/1986 |
| EP | 0 184 909 | 6/1986 |
| EP | 0 206 218 | 12/1986 |
| EP | 0 230 472 | 8/1987 |
| EP | 0 241 309 | 10/1987 |
| EP | 0 245 073 | 11/1987 |
| EP | 0 255 291 | 2/1988 |
| EP | 0 278 647 | 8/1988 |
| EP | 0 319 277 A1 | 6/1989 |
| EP | 0320109 | 6/1989 |
| EP | 0353328 | 2/1990 |
| EP | 0 359 831 | 3/1990 |
| EP | 0 368 209 | 5/1990 |
| EP | 0390390 | 10/1990 |
| EP | 0396788 | 11/1990 |

| | | |
|---|---|---|
| EP | 0 400 918 | 12/1990 |
| EP | 0 453 283 | 10/1991 |
| EP | 0 470 290 | 2/1992 |
| EP | 0 567 725 | 11/1993 |
| EP | 0286118 | 1/1995 |
| EP | 0680727 | 11/1995 |
| EP | 0724859 | 8/1996 |
| EP | 0805574 | 11/1997 |
| EP | 0973289 | 1/2000 |
| EP | 0678308 | 5/2000 |
| EP | 1048264 | 11/2000 |
| EP | 1177802 | 2/2002 |
| EP | 0 729 366 | 7/2002 |
| EP | 1292218 | 3/2003 |
| EP | 1077634 | 7/2003 |
| EP | 1 092 390 | 7/2004 |
| EP | 1568309 | 8/2005 |
| EP | 1 630 898 | 3/2006 |
| EP | 1 669 020 | 6/2006 |
| EP | 1666091 | 6/2006 |
| EP | 1 704 889 | 9/2006 |
| EP | 1703697 | 9/2006 |
| EP | 1704893 | 9/2006 |
| EP | 1 729 128 | 12/2006 |
| EP | 0987982 | 1/2007 |
| EP | 1956371 | 8/2008 |
| EP | 2031534 | 3/2009 |
| EP | 2060284 | 5/2009 |
| EP | 1897487 | 11/2009 |
| EP | 1897492 | 11/2009 |
| EP | 2113864 | 11/2009 |
| EP | 1897488 | 12/2009 |
| EP | 1681992 | 4/2010 |
| EP | 2201969 | 6/2010 |
| EP | 1448489 | 8/2010 |
| EP | 1971396 | 8/2010 |
| EP | 1725163 | 12/2010 |
| EP | 2260757 | 12/2010 |
| EP | 1413245 | 6/2011 |
| EP | 2327362 | 6/2011 |
| EP | 2327984 | 6/2011 |
| EP | 2335587 | 6/2011 |
| EP | 2153382 | 2/2012 |
| EP | 2284773 | 2/2012 |
| EP | 1 789 116 B1 | 5/2013 |
| EP | 2 713 879 B1 | 7/2017 |
| EP | 2 393 417 B1 | 1/2019 |
| EP | 3 251 597 B1 | 11/2019 |
| EP | 3 632 314 A1 | 4/2020 |
| EP | 3 632 315 A1 | 4/2020 |
| EP | 3 851 045 A1 | 7/2021 |
| EP | 3 730 044 B1 | 12/2021 |
| EP | 3 730 045 B1 | 3/2022 |
| EP | 3 766 408 B1 | 4/2022 |
| EP | 3 928 688 B1 | 6/2022 |
| EP | 3 831 283 B1 | 4/2023 |
| EP | 4 111 949 B1 | 7/2023 |
| EP | 4 344 633 A2 | 4/2024 |
| EP | 4 203 819 B1 | 7/2024 |
| GB | 1 394 171 | 5/1975 |
| GB | 1 599 241 | 9/1981 |
| GB | 2 073 891 | 10/1981 |
| GB | 2 067 764 B | 1/1984 |
| GB | 2 154 003 | 8/1985 |
| GB | 2 204 408 | 11/1988 |
| GB | 2 254 436 | 10/1992 |
| GB | 2409951 | 7/2005 |
| JP | 54-041191 | 4/1979 |
| JP | 55-010581 | 1/1980 |
| JP | 55-010583 | 1/1980 |
| JP | 55-010584 | 1/1980 |
| JP | 55-012406 | 1/1980 |
| JP | 56-163447 | 12/1981 |
| JP | 57-070448 | 4/1982 |
| JP | 60-173457 | 9/1985 |
| JP | 60-173458 | 9/1985 |
| JP | 60-173459 | 9/1985 |
| JP | 62-085855 | 4/1987 |
| JP | 62-114747 | 5/1987 |

(56) References Cited

FOREIGN PATENT DOCUMENTS

| | | |
|---|---|---|
| JP | 63-058149 | 3/1988 |
| JP | 63-128252 | 5/1988 |
| JP | 63-139246 | 6/1988 |
| JP | 63-294799 | 12/1988 |
| JP | 63-317757 | 12/1988 |
| JP | 63-317758 | 12/1988 |
| JP | 01-114746 | 5/1989 |
| JP | 01-114747 | 5/1989 |
| JP | 01-124060 | 5/1989 |
| JP | 01-134244 | 5/1989 |
| JP | 01-156658 | 6/1989 |
| JP | 02-062958 | 3/1990 |
| JP | 02-120655 | 5/1990 |
| JP | 02-287145 | 11/1990 |
| JP | 02-310457 | 12/1990 |
| JP | 03-020752 | 1/1991 |
| JP | 03-026956 | 2/1991 |
| JP | 03-028752 | 2/1991 |
| JP | 03-500940 | 2/1991 |
| JP | 03-194458 | 8/1991 |
| JP | 03-202764 | 9/1991 |
| JP | 05-072171 | 3/1993 |
| JP | 05-196595 | 8/1993 |
| JP | 06-190050 | 7/1994 |
| JP | 07-055757 | 3/1995 |
| JP | 07-072585 | 3/1995 |
| JP | 07-182462 | 7/1995 |
| JP | 07-311196 | 11/1995 |
| JP | 08-285814 | 11/1996 |
| JP | 08-285815 | 11/1996 |
| JP | 09-021778 | 1/1997 |
| JP | 09-101280 | 4/1997 |
| JP | 09-285459 | 4/1997 |
| JP | 10-170471 | 6/1998 |
| JP | 10-305016 | 11/1998 |
| JP | 11-506629 | 6/1999 |
| JP | 11-225359 | 8/1999 |
| JP | 2003-144417 | 5/2003 |
| JP | 2004-033438 | 2/2004 |
| JP | 2004-214014 A | 7/2004 |
| JP | 2004-520103 | 7/2004 |
| JP | 2004-520898 | 7/2004 |
| JP | 2004-358016 | 12/2004 |
| JP | 2006-021031 | 1/2006 |
| JP | 2006-280464 | 10/2006 |
| JP | 2006-527036 | 11/2006 |
| JP | 2007-510499 | 4/2007 |
| JP | 2007-152037 | 6/2007 |
| JP | 2008-506468 | 3/2008 |
| KR | 10-2017-0068694 | 6/2017 |
| SU | 1281988 | 1/1987 |
| WO | WO 89/05119 | 6/1989 |
| WO | WO 89/08713 | 9/1989 |
| WO | WO 90/05300 | 5/1990 |
| WO | WO 90/05910 | 5/1990 |
| WO | WO 91/01680 | 2/1991 |
| WO | WO 91/04704 | 4/1991 |
| WO | WO-1991/015993 | 10/1991 |
| WO | WO-1992/013271 | 8/1992 |
| WO | WO-1994/020602 | 9/1994 |
| WO | WO-95/28878 | 2/1995 |
| WO | WO-1996/039977 | 5/1996 |
| WO | WO-1996/025089 | 8/1996 |
| WO | WO-96/35370 | 11/1996 |
| WO | WO 97/02847 | 1/1997 |
| WO | WO 97/19344 | 5/1997 |
| WO | WO 97/21457 | 6/1997 |
| WO | WO-97/33513 | 9/1997 |
| WO | WO 97/42882 | 11/1997 |
| WO | WO 97/42883 | 11/1997 |
| WO | WO 97/42886 | 11/1997 |
| WO | WO 97/42888 | 11/1997 |
| WO | WO 97/43962 | 11/1997 |
| WO | WO-98/04902 | 2/1998 |
| WO | WO-1998/035053 | 8/1998 |
| WO | WO-1998/056293 | 12/1998 |
| WO | WO-99/27849 | 6/1999 |
| WO | WO-99/28736 | 6/1999 |
| WO | WO-1999/033504 | 7/1999 |
| WO | WO-1999/056613 | 11/1999 |
| WO | WO 00/40159 | 7/2000 |
| WO | WO-2000/049940 | 8/2000 |
| WO | WO-00/60350 | 10/2000 |
| WO | WO-2000/059370 | 10/2000 |
| WO | WO-00/74753 | 12/2000 |
| WO | WO-2000/078992 | 12/2000 |
| WO | WO 01/17875 A1 | 3/2001 |
| WO | WO 01/52727 A1 | 7/2001 |
| WO | WO-2001/052935 | 7/2001 |
| WO | WO 01/58348 A2 | 8/2001 |
| WO | WO-2001/054753 | 8/2001 |
| WO | WO 02/15778 A1 | 2/2002 |
| WO | WO-2002/016905 | 2/2002 |
| WO | WO-2002/050534 | 6/2002 |
| WO | WO-2002/058537 | 8/2002 |
| WO | WO 02/100457 | 12/2002 |
| WO | WO 03/026728 A2 | 4/2003 |
| WO | WO-2003/028784 | 4/2003 |
| WO | WO 03/056319 A2 | 7/2003 |
| WO | WO-03/057027 | 7/2003 |
| WO | WO 03/072164 | 9/2003 |
| WO | WO 03/073936 | 9/2003 |
| WO | WO 03/076893 | 9/2003 |
| WO | WO-2003/076893 | 9/2003 |
| WO | WO-03/085372 | 10/2003 |
| WO | WO-2003/082091 | 10/2003 |
| WO | WO 2004/006982 | 1/2004 |
| WO | WO-2004/015539 | 2/2004 |
| WO | WO-2004/028337 | 4/2004 |
| WO | WO 2004/030726 | 4/2004 |
| WO | WO 2004/034024 | 4/2004 |
| WO | WO-2004/047445 | 6/2004 |
| WO | WO 2004/049237 A2 | 6/2004 |
| WO | WO 2004/054445 | 7/2004 |
| WO | WO-2004/060436 | 7/2004 |
| WO | WO-2004/061420 | 7/2004 |
| WO | WO-2004/090503 | 10/2004 |
| WO | WO-2004/098405 | 11/2004 |
| WO | WO 2004/098682 A2 | 11/2004 |
| WO | WO 2004/098683 A1 | 11/2004 |
| WO | WO-2004/098684 | 11/2004 |
| WO | WO 2004/098685 | 11/2004 |
| WO | WO 2004/107971 | 12/2004 |
| WO | WO-2004/112602 | 12/2004 |
| WO | WO 2005/011779 A1 | 2/2005 |
| WO | WO 2005/018450 A2 | 3/2005 |
| WO | WO 2005/037184 | 4/2005 |
| WO | WO-2005/041766 | 5/2005 |
| WO | WO 2005/044116 | 5/2005 |
| WO | WO-2005/045744 | 5/2005 |
| WO | WO 2005/046780 A1 | 5/2005 |
| WO | WO-2005/051170 | 6/2005 |
| WO | WO-2005/057175 | 6/2005 |
| WO | WO-2005/065538 | 7/2005 |
| WO | WO-2005/084534 | 9/2005 |
| WO | WO-2005/089103 | 9/2005 |
| WO | WO 2005/092177 | 10/2005 |
| WO | WO-2005/121785 | 12/2005 |
| WO | WO 2005/123186 A1 | 12/2005 |
| WO | WO 2006/001024 | 1/2006 |
| WO | WO 2006/015922 | 2/2006 |
| WO | WO-2006/017358 | 2/2006 |
| WO | WO-2006/020212 | 2/2006 |
| WO | WO-2006/024671 | 3/2006 |
| WO | WO-2006/026741 | 3/2006 |
| WO | WO-2006/032653 | 3/2006 |
| WO | WO 2006/036145 | 4/2006 |
| WO | WO 2006/040083 A1 | 4/2006 |
| WO | WO-2006/042811 | 4/2006 |
| WO | WO 2006/061354 | 6/2006 |
| WO | WO-2006/064397 | 6/2006 |
| WO | WO-2006/072035 | 7/2006 |
| WO | WO-2006/079114 | 7/2006 |
| WO | WO 2006/086423 A2 | 8/2006 |

(56)                References Cited

FOREIGN PATENT DOCUMENTS

| WO | WO 2006/094513 A2 | 9/2006 |
| WO | WO-2006/108809 | 10/2006 |
| WO | WO 2006/110742 | 10/2006 |
| WO | WO 2006/114297 A1 | 11/2006 |
| WO | WO-2006/118947 | 11/2006 |
| WO | WO 2006/121921 A2 | 11/2006 |
| WO | WO-2006/124099 | 11/2006 |
| WO | WO 2007/002189 | 1/2007 |
| WO | WO-2007/007459 | 1/2007 |
| WO | WO-2007/016399 | 2/2007 |
| WO | WO-2007/019289 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/056638 | 5/2007 |
| WO | WO-2007/065285 | 6/2007 |
| WO | WO-2007/089738 | 8/2007 |
| WO | WO-2007/092618 | 8/2007 |
| WO | WO 2007/097754 A1 | 8/2007 |
| WO | WO-2007/101223 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2007/149319 | 12/2007 |
| WO | WO-20071140783 | 12/2007 |
| WO | WO-2008/001366 | 1/2008 |
| WO | WO 2008/014792 A1 | 2/2008 |
| WO | WO-2008/021913 | 2/2008 |
| WO | WO 2008/031106 | 3/2008 |
| WO | WO 2008/031110 | 3/2008 |
| WO | WO 2008/039944 | 4/2008 |
| WO | WO-2008/042760 | 4/2008 |
| WO | WO-2008/048452 | 4/2008 |
| WO | WO 2008/051920 | 5/2008 |
| WO | WO 2008/051924 | 5/2008 |
| WO | WO-2008/052374 | 5/2008 |
| WO | WO-2008/062099 | 5/2008 |
| WO | WO 2008/065646 | 6/2008 |
| WO | WO 2008/073813 | 6/2008 |
| WO | WO-2008/086541 | 7/2008 |
| WO | WO 2008/103620 | 8/2008 |
| WO | WO 2008/114223 | 9/2008 |
| WO | WO 2008/115409 A1 | 9/2008 |
| WO | WO-2008/128210 | 10/2008 |
| WO | WO 2008/129532 A2 | 10/2008 |
| WO | WO-2008/130896 | 10/2008 |
| WO | WO-2008/130897 | 10/2008 |
| WO | WO-2008/130898 | 10/2008 |
| WO | WO 2008/133702 | 11/2008 |
| WO | WO 2008/138006 A2 | 11/2008 |
| WO | WO-2008/143943 | 11/2008 |
| WO | WO-2008/144445 | 11/2008 |
| WO | WO 2008/147921 | 12/2008 |
| WO | WO 2008/150917 | 12/2008 |
| WO | WO-2008/153693 | 12/2008 |
| WO | WO 2008/155377 | 12/2008 |
| WO | WO 2008/157821 A1 | 12/2008 |
| WO | WO 2009/007287 | 1/2009 |
| WO | WO 2009/010396 | 1/2009 |
| WO | WO 2009/016635 | 2/2009 |
| WO | WO 2009/016638 | 2/2009 |
| WO | WO-2009/018058 | 2/2009 |
| WO | WO-2009/035773 | 3/2009 |
| WO | WO 2009/039013 | 3/2009 |
| WO | WO 2009/062674 | 5/2009 |
| WO | WO-2009/062675 | 5/2009 |
| WO | WO 2009/066288 A1 | 5/2009 |
| WO | WO 2009/068661 | 6/2009 |
| WO | WO-2009/086216 | 7/2009 |
| WO | WO-2009/096992 | 8/2009 |
| WO | WO 2009/097594 | 8/2009 |
| WO | WO-2010/062898 | 6/2010 |
| WO | WO-2010/077329 | 7/2010 |
| WO | WO 2010/091005 | 8/2010 |
| WO | WO 2010/099507 | 9/2010 |
| WO | WO 2010/112521 | 10/2010 |
| WO | WO 2010/141922 | 12/2010 |
| WO | WO-2011/000528 | 1/2011 |
| WO | WO-20111002815 | 1/2011 |
| WO | WO 2011/015659 | 2/2011 |
| WO | WO-2011/022418 | 2/2011 |
| WO | WO 2011/025549 | 3/2011 |
| WO | WO-2011/104616 | 9/2011 |
| WO | WO 2011/119896 | 9/2011 |
| WO | WO 2011/119898 A1 | 9/2011 |
| WO | WO 2012/103429 | 8/2012 |
| WO | WO 2013/090215 | 6/2013 |
| WO | WO 2016/183493 A1 | 11/2016 |
| WO | WO 2017/027749 | 2/2017 |
| WO | WO 2017/116915 A1 | 7/2017 |
| WO | WO 2017/134227 | 8/2017 |
| WO | WO 2018/136898 | 7/2018 |
| WO | WO 2018/166963 | 9/2018 |
| WO | WO 2019/005627 A1 | 1/2019 |
| WO | WO 2019/236850 | 12/2019 |
| WO | WO 2019/236859 | 12/2019 |
| WO | WO 2019/236876 | 12/2019 |
| WO | WO 2022/046416 A1 | 3/2022 |
| WO | WO 2022/060677 A1 | 3/2022 |

OTHER PUBLICATIONS

Bennion, N., et al., "Alternate Site Glucose Testing: A Crossover Design", Diabetes Technology & Therapeutics, vol. 4, No. 1, 2002, pp. 25-33.

Claremont, D. J., et al., "Biosensors for Continuous In Vivo Glucose Monitoring", Proceedings of the Annual International Conference of the IEEE Engineering in Medicine and Biology Society, vol. 10, 1988.

Clark Jr., L. C., et al., "Electrode Systems for Continuous Monitoring in Cardiovascular Surgery", Annals New York Academy of Sciences, 1962, pp. 29-45.

Clark Jr., L. C., et al., "Long-term Stability of Electroenzymatic Glucose Sensors Implanted in Mice", American Society of Artificial Internal Organs Transactions, vol. XXXIV, 1988, pp. 259-265.

Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.

Csoregi, E., et al., "Design, Characterization, and One-Point in Vivo Calibration of a Subcutaneously Implanted Glucose Electrode", Analytical Chemistry, vol. 66 No. 19, 1994, pp. 3131-3138.

Feldman, B., et al., "A Continuous Glucose Sensor Based on Wired Enzyme™ Technology—Results from a 3-Day Trial in Patients with Type 1 Diabetes", Diabetes Technology & Therapeutics, vol. 5, No. 5, 2003, pp. 769-779.

Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.

Isermann, R., "Supervision, Fault-Detection and Fault-Diagnosis Methods—An Introduction", Control Engineering Practice, vol. 5, No. 5, 1997, pp. 639-652.

Gunasingham, et al., "Electrochemically Modulated Optrode for Glucose", Biosensors & Bioelectronics, vol. 7, 1992, pp. 353-359.

Ikeda, T., et al., "Artificial Pancreas—Investigation of the Stability of Glucose Sensors Using a Telemetry System" (English language translation of abstract), Jpn. J. Artif. Organs, vol. 19, No. 2, 1990, 889-892.

Isermann, R., et al., "Trends in the Application of Model-Based Fault Detection and Diagnosis of Technical Processes", Control Engineering Practice, vol. 5, No. 5, 1997, pp. 709-719.

Johnson, P. C., "Peripheral Circulation", John Wiley & Sons, 1978, pp. 198.

Jungheim, K., et al., "How Rapid Does Glucose Concentration Change in Daily Life of Patients with Type 1 Diabetes?", 2002, pp. 250.

(56) References Cited

OTHER PUBLICATIONS

Jungheim, K., et al., "Risky Delay of Hypoglycemia Detection by Glucose Monitoring at the Arm", Diabetes Care, vol. 24, No. 7, 2001, pp. 1303-1304.

Koudelka, M., et al., "In-Vivo Behaviour of Hypodermically Implanted Microfabricated Glucose Sensors", Biosensors & Bioelectronics, vol. 6, 1991, pp. 31-36.

Lager, W., et al., "Implantable Electrocatalytic Glucose Sensor", Hormone Metabolic Research, vol. 26, 1994, pp. 526-530.

Minimed Technologies, "Tape Tips and Other Infusion Site Information", 1995.

Moatti-Sirat, D., et al., "Evaluating In Vitro and In Vivo the Interference of Ascorbate and Acetaminophen on Glucose Detection by a Needle-Type Glucose Sensor", Biosensors & Bioelectronics, vol. 7, 1992, pp. 345-352.

Moatti-Sirat, D., et al., "Reduction of Acetaminophen Interference in Glucose Sensors by a Composite Nafion Membrane: Demonstration in Rats and Man", Diabetologia, vol. 37, 1994, pp. 610-616.

Olievier, C. N., et al., "In Vivo Measurement of Carbon Dioxide Tension with a Miniature Electrodes", Pflugers Archiv: European Journal of Physiology, vol. 373, 1978, pp. 269-272.

Pickup, J., "Developing Glucose Sensors for In Vivo Use", Tibtech, vol. 11, 1993, pp. 285-291.

Pickup, J., et al., "Implantable Glucose Sensors: Choosing the Appropriate Sensing Strategy", Biosensors, vol. 3, 1987/88, pp. 335-346.

Pickup, J., et al., "Potentially-Implantable, Amperometric Glucose Sensors with Mediated Electron Transfer: Improving the Operating Stability", Biosensors, vol. 4, 1989, pp. 109-119.

Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", Diabetolgia, vol. 36, 1993, pp. 658-663.

Poitout, V., et al., "Calibration in Dogs of a Subcutaneous Miniaturized Glucose Sensor Using a Glucose Meter for Blood Glucose Determination", Biosensors & Bioelectronics, vol. 7, 1992, pp. 587-592.

Quinn, C. P., et al., "Kinetics of Glucose Delivery to Subcutaneous Tissue in Rats Measured with 0.3-mm Amperometric Microsensors", The American Physiological Society, 1995, E155-E161.

Roe, J. N., et al., "Bloodless Glucose Measurements", Critical Review in Therapeutic Drug Carrier Systems, vol. 15, Issue 3, 1998, pp. 199-241.

Salehi, C., et al., "A Telemetry-Instrumentation System for Long-Term Implantable Glucose and Oxygen Sensors", Analytical Letters, vol. 29, No. 13, 1996, pp. 2289-2308.

Scheller, F., et al., "Enzyme Electrodes and Their Application", Philosophical Transactions of the Royal Society of London B, vol. 316, 1987, pp. 85-94.

Schmidt, F. J., et al., "Calibration of a Wearable Glucose Sensor", The International Journal of Artificial Organs, vol. 15, No. 1, 1992, pp. 55-61.

Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.

Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.

Shichiri, M., et al., "Membrane Design for Extending the Long-Life of an Implantable Glucose Sensor", Diabetes Nutrition and Metabolism, vol. 2, 1989, pp. 309-313.

Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.

Thompson, M., et al., "In Vivo Probes: Problems and Perspectives", Clinical Biochemistry, vol. 19, 1986, pp. 255-261.

Velho, G., et al., "In Vitro and In Vivo Stability of Electrode Potentials in Needle-Type Glucose Sensors", Diabetes, vol. 38, No. 2, 1989, pp. 164-171.

Von Woedtke, T., et al., "In Situ Calibration of Implanted Electro-chemical Glucose Sensors", Biomedica Biochimica Acta, vol. 48, 1989, pp. 943-952.

Chinese Patent Application No. CN 2010800064817, Original Language and English Translation of Office Action dated Dec. 2, 2014.

European Patent Application No. 10739015.5, Extended European Search Report dated May 10, 2013.

Ambade, V. N., et al., "Methods for Estimation of Blood Glucose: A Comparative Evaluation", Medical Journal Armed Forces India, 1998, vol. 54, No. 2, pp. 131-133.

ASTM International, Designation D2240-05, 2010, pp. 1-13.

Biosensors: Fundamentals and Applications, Turner et al., Eds., 1987, pp. 1-786.

Bluetooth Core Specification 4.0, Jun. 30, 2010, Master Table of Contents & Compliance Requirements, pp. 1-89.

Clarke, W., et al., "Statistical Tools to Analyze Continuous Glucose Monitor Data", Diabetes Technology & Therapeutics, 2009, vol. 11, Suppl. 1, pp. S-45-S-54.

In Vivo Glucose Sensing, Cunningham et al., Eds., 2010, Chemical Analysis, vol. 174, pp. 1-466.

Decuir, J., "Bluetooth 4.0: Low Energy", IEEE SCV Consultants' Network of Silicon Valley, 2012, pp. 1-68.

Dementyev, A., et al., "Power Consumption Analysis of Bluetooth Low Energy, ZigBee and ANT Sensor Nodes in a Cyclic Sleep Scenario", IEEE International Wireless Symposium (IWS), 2013, Beijing, China, pp. 1-4.

DexCom™ STS™ Continuous Glucose Monitoring System User's Guide, 2006, pp. 1-57.

ECMA International Standard ECMA-340, Near Field Communication Interface and Protocol (NFCIP-1), 2nd Edition, 2004, pp. 1-65.

Facchinetti, A., et al., "A New Index to Optimally Design and Compare Continuous Glucose Monitoring Glucose Prediction Algorithms", Diabetes Technology & Therapeutics, 2011, vol. 13, No. 2, pp. 111-119.

Fujipoly Silver ZEBRA® Connector Data Sheet FSDS 01-34, Version 5, 2006, pp. 1-7.

Gilligan, B. J., et al., "Evaluation of a Subcutaneous Glucose Sensor out to 3 Months in a Dog Model", Diabetes Care, 1994, vol. 17, No. 8, pp. 882-887.

Guerra, S., et al., "A Dynamic Risk Measure from Continuous Glucose Monitoring Data", Diabetes Technology & Therapeutics, 2011, vol. 13, No. 8, pp. 843-852.

Heise, T., et al., "Hypoglycemia Warning Signal and Glucose Sensors: Requirements and Concepts", Diabetes Technology & Therapeutics, 2003, vol. 5, No. 4, pp. 563-571.

Heller, A., "Implanted Electrochemical Glucose Sensors for the Management of Diabetes", Annnu. Rev. Biomed. Eng., 1999, vol. 1, pp. 153-175.

"In Vitro Diagnostic Products for Human Use", Federal Register, 1974, vol. 39, No. 126, pp. 24136-24147.

Klonoff, D. C., "A Review of Continuous Glucose Monitoring Technology", Diabetes Technology & Therapeutics, 2005, vol. 7, No. 5, pp. 770-775.

León, L. P., et al., "Continuous-Flow Analysis for Glucose in Serum, with Use of Hexokinase and Glucose-6-Phosphate Dehydrogenase Co-Immobilized in Tubular Form", Clinical Chemistry, 1980, vol. 26, No. 1, pp. 123-129.

Morak, J., et al., "Design and Evaluation of a Telemonitoring Concept Based on NFC-Enabled Mobile Phones and Sensor Devices", IEEE Transactions on Information Technology in Biomedicine, 2012, vol. 16, No. 1, pp. 17-23.

Movassaghi, S., et al., "Wireless Technologies for Body Area Networks: Characteristics and Challenges", 2012 International Symposium on Communications and Information Technologies (ISCIT), 2012, Gold Coast, QLD, Australia, pp. 42-47.

Passey, R. B., et al., "Evaluation and Comparison of 10 Glucose Methods and the Reference Method Recommendation in the Proposed Product Class Standard (1974)", Clinical Chemistry, 1977, vol. 23, No. 1, pp. 131-139.

Sandham, W., et al., "Blood Glucose Prediction for Diabetes Therapy Using a Recurrent Artificial Neural Network", 9th European Signal Processing Conference, 1998, Rhodes, Greece, pp. 1-4.

(56)        References Cited

OTHER PUBLICATIONS

Sparacino, G., et al., "Glucose Concentration Can Be Predicted Ahead in Time from Continuous Glucose Monitoring Sensor Time-Series", IEEE Transactions on Biomedical Engineering, 2007, vol. 54, No. 5, pp. 931-937.

Townsend, K., et al., "Getting Started with Bluetooth Low Energy—Chapter 1", 2014, pp. 1-26.

U.S. Appl. No. 60/587,787, filed Jul. 13, 2004, pp. 1-69.

U.S. Appl. No. 60/606,334, filed Aug. 31, 2004, pp. 1-38.

Wang, X.H., et al., "Bluetooth: Opening a blue sky for healthcare", Mobile Information Systems, 2006, vol. 2, pp. 151-167.

Z-Carbon Connector, retrieved from http://www.zaxisconnector. com/SS_zc.shtml, 2004, 2 pages.

Z-Silver Connector, retrieved from http://www.zaxisconnector.com/ SS_zs.shtml, 2004, 2 pages.

Alcock & Turner, "Continuous analyte monitoring to aid clinical practice," IEEE Engineering in Medicine & BioloXY Magazine, 13:319-25 (1994).

Armour et al., "Application of Chronic Intravascular Blood Glucose Sensor in Dogs," Diabetes, vol. 39, pp. 1519-1526, Dec. 1990.

Bindra, D.S. et al., "Design and in Vitro Studies of a Needle-Type Glucose Sensor for Subcutaneous Monitoring," Anal. Chem., 63(17):1692-1696 (Sep. 1, 1991).

Bobbioni-Harsch, E. et al., "Lifespan of subcutaneous glucose sensors and their performances during dynamic glycaemia changes in rats," J. Biomed. Eng. 15:457-463 (1993).

Cass, A.E.G. et al., "Ferrocene-Mediated Enzyme Electrode for Amperometric Determination of Glucose," Anal. Chem., 56(4):667-671 (Apr. 1984).

Gregg, B. A. et al., "Cross-Linked Redox Gels Containing Glucose Oxidase for Amperometric Biosensor Applications," Analytical Chemistry, 62(3):258-263 (Feb. 1, 1990).

Harrison, DJ. et al., "Characterization of Perfluorosulfonic Acid Polymer Coated Enzyme Electrodes and a Miniaturized Integrated Potentiostat for Glucose Analysis in Whole Blood," Anal. Chem., 60 (19):2002-2007 (Oct. 1, 1988).

Heller, A., "Electrical Connection of Enzyme Redox Centers to Electrodes," J. Phys. Chern., 96 (9):3579-3587 (1992).

Heller, A., "Electrical Wiring of Redox Enzymes," Acc. Chem. Res., 23(5):129-134 (1990).

International Search Report and Written Opinion from PCT/US2010/ 022860 dated Mar. 23, 2010.

International Search Report and Written Opinion from PCT/US2010/ 047381 dated Oct. 15, 2010.

International Search Report and Written Opinion from PCT/US2010/ 050772 dated Dec. 3, 2010.

International Search Report and Written Opinion from PCT/US2010/ 050888 dated Nov. 29, 2010.

International Search Report and Written Opinion from PCT/US2010/ 051861 dated Nov. 30, 2010.

Johnson, K., et al., "In vivo evaluation of an electroenzymatic glucose sensor implanted in subcutaneous tissue," Biosensors and Bioelectronics. 1992, vol. 7, pp. 709-714.

Maidan, R. et al., "Elimination of Electroaxidizable Interferant-Produced Currents in Amperometric Biosensors," Analytical Chemistry, 64(23):2889-2896 (Dec. 1, 1992).

Mastrototaro, J.J., et al., "An Electroenzymatic Glucose Sensor Fabricated on a Flexible Substrate," Sensors and Biosensors B Chemical, B5: 139-144 (1991).

McKean, B., et al., "A Telemetry-Instrumentation System for Chronically Implanted Glucose and Oxygen Sensors," IEEE Transactions on Biomedical Engineering, vol. 35, No. 7, (Jul. 1988), pp. 526-532.

Moatti-Sirat, D., et al., "Towards continuous glucose monitoring: in vivo evaluation of a miniaturized glucose sensor implanted for several days in rat subcutaneous tissue," Diabetolocia, 35(3) (1 page—Abstract only) (Mar. 1992).

Ohara, T. J., et al., "Glucose Electrodes Based on Cross-Linked [Os(bpy)$_2$Cl]$^{+/2+}$ Complexed Poly(1-vinylimadazole) Films," Analytical Chemistry, 65(23):3512-3516 (Dec. 1, 1993).

Opinion of the Court, Supreme Court of the United States, No. 04-1350, KSR *International co.*, Petitioner v. *Teleflex Inc, et al.*, Apr. 30, 2007.

Pickup, J. C., et al., "In vivo molecular sensing in diabetes mellitus: an implantable glucose sensor with direct electron transfer," Diabetologia, 32(3):213-217 (1989).

Pishko, M. V., et al., "Amperometric Glucose Microelectrodes Prepared Through Immobilization of Glucose Oxidase in Redox Hydrogels," Anal. Chem., 63(20):2268-2272 (Oct. 15, 1991).

Poitout, V., et al., "In vitro and in vivo evaluation in dogs of a miniaturized glucose sensor," ASAIO Transactions, 37(3) (1 page—Abstract only) (Jul.-Sep. 1991).

Reach, G., et al., "Can Continuous Glucose Monitoring Be Used for the Treatment of Diabetes?," Analytical Chemistry, 64(6):381-386 (Mar. 15, 1992).

Rebrin, K., et al., "Automated Feedback Control of Subcutaneous Glucose Concentration in Diabetic Dogs," Diabetologia, 32(8):573-576 (Aug. 1989).

Sakakida, M., et al., "Ferrocene-mediate needle-type glucose sensor covered with newly designed biocompatible membrane," Sensors and Actuators B, 13-14:319-322 (1993).

Sakakida, M., et al., "Development of ferrocene-mediated needle-type glucose sensor as a measure of true subcutaneous tissue glucose concentrations", Artif Organs Today. 1992, vol. 2, No. 2, pp. 145-458.

Shichiri, M., et al., "Glycaemic Control in Pancrearetomized Dogs with a Wearable Artificial Endocrine Pancreas," Diabetologia, 24(3):179-184 (Mar. 1983).

Shichiri, M., et al., "Telemetry Glucose Monitoring Device with Needle-type Glucose Sensor: A Useful Tool for Blood Glucose Monitoring in Diabetic Individuals," Diabetes Care, vol. 9, No. 3 (May-Jun. 1986), pp. 298-301.

Shichiri, M., et al., "In vivo characteristics of needle-type glucose sensor—Measurement of subcutaneous glucose concentrations in human volunteers," Horm Metab Res Suppl. 1988, vol. 20, pp. 17-20.

Shichiri, M., et al., "Wearable artificial endocrine pancreas with needle-type glucose sensor," The Lancet, 1982, vol. 2, No. 8308, pp. 1129-1131.

Shults, M., "A Telemetry-Instrumentation System for Monitoring Multiple Subcutaneously Implanted Glucose Sensors," IEEE Transactions on Biomedical Engineering, vol. 41, No. 10 (Oct. 1994), pp. 937-942.

Sternberg, R., et al., "Study and Development of Multilayer Needle-type Enzyme-based Glucose Microsensors," Biosensors, 4:27-40 (1988).

Turner, A.P.F., et al., "Diabetes Mellitus: Biosensors for Research and Management", Biosensors, 1:85-115 (1985).

Updike, S. et al., "Principles of Long-term Fully Implanted Sensors with Emphasis on Radiotelemetric Monitoring of Blood Glucase from Inside a Subcataneous Foreign Body Capsule (FBC)" in "Biosensors in the Body: Continuous in vivo Monitoring" (John Wiley & Sons, Ltd., 1997) Chapter 4, pp. 117-137.

Updike, S. J., et al., "A Subcutaneous Glucose Sensor With Improved Longevity, Dynamic Range, and Stability of Calibration", Diabetes Care, 2000, vol. 23, pp. 208-214.

Velho, G. et al., "Strategies for calibrating a subcutaneous glucose sensor," Biomed. Biochim. Acta, 48 (11112):957-964 (1989).

Wilson, G. S. et al., "Progress toward the Development of an Implantable Sensor for Glucose," Clinical Chemistry, 38(9):1613-1617 (1992).

Ye, L. et al., "High Current Density "Wired" Quinoprotein Glucose Dehydrogenase Electroade," Anal. Chem., 65(3):238-241 (Feb. 1, 1993).

Australian Examination Report from 2011269796 dated Apr. 3, 2014.

Netherlands Search Report from 2009963 dated Aug. 12, 2013.

European Extended Search Report from 11760268.0 dated Apr. 14, 2014.

International Search Report and Written Opinion from PCT/US2012/ 068839 dated Feb. 22, 2013.

International Search Report and Written Opinion from PCT/US2016/ 032485 dated Sep. 12, 2016.

(56) References Cited

OTHER PUBLICATIONS

European Search Report from 19151577.4 dated Aug. 16, 2019.
Ahson, S., et al., "RFID Handbook: Applications, Technology, Security, and Privacy", 2008, Chapter 4, Far-Field Tag Antenna Design Methodology, and Chapter 13, RFID Tags for Metallic Object Identification, pp. 71 and 253-254.
Application Note AN048, Antenna Part No. FR05-S1-N-0-102, Company Reach Xtend™, Bluetooth®, 802.11b/g WLAN Chip Antenna, 2008, pp. 1-13.
Application Note AVR2023—AT86RF231 PCB reference design for antenna diversity, Atmel Corporation, 2008, pp. 1-15.
Application Note nRF9E5 RF and antenna layout, Nordic Semiconductor, 2006, pp. 1-13.
Benkič, K., et al., "Using RSSI value for distance estimation in Wireless sensor networks based on ZigBee", 15th International Conference on Systems, Signals and Image Processing, Bratislava, Slovakia, 2008, pp. 1-4.
"Bluetooth Antenna Design", National Semiconductor Application Note, 2005, pp. 1-16.
Callaway, Jr., E. H., "Wireless Sensor Networks: Architectures and Protocols", 2004, Chapters, Antennas and the Definition of RF Performance, pp. 201-202.
Frenzel, L. E., "Printed-Circuit-Board Antennas, retrieved from https://www.electronicdesign.com/technologies/boards/article/21751417/printedcircuitboard-antennasprint/3266", Electronic Design, 2005, pp. 1-4.
Gonzalez, O. L., et al., "Low-Cost Wireless Sensors—Designer Reference Manual", Freescale Semiconductor, 2007, pp. 1-146.
Güler, N. F., et al., "Theory and Applications of Biotelemetry", Journal of Medical Systems, 2002, vol. 26, No. 2, pp. 159-178.
Heftman, G., "Chip Antenna Reduces Cell-Phone Dimensions", Microwaves & RF, 1999, p. 182.
Huang, Y., et al., "Antennas from Theory to Practice", 2008, Chapter 8, Antenna Diversity, pp. 322-325.
James, Jr., et al., "Handbook of Microstrip Antennas", 1969, pp. 1038-1047.
Loy, M., et al., "ISM—Band and Short Range Device Antennas", Texas Instruments Application Report, 2005, pp. 1-38.
Microchip Technology Inc., MRF24J40MA Data Sheet, 2008, pp. 1-30.
Moore, B., "The Potential Use of Radio Frequency Identification Devices for Active Monitoring of Blood Glucose Levels", Journal of Diabetes Science and Technology, 2009, vol. 3, No. 1, pp. 180-183.
"Murata Puts Antenna on a Chip", Passives, 1999, vol. 44, 1 page.
Schoepke, E., "Chip Antenna Layout Considerations for 802.11 Applications", Johanson Technology, 2006, retrieved from https://www.johansontechnology.com/chip-antenna-layout-considerations-for-802-11-applications, pp. 1-7.
Sharawi, M. S., "Use of low-cost patch antennas in modern wireless technology", IEEE Potentials, 2006, pp. 35-38 and 47.
Waterhouse, R., "Printed Antennas for Wireless Communications," 2007, pp. 116-129 and 284-289.
Wong, KL, "Planar Antennas for Wireless Communications," 2003, Chapter 1, Introduction and Overview, pp. 4-17, 38-45, and 218-221.
EP, 10739015.5 Extended Search Report, dated May 10, 2013.
EP, 19151577.4 Extended Search Report, dated Aug. 16, 2019.
EP, 17201183.5 Extended Search Report, dated May 7, 2018.
EP, 20177703.4 Extended Search Report, dated Sep. 25, 2020.
EP, 20177712.5 Extended Search Report, dated Sep. 30, 2020.
EP, 21192910.4 Extended Search Report, dated Jan. 31, 2022.
Armour, J. C., et al., "Application of Chronic Intravascular Blood Glucose Sensor in Dogs", Diabetes, vol. 39, 1990, pp. 1519-1526.
Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.

Brooks, S. L., et al., "Development of an On-Line Glucose Sensor for Fermentation Monitoring", Biosensors, vol. 3, 1987/88, pp. 45-56.
Diem, P., et al., "Clinical Performance of a Continuous Viscometric Affinity Sensor for Glucose", Diabetes Technology & Therapeutics, vol. 6, 2004, pp. 790-799.
El-Khatib, F. H, et al., "Adaptive Closed-Loop Control Provides Blood-Glucose Regulation Using Subcutaneous Insulin and Glucagon Infusion in Diabetic Swine", Journal of Diabetes Science and Technology, vol. 1, No. 2, 2007, pp. 181-192.
Garg, S., et al., "Improvement in Glycemic Excursions with a Transcutaneous, Real-Time Continuous Glucose Sensor", Diabetes Care, vol. 29, No. 1, 2006, pp. 44-50.
Kaplan, S. M., "Wiley Electrical and Electronics Engineering Dictionary", IEEE Press, 2004, pp. 141, 142, 548, 549.
Kondepati, V., et al., "Recent Progress in Analytical Instrumentation for Glycemic Control in Diabetic and Critically Ill Patients", Analytical Bioanalytical Chemistry, vol. 388, 2007, pp. 545-563.
Lo, B., et al., "Key Technical Challenges and Current Implementations of Body Sensor Networks", Body Sensor Networks, 2005, pp. 1-5.
Lodwig, V., et al., "Continuous Glucose Monitoring with Glucose Sensors: Calibration and Assessment Criteria", Diabetes Technology & Therapeutics, vol. 5, No. 4, 2003, pp. 573-587.
Lortz, J., et al., "What is Bluetooth? We Explain the Newest Short-Range Connectivity Technology", Smart Computing Learning Series, Wireless Computing, vol. 8, Issue 5, 2002, pp. 72-74.
Malin, S. F., et al., "Noninvasive Prediction of Glucose by Near-Infrared Diffuse Reflectance Spectroscopy", Clinical Chemistry, vol. 45, No. 9, 1999, pp. 1651-1658.
McGarraugh, G., et al., "Glucose Measurements Using Blood Extracted from the Forearm and the Finger", TheraSense, Inc., 2001, 16 Pages.
McGarraugh, G., et al., "Physiological Influences on Off-Finger Glucose Testing", Diabetes Technology & Therapeutics, vol. 3, No. 3, 2001, pp. 367-376.
McKean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.
Rodriguez, N., et al., "Flexible Communication and Control Protocol for Injectable Neuromuscular Interfaces", IEEE Transactions on Biomedical Circuits and Systems, IEEE, vol. 1, No. 1, 2007, pp. 19-27.
Salditt, P., "Trends in Medical Device Design and Manufacturing", SMTA News and Journal of Surface Mount Technology, vol. 17, 2004, pp. 19-24.
Sternberg, R., et al., "Study and Development of Multilayer Needle-Type Enzyme-Based Glucose Microsensors", Biosensors, vol. 4, 1988, pp. 27-40.
Tung, S., "Layers of Security for Active RFID Tags", RFID Handbook: Applications, Technology, Security, and Privacy, Edited by Ehson, et al., Chapter 33, 2008, pp. 1-28.
Australian Patent Application No. 2008265541, Examiner's Report dated Nov. 29, 2013.
Australian Patent Application No. 2008265541, Examiner's Report dated Oct. 15, 2012.
Australian Patent Application No. 2016201703, Examiner's Report dated Mar. 22, 2017.
Australian Patent Application No. 2017254903, Examiner's Report dated Dec. 11, 2018.
Australian Patent Application No. 2018200899, Examiner's Report dated Dec. 6, 2018.
Canadian Patent Application No. 2,765,712, Examiner's Report dated Apr. 10, 2017.
Canadian Patent Application No. 2,765,712, Examiner's Report dated Mar. 27, 2018.
Chinese Patent Application No. 201080006480.2, Original Language & English Translation of Office Action dated Dec. 11, 2013.
Chinese Patent Application No. 201080006480.2, Original Language & English Translation of Office Action dated May 6, 2013.
Chinese Patent Application No. 201080027344.1, Original Language & English Translation of Office Action dated Feb. 6, 2015.

(56) References Cited

OTHER PUBLICATIONS

Chinese Patent Application No. 201080027344.1, Original Language & English Translation of Office Action dated Jun. 5, 2014.
Chinese Patent Application No. 20160144860.1, Original Language & English Translation of Office Action dated Mar. 23, 2018.
Chinese Patent Application No. 20160144860.1, Original Language & English Translation of Office Action dated Dec. 10, 2018.
Chinese Patent Application No. 20160144860.1, Original Language & English Translation of Office Action dated May 23, 2019.
European Patent Application No. 13000105.0, Examination Report dated Oct. 18, 2016.
European Patent Application No. 13000105.0, Minutes of the Oral Proceedings mailed Oct. 18, 2016.
European Patent Application No. 10739031.2, Extended European Search Report dated May 7, 2013.
European Patent Application No. 10739031.2, Examination Report dated Oct. 28, 2016.
European Patent Application No. 10739031.2, Opposition filed Dec. 20, 2018.
European Patent Application No. 10812438.9, Extended European Search Report dated Dec. 10, 2013.
European Patent Application No. 13000105.0, Opposition filed Jan. 4, 2019.
European Patent Application No. 15184320.8, Examination Report dated Apr. 18, 2017.
European Patent Application No. 17201183.5, Examination Report dated May 17, 2019.
European Patent Application No. 18192278.2, Extended European Search Report dated Mar. 13, 2019.
European Patent Application No. 18208224.8, Extended European Search Report dated Oct. 11, 2019.
Japanese Patent Application No. 2012-526736, Original Language & English Translation of Office Action dated Apr. 15, 2014.
Japanese Patent Application No. 2012-526736, Original Language & English Translation of Office Action dated Dec. 16, 2014.
Japanese Patent Application No. 2015-159805, Original Language & English Translation of Office Action dated Aug. 9, 2016,.
PCT Application No. PCT/US2010/002401, International Preliminary Report on Patentability and Written Opinion of the International Searching Authority dated Mar. 15, 2012.
PCT Application No. PCT/US2010/002401, International Search Report and Written Opinion of the International Searching Authority dated Nov. 12, 2010.
PCT Application No. PCT/US2010/022928, International Preliminary Report on Patentability and Written Opinion of the International Searching Authority dated Aug. 18, 2011.
PCT Application No. PCT/US2010/022928, International Search Report and Written Opinion of the International Searching Authority dated Mar. 21, 2010.
U.S. Appl. No. 12/698,124, Office Action dated Aug. 12, 2012.
U.S. Appl. No. 12/698,124, Office Action dated Dec. 4, 2013.
U.S. Appl. No. 12/698,124, Office Action dated Jun. 6, 2013.
U.S. Appl. No. 12/698,124, Office Action dated Mar. 20, 2015.
U.S. Appl. No. 12/698,124, Office Action dated Nov. 21, 2012.
U.S. Appl. No. 12/807,278, Advisory Action dated Jul. 28, 2014.
U.S. Appl. No. 12/807,278, Advisory Action dated Jun. 13, 2013.
U.S. Appl. No. 12/807,278, Advisory Action dated Oct. 8, 2014.
U.S. Appl. No. 12/807,278, Office Action dated Aug. 21, 2012.
U.S. Appl. No. 12/807,278, Office Action dated Feb. 1, 2013.
U.S. Appl. No. 12/807,278, Office Action dated Mar. 29, 2013.
U.S. Appl. No. 12/807,278, Office Action dated Mar. 5, 2015.
U.S. Appl. No. 12/807,278, Office Action dated Jul. 5, 2016.
U.S. Appl. No. 12/807,278, Office Action mailed Apr. 3, 2017.
U.S. Appl. No. 12/807,278, Office Action mailed Feb. 1, 2018.
U.S. Appl. No. 12/807,278, Notice of Allowance mailed Jul. 5, 2018.
U.S. Appl. No. 14/094,719, Office Action mailed Dec. 26, 2018.
U.S. Appl. No. 14/094,719, Office Action mailed Jul. 10, 2019.
U.S. Appl. No. 14/741,459, Office Action mailed Jun. 5, 2017.
U.S. Appl. No. 14/741,459, Office Action mailed Dec. 14, 2017.
U.S. Appl. No. 14/741,459, Advisory Action mailed Apr. 13, 2018.
U.S. Appl. No. 14/741,459, Office Action mailed Aug. 2, 2019.
U.S. Appl. No. 14/741,459, Office Action mailed Jan. 7, 2020.
U.S. Appl. No. 14/841,122, Office Action mailed Aug. 25, 2016.
U.S. Appl. No. 14/841,122, Office Action mailed Mar. 7, 2017.
U.S. Appl. No. 14/841,122, Office Action mailed Feb. 8, 2018.
U.S. Appl. No. 14/841,122, Office Action mailed Sep. 18, 2018.
U.S. Appl. No. 14/841,122, Office Action mailed May 1, 2019.
U.S. Appl. No. 14/841,224, Office Action mailed Nov. 3, 2016.
U.S. Appl. No. 14/841,224, Office Action mailed Jan. 17, 2017.
U.S. Appl. No. 14/841,224, Advisory Action mailed Jun. 2, 2017.
U.S. Appl. No. 14/841,224, Office Action mailed Jul. 31, 2017.
U.S. Appl. No. 14/841,224, Office Action mailed Feb. 8, 2018.
U.S. Appl. No. 14/841,224, Office Action mailed Apr. 17, 2018.
U.S. Appl. No. 14/841,224, Office Action mailed Sep. 26, 2018.
U.S. Appl. No. 14/841,224, Advisory Action mailed Jan. 28, 2019.
U.S. Appl. No. 14/841,224, Office Action mailed Feb. 19, 2019.
U.S. Appl. No. 14/841,224, Notice of Allowance mailed Jul. 25, 2019.
U.S. Appl. No. 14/841,429, Office Action mailed Oct. 27, 2016.
U.S. Appl. No. 14/841,429, Office Action mailed Feb. 8, 2017.
U.S. Appl. No. 14/841,429, Office Action mailed Feb. 8, 2018.
U.S. Appl. No. 14/841,429, Advisory Action mailed May 2, 2018.
U.S. Appl. No. 14/841,429, Office Action mailed Sep. 21, 2018.
U.S. Appl. No. 14/841,429, Office Action mailed Jun. 12, 2019.
U.S. Appl. No. 15/985,615, Office Action mailed Jul. 27, 2018.
U.S. Appl. No. 15/985,615, Office Action mailed Mar. 7, 2019.
AU, 2007309066 Examiner's Report, Jul. 12, 2012.
AU, 2007309066 Examiner's Report, Aug. 16, 2012.
AU, 2010286917 Examiner's Report, Sep. 8, 2014.
AU, 2011230596 Examiner's Report, Feb. 28, 2014.
CN, 200780045373.9 Notice of Allowance, May 18, 2011.
CN, 200780045373.9 Office Action, Apr. 14, 2010.
CN, 201180002616.7 Office Action, Apr. 24, 2014.
CN, 201180002617.1 Office Action, Jul. 3, 2014.
EP, 06804122.7 Decision to Refuse the Application, Feb. 25, 2013.
EP, 06804122.7 Examination Report, Nov. 30, 2011.
EP, 06804122.7 Examination Report, Jan. 25, 2011.
EP, 06815715.5 Extended Search Report, Oct. 30, 2009.
EP, 07842173.2 Examination Report, Mar. 21, 2013.
EP, 07842173.2 Extended Search Report, Dec. 29, 2010.
EP, 07842180.7 Examination Report, Oct. 23, 2012.
EP, 07842180.7 Examination Report, Dec. 14, 2011.
EP, 07842180.7 Examination Report, Feb. 23, 2011.
EP, 07842180.7 Extended Search Report, Sep. 28, 2009.
EP, 10739031.2 Reply to Notice of Opposition, May 21, 2019.
EP, 10739031.2 Reply to Notice of Opposition Reply, Aug. 8, 2019.
EP, 10739031.2 Summons to Attend Oral Proceedings, Sep. 17, 2019.
EP, 10739031.2 Written Submissions, Dec. 3, 2019.
EP, 10739031.2 Response to Written Submissions, Jan. 24, 2020.
EP, 10739031.2 Summons to Attend Oral Proceedings, May 20, 2020.
EP, 10739031.2 Written Submissions, Nov. 20, 2020.
EP, 10739031.2 Response to Written Submissions, Jan. 7, 2021.
EP, 10739031.2 Decision and Grounds for Revoking Patent, Jun. 9, 2021.
EP, 10739031.2 Grounds of Appeal, Oct. 19, 2021.
EP, 10739031.2 Response to Grounds of Appeal, Mar. 1, 2022.
EP, 10739031.2 Response to Response to Grounds of Appeal, Mar. 1, 2022.
EP, 11760268.0 Decision of the Oral Proceedings, Sep. 27, 2022.
EP, 11760268.0 Minutes of Oral Proceedings, Aug. 11, 2022.
EP, 11760268.0 Communication from Board of Appeals, Mar. 31, 2022.
EP, 11760268.0 Response to Written Submissions, Jan. 14, 2020.
EP, 11760268.0 Response to Notice of Appeal, Sep. 5, 2019.
EP, 11760268.0 Statement of Grounds of Appeal, Apr. 23, 2019.
EP, 11760268.0 Grounds of Appeal, Apr. 18, 2019.
EP, 11760268.0 Notice of Appeal Abbott Diabetes Care Inc., Feb. 25, 2019.
EP, 11760268.0 Notice of Appeal Dexcom, Feb. 22, 2019.
EP, 11760268.0 Interlocutory Decision, Dec. 13, 2018.

(56) References Cited

OTHER PUBLICATIONS

EP, 11760268.0 Response to Summons to Attend Oral Proceedings, Sep. 13, 2018.
EP, 11760268.0 Letter Regarding the Opposition Procedure, Sep. 12, 2018.
EP, 11760268.0 Summons to Attend Oral Proceedings, Mar. 22, 2018.
EP, 11760268.0 Comments on Reply to Notice of Opposition, Dec. 27, 2017.
EP, 11760268.0 Reply to Notice of Opposition, Sep. 4, 2017.
EP, 11760268.0 Notice of Opposition, Mar. 29, 2017.
EP, 16176370.1 Extended Search Report, Dec. 7, 2016.
EP, 16793637.6 Extended Search Report, Oct. 9, 2018.
EP, 17182379.2 Extended Search Report, Feb. 21, 2018.
EP, 18741791.0 Extended Search Report, Sep. 23, 2020.
EP, 19151577.4 Examination Report, May 27, 2022.
EP, 19184881.1 Extended Search Report, Nov. 21, 2019.
EP, 19900891.3 Extended Search Report, Sep. 26, 2022.
EP, 20177703.4 Grounds of Opposition, Sep. 28, 2022.
EP, 20177703.4 Notice of Opposition. Sep. 28, 2022.
EP, 20177703.4 Examination Report, Jun. 25, 2021.
EP, 20195922.8 Extended Search Report, Dec. 16, 2020.
EP, 21152231.3 Extended Search Report, May 11, 2021.
EP, 21211041.5 Extended Search Report, Mar. 3, 2022.
EP, 22168031.7 Extended Search Report, Aug. 17, 2022.
EP, 22169853.3 Extended Search Report, Sep. 2, 2022.
GB, Claim No. HP-2021-000026 Re-Amended Grounds of Invalidity, Aug. 26, 2022.
GB, Claim No. HP-2021-000025 Amended Reply and Defence to Counterclaim, Apr. 19, 2022.
GB, Claim No. HP-2021-000025 Amended Defence and Counterclaim, Mar. 28, 2022.
GB, Claim No. HP-2021-000025 Amended Grounds of Invalidity, Aug. 26, 2022.
IL, 198329 Office Action, Mar. 5, 2012.
JP, 2009-534798 Office Action, Sep. 25, 2012.
JP, 2013-501503 Office Action, Mar. 3, 2015.
JP, 2016-44196 Office Action, Apr. 11, 2017.
MX, MX/a/2009/004398 Office Action, Sep. 24, 2012.
MY, PI2021004760 Examination Report, Mar. 30, 2022.
MY, PI2021005830 Examination Report, Sep. 30, 2022.
MY, PI2021005830 Examination Report, Aug. 29, 2022.
US, Institution Decision, IPR No. 2022-00605, Jul. 27, 2022.
US, Patent Owner's Preliminary Sur-Reply, IPR No. 2022-00605, Jun. 28, 2022.
US, Petitioner's Preliminary Reply to Patent Owner's Preliminary Response, IPR No. 2022-00605, Jun. 21, 2022.
US, Patent Owner's Preliminary Response, IPR No. 2022-00605, May 24, 2022.
US, Petition For Inter Partes Review Of U.S. Pat. No. 10,945,649, IPR No. 2022-00605, Feb. 15, 2022.
US, Institution Decision, IPR No. 2022-00637, Jul. 27, 2022.
US, Patent Owner's Preliminary Sur-Reply, IPR No. 2022-00637, Jun. 28, 2022.
US, Petitioner's Preliminary Reply to Patent Owner's Preliminary Response, IPR No. 2022-00637, Jun. 21, 2022.
US, Patent Owner's Preliminary Response, IPR No. 2022-00637, Jun. 9, 2022.
US, Petition For Inter Partes Review Of U.S. Pat. No. 11,013,440, IPR No. 2022-00637, Feb. 8, 2022.
US, Reexamination U.S. Appl. No. 95/002,162 Request to Review Order Denying Request for Reexamination, Dec. 13, 2012.
US, Rexamination U.S. Appl. No. 95/002,162 Order Denying Request for Reexamination, Nov. 13, 2012.
US, Request for Reexamination U.S. Appl. No. 95/002,162 of U.S. Pat. No. 8,175,673, Sep. 7, 2012.
US, Reexamination U.S. Appl. No. 95/002,113 Request to Review Order Denying Request for Reexamination, Dec. 13, 2012.
US, Reexamination U.S. Appl. No. 95/002,113 Order Denying Request for Reexamination, Nov. 13, 2012.

US, Request for Reexamination U.S. Appl. No. 95/002,113 of U.S. Pat. No. 6,990,366, Aug. 30, 2012.
US, Reexamination U.S. Appl. No. 90/011,730 Notice of Intent to Issue Ex Parte Reexamination Certificate, Apr. 5, 2012.
US, Reexamination U.S. Appl. No. 90/011,730 Office Action, Jan. 11, 2012.
US, Reexamination U.S. Appl. No. 90/011,730 Order Granting Request for Reexamination, Aug. 24, 2011.
US, Request for Reexamination U.S. Appl. No. 90/011,730 of U.S. Pat. No. 6,990,366, Jun. 3, 2011.
US, Reexamination U.S. Appl. No. 90/010,791 Ex Parte Reexamination Certificate, May 17, 2011.
US, Reexamination U.S. Appl. No. 90/010,791 Office Action. Dec. 17, 2010.
US, Reexamination U.S. Appl. No. 90/010,791 Office Action, May 28, 2010.
US, Reexamination U.S. Appl. No. 90/010,791 Order Granting Request for Reexamination, Feb. 22, 2010.
US, Request for Reexamination U.S. Appl. No. 90/010,791 of U.S. Pat. No. 6,990,366, Dec. 22, 2009.
US, Reexamination U.S. Appl. No. 90/009,328 Notice of Intent to Issue Ex Parte Reexamination Certificate, Nov. 20, 2009.
US, Reexamination U.S. Appl. No. 90/009,328 Office Action, Sep. 30, 2009.
US, Reexamination U.S. Appl. No. 90/009,328 Office Action, Aug. 4, 2009.
US, Reexamination U.S. Appl. No. 90/009,328 Order Granting Request for Reexamination, Dec. 9, 2008.
US, Request for Reexamination U.S. Appl. No. 90/009,328 of U.S. Pat. No. 6,990,366, Nov. 10, 2008.
US, Reexamination U.S. Appl. No. 90/009,104 Notice of Intent to Issue Ex Parte Reexamination Certificate, Nov. 20, 2009.
US, Reexamination U.S. Appl. No. 90/009,104 Office Action, Sep. 30, 2009.
US, Reexamination U.S. Appl. No. 90/009,104 Office Action, Aug. 4, 2009.
US, Reexamination U.S. Appl. No. 90/009,104 Office Action, Oct. 16, 2008.
US, Reexamination U.S. Appl. No. 90/009,104 Order Granting Request for Reexamination, Jun. 5, 2008.
US, Request for Reexamination U.S. Appl. No. 90/009,104 of U.S. Pat. No. 6,990,366, Apr. 8, 2008.
US, Reexamination U.S. Appl. No. 90/008,457 Notice of Intent to Issue Ex Parte Reexamination Certificate, Mar. 13, 2008.
US, Reexamination U.S. Appl. No. 90/008,457 Order Granting Request for Reexamination, Feb. 23, 2007.
US, Request for Reexamination U.S. Appl. No. 90/008,457 of U.S. Pat. No. 6,990,366, Jan. 23, 2007.
US, Request for Reexamination U.S. Appl. No. 90/008,172 of U.S. Pat. No. 6,990,366, Aug. 16, 2008.
US, Reexamination U.S. Appl. No. 90/007,910 Patent Board Decision, May 17, 2013.
US, Reexamination U.S. Appl. No. 90/007,910 Decision on Appeal, Jan. 18, 2011.
US, Reexamination U.S. Appl. No. 90/007,910 Advisory Action, Jul. 30, 2009.
US, Reexamination U.S. Appl. No. 90/007,910 Advisory Action, Feb. 6, 2009.
US, Reexamination U.S. Appl. No. 90/007,910 Examiner's Answer to Appeal Brief, Nov. 19, 2009.
US, Reexamination U.S. Appl. No. 90/007,910 Office Action, Oct. 2, 2008.
US, Reexamination U.S. Appl. No. 90/007,910 Office Action, Feb. 13, 2008.
US, Reexamination U.S. Appl. No. 90/007,910 Order Granting Request for Reexamination, Mar. 27, 2006.
US, Request for Reexamination U.S. Appl. No. 90/007,910 of U.S. Pat. No. 6,175,752, Feb. 1, 2006.
US, Reexamination U.S. Appl. No. 90/009,270 Order Denying Request for Reexamination, Dec. 1, 2008.
US, Request for Reexamination U.S. Appl. No. 90/009,270 of U.S. Pat. No. 6,175,752, Sep. 8, 2008.

(56) References Cited

OTHER PUBLICATIONS

US, Reexamination U.S. Appl. No. 90/009,497 Notice of Intent to Issue Reexamination Certificate, Aug. 30, 2010.
US, Reexamination U.S. Appl. No. 90/009,497 Order Granting Request, Jul. 30, 2009.
US, Request for Reexamination U.S. Appl. No. 90/009,497 of U.S. Pat. No. 6,175,752, Jun. 17, 2009.
WO, PCT/US2006/037312 ISR and Written Opinion, Apr. 17, 2007.
WO, PCT/US2006/037928 ISR and Written Opinion, Jul. 11, 2008.
WO, PCT/US2007/078065 ISR and Written Opinion, Apr. 11, 2008.
WO, PCT/US2007/078073 ISR and Written Opinion, Apr. 11, 2008.
WO, PCT/US2007/082114 ISR and Written Opinion, May 9, 2008.
WO, PCT/US2011/029881 ISR and Written Opinion, May 20, 2011.
WO, PCT/US2011/029883 ISR and Written Opinion, Jun. 2, 2011.
WO, PCT/US2011/029884 ISR and Written Opinion, Jun. 1, 2011.
WO, PCT/US2013/052397 ISR and Written Opinion, Dec. 2, 2013.
WO, PCT/US2018/014745 ISR and Written Opinion, Jun. 4, 2018.
WO, PCT/US2019/035843 ISR and Written Opinion, Sep. 18, 2019.
WO, PCT/US2021/040541 ISR and Written Opinion, Dec. 20, 2021.
WO, PCT/US2021/045576 Isr and Written Opinion, Jan. 27, 2022.
WO, PCT/US2021/048086 ISR and Written Opinion, Feb. 28, 2022.
WO, PCT/US2021/050672 ISR and Written Opinion, Jan. 5, 2022.
WO, PCT/US22/37291 Invitation to Pay Additional Fees, Sep. 29, 2022.
Abruna, H. D., et al., "Rectifying Interfaces Using Two-Layer Films of Electrochemically Polymerized Vinylpyridine and Vinylbipyridine Complexes of Ruthenium and Iron on Electrodes", Journal of the American Chemical Society, 1981, vol. 103, No. 1, pp. 1-5.
ACCU-CHEK Compact Plus Owner's Booklet, 2008, pp. 1-100.
ACCU-CHEK Softclix Plus Lancet Device retrieved from https://web.archive.org/web/20061018055737/http://www.accu-check.com/us/rewrite/content/en_US/2.1.7.1:10/article/ACCM_general_article_3303.htm, 2006, pp. 1-2.
Albery, W.J., et al., "Amperometric Enzyme Electrodes Part II: Conducting Salts as Electrode Materials for the Oxidation of Glucose Oxidase", Journal of ElectroAnalytical Chemistry, 1985, vol. 194, pp. 223-235.
Albery, W.J., et al., "Amperometric Enzyme Electrodes", Philosophical Transactions of the Royal Society of London, 1987, vol. 316, pp. 107-119.
Anderson, L. B., et al., "Thin-Layer Electrochemistry: Steady-State Methods of Studying Rate Processes", Journal of ElectroAnalytical Chemistry, 1965, vol. 10, pp. 295-305.
Bartlett, P. N., et al., "Covalent Binding of Electron Relays to Glucose Oxidase", Journal of the Chemical Society, Chemical Communications, 1987, pp. 1603-1604.
Bartlett, P. N., et al., "Modification of Glucose Oxidase by Tetrathiafulvalene", Journal of the Chemical Society, Chemical Communications, 1990, pp. 1135-1136.
Bindra, D.S., et al., "Pulsed Amperometric Detection of Glucose in Biological Fluids at a Surface-Modified Gold Electrode", American Chemical Society, 1989, vol. 61, No. 22, pp. 2566-2570.
Bonnett, A. H., et al., "Squirrel-Cage Rotor Options for AC Induction Motors", IEEE Transactions on Industry Applications, 2001, vol. 37, No. 4, pp. 1197-1209.
Brandt, J., et al., "Covalent Attachment of Proteins to Polysaccharide Carriers by Means of Benzoquinone", Biochimica et Biophysica Acta, 1975, vol. 386, pp. 196-202.
Brownlee, M., et al., "A Glucose-Controlled Insulin-Delivery System: Semisynthetic Insulin Bound to Lectin", Science, 1979, vol. 206, pp. 1190-1191.
Bühling, K. J., et al., "Optimal timing for postprandial glucose measurement in pregnant women with diabetes and a non-diabetic pregnant population evaluated by the Continuous Glucose Monitoring System (CGMS®)", Journal of Perinatal Medicine, 2005, vol. 33, No. 2, pp. 125-131.
Cass, A.E.G et al., "Ferricinium Ion as an Electron Acceptor for Oxido-Reductases", Journal of ElectroAnalytical Chemistry, 1985, vol. 190, pp. 117-127.

Castner, J. F., et al., "Mass Transport and Reaction Kinetic Parameters Determined Electrochemically for Immobilized Glucose Oxidase", Biochemistry, 1984, vol. 23, No. 10, pp. 2203-2210.
Cheyne, E.H., et al., "Performance of a Continuous Glucose Monitoring System During Controlled Hypoglycaemia in Healthy Volunteers", Diabetes Technology & Therapeutics, 2002, vol. 4, No. 5, pp. 607-613.
Clark Jr., L. C., et al., "Differential Anodic Enzyme Polarography for the Measurement of Glucose", Oxygen Transport to Tissue: Instrumentation, Methods, and Physiology, 1973, pp. 127-133.
Clarke, W. L., et al., "Evaluating Clinical Accuracy of Systems for Self-Monitoring of Blood Glucose", Diabetes Care, 1987, vol. 10, No. 5, pp. 622-628.
Cleo™ 90 Infusion Set, 510(k) Summary of Safety and Effectiveness, Aug. 10, 2004, pp. 1-618.
Cleo® 90 Infusion Set Training Guide, 2011, 1 page.
Compact Plus Blood Glucose Meter retrieved from https://web.archive.org/web/20090316065810/http://www.accu-check.com/us/rewrite/content/en_US/2.1.9:0/article/ACCM_general_article_5136.htm, 2009, pp. 1-3.
Complaint Abbott Diabetes Care Inc. v. Dexcom, Inc. U.S. District Court Delaware C.A. No. 05-590 filed Aug. 11, 2005.
Complaint, Amended, Abbott Diabetes Care Inc. v. Dexcom, Inc. U.S. District Court Delaware C.A. No. 05-590 filed Jun. 27, 2006.
Complaint Abbott Diabetes Care Inc. v. Dexcom, Inc. U.S. District Court Delaware C.A. No. 06-514 filed Aug. 17, 2006.
Cox, M., "An Overview of Continuous Glucose Monitoring Systems", Journal of Pediatric Health Care, 2009, vol. 23, No. 5, pp. 344-347.
Csöregi, E., et al., "On-Line Glucose Monitoring by Using Microdialysis Sampling and Amperometric Detection Based on 'Wired' Glucose Oxidase in Carbon Paste", Mikrochimica Acta, 1995, vol. 121, pp. 31-40.
Cullen, M.T., et al., "The Changing Presentations of Diabetic Ketoacidosis During Pregnancy", Amer. J. Perinatol, 1996, vol. 13, No. 7, pp. 449-451 (abstract only).
Darley, J., "Is your user experience as good as your technology?", 2019, retrieved from https://www.massdevice.com/is-your-user-experience-as-good-as-your-technology/, pp. 1-16.
Davis, G., "Electromechanical Techniques for the Development of Amperometric Biosensors", Biosensors, 1985, vol. 1, pp. 161-178.
IPR2022-00605 (Ex. 2001) Declaration of Michael Cima, Ph.D dated May 24, 2022, pp. 1-70.
IPR2022-00637 (Ex. 2001) Declaration of Michael Cima, Ph.D dated Jun. 9, 2022, pp. 1-79.
IPR2022-00605 (Ex. 1003) Declaration of Gary D. Fletcher, Ph.D dated Feb. 15, 2022, pp. 1-122.
IPR2022-00605 (Ex. 1003) Corrected Declaration of Gary D. Fletcher, Ph.D dated Feb. 18, 2022, pp. 1-124.
IPR2022-00637 (Ex. 1035) Second Declaration of Gary D. Fletcher, Ph.D dated Feb. 28, 2022, pp. 1-136.
Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", The Journal of Physical Chemistry, 1987, vol. 91, No. 6, pp. 1285-1289.
Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", Journal of the American Chemical Society, 1988, vol. 110, No. 8, pp. 2615-2620.
Degani, Y., et al., "Electrical Communication Between Redox Centers of Glucose Oxidase and Electrodes via Electrostatically and Covalently Bound Redox Polymers", Journal of the American Chemical Society, 1989, vol. 111, pp. 2357-2358.
Dehez, B., et al., "Development of a Spherical Induction Motor With Two Degrees of Freedom", IEEE Transactions on Magnetics, 2006, vol. 42, No. 8, pp. 2077-2089.
Delve Talks: Jake Leach, Dexcom, retrieved from https://www.delve.com/podcasts/delve-talks-jake-leach-dexcom, pp. 1-9.
Denisevich, P., et al., "Unidirectional Current Flow and Charge State Trapping at Redox Polymer Interfaces on Bilayer Electrodes:

(56) References Cited

OTHER PUBLICATIONS

Principles, Experimental Demonstration, and Theory", Journal of the American Chemical Society, 1981, vol. 103, pp. 4727-4737.
"Dexcom CEO tells investors not to fear new competition from Abbott's Freestyle Libre", 2017, retrieved from https://www.mobihealthnews.com/content/dexcom-ceo-tells-investors-not-fear-new-competition-abbotts-freestyle-libre, pp. 1-3.
Dexcom G5 Mobile System User Guide, 2020, pp. 1-410.
Dexcom G6, Winner Health & Wellness Award, Core77 Design Awards, 2019, retrieved from https://designawards.core77.com/health-wellness/85111/Dexcom-G6, pp. 1-8.
Dicks, J.M., et al., "Ferrocene Modified Polypyrrole with Immobilised Glucose Oxidase and its Application in Amperometric Glucose Microbiosensors", Annales de Biologie Clinique, 1989, vol. 47, pp. 607-619.
Ellis, C. D., et al., "Selectivity and Directed Charge Transfer through an Electroactive Metallopolymer Film", Journal of the American Chemical Society, 1981, vol. 103, No. 25, pp. 7480-7483.
Engstrom, R. C., "Electrochemical Pretreatment of Glassy Carbon Electrodes", Analytical Chemistry, 1982, vol. 54, No. 13, pp. 2310-2314.
Engstrom, R. C., et al., "Characterization of Electrochemically Pretreated Glassy Carbon Electrodes", Analytical Chemistry, 1984, vol. 56, No. 2, pp. 136-141.
Feldman, B., et al., "Electron Transfer Kinetics at Redox Polymer/Solution Interfaces Using Microelectrodes and Twin Electrode Thin Layer Cells", Journal of ElectroAnalytical Chemistry, 1985, vol. 194, pp. 63-81.
File History of U.S. Pat. No. 10,292,632.
File History of U.S. Pat. No. 10,945,649.
File History of U.S. Pat. No. 11,013,440.
U.S. Appl. No. 12/250,760.
Fischer, H., et al., "Intramolecular Electron Transfer Medicated by 4,4'-Bypyridine and Related Bridging Groups", Journal of the American Chemical Society, 1976, vol. 98, No. 18, pp. 5512-5517.
Foulds, N. C., et al., "Enzyme Entrapment in Electrically Conducting Polymers: Immobilisation of Glucose Oxidase in Polypyrrole and its Application in Amperometric Glucose Sensors", Journal of the Chemical Society, Faraday Transactions 1, 1986, vol. 82, pp. 1259-1264.
Foulds, N. C., et al., "Immobilization of Glucose Oxidase in Ferrocene-Modified Pyrrole Polymers", Analytical Chemistry, 1988, vol. 60, No. 22, pp. 2473-2478.
Freedman, D., et al., Statistics: Second Edition, 1991, Chapter 5, p. 74.
Freestyle Navigator Continuous Glucose Monitor FDA Premarket Approval (PMA), May 2022, pp. 1-6.
Freestyle Navigator Summary of Safety and Effectiveness Data, 2008, pp. 1-27.
Freestyle Navigator User's Guide, 2008, pp. 1-195.
Frew, J. E., et al., "Electron-Transfer Biosensors", Philosophical Transactions of the Royal Society of London, 1987, vol. 316, pp. 95-106.
Garibotto, J., et al., "An Innovative Application of Shape Memory Alloy Technology Yields a Novel Therapeutic Approach to Diabetes Management", Insulet Corporation, p. A41.
Gonzales, W. V., et al., "The Progress of Glucose Monitoring—A Review of Invasive to Minimally and Non-Invasive Techniques, Devices and Sensors", Sensors, 2019, vol. 19, No. 800, pp. 1-45.
Gorton, L., et al., "Selective Detection in Flow Analysis Based on the Combination of Immobilized Enzymes and Chemically Modified Electrodes", Analytica Chimica Acta, 1991, vol. 250, pp. 203-248.
Gregg, B. A., et al., "Redox Polymer Films Containing Enzymes. 1. A Redox-Conducting Epoxy Cement: Synthesis, Characterization, and Electrocatalytic Oxidation of Hydroquinone", Journal of Physical Chemistry, 1991, vol. 95, No. 15, pp. 5970-5975.
Gregg, T. H., "How Continuous Glucose Monitoring is Transforming Diabetes Treatment", Qualcomm Life Connect, 2013, pp. 1-33.

Guardian® RT Continuous Glucose Monitoring System Ref MMT-7900 User Guide, 2005, pp. 1-128.
Hale, P. D., et al., "A New Class of Amperometric Biosensor Incorporating a Polymeric Electron-Transfer Mediator", Journal of the American Chemical Society, 1989, vol. 111, No. 9, pp. 3482-3484.
Hao, Y., "Wireless body sensor networks for health-monitoring applications", Physiol. Meas., 2008, vol. 29, R27-R56.
Hawkridge, F. M., et al., "Indirect Coulometric Titration of Biological Electron Transport Components", Analytical Chemistry, 1973, vol. 45, No. 7, pp. 1021-1027.
Heller, A., et al., "Amperometric Biosensors Based on Three-Dimensional Hydrogel-Forming Epoxy Networks", Sensors and Actuators B, 1993, vol. 13-14, pp. 180-183.
Hirsch, I. B., "Introduction: History of Glucose Monitoring", Clinical Compendia, 2018, vol. 2018, No. 1, 1 page.
Hoel, p. G., Elementary Statistics: Fourth Edition, 1976, Chapter 5, pp. 113-114.
Howe, D., "Comparing the Dexcom G6 To the G5", 2018, retrieved from https://beyondtype1.org/comparing-the-dexcom-g6-to-the-g5/, pp. 1-10.
Ianniello, R. M., et al., "Immobilized Enzyme Chemically Modified Electrode as an Amperometric Sensor", Analytical Chemistry, 1981, vol. 53, No. 13, pp. 2090-2095.
Ianniello, R. M., et al., "Differential Pulse Voltammetric Study of Direct Electron Transfer in Glucose Oxidase Chemically Modified Graphite Electrodes", Analytical Chemistry, 1982, vol. 54, No. 7, pp. 1098-1101.
Ikeda, T., et al., "Kinetics of Outer-Sphere Electron Transfers Between Metal Complexes in Solutions and Polymeric Films on Modified Electrodes", Journal of the American Chemical Society, 1981, vol. 103, No. 25, pp. 7422-7425.
Ikeda, T., et al., "Glucose Oxidase- Immobilized Benzoquinone-Carbon Paste Electrode as a Glucose Sensor", Agricultural and Biological Chemistry, 1985, vol. 49, No. 2, pp. 541-543.
Jain, A.K., et al., "Wound Rotor Induction Generator With Sensorless Control and Integrated Active Filter for Feeding Nonlinear Loads in a Stand-Alone Grid", IEEE Transactions on Industrial Electronics, 2008, vol. 55, No. 1, pp. 218-228.
Johnson, J. M., et al., "Potential-Dependent Enzymatic Activity in an Enzyme Thin-Layer Cell", Analytical Chemistry, 1982, vol. 54, No. 8, pp. 1377-1383.
Johnson, K. W., "Reproducible Electrodeposition of Biomolecules for the Fabrication of Miniature Electroenzymatic Biosensors", Sensors and Actuators B, 1991, vol. 5, pp. 85-89.
Jönsson, G., et al., "An Amperometric Glucose Sensor Made by Modification of a Graphite Electrode Surface With Immobilized Glucose Oxidase and Adsorbed Mediator", Biosensors, 1985, vol. 1, pp. 355-368.
Josowicz, M., et al., "Electrochemical Pretreatment of Thin Film Platinum Electrodes", Journal of the Electrochemical Society, 1988, vol. 135, No. 1, pp. 112-115.
Jovanovic, L., "The Role of Continuous Glucose Monitoring in Gestational Diabetes Mellitus", Diabetes Technology & Therapeutics, 2000, vol. 2, Supplement 1, pp. S-67-S-71.
Katakis, I., et al., "L-α-Glycerophosphate and L-Lactate Electrodes Based on the Electrochemical 'Wiring' of Oxidases", Analytical Chemistry, 1992, vol. 64, No. 9, pp. 1008-1013.
Katakis, I., et al., "Electrostatic Control of the Electron Transfer Enabling Binding of Recombinant Glucose Oxidase and Redox Polyelectrolytes", Journal of the American Chemical Society, 1994, vol. 116, No. 8, pp. 3617-3618.
Kenausis, G., et al., "'Wiring' of Glucose Oxidase and Lactate Oxidase Within a Hydrogel Made with Poly(vinyl pyridine) complexed with $[Os(4,4'-dimethoxy-2,2'-bipyridine) 2Cl]^{+/2+}$", Journal of the Chemical Society, Faraday Transactions, 1996, vol. 92, No. 20, pp. 4131-4136.
Kulys, J., et al., "Mediatorless Peroxidase Electrode and Preparation of Bienzyme Sensors", Bioelectrochemistry and Bioenergetics, 1990, vol. 24, pp. 305-311.

(56) References Cited

OTHER PUBLICATIONS

Lindner, E., et al., "Flexible (Kapton-Based) Microsensor Arrays of High Stability for Cardiovascular Applications", Journal of the Chemical Society, Faraday Transactions, 1993, vol. 89, No. 2, pp. 361-367.

McNeil, C. J., et al., "Thermostable Reduced Nicotinamide Adenine Dinucleotide Oxidase: Application to Amperometric Enzyme Assay", Analytical Chemistry, 1989, vol. 61, No. 1, pp. 25-29.

Medtronic Guardian® REAL-Time Continuous Glucose Monitoring System User Guide, 2006, pp. 1-184.

IPR2022-00605 (Ex. 1027) The Merriam-Webster Dictionary, Merriam Webster, Incorporated (2005), pp. 66, 403, and 415.

IPR2022-00605 (Ex. 2008) MiniMed® Glucose Sensor, Ref MMT-7002, Instructions for Use, pp. 1-4.

MINIMED Quick-set™ retrieved from https://web.archive.org/web/20010412224824/http://www.minimed.com/patientfam/pf_ipt_pumpinfusion_quickset.shtml, Apr. 12, 2001, pp. 1-2.

MINIMED Sof-set Micro QRR Sof-set Ultimate QR® retrieved from https://web.archive.org/web/20010412225617/http://www.minimed.com/patientfam/pf_ipt_pumpinfusion_sofset.shtml, Apr. 12, 2001, pp. 1-2.

Miyawaki, O., et al., "Electrochemical and Glucose Oxidase Coenzyme Activity of Flavin Adenine Dinucleotide Covalently Attached to Glassy Carbon at the Adenine Amino Group", Biochimica et Biophysica Acta, 1985, vol. 838, pp. 60-68.

IPR2022-00605 (Ex. 2003) "Monitoring Your Blood Sugar", retrieved from https://www.cdc.gov/diabetes/managing/managing-blood-sugar/bloodglucosemonitoring.html, pp. 1-3.

Morbiducci, U., et al., "Improved Usability of the Minimal Model of Insulin Sensitivity Based on an Automated Approach and Genetic algorithms for Parameter Estimation", Clinical Science, vol. 112, 2007, pp. 257-263.

Mougiakakou, S. G., et al., "A Real Time Simulation Model of Glucose-Insulin Metabolism for Type 1 Diabetes Patients", Proceedings of the 2005 IEEE, 2005, pp. 298-301.

Nagy, G., et al., "A New Type of Enzyme Electrode: The Ascorbic Acid Eliminator Electrode", Life Sciences, 1982, vol. 31, No. 23, pp. 2611-2616.

Nakamura, S., et al., "Effect of Periodate Oxidation on the Structure and Properties of Glucose Oxidase", Biochimica et Biophysica Acta., 1976, vol. 445, pp. 294-308.

Narasimham, K., et al., "p. Benzoquinone Activation of Metal Oxide Electrodes for Attachment of Enzymes", Enzyme and Microbial Technology, 1985, vol. 7, pp. 283-286.

Ohara, T. J., et al., "'Wired' Enzyme Electrodes for Amperometric Determination of Glucose or Lactate in the Presence of Interfering Substances", Analytical Chemistry, 1994, vol. 66, No. 15, pp. 2451-2457.

Ohara, T. J., "Osmium Bipyridyl Redox Polymers Used in Enzyme Electrodes", Platinum Metals Review, 1995, vol. 39, No. 2, pp. 54-62.

OmniPod Insulet UST400 User Manual, 2011, pp. 1-190.

Osmonics, Poretics® Polycarbonate Membrane; Product Leaflet; Engineering Purity, 2002, pp. 1-2.

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", Journal of ElectroAnalytical Chemistry, 1989, vol. 260, pp. 487-494.

Palleschi, G., et al., "A Study of Interferences in Glucose Measurements in Blood by Hydrogen Peroxide Based Glucose Probes", Analytical Biochemistry, 1986, vol. 159, pp. 114-121.

Pankratov, I., et al., "Sol-Gel Derived Renewable-Surface Biosensors", Journal of ElectroAnalytical Chemistry, 1995, vol. 393, pp. 35-41.

Parker, R., et al., "Robust H∞ Glucose Control in Diabetes Using a Physiological Model", AIChE Journal, 2000, vol. 46, No. 12, 2000, pp. 2537-2549.

Pathak, C., et al., "Rapid Photopolymerization of Immunoprotective Gels in Contact with Cells and Tissue", Journal of the American Chemical Society, 1992, vol. 114, No. 21, pp. 8311-8312.

Patton, S. R., et al., "Continuous Glucose Monitoring Versus Self-monitoring of Blood Glucose in Children with Type 1 Diabetes—Are there Pros and Cons for Both?", US Endocrinol., 2012, vol. 8, No. 1, pp. 27-29.

Pollak, A., et al., "Enzyme Immobilization by Condensation Copolymerization into Cross-Linked Polyacrylamide Gels", Journal of the American Chemical Society, 1980, vol. 102, No. 20, pp. 6324-6336.

Ratner, B. D., "Reducing Capsular Thickness and Enhancing Angeiogenesis Around Implant Drug Release Systems", Journal of Controlled Release, 2002, vol. 78, pp. 211-218.

Repas, R., "Sensor Sense: RFID for smart position sensing", retrieved from https://www/machinedesign/com/automation-iiot/article/21818777/sensor-sense-rfid-for-smart-position-sensing, 2010, pp. 1-2.

IPR2022-00605 (Ex. 1024) "Rotor," Dictionary of Mechanical Engineering, Fourth Ed., G.H.F. Nayler, Society of Automotive Engineers, Inc., 1996, p. 328.

IPR2022-00605 (Ex. 1025) "Rotor," Random House Kernerman Webster's College Dictionary, K Dictionaries Ltd. (2010), available at https://www.thefreedictionary.com/rotor.

IPR2022-00605 (Ex. 1026) "Rotate," Random House Kernerman Webster's College Dictionary, K Dictionaries Ltd. (2010), available at https://www.thefreedictionary.com/rotate.

Samuels, G. J., et al., "An Electrode-Supported Oxidation Catalyst Based on Ruthenium (IV). pH "Encapsulation" in a Polymer Film", Journal of the American Chemical Society, 1981, vol. 103, No. 2, pp. 307-312.

Sasso, S. V., et al., "Electropolymerized 1,2-Diaminobenzene as a Means to Prevent Interferences and Fouling and to Stabilize Immobilized Enzyme in Electrochemical Biosensors", Analytical Chemistry, 1990, vol. 62, No. 11, pp. 1111-1117.

IPR2022-00605 (Ex. 1013) Scheduling Order in *Abbott Diabetes Care Inc., et al. v. Dexcom, Inc.*, 1:21-cv-00977 (D. Del.), dated Dec. 2, 2021.

Schmehl, R. H., et al., "The Effect of Redox Site Concentration on the Rate of Mediated Oxidation of Solution Substrates by a Redox Copolymer Film", Journal of ElectroAnalytical Chemistry, 1983, vol. 152, pp. 97-109.

Sittampalam, G., et al., "Surface-Modified Electrochemical Detector for Liquid Chromatography", Analytical Chemistry, 1983, vol. 55, No. 9, pp. 1608-1610.

Soegijoko, S., et al., "External Artificial Pancreas: A New Control Unit Using Microprocessor", Hormone and Metabolic Research Supplement Series, 1982, vol. 12, pp. 165-169.

Sprules, S. D., et al., "Evaluation of a New Disposable Screen-Printed Sensor Strip for the Measurement of NADH and Its Modification to Produce a Lactate Biosensor Employing Microliter Volumes", Electroanalysis, 1996, vol. 8, No. 6, pp. 539-543.

Sternberg, F., et al., "Calibration Problems of Subcutaneous Glucosensors when Applied "In-Situ" in Man", Hormone and Metabolic Research, 1994, vol. 26, pp. 523-526.

Sternberg, R., et al., "Covalent Enzyme Coupling on Cellulose Acetate Membranes for Glucose Sensor Development", Analytical Chemistry, 1988, vol. 60, No. 24, pp. 2781-2786.

Suekane, M., et al., "Immobilization of Glucose Isomerase", Zettschrift fur Allgemeine Mikrobiologie, 1982, vol. 22, No. 8, pp. 565-576.

Tajima, S., et al., "Simultaneous Determination of Glucose and 1,5-Anydroglucitol", Chemical Abstracts, 1989, vol. 111, No. 25, p. 394.

Tarasevich, M. R., "Bioelectrocatalysis", Comprehensive Treatise of Electrochemistry, 1985, vol. 10, pp. 231-295.

Tatsuma, T., et al., "Enzyme Monolayer- and Bilayer-Modified Tin Oxide Electrodes for the Determination of Hydrogen Peroxide and Glucose", Analytical Chemistry, 1989, vol. 61, No. 21, pp. 2352-2355.

Taylor, C., et al., ""Wiring" of Glucose Oxidase Within a Hydrogel Made with Polyvinyl Imidazole Complexed with [(Os-4,4'-dimethoxy-2,2'-bipyridine)CI]$^{+/2+}$", Journal of ElectroAnalytical Chemistry, 1995, vol. 396, pp. 511-515.

(56) References Cited

OTHER PUBLICATIONS

Trojanowicz, M., et al., "Enzyme Entrapped Polypyrrole Modified Electrode for Flow-Injection Determination of Glucose", Biosensors & Bioelectronics, 1990, vol. 5, pp. 149-156.

Turner, R.F.B., et al., "A Biocompatible Enzyme Electrode for Continuous in vivo Glucose Monitoring in Whole Blood", Sensors and Actuators B, 1990, vol. 1, pp. 561-564.

Tuzhi, P., et al., "Constant Potential Pretreatment of Carbon Fiber Electrodes for in Vivo Electrochemistry", Analytical Letters, 1991, vol. 24, No. 6, pp. 935-945.

Umana, M., "Protein-Modified Electrochemically Active Biomaterial Surface", U.S. Army Research Office, Analytical and Chemical Sciences Research Triangle Institute, 1988, pp. 1-9.

United States Court of Appeals for the Federal Circuit, No. 06-1402, *Leapfrog Enterprises, Inc.* v. *Fisher-Price, Inc. and Mattel, Inc.*, May 9, 2007.

Urban, G., et al., "Miniaturized Thin-Film Biosensors Using Covalently Immobilized Glucose Oxidase", Biosensors & Bioelectronics, 1991, vol. 6, pp. 555-562.

Vreeke, M. S., et al., "Hydrogen Peroxide Electrodes Based on Electrical Connection of Redox Centers of Various Peroxidases to Electrodes through a Three-Dimensional Electron-Relaying Polymer Network", Diagnostic Biosensors Polymers, Chapter 15, 1993, pp. 180-193.

Vreeke, M., et al., "Hydrogen Peroxide and β-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", Analytical Chemistry, 1992, vol. 64, No. 24, pp. 3084-3090.

Wang, D. L., et al., "Miniaturized Flexible Amperometric Lactate Probe", Analytical Chemistry, 1993, vol. 65, No. 8, pp. 1069-1073.

Wang, J., et al., "Activation of Glassy Carbon Electrodes by Alternating Current Electrochemical Treatment", Analytica Chimica Acta, 1985, vol. 167, pp. 325-334.

Wang, J., et al., "Amperometric Biosensing of Organic Peroxides with Peroxidase-Modified Electrodes", Analytica Chimica Acta, 1991, vol. 254, pp. 81-88.

Wang, J., et al., "Screen-Printable Sol-Gel Enzyme-Containing Carbon Inks", Analytical Chemistry, 1996, vol. 68, No. 15, pp. 2705-2708.

Wang, J., et al., "Sol-Gel-Derived Metal-Dispersed Carbon Composite Amperometric Biosensors", Electroanalysis, 1997, vol. 9, No. 1, pp. 52-55.

Williams, D. L., et al., "Electrochemical-Enzymatic Analysis of Blood Glucose and Lactate", Analytical Chemistry, 1970, vol. 42, No. 1, pp. 118-121.

Yabuki, S., et al., "Electro-Conductive Enzyme Membrane", Journal of the Chemical Society, Chemical Communications, 1989, pp. 945-946.

Yang, L., et al., "Determination of Oxidase Enzyme Substrates Using Cross-Flow Thin-Layer Amperometry", Electroanalysis, 1996, vol. 8, No. 8-9, pp. 716-721.

Yao, S. J., et al., "The Interference of Ascorbate and Urea in Low-Potential Electrochemical Glucose Sensing", Proceedings of the Twelfth Annual International Conference of the IEEE Engineering in Medicine and Biology Society, 1990, vol. 12, Part 2, pp. 487-489.

Yao, T., "A Chemically-Modified Enzyme Membrane Electrode as an Amperometric Glucose Sensor", Analytica Chimica Acta, 1983, vol. 148, pp. 27-33.

Yildiz, A., et al., "Evaluation of an Improved Thin-Layer Electrode", Analytical Chemistry, 1968, vol. 40, No. 7, pp. 1018-1024.

Zamzow, K., et al., "New Wearable Continuous Blood Glucose Monitor (BGM) and Artificial Pancreas (AP)", Diabetes, 1990, vol. 39, p. 5A-20.

Zhang, Y., et al., "Application of Cell Culture Toxicity Tests to the Development of Implantable Biosensors", Biosensors & Bioelectronics, 1991, vol. 6, pp. 653-661.

Zhang, Y., et al., "Elimination of the Acetaminophen Interference in an Implantable Glucose Sensor", Analytical Chemistry, 1994, vol. 66, No. 7, pp. 1183-1188.

Zhu, J., et al., "Fabrication and Characterization of Glucose Sensors Based on a Microarray $H_2O_2$ electrode", Biosensors & Bioelectronics, 1994, vol. 9, pp. 295-300.

Zisser, H. C., "The OmniPod Insulin Management System: the Latest Innovation in Insulin Pump Therapy", Diabetes Ther, 2010, vol. 1, No. 1, pp. 10-24.

Affidavit of Richard Paragas signed on May 18, 2016, pp. 1-4.

Affidavit of Paul Neale signed on May 18, 2016, pp. 1-2.

Choleau, C., et al., "Calibration of a Subcutaneous Amperometric Glucose Sensor Implanted for 7 Days in Diabetic Patients Part 2. Superiority of the One-Point Calibration Method", Biosensor & Bioelectronics, 2002, vol. 17, No. 8, pp. 647-654.

Choleau, C., et al., "Calibration of a Subcutaneous Amperometric Glucose Sensor Part 1. Effect of Measurement Uncertainties on the Determination of Sensor Sensitivity and Background Current", Biosensor & Bioelectronics, 2002, vol. 17, No. 8, pp. 641-646.

Guerci, B., et al., "Clinical Performance of CGMS in Type 1 Diabetic Patients Treated by Continuous Subcutaneous Insulin Infusion Using Insulin Analogs", Diabetes Care, 2003, vol. 26, No. 3, pp. 582-589.

Kovatchev, B. P., et al., "Evaluating the Accuracy of Continuous Glucose-Monitoring Sensors", Diabetes Care, 2004, vol. 27, No. 8, pp. 1922-1928.

Mauras, N., et al., "Lack of Accuracy of Continuous Sensors in Healthy, Nondiabetic Children: Results of the Diabetes Research in Children Network (DirecNet) Accuracy Study", Journal of Pediatrics, 2004, pp. 770-775.

Schmidtke, D. W., et al., "Accuracy of the One-Point In Vivo Calibration of "Wired" Glucose Oxidase Electrodes Implanted in Jugular Veins of Rats in Periods of Rapid Rise and Decline of the Glucose Concentration", Analytical Chemistry, 1998, vol. 70, No. 10, pp. 2149-2155.

Tierney, M. J., et al., "Effect of Acetaminophen on the Accuracy of Glucose Measurements Obtained with the GlucoWatch Biographer", Diabetes Technology & Therapeutics, 2000, vol. 2, No. 2, pp. 199-207.

Tsalikian, e., et al., "Accuracy of the GlucoWatch G2® Biographer and the Continuous Glucose Monintoring System During Hypoglycemia: Experience of the Diabetes Research in Children Network", Diabetes Care, 2004, vol. 27, No. 3, pp. 722-726.

Ward, W. K., et al., "Rise in Background Current Over Time in a Subcutaneous Glucose Sensor in the Rabbit: Relevance to Calibration and Accuracy", Biosensors & Bioelectronics, 2000, vol. 15, pp. 53-61.

CA, 2,872,576 Examiner's Report, Feb. 17, 2015.

CA, 2,872,576 Examiner's Report, Feb. 19, 2016.

EP, 06851063.5 Extended Search Report, Sep. 21, 2009.

EP, 07843396.8 Extended Search Report, Dec. 22, 2010.

EP, 13000104.3 Extended Search Report, Mar. 12, 2013.

EP, 14179905.6 Summons to Attend Oral Proceedings, Apr. 10, 2017.

EP, 14179905.6 Notice of Opposition, May 19, 2016.

EP, 14179905.6 Extended Search Report, Dec. 23, 2014.

EP, 15002441.2 Extended Search Report, Dec. 18, 2015.

EP, 20177712.5 Notice of Opposition Guide & Partner Patent, Dec. 22, 2022.

EP, 20177712.5 Notice of Opposition Dexcom, Dec. 22, 2022.

WO, PCT/US2006/062690 ISR and Written Opinion, Jan. 2, 2008.

WO, PCT/US2007/079774 ISR and Written Opinion, Apr. 1, 2008.

WO, PCT/US2022/037291 ISR and Written Opinion, Nov. 22, 2022.

Certified U.S. Appl. No. 60/424,099, filed Nov. 5, 2002.

De Block, C., et al., "Minimally-Invasive and Non-Invasive Continuous Glucose Monitoring Systems: Indications, Advantages, Limitations and Clinical Aspects", Current Diabetes Reviews, 2008, vol. 4, No. 3, pp. 159-168.

File wrapper of U.S. Appl. No. 10/633,367.

Medtronic MiniMed Sen-Serter® User Guide, 2006, pp. 1-96.

CA, 3,120,335 Examiner's Report, Mar. 31, 2023.

CA, 3,182,961 Examiner's Report, Mar. 29, 2023.

(56)                    References Cited

OTHER PUBLICATIONS

CN, 201980082748.1 First Office Action, Jan. 10, 2023.
DE, Claim, Case 2006593/20—ABB34.D1000, Feb. 20, 2023.
EP, 10739031.2 Response to Response to Response to Grounds of Appeal, Jan. 18, 2023.
EP, 20177703.4 Reply to Opposition, Feb. 22, 2023.
EP, 20177712.5 Grounds of Opposition Gulde & Partner Patent, Dec. 22, 2022.
EP, 20177712.5 Grounds of Opposition Dexcom, Dec. 22, 2022.
EP, 20195922.8 Grounds of Opposition Dexcom, Jan. 26, 2023.
EP, 20195922.8 Notice of Opposition Dexcom, Jan. 26, 2023.
GB, Claim No. HP-2021-000025 Re-Amended Reply and Defence to Counterclaim, Apr. 19, 2023.
GB, Claim No. HP-2021-000025 Consent Order, Mar. 14, 2023.
GB, Claim No. HP-2021-000025 Re-Re-Re-Amended Grounds of Invalidity, Mar. 14, 2023.
GB, Claim No. HP-2021-000025 First Expert Report of Dr Michael Schoemaker, Feb. 28, 2023.
GB, Claim No. HP-2021-000026 First Expert Report of Dr Michael Schoemaker, Feb. 28, 2023.
JP, 2021-531135 Office Action, Feb. 22, 2023.
US, Dexcom, Inc.'s Amended Answer to Second Amended Complaint, Case 21-CV-977-KAJ, Mar. 17, 2023.
US, Complaint, Case 23-CV-239-UNA, Mar. 3, 2023.
WO, PCT/US2023/010054 Invitation to Pay Additional Fees. Mar. 24, 2023.
GB, Claim No. HP-2021-000026 Grounds of Opposition to Amendment of EP (UK) 3,730,044, Nov. 28, 2022.
GB, Claim No. HP-2021-000026 Grounds of Opposition to Amendment of EP (UK) 2,393,418, Nov. 28, 2022.
GB, Claim No. HP-2021-000026 Statement of Grounds of Amendment of EP (UK) 3,730,044, Oct. 10, 2022.
GB, Claim No. HP-2021-000026 Statement of Grounds of Amendment of EP (UK) 2,393,418, Oct. 10, 2022.
GB, Claim No. HP-2021-000025 Grounds of Opposition to Amendment of EP (UK) 3,730,044, Nov 28, 2022.
GB, Claim No. HP-2021-000025 Grounds of Opposition to Amendment of EP (UK) 2,393,418, Nov. 28, 2022.
GB, Claim No. HP-2021-000025 Re-Amended Grounds of Invalidity, Nov. 24, 2022.
GB, Claim No. HP-2021-000025 Statement of Grounds of Amendment of EP (UK) 3,370,044, Oct. 10, 2022.
GB, Claim No. HP-2021-000025 Statement of Grounds of Amendment of EP (UK) 2,393,418, Oct. 10, 2022.
201980082748.1 Second Office Action.
20177703.4 Reply to Reply to Notice of Opposition.
20177703.4 Notice of Intervention.
20177712.5 Notice of Intervention.
20177712.5 Reply to Notice of Opposition.
20195922.8 Reply to Notice of Opposition.
20195922.8 Notice of Intervention.
Particulars of Claim (EP 3730045).
Claimant's Initial List of Disclosure Documents (EP 3730045).
Grounds of Invalidity (EP 3730045).
Claim No. HP-2021-000025 Dexcom's Closing Submissions.
Claim No. HP-2021-000025 Abbott's Closing Skeleton Argument.
Claim No. HP-2021-000025 Re-Re-Amended Reply and Defence to Counterclaim.
Claim No. HP-2021-000025 Re-Re-Re-Re-Amended Grounds of Invalidity.
Claim No. HP-2021-000025 Corrected PTR Order for Trial B.
Claim No. HP-2021-000025 Trial B—Joint CGK Statement.
Claim No. HP-2021-000025 Dexcom Trial Skeleton.
Claim No. HP-2021-000025 Abbott's Opening Skeleton Argument.
Claim No. HP-2021-000025 Second Expert Report of Dr Michael Schoemaker.
Claim No. HP-2021-000025 Exhibits MS1-MS3 of First Expert Report of Dr Michael Schoemaker.
Claim No. HP-2021-000026 Corrected PTR Order for Trial B.
Claim No. HP-2021-000026 Dexcom Trial Skeleton.
Claim No. HP-2021-000026 Dexcom's Closing Submissions.
Claim No. HP-2021-000026 Second Expert Report of Dr Michael Schoemaker.
Claim No. HP-2021-000026 Exhibits MS1-MS3 of First Expert Report of Dr Michael Schoemaker.
PI2022007295 Examination Report.
Final Written Decision, IPR No. 2022-00605.
PCT/US2012/062551 ISR and Written Opinion.
PCT/US2023/010054 ISR and Written Opinion.
"Abbott Receives CE Mark for Freestyle® Libre, A Revolutionary Glucose Monitoring System for People With Diabetes", 2014, 7 pages.
"Alcove", Webster's New College Dictionary, 2001, p. 26.
Boise, M., "Dexcom CEO Kevin Sayer Explains G6", 2018, retrieved from https://beyondtype1.org/dexcom-ceo-kevin-sayer-explains-g6/, 9 pages.
Certified True Copy of Preliminary Amendment filed on Apr. 20, 2018 for U.S. Pat. No. 10,827,954, 7 pages.
Excerpts of the File History of U.S. Pat. No. 10,973,442, 22 pages.
CGMs Changing Diabetes Management: Kevin Sayer, DIC Interview Transcript, 2019, retrieved from https://www.diabetesincontrol.com/cgms-changing-diabetes-management-kevin-sayer-dic-interview-transcript/, 10 pages.
"Deciding When to Submit a 510(k) for a Change to an Existing Device, Guidance for Industry and Food and Drug Administration Staff", 2017, pp. 1-77.
"Deciding When to Submit a 510(k) for a Software Change to an Existing Device, Guidance for Industry and Food and Drug Administration Staff", 2017, pp. 1-31.
Dexcom CEO- Prime Position in Our Market—Mad Money—CNBC.mp4, Transcript 2023 by Sonix, 2 pages.
DexCom (DXCM) 2017 Q4 Earnings Call Transcript, 2017, retrieved from https://docoh.com/transcript/1093557/2017Q4/DXCM, 11 pages.
DexCom (Dxcm) Q1 2018 Results—Earnings Call Transcript, 2018, retrieved from https://seekingalpha.com/article/4168949-dexcom-dxcm-q1-2018-results-earnings-call- transcript, 4 pages.
Dexcom, Inc. NasdaqGS:DXCM Company Conference Presentation, 2019, 10 pages.
Dexcom, Inc. NasdaqGS:DXCM Company Conference Presentation, 2020, 9 pages.
Dexcom, Inc. NasdaqGS:DXCM Company Conference Presentation, 2021, 16 pages.
Dexcom G6 Continuous Glucose Monitoring System User Guide, pp. 1-22.
Dexcom G6 Start Here Set up Guide, pp. 1-8.
Dexcom G6 Using Your G6 Guide, Mar. 2020, pp. 1-7.
Dexcom G7 Inserting Sensor Instructions for Use, 2021, pp. 1-2.
Dexcom G7, Start Here, Operational Manual, 2022, pp. 1-9 (English Abstract).
Dexcom G7, User Guide, 2022, p. 1-179 (English Abstract).
Dexcom Seven® Plus Continuous Glucose Monitoring System User's Guide, 2011, pp. 1-144.
DexCom™ STS™ Continuous Glucose Monitoring System FDA Premarket Approval (PMA), 2006, pp. 1-7.
DexCom™ STS™ Continuous Glucose Monitoring System Summary of Safety and Effectiveness Data, 2006, 20 pages.
DexCom™ STS™ Sensor Instructions for Use, 2006, pp. 1-6.
Dexcom STS-7 Continuous Glucose Monitoring System FDA Premarket Approval (PMA), 2007, pp. 1-7.
Dexcom STS®-7 Continuous Glucose Monitoring System Summary of Safety and Effectiveness Data, 2007, 14 pages.
Dexcom STS®-7 Continuous Glucose Monitoring System User's Guide, 2007, pp. 1-74.
Diglas, J., et al., "Reduced pain perception with Pen Mate™, an automatic needle insertion device for use with an insulin pen", Practical Diabetes International, 1999, vol. 16, No. 2, pp. 39-41.
"Does Dexcom Really Have a Future If It Can't Match Abbott's Scale", 2019, retrieved from https://www.sprucepointcap.com/reports/dxcm_research_thesis_3-21-2019.pdf, p. 46.
Email from John Shaw of Shaw & Keller dated May 16, 2023, 2 pages.
Email chain from Sophie Hood, oldest email dated Jan. 24, 2023, 5 pages.

(56)                    References Cited

OTHER PUBLICATIONS

European Standard, ISO 11607-1, Packaging for terminally steril-ized medical devices—Part 1: Requirements for materials, sterile barrier systems and packaging systems, 2006, 32 pages.
European Standard, ISO 13485, Medical devices—Quality man-agement systems—Requirement for regulatory purposes, 2003, 69 pages.
European Standard, ISO 15197, In vitro diagnostic test systems—Requirements for blood glucose monitoring systems for self-testing in managing diabetes mellitus, 2003, 43 pages.
Explore The Monroe Street Market Community, Retrieved from https://www.monroestreetmarket.com/floor-plans/apartment/B-231, 2 pages.
"FDA authorizes first fully interoperable continuous glucose moni-toring system, streamlines review pathway for similar devices", FDA News Release, 2018, retrieved from https://www.fda.gov/news-events/press-announcements/fda-authorizes-first-fully-interoperable-continuous-glucose-monitoring-system-streamlines-review, 3 pages.
Food and Drug Administration, HHS, 2009, Code of Federal Regulation § 820.30, Subpart C-Design Controls, pp. 147-148.
Freestyle Libre Pro Flash Glucose Monitoring System Summary of Safety and Effectiveness Data, 2016, 31 pages.
FreeStyle Lite Blood Glucose Monitoring System Owner's Booklet, 2006, 15 pages.
FreeStyle Navigator Continuous Glucose Monitoring System FDA Premarket Approval (PMA), 2008, pp. 1-7.
Hemmerich, K. J., et al., "Sterilization Methods Stand the Test of Time", 2004, retrieved from https://www.mddionline.com/sterilization/sterilization-methods-stand-test-time, pp. 1-8.
Hirsch, I. B., "Realistic Expectations and Practical Use of Continu-ous Glucose Monitoring for the Endocrinologist", The Journal of Clinical Endocrinology & Metabolism, 2009, VI. 94, No. 7, pp. 2232-2238.
Hoss, U., et al., "Continuous glucose monitoring in the tissue: Do we really need to calibrate in-vivo?", pp. 1-21.
Hoss, U., et al., "Continuous Glucose Monitoring in Subcutaneous Tissue Using Factory-Calibrated Sensors: A Pilot Study", Diabetes Technology & Therapeutics, 2010, vol. 12, No. 8, pp. 591-597.
Hoss, U., et al., "Feasibility of Factory Calibration for Subcutaneous Glucose Sensors in Subjects With Diabetes", Journal of Diabetes Science and Technology, 2014, vol. 8, No. 1, pp. 89-94.
"Housing", "recess", "release", and "retain", Merriam-Webster's Collegiate Dictionary, Tenth Edition, 1999, pp. 563, 975, 987, and 999.
"Housing" and "recess", The New Penguin English Dictionary, 2000, pp. 678 and 1167.
Hughes, M. D., "The Business of Self-Monitoring of Blood Glu-cose: A Market Profile", Journal of Diabetes Science and Technol-ogy, 2009, vol. 3, No. 5, pp. 1219-1223.
IEEE 100 The Authoritative Dictionary of IEEE Standards Terms, Seventh Edition, 2000, 3 pages.
International Standard, ISO 14971, Medical devices—Application of risk management to medical devices, 2007, 90 pages.
"An Interview with Kevin Sayer, President and CEO of Dexcom, About The New G6", 2021, 5 pages.
Klueh, U., et al., "Inflammation and Glucose Sensors: Use of Dexamethasone to Extend Glucose Sensor Function and Life Span in Vivo", Journal of Diabetes Science and Technology, 2007, vol. 1, No. 4, pp. 496-504.
Klueh, U., et al., "Blood-Induced Interference of Glucose Sensor Function in Vitro: Implications for in Vivo Sensor Function", Journal of Diabetes Science and Technology, 2007, vol. 1, No. 6, pp. 842-849.
Medtronic Guardian® REAL-Time Continuous Glucose Monitor-ing System User Guide, 2006, pp. 1-181.
Medtronic MiniMed Guardian Rt Fda Premarket Approval (PMA), 2005, pp. 1-6.
Medtronic MiniMed Guardian RT Summary of Safety and Effec-tiveness Data, 2005, 13 pages.

Medtronic MiniMed Paradigm® REAL-Time 522 and 722 Insulin Pumps User Guide, 2008, pp. 1-262.
Occupational Safety and Health Admin., Labor, 2003, 29 CFR § 1910.1030 Bloodborne pathogens, pp. 260-273.
Omnipod image, Exhibit 182 of ADC Reply Brief SJ, Daubert, Sep. 22, 2022, 2 pages.
OneTouch® Ultra™ Blood Glucose Monitoring System Owner's Booklet, 2000, 23 pages.
OneTouch Ultra2 Blood Glucose Monitoring System Owner's Book-let, 2005, 34 pages.
Order, Federal Communications Commission, 2006, pp. 1-8.
Program, 2nd International Conference on Advanced Technologies & Treatments for Diabetes, Athens, Greece, 2009, 3 pages.
"Recess", Cambridge Dictionary of American English, 2000, pp. 710-711.
"Retract", The Chambers Dictionary, 1998, p. 1410.
"Retract", The New Oxford American Dictionary, 2001, p. 1455.
"Retract", Webster's Third New International Dictionary, 1993, pp. 1939-1940.
"Submission and Review of Sterility Information in Premarket Notification (510(k)) Submissions for Devices Labeled as Sterile, Guidance for Industry and Food and Drug Administration Staff", 2016, pp. 1-11.
Tegnestedt, C., et al., "Levels and sources of sound in the intensive care unit - an observational study of three room types", Acta Anaesthiesiologica Scandinavica, 2013, pp. 1-10.
Watkin, J., "An Introduction to Flash Glucose Monitoring", 14 pages.
CA, 2,984,939 Examiner's Report, Nov. 15, 2023.
EP, 20177703.4 Reply to Notice of Intervention, Nov. 17, 2023.
EP, 20177712.5 Reply to Notice of Intervention, Nov. 17, 2023.
EP, 20177712.5 Reply to Reply to Notice of Opposition Dexcom, Sep. 27, 2023.
EP, 20177712.5 Reply to Reply to Notice of Opposition Gulde & Partner Patent, Aug. 30, 2023.
EP, 20195922.8 Summons to Attend Oral Proceedings, Sep. 21, 2023.
EP, 20195922.8 Reply to Notice of Intervention, Aug. 29, 2023.
EP, 20195922.8 Reply to Reply to Notice of Opposition, Aug. 21, 2023.
EP, 23166498.8 Extended Search Report, Nov. 17, 2023.
EP, 23190032.5 Extended Search Report, Nov. 17, 2023.
JP, 2021-531135 Office Action, Aug. 9, 2023.
US, Petition For Inter Partes Review Of U.S. Pat. No. 11,202,591, IPR No. 2023-01409, Oct. 11, 2023.
US, Petition For Inter Partes Review Of U.S. Pat. No. 11,266,335, IPR No. 2023-01397, Oct. 6, 2023.
US, Petition For Inter Partes Review Of U.S. Pat. No. 11,266,335, IPR No. 2023-01396, Oct. 6, 2023.
US, Record of Oral Hearing, IPR No. 2022-00605, Apr. 26, 2023.
US, Petitioner's Reply to Patent Owner's Response to Petition, IPR No. 2022-00605, Jan. 11, 2023.
US, Supplemental Declaration of Gary D. Fletcher, Ph.D, IPR No. 2022-00605, Jan. 11, 2023.
US, Second Declaration by Dr. Michael Cima in Support of Patent Owner's Response, IPR No. 2022-00605, Oct. 19, 2022.
US, Patent Owner's Response, IPR No. 2022-00605, Oct. 19, 2022.
US, Amended [Proposed] Final Pretrial Order, Case No. 21- CV-977-KAJ (D. Delaware), Sep. 20, 2023.
US, Exhibit 3P to the Proposed Pretrial Order Abbott's Statement of Issues of Law Which Remain to be Litigated, Case No. 21-CV-977-KAJ (D. Delaware), Sep. 20, 2023.
US, Exhibit 3D to the Proposed Pretrial Order Dexcom's Statement of Issues of Law Which Remain to be Litigated, Case No. 21-CV-977-KAJ (D. Delaware), Sep. 20, 2023.
US, Exhibit 2P to the Proposed Pretrial Order Abbott's Statement of Issues of Fact Which Remain to be Litigated, Case No. 21-CV-977-KAJ (D. Delaware), Sep. 20, 2023.
US, Exhibit 2D to Proposed Pretrial Order Dexcom's Statement of Contested Facts, Case No. 21-CV-977-KAJ (D. Delaware), Sep. 20, 2023.

(56) References Cited

OTHER PUBLICATIONS

US, 1 to the Proposed Pretrial Order Parties' Joint Statement of Uncontroverted Facts, Case No. 21-CV- 977-KAJ (D. Delaware), Sep. 20, 2023.

US, Memorandum Opinion, Case No. 21-CV-977-KAJ (D. Delaware)—Public Version, Aug. 15, 2023.

US, Order, Case No. 21-CV-977-KAJ (D. Delaware), Aug. 15, 2023.

US, Appendix of Attachments and Exhibits for Plaintiffs' Opening Letter Brief in Support of Plaintiffs' Motion to Strike Defendant's New Claim Constructions, Case No. 21-CV-977-KAJ (D. Delaware)—Public Version, Aug. 10, 2023.

US, Opening Letter Brief in Support of Plaintiffs' Motion to Strike Defendant's New Claim Constructions, Case No. 21-CV-977-KAJ (D. Delaware)—Public Version, Aug. 10, 2023.

US, Dexcom's Letter Brief in Opposition to Abbott's Motion to Strike, Case No. 21-CV-977-KAJ (D. Delaware)—Public Version, Aug. 9, 2023.

US, Plaintiffs' Motion to Strike Defendant's New Claim Constructions, Case No. 21-CV-977-KAJ (D. Delaware), Aug. 3, 2023.

US, Plaintiffs' Letter Response to the Court's Questions Regarding the IPR Final Written Decision Relating to U.S. Pat. No. 10,945,649, Case No. 21-CV-977-KAJ (D. Delaware)—Public Version, Jul. 26, 2023.

US, Letter to Hon. Kent Jordan re Impact of Final Written Decision, Case No. 21-CV-977-KAJ (D. Delaware), Jul. 19, 2023.

US, *Abbott* v *Dexcom*—Trial C—Construction Schedule, Case No. 21-CV-977-KAJ (D. Delaware), Jul. 18, 2023.

US, Notice of Final Written Decision Re Inter Partes Review of the '649 Patent, Case No. 21-CV-977-KAJ (D. Delaware), Jul. 13, 2023.

US, Transcript of Motion Hearing, Case No. 21-CV-977-KAJ (D. Delaware), Jun. 30, 2023.

US, Defendant Dexcom, Inc.'s Reply Brief in Support of its Motion to Strike Abbott's Late-Disclosed Supplemental Declarations, Case No. 21-CV-977-KAJ (D. Delaware)—Public Version, Jun. 26, 2023.

US, Appendix of Exhibits in Support of Dexcom, Inc.'s Opposition to Plaintiffs' Motion for Summary Judgement and Daubert Challenges—vol. 2, Case No. 21-CV- 977-KAJ (D. Delaware)—Public Version, Jun. 23, 2023.

US, Appendix of Exhibits in Support of Dexcom, Inc.'s Opposition to Plaintiffs' Motion for Summary Judgement and Daubert Challenges—vol. 1, Case No. 21-CV- 977-KAJ (D. Delaware)—Public Version, Jun. 23, 2023.

US, Defendant Dexcom, Inc.'s Appendix to Brief in Support of its Reply to Abbott Diabetes Care Inc. and Abbott Diabetes Care Limited's Opposition to Dexcom Inc.'s Motions for Summary Judgement, Case No. 21-CV-977-KAJ (D. Delaware)—Public Version, Jun. 23, 2023.

US, Appendix of Exhibits and Attachments for Plaintiffs' Responsive Letter Brief In Opposition to Dexcom's Motion to Strike Expert Declarations (D.I. 408), Case No. 21-CV-977-KAJ (D. Delaware)—Public Version, Jun. 23, 2023.

US, Plaintiffs' Responsive Letter Brief in Opposition to Defendant's Motion to Strike Expert Declarations, Case No. 21-CV-977-KAJ (D. Delaware)—Public Version, Jun. 23, 2023.

US, Defendant Dexcom, Inc.'s Appendix to Brief in Support of its Reply to Abbott Diabetes Care Inc. and Abbott Diabetes Care Limited's Opposition to Dexcom Inc.'s Motions to Exclude Expert Reports and Testimony, Case No. 21-CV-977-KAJ (D. Delaware)—Public Version, Jun. 16, 2023.

US, Defendant Dexcom, Inc.'s Opening Brief in Support of its Motion to Strike Abbott's Late-Disclosed Supplemental Declarations, Case No. 21-CV-977-KAJ (D. Delaware)—Public Version, Jun. 16, 2023.

US, Dexcom, Inc.'s Motion to Strike Plaintiffs' Untimely Expert Opinions, Case No. 21-CV-977-KAJ (D. Delaware), Jun. 16, 2023.

US, Appendix of Exhibits (vol. 3 of 3, Exhibits 151-171) for Plaintiffs' Answering Briefs In Opposition to Dexcom's Motions for Summary Judgement (D.I. 331) and to Exclude Expert Reports and Testimony (D.I. 337), Case No. 21-CV-977-KAJ (D. Delaware)—Public Version, Jun. 7, 2023.

US, Appendix of Exhibits (vol. 2 of 3, Exhibits 138-150) for Plaintiffs' Answering Briefs In Opposition to Dexcom's Motions for Summary Judgement (D.I. 331) and to Exclude Expert Reports and Testimony (D.I. 337), Case No. 21-CV-977-KAJ (D. Delaware)—Public Version, Jun. 7, 2023.

US, Appendix of Exhibits (vol. 1 of 3, Exhibits 98-137) for Plaintiffs' Answering Briefs In Opposition to Dexcom's Motions for Summary Judgement (D.I. 331) and to Exclude Expert Reports and Testimony (D.I. 337), Case No. 21-CV-977-KAJ (D. Delaware)—Public Version, Jun. 7, 2023.

US, Supplemental Declaration of Karl R. Leinsing, MSME, PE, Regarding Validity, Case No. 21-CV-977-KAJ (D. Delaware)—Public Version, Jun. 7, 2023.

US, Declaration of John L. Smith, PH.D., on Validity, in Support of Plaintiffs' Answering Brief in Opposition to Dexcom's Motions for Summary Judgement and Plaintiffs' Answering Brief in Opposition to Dexcom's Motions to Exclude Expert Reports and Testimony, Case No. 21-CV-977-KAJ (D. Delaware)—Public Version, Jun. 7, 2023.

US, Declaration of John L. Smith, PH.D., Regarding Infringement, in Support of Plaintiffs' Answering Brief in Opposition to Dexcom's Motions for Summary Judgement and Plaintiffs' Answering Brief in Opposition to Dexcom's Motions to Exclude Expert Reports and Testimony, Case No. 21-CV-977-KAJ (D. Delaware)—Public Version, Jun. 7, 2023.

US, Declaration of Dr. John E. Anderson in Opposition to Defendant Dexcom, Inc.'s Motions to Exclude Expert Reports and Testimony, Case No. 21-CV-977-KAJ (D. Delaware)—Public Version, Jun. 7, 2023.

US, Declaration of Dr. Eden M. Miller in Opposition to Defendant Dexcom, Inc.'s Motions to Exclude Expert Reports and Testimony, Case No. 21-CV-977-KAJ (D. Delaware)—Public Version, Jun. 7, 2023.

US, Declaration of Catherine M. Lawton in Opposition to Defendant Dexcom, Inc.'s Motions to Exclude Expert Reports and Testimony, Case No. 21-CV-977-KAJ (D. Delaware)—Public Version, Jun. 7, 2023.

US, Declaration of Eric B. Hanson in Support of Dexcom's Opposition to Plaintiffs' Motion for Summary Judgement and Daubert Challenges, Case No. 21-CV-977-KAJ (D. Delaware), Jun. 6, 2023.

US, Defendant Dexcom, Inc.'s Opening Brief in Support of Its Motions to Exclude Expert Reports and Testimony, Case No. 21-CV-977-KAJ (D. Delaware)—Public Version, May 19, 2023.

US, Declaration of Karl R. Leinsing, Msme, Pe, in Support of Abbott's Motion for Summary Judgement, Case No. 21- CV-977-KAJ (D. Delaware)—Public Version, May 19, 2023.

Video-Recorded Deposition of Neil Sheehan, Ph.D, Case No. 21-CV-977-KAJ (D. Delaware), May 4, 2023.

US, Video Deposition of Karl R. Leinsing, MSME, PE, Vol. I, Case No. 21-CV-977-KAJ (D. Delaware), May 3, 2023.

US, Videotaped Deposition of John Mastrototaro, Ph.D, Case No. 21-CV-977-KAJ (D. Delaware), Apr. 26, 2023.

US, Video-Recorded Deposition of John Smith, Ph.D, Case No. 21-CV-977-KAJ (D. Delaware), Apr. 21, 2023.

US, Expert Report of John L. Smith, Ph.D., on Infringement of the Asserted Claims of U.S. Pat. No. 10,827,954, Case No. 21-CV-977-KAJ (D. Delaware), Mar. 14, 2023.

US, Oral Argument Hearing Before Hon. Kent A. Jordan, U.S. Circuit Court Judge, Case No. 21-CV-977-KAJ (D. Delaware), Mar. 9, 2023.

US, Defendant Dexcom, Inc.'s Supplemental Responses to Plaintiffs Abbott Diabetes Care Inc's. and Abbott Diabetes Care Limited's Notice of Rule 30(b)(6) Deposition, Case No. 21-CV-977-KAJ (D. Delaware), Feb. 8, 2023.

US, Telephone Conference Before Kent A. Jordan, U.S. Circuit Court Judge, Case No. 21-CV-977-KAJ (D. Delaware), Jan. 3, 2023.

US, Letter to the Honorable Kent A. Jordan Regarding Discovery Disputes, Case No. 21-CV-977-KAJ (D. Delaware), Dec. 28, 2022.

US, Order Denying Evenflo's Motion for Summary Judgement of Non-Infringement and Granting in Part and Denying in Part Won-

(56) References Cited

OTHER PUBLICATIONS derland's Motion for Partial Summary Judgement, Case 20-CV-727-JPM (D. Delaware), Dec. 6, 2022.

US, Defendant Dexcom, Inc.'s Notice of Deposition to Plaintiff Abbott Diabetes Care Limited, Case No. 21-CV-977-KAJ (D. Delaware), Aug. 19, 2022.

US, Defendant Dexcom, Inc.'s Notice of Deposition to Plaintiff Abbott Diabetes Care Inc., Case No. 21-CV-977-KAJ (D. Delaware), Aug. 19, 2022.

US, Plaintiffs' Proposed Claim Constructions, Case 21-CV-977-KAJ, May 27, 2022.

US, Plaintiffs' Identification of Claim Terms For Construction, Case 21-CV-977-KAJ (D. Delaware), May 13, 2022.

US, Joint Claim Construction Brief, Case 20-1679-RGA-JLH (D. Delaware), Feb. 11, 2022.

US, Plaintiff Dexcom, Inc.'s Amended Preliminary Disclosure of Asserted Claims and Infringement Contentions to Abbott Diabetes Care Inc. and Abbott Diabetes Care Sales Corp., Case 21-CV-690-ADA ((D. Texas), Jan. 5, 2022.

US, Findings of Fact and Conclusions of Law Regrading Subject Matter Eligibility of U.S. Pat. No. 6,975,308 Under 35 U.S.C. §101, Case 20-CV-101-ADA (D. Texas), Dec. 7, 2021.

US, Non-Final Office Action issued in U.S. Appl. No. 17/030,030, Dec. 17, 2021.

US, Non-Final Office Action issued in U.S. Appl. No. 17/017,590, Jan. 8, 2021.

US, Notice of Allowance issued in U.S. Appl. No. 15/963,828, Mar. 3, 2021.

US, Response to Non-Final Office Action filed in U.S. Appl. No. 15/963,828, Dec. 8, 2020.

US, Request Under 37 CRR 1.48(a) to Correct Inventorship filed in U.S. Appl. No. 15/963,828, Dec. 8, 2020.

Joint Declaration Under 37 C.F.R. 1.131 filed in U.S. Appl. No. 15/963,828, Nov. 30, 2020.

US, Non-Final Office Action issued in U.S. Appl. No. 14/884,622, Jun. 13, 2018.

US, Response to Restriction Requirement, and Acknowledgement Receipt, filed in U.S. Appl. No. 14/884,622, Apr. 5, 2018.

Breton, M. D., et al., "Optimum Subcutaneous Glucose Sampling and Fourier Analysis of Continuous Glucose Monitors", Journal of Diabetes Science and Technology, 2008, vol. 2, No. 3, pp. 495-500.

Panteleon, A. E., et al., "The Role of the Independent Variable to Glucose Sensor Calibration", Diabetes Technology & Therapeutics, 2003, vol. 5, No. 3, pp. 401-410.

Parker, S. P., ed., McGraw-Hill Dictionary of Mechanical and Design Engineering, 1984 (excerpted), pp. 1-4.

Shenoi, B. A., ed., Introduction to Digital Signal Processing and Filter Design, 2006, "Introduction", Chapter 1, pp. 1-30.

Smith, S. S., ed., The Scientist and Engineer's Guide to Digital Signal Processing, Second Edition, 1997-1999, "Digital Signal Processors", Chapter 28, pp. 503-534.

2,617,192 Examiner's Report.

3,182,961 Examiner's Report.

200780039416.2 Second Office Action.

200780039416.2 First Office Action.

200880005388.7 Second Office Action.

200880005388.7 First Office Action.

201980082748.1 Final Office Action.

Application for Enforcement Security in Patent Infringement of European Patent No. 3 730 045.

06788869.3 Examination Report.

06788869.3 Extended Search Report.

06813967.4 Extended Search Report.

07854298.2 Extended Search Report.

08730066.1 Extended Search Report.

10739031.2 Communication from Board of Appeals.

10739031.2 Summons to Attend Oral Proceedings.

18741791.0 Examination Report.

20177703.4 Reply to Reply to Reply to Notice of Opposition ADC.

20177712.5 Response to Written Submissions Dexcom.

20177712.5 Written Submissions ADC.

20177712.5 Reply to Reply to Reply to Notice of Opposition ADC.

20195922.8 Response to Summons to Attend Oral.

EP, 20195922.8 Written Submissions Dexcom, Dec. 12, 2023

EP, 20195922.8 Written Submissions ADC, Oct. 23, 2023.

GB, Order for Directions—Trial D, Claim No. HP-2023-000012, Jul. 18, 2023.

GB, Reply and Defence to Counterclaim, Claim No. HP-2023-000012, Jul. 5, 2023.

GB, Application Notice, Claim No. HP-2023-000012, Jun. 19, 2023.

GB, Defence and Counterclaim, Claim No. HP-2023-000012, Jun. 14, 2023.

JP, 2009-534799 Final Office Action, Feb. 19, 2023.

JP, 2009-534799 Office Action, Sep. 27, 2011.

MX, MX/a/2009/004322 Office Action, Mar. 11, 2013.

MX, MX/a/2009/004322 Office Action, Sep. 19, 2012.

MY, PI2023005466 Examination Report, Dec. 28, 2023.

RU, 2009119430 Office Action, Jun. 5, 2011.

RU, 2009135048 Office Action, Dec. 20, 2011.

US, Third Declaration of Gary Fletcher, Ph.D., IPR No. 2024-00520, Jan. 31, 2024.

US, Petition For Inter Partes Review Of U.S. Pat. No. 11,266,335, IPR No. 2024-00520, Jan. 31, 2024.

US, Patent Owner's Preliminary Response, IPR No. 2023-01409, Jan. 18, 2024.

US, Notice of Filing Date Accorded to Petition and Time for Filing Patent Owner Preliminary Response, IPR No. 2023-01409, Oct. 18, 2023.

US, Patent Owner's Response to Petitioner's Explanation of Material Differences Between Petitions, IPR Nos. 2023-01396 and 2023-01397, Jan. 18, 2024.

US, Petitioner's Explanation of Material Differences Between Petitions, IPR No. 2023-01397, Oct. 6, 2023.

US, Declaration of Gary D. Fletcher, Ph.D, IPR No. 2023-01396 and IPR No. 2023-01397, Oct. 6, 2023.

US, Petitioner's Explanation of Material Differences Between Petitions, IPR No. 2023-01396, Oct. 6, 2023.

US, Notice of Final Written Decision re Inter Partes Review of the '649 Patent, IPR No. 2022-00605, Jul. 13, 2023.

US, Reexamination U.S. Appl. No. 90/019,329 Order Granting Request for Reexamination of U.S. Pat. No. 11,013,440, Jan. 23, 2024.

US, Request for Ex Parte Reexamination Under 35.U.S.C. §§ 302-307 and 37 C.F.R. § 1.510 of U.S. Pat. No. 11,013,440, Dec. 11, 2023.

US, Request for Ex Parte Reexamination Under 35.U.S.C. §§ 302-307 and 37 C.F.R. § 1.510 of U.S. Pat. No. 11,000,216, Dec. 11, 2023.

US, Reexamination U.S. Appl. No. 90/019,307 Order Granting Request for Reexamination of U.S. Pat. No. 10,973,443, Dec. 22, 2023.

US, Request for Ex Parte Reexamination Under 35.U.S.C. §§ 302-307 and 37 C.F.R. § 1.510 of U.S. Pat. No. 10,973,443, Nov. 27, 2023.

US, Request for Ex Parte Reexamination Under 35.U.S.C. §§ 302-307 and 37 C.F.R. § 1.510 of U.S. Pat. No. 10,959,654, Dec. 11, 2023.

WO, PCT/US2006/029541 ISR and Written Opinion, Apr. 24, 2007.

WO, PCT/US2006/033885 ISR and Written Opinion, Aug. 3, 2007.

WO, PCT/US2007/082121 ISR and Written Opinion, May 9, 2008.

WO, PCT/US2008/054186 ISR and Written Opinion, Aug. 8, 2008.

WO, PCT/US2008/065154 ISR and Written Opinion, Sep. 3, 2008.

WO, PCT/US2010/047065 ISR and Written Opinion, Dec. 21, 2010.

WO, PCT/US2010/047414 ISR and Written Opinion, Dec. 27, 2010.

WO, PCT/US2010/047415 ISR and Written Opinion, Oct. 25, 2010.

CA, 3,120,335 Examiner's Report, May 27, 2024.

EP, 10739031.2 Decision of Oral Proceedings, Jun. 11, 2024.

EP, 10739031.2 Minutes of Oral Proceedings, May 10, 2024.

EP, 20177703.4 Summons to Attend Oral Proceedings, Apr. 29, 2024.

(56) References Cited

OTHER PUBLICATIONS

EP, 20177712.5 Summons to Attend Oral Proceedings, Jul. 2, 2024.
EP, 20195922.8 Written Submissions Dexcom, May 9, 2024.
EP, 20195922.8 Decision Revoking the European Patent, May 8, 2024.
EP, 20195922.8 Minutes of the Oral Proceedings, May 8, 2024.
EP, 20195922.8 Written Submissions Dexcom, Mar. 15, 2024.
EP, 21211041.5 Grounds of Opposition Dexcom, Mar. 28, 2024.
EP, 21211041.5 Notice of Opposition Dexcom, Mar. 28, 2024.
EP, 24152079.0 Partial Search Report, Jun. 14, 2024.
GB, Claim No. HP-2023-000012 Amended Grounds of Invalidity, Mar. 15, 2024.
GB, Claim No. HP-2023-000012 Order, Mar. 7, 2024.
GB, Claim No. HP-2023-000012 Dexcom's Statement of Case on Validity, Feb. 8, 2024.
GB, Claim No. HP-2021-000025 Approved Judgement, Oct. 18, 2021.
UP, Counterclaim for Revocation in the Infringement Action Regarding EP 3 977 921 B1, Mar. 28, 2024.
US, Notice of Filing Date Accorded to Petition and Time for Filing Patent Owner Preliminary Response, IPR No. 2024-00860, May 23, 2024.
US, Declaration of Dr. Cameron Riviere, Ph.D., IPR No. 2024-00860, May 9, 2024.
US, Petition For Inter Partes Review Of U.S. Pat. No. 11,510,625, IPR No. 2024-00860, May 9, 2024.
US, Patent Owner's Authorized Sur-Reply to Petitioner's Reply to Patent Owner's Preliminary Response, IPR No. 2024-00520, Jun. 11, 2024.
US, Petitioner's Authorized Reply to Patent Owner's Preliminary Response, IPR No. 2024-00520, May 31, 2024.
US, Patent Owner's Preliminary Response, IPR No. 2024-00520, May 8, 2024.
US, Patent Owner's Exhibit List, IPR2024-00520, Mar. 25, 2024.
US, Telephonic Hearing, IPR2024-00520, Mar. 13, 2024.
US, Petitioner's Explanation of Material Differences Between the Petition in IPR2024-00520 and Previously Filed Petitions in IPR2023-01396 and IPR2023-01397, IPR No. 2024-00520, Jan. 31, 2024.
US, Order, IPR No. 2023-01409, May 30, 2024.
US, Notice of Stipulation, IPR No. 2023-01409, May 29, 2024.
US, Patent Owner's Objections to Petitioner's Exhibits to the Petition, IPR No. 2023-01409, Apr. 29, 2024.
US, Patent Owner's Request for Rehearing by the Director, IPR 2023-01409, Apr. 29, 2024.
US, Email of Peter McAndrews, IPR 2023-01409, Apr. 29, 2024.
US, Decision Granting Institution of Inter Partes Review, IPR No. 2023-01409, Apr. 15, 2024.
US, Scheduling Order, IPR 2023-01409, Apr. 15, 2024.
US, Order Conduct of the Proceeding 37 C.F.R. § 42.5, IPR No. 2023-01409, Feb. 6, 2024.
US, Telephonic Conference Call, IPR No. 2023-01409, Feb. 2, 2024.
US, Petitioner's Updated Exhibit List, IPR No. 2023-01409, Feb. 5, 2024.
US, Patent Owner's Updated Mandatory Notices, IPR No. 2023-01409, Feb. 2, 2024.
US, Email of Andrew M. Mason, IPR 2023-01409, Jan. 30, 2024.
US, Decision Denying Institution of Inter Partes Review, IPR No. 2023-01397, Apr. 16, 2024.
US, Patent Owner's Updated Exhibit List, IPR2023-01397, Mar. 25, 2024.
US, Telephonic Hearing, IPR2023-01397, Mar. 13, 2024.
US, Petitioner's Updated Mandatory Notices Pursuant to 37 C.F.R. § 42.8(a)(3), IPR No. 2023-01397, Feb. 19, 2024.
US, Patent Owner's Updated Mandatory Notices, IPR No. 2023-01397, Feb. 2, 2024.
US, Patent Owner's Preliminary Response, IPR No. 2023-01397, Jan. 18, 2024.
US, Petitioner's Request for Rehearing of Decision Denying Institution, IPR No. 2023-01396, May 16, 2024.

US, Decision Denying Institution of Inter Partes Review, IPR No. 2023-01396, Apr. 16, 2024.
US, Patent Owner's Updated Exhibit List, IPR No. 2023-01397, Mar. 25, 2024.
US, Telephonic Hearing, IPR2023-01396, Mar. 13, 2024.
US, Petitioner's Updated Mandatory Notices Pursuant to 37 C.F.R. § 42.8(a)(3), IPR No. 2023-01396, Feb. 19, 2024.
US, Patent Owner's Preliminary Response, IPR No. 2023-01396, Jan. 18, 2024
US, Notice of Filing Date Accorded to Petition and Time for Filing Patent Owner Preliminary Response, IPR No. 2023-01396, Oct. 18, 2023.
US, Reexamination U.S. Appl. No. 90/019,329 Notification of Concurrent Proceedings, May 15, 2024.
US, Petition Under 37 CFR § 1.181 and/or § 1.182 to Terminate Reexamination U.S. Appl. No. 90/019,329, Apr. 26, 2024.
US, Reexamination U.S. Appl. No. 90/019,329 Order Granting Request for Reexamination of U.S. Patent No, Jan. 30, 2024.
US, Reexamination U.S. Appl. No. 90/019,329 Declaration of Gary D. Fletcher, Ph.D, Dec. 11, 2023.
US, Reexamination U.S. Appl. No. 90/019,331 Notification of Concurrent Proceedings, May 15, 2024.
US, Reexamination U.S. Appl. No. 90/019,331 Order Granting Request for Reexamination of U.S. Pat. No. 11,000,216, Jan. 23, 2024.
US, Reexamination U.S. Appl. No. 90/019,330 Notice of Intent to Issue Ex Parte Reexamination Certificate of U.S. Pat. No. 11,013,440, Jul. 1, 2024.
US, Reexamination U.S. Appl. No. 90/019,330 Notification of Concurrent Proceedings, May 15, 2024.
US, Reexamination U.S. Appl. No. 90/019,330 Order Granting Request for Reexamination of U.S. Pat. No. 10,959,654, Jan. 23, 2024.
US, Reexamination U.S. Appl. No. 90/019,330 Declaration of John Mastrototaro, Ph.D, Dec. 11, 2023.
US, [Joint Proposed] Final Jury Instructions, Case No. 21-CV-977-KAJ (D. Delaware), Mar. 17, 2024.
US, [Joint Proposed] Final Jury Instructions, Case No. 21-CV-977-KAJ (D. Delaware), Mar. 7, 2024.
US Exhibit 7P to the Proposed Pretrial Order Abbott's Brief Summary of Opinion Testimony, Case No. 21-CV-977-KAJ (D. Delaware), Mar. 7, 2024.
US, Exhibit 7D to the Proposed Pretrial Order Dexcom's Brief Summary of Opinion Testimony, Case No. 21-CV-977-KAJ (D. Delaware), Mar. 7, 2024.
US, Exhibit 6P to the Proposed Pretrial Order Abbott's Deposition Designations, Case No. 21-CV-977-KAJ (D. Delaware), Mar. 7, 2024.
US, Exhibit 6D to the Proposed Pretrial Order Dexcom's Deposition Designations, Case No. 21-CV-977-KAJ (D. Delaware), Mar. 7, 2024.
US, Exhibit 5P to the Proposed Pretrial Order Abbott's List of Trial Exhibits, Case No. 21-CV-977-KAJ (D. Delaware), Mar. 7, 2024.
US, Exhibit 5D to the Proposed Pretrial Order Dexcom's List of Trial Exhibits, Case No. 21-CV-977-KAJ (D. Delaware), Mar. 7, 2024.
US, Exhibit 3P to the Proposed Pretrial Order Abbott's Statement of Issues of Law Which Remain to be Litigated, Case No. 21-CV-977-KAJ (D. Delaware), Mar. 7, 2024.
US, Exhibit 3D to the Proposed Pretrial Order Dexcom's Statement of Issues of Law Which Remain to be Litigated, Case No. 21-CV-977-KAJ (D. Delaware), Mar. 7, 2024.
US, Exhibit 2P to the Proposed Pretrial Order Abbott's Statement of Issues of Fact Which Remain to be Litigated, Case No. 21-CV-977-KAJ (D. Delaware), Mar. 7, 2024.
US, Exhibit 2D to Proposed Pretrial Order Dexcom's Statement of Contested Facts, Case No. 21-CV-977-KAJ (D. Delaware), Mar. 7, 2024.
US, Exhibit 1 to the Proposed Pretrial Order Parties' Joint Statement of Uncontroverted Facts, Case No. 21-CV-977-KAJ (D. Delaware), Mar. 7, 2024.
US, [Proposed] Final Pretrial Order, Case No. 21-CV-977-KAJ (D. Delaware), Mar. 7, 2024.

(56) References Cited

OTHER PUBLICATIONS

US, Joint Stipulation and [Proposed] Order Regarding Dismissal of Certain Asserted Patent Claims, Case No. 21-CV-977-KAJ (D. Delaware), Mar. 1, 2024.

US, Defendant Dexcom, Inc.'s Notice Pursuant to 35 U.S.C. § 282, Case No. 21-CV-977-KAJ (D. Delaware), Feb. 9, 2024.

US, Letter to the Honorable Kent A. Jordan Regarding Pretrial Order, Case No. 21-CV-977-KAJ (D. Delaware), Feb. 2, 2024.

US, Letter to the Honorable Kent A. Jordan From Nathan R. Hoeschen Regarding Pretrial Order, Case No. 21-CV-977-KAJ (D. Delaware)—Public Version, Feb. 1, 2024.

US, [Joint Proposed] Final Jury Instructions, Case No. 21-CV-977-KAJ (D. Delaware), Jan. 31, 2024.

WO, PCT/US24/11756 Invitation to Pay Additional Fees, May 7, 2024.

WO, PCT/US24/16127 Invitation to Pay Additional Fees, Jun. 4, 2024.

WO, PCT/US24/18665 ISR and Written Opinion, Jun. 21, 2024.

Continuous Glucose Monitoring Systems Product Reference Guide, Diabetes Health, 2006-2007, pp. 50-51.

Das, S. D., et al., "Review—Electrochemistry and Other Emerging Technologies for Continuous Glucose Monitoring Devices", ECS Sensors Plus, 2022, 19 pages.

Dexcom G6 Continuous Glucose Monitoring System User Guide, 2022, 346 pages.

Englert, K., et al., "Skin and Adhesive Issues With Continuous Glucose Monitors: A Sticky Situation", Journal of Diabetes Science and Technology, 2014, vol. 8, No. 4, pp. 745-751.

File Wrapper of U.S. Appl. No. 61/317,243.

File Wrapper of U.S. Appl. No. 61/345,562.

File Wrapper of U.S. Appl. No. 61/361,374.

File Wrapper of U.S. Appl. No. 61/411,262.

Freckmann, G., et al., "Performance Evaluation of Three Continuous Glucose Monitoring Systems: Comparison of Six Sensors per Subject in Parallel", Journal of Diabetes Science and Technology, 2013, vol. 7, No. 4, pp. 842-853.

Freestyle Libre Brochure, 2016, 10 pages.

Freestyle Libre Fact Sheet, 2016, retrieved from www.FreeStyleLibre.de, 2 pages.

Harris, J. M., et al., "Common Causes of Glucose Oxidase Instability in In Vivo Biosensing: A Brief Review", Journal of Diabetes Science and Technology. 2013, vol. 7, No. 4, pp. 1030-1038.

Hovorka, R., "Continuous glucose monitoring and closed-loop systems", Diabetic Medicine, 2005, vol. 23, pp. 1-12.

Medtronic Enlite Serter User Guide, 2014, 26 pages.

Medtronic MiniMed iPro2 User Guide, 2010, pp. 1-99.

Meltsner, M A, et al., "Observations on rotating needle insertions using a brachytherapy robot", Phys. Med. Biol., 2007, vol. 52, pp. 6027-6037.

Nichols, S. P., et al., "Biocompatible Materials for Continuous Glucose Monitoring Devices", Chem Rev., 2013, vol. 113, No. 4, pp. 2528-2549.

Rice, M. J., et al., "Continuous Measurement of Glucose: Facts and Challenges", Anesthesiology, 2012, vol. 116, No. 1, pp. 199-204.

Rigo, R. S., et al., "Cutaneous Reactions to Continuous Glucose Monitoring and Continuous Subcutaneous Insulin Infusion Devices in Type 1 Diabetes Mellitus", Journal of Diabetes Science and Technology, 2021, vol. 15, No. 4, pp. 786-791.

Rocchitta, G., et al., "Enzyme Biosensors for Biomedical Applications: Strategies for Safeguarding Analytical Performances in Biological Fields", Sensors, 2016. Vol. 16, No. 6, 21 pages.

Sclater, N., et al., eds., Mechanisms and Mechanical Devices Sourcebook, Fourth Edition, 2007, Chapter 12—Shaft Couplings and Connections, pp. 290-307.

"Transcutaneous", Webster's Third New International Dictionary, 2002, p. 2426.

Tsumura, R., et al., "Histological Evaluation of Tissue Damage Caused by Rotational Needle Insertion", Proceedings of the Annual International Conference of the IEEE Engineering in Medicine and Biology Society, 2016, pp. 5120-5123.

Xu, J., et al., "Anti-Biofouling Strategies for Long-Term Continuous Use of Implantable Sensors", Chemosensors, 2020, vol. 20 No. 3, 29 pages.

Anderson, A. J., "Foundations of Computer Technology", 1994, pp. 55-57.

Kal, S., "Basic Electronics—Devices, Circuits and IT Fundamentals", 2006, Chapter 13, Microcomputers and Microprocessors, p. 412.

CN, 201980082748.1 Second Office Action, Jul. 10, 2023.

EP, 20177703.4 Reply to Reply to Notice of Opposition, Jun. 29, 2023.

EP, 20177703.4 Notice of Intervention, Jun. 23, 2023.

EP, 20177712.5 Notice of Intervention, Jun. 23, 2023.

EP, 20177712.5 Reply to Notice of Opposition, May 23, 2023.

EP, 20195922.8 Reply to Notice of Opposition, Jun. 20, 2023.

EP, 20195922.8 Notice of Intervention, Jun. 13, 2023.

GB, Particulars of Claim (EP 3730045), May 15, 2023.

GB, Claimant's Initial List of Disclosure Documents (EP 3730045), May 15, 2023.

GB, Grounds of Invalidity (EP 3730045), May 15, 2023.

GB, Claim No. HP-2021-000025 Dexcom's Closing Submissions, May 3, 2023.

GB, Claim No. HP-2021-000025 Abbott's Closing Skeleton Argument, May 3, 2023.

GB, Claim No. HP-2021-000025 Re-Re-Amended Reply and Defence to Counterclaim, Apr. 28, 2023.

GB, Claim No. HP-2021-000025 Re-Re-Re-Re-Amended Grounds of Invalidity, Apr. 24, 2023.

GB, Claim No. HP-2021-000025 Corrected PTR Order for Trial B, Apr. 21, 2023.

GB, Claim No. HP-2021-000025 Trial B—Joint CGK Statement, Apr. 18, 2023.

GB, Claim No. HP-2021-000025 Dexcom Trial Skeleton, Apr. 19, 2023.

GB, Claim No. HP-2021-000025 Abbott's Opening Skeleton Argument, Apr. 19, 2023.

GB, Claim No. HP-2021-000025 Second Expert Report of Dr Michael Schoemaker, Mar. 27, 2023.

GB, Claim No. HP-2021-000025 Exhibits MS1-MS3 of First Expert Report of Dr Michael Schoemaker, Feb. 28, 2023.

GB, Claim No. HP-2021-000026 Corrected PTR Order for Trial B, Apr. 21, 2023.

GB, Claim No. HP-2021-000026 Dexcom Trial Skeleton, Apr. 19, 2023.

GB, Claim No. HP-2021-000026 Dexcom's Closing Submissions, May 3, 2023.

GB, Claim No. HP-2021-000026 Second Expert Report of Dr Michael Schoemaker, Mar. 27, 2023.

GB, Claim No. HP-2021-000026 Exhibits MS1-MS3 of First Expert Report of Dr Michael Schoemaker, Feb. 28, 2023.

MY, PI2022007295 Examination Report, Jul. 11, 2023.

US, Final Written Decision, IPR No. 2022-00605, Jul. 10, 2023.

WO, PCT/US2012/062551 ISR and Written Opinion, Jan. 2, 2013.

WO, PCT/US2023/010054 ISR and Written Opinion, May 15, 2023.

CA, 2,984,939 Examiner's Report, Aug. 7, 2024.

CN, 200880005149.1 Notice of Allowance, Jun. 21, 2013.

CN, 200880005149.1 Fourth Office Action, Dec. 3, 2012.

CN, 200880005149.1 Third Office Action, Feb. 16, 2012.

CN, 200880005149.1 Second Office Action, Aug. 17, 2011.

CN, 200880005149.1 First Office Action, Jul. 29, 2010.

DE, Complaint in Litigation of EP 3300658, Mar. 20, 2024.

EP, 17182379.2 Grounds of Opposition, Jul. 12, 2024.

EP, 17182379.2 Notice of Opposition, Jul. 12, 2024.

EP, 17182379.2 Reply to Examination Report, Apr. 9, 2021.

EP, 17182379.2 Reply to Search Report, Oct. 3, 2018.

EP, 19151577.4 Examination Report, Oct. 7, 2018.

EP, 20177712.5 Summons to Attend Oral Proceedings, Oct. 1, 2018.

EP, 20177712.5 Response to Summons to Attend Oral Proceedings, Aug. 30, 2024.

EP, 20195922.8 Grounds of Appeal, Sep. 6, 2024.

EP, 20195922.8 Notice of Appeal, Jul. 4, 2024.

(56)                    References Cited

OTHER PUBLICATIONS

EP, 21211041.5 Summons to Attend Oral Proceedings, Sep. 23, 2024.
EP, 21211041.5 Reply to Notice of Opposition, Jul. 17, 2024.
EP, 23166498.8 Examination Report, Sep. 2, 2024.
EP, 24152079.0 Extended Search Report, Sep. 4, 2024.
EP, 24183336.7 Extended Search Report, Oct. 11, 2024.
EP, 24187206.8 Extended Search Report, Oct. 9, 2024.
GB, Claim No. HP-2024-000010 Tomlin Order, Jul. 25, 2024.
GB, Claim No. HP-2024-000010 Order, May 20, 2024.
GB, Claim No. HP-2024-000010 Particulars of Infringement, Mar. 20, 2024.
GB, Claim No. HP-2024-000010 Particulars of Claim, Mar. 20, 2024.
GB, Claim No. HP-2023-000012 and Claim No. HP-2023-000016 Order, Jul. 16, 2024.
GB, Claim No. HP-2021-000025 and Claim No. HP-2021-000026 Approved Judgment, Jun. 28, 2024.
GB, Claim No. HP-2021-000025 and Claim No. HP-2021-000026 Third Letter, Jan. 24, 2023.
RU, 2009134334 Office Action, Feb. 7, 2012.
UP, Reply to the Defence to the Counterclaim and Defence to the Application to Amend the Patent (R.29(d) RoP) in the Counterclaim Regarding EP 3 977 921 B1, Aug. 12, 2024.
UP, Expert Statement of Pantelis Georgiou in Litigation of EP 3 977 921, Aug. 9, 2024.
UP, Expert Statement of Andrew Vardé in Litigation of EP 3 977 921, Aug. 9, 2024.
UP, First Expert Opinion of Dr Michael Schoemaker in Litigation of EP 3 977 921, Jun. 11, 2024.
UP, Reply to the Statement of Defence Including a Defence to the Counterclaim Including an Application to Amend the Patent in Litigation of EP 3 977 921, Jun. 11, 2024.
UP, Decision in Litigation of EP 2 393 417, Jul. 3, 2024.
UP, Request pursuant to R. 9 ROP for admitting further submissions with respect to the Application for Provisional Measures ACT_15000/2024 UPC_CFI_133/2024 in Litigation of EP 2 393 417, Jun. 27, 2024.
UP, Rejoinder to Application for Provisional Measures in Litigation of EP 2 393 417, May 17, 2024.
UP, Reply to the Objection to Application for Provisional Measures in Litigation of EP 2 393 417, May 10, 2024.
UP, Objection to Application for Provisional Measures in Litigation of EP 2 393 417, May 2, 2024.
UP, Application for Preliminary Injunction and Other Provisional Measures in the Litigation of EP 2 393 417, Mar. 20, 2024.
US, Decision Denying Institution of Inter Partes Review, IPR No. 2024-00520, Aug. 8, 2024.
US, Declaration of Karl R. Leinsing, MSME, PE, IPR No. 2023-01409, Jul. 19, 2024.
US, Patent Owner's Response, IPR No. 2023-01409, Jul. 19, 2024.
US, Deposition of Gary Fletcher, Ph.D., IPR No. 2023-01409, Jun. 26, 2024.
US, Reexamination U.S. Appl. No. 90/019,307 Petition Under 37 CFR § 1.181 to Terminate, Aug. 15, 2024.
US, Reexamination U.S. Appl. No. 90/019,307 Decision on Petitions, Aug. 7, 2024.
US, Reexamination U.S. Appl. No. 90/019,307 Petition Under 37 CFR § 1.59 to Expunge Application Papers, Aug. 1, 2024.
US, Reexamination U.S. Appl. No. 90/019,307 Petition Under 37 CFR § 1.59 to Expunge Application Papers, Jun. 12, 2024.
US, Reexamination U.S. Appl. No. 90/019,307 Notification of Concurrent Proceedings, May 15, 2024.
US, Reexamination U.S. Appl. No. 90/019,307 Petition Under 37 CFR §§ 1.182 and/or § 1.183 to Allow Filing and Consideration of Response to Patent Owner's Extraordinary Petition to Suspend, Mar. 19, 2024.
US, Reexamination U.S. Appl. No. 90/019,307 Petition Under 37 CFR § 1.181 and/or § 1.183 to Suspend, Mar. 1, 2024.

US, Reexamination U.S. Appl. No. 90/019,329 Ex Parte Reexamination Certificate, Oct. 30, 2024.
US, Reexamination U.S. Appl. No. 90/019,329 Notice of Intent to Issue Ex Parte Reexamination Certificate, Oct. 8, 2024.
US, Reexamination U.S. Appl. No. 90/019,329 Decision on Petition Under 37 C.F.R. § 1.59, Sep. 16, 2024.
US, Reexamination U.S. Appl. No. 90/019,329 Statutory disclaimer per Manual of Patent Examining Procedure (MPEP) 1490, Sep. 3, 2024.
US, Reexamination U.S. Appl. No. 90/019,329 Petition Under 37 C.F.R. § 1.182 to Seal Document Versions Filed via IDS and Substitute Redacted Document Versions Therfor, Aug. 1, 2024.
US, Reexamination No. U.S. Appl. No. 90/019,329 Petition Under 37 CFR § 1.59 to Expunge Application Papers, Aug. 1, 2024.
US, Reexamination U.S. Appl. No. 90/019,329 Ex Parte Reexamination Interview Summary, Jul. 25, 2024.
US, Reexamination U.S. Appl. No. 90/019,329 Decision on Petition Under 37 C.F.R. § 1.59, Jul 22, 2024.
US, Reexamination U.S. Appl. No. 90/019,329 Decision Sua Sponte Vacating Notice of Intent to Issue Ex Parte Reexamination Certificate, Jul. 3, 2024.
US, Reexamination U.S. Appl. No. 90/019,329 Petition Under 37 CFR § 1.59 to Expunge Application Papers, Jun. 12, 2024.
US, Reexamination U.S. Appl. No. 90/019,331 Notice of Intent to Issue Ex Parte Reexamination Certificate, Oct. 15, 2024.
US, Reexamination U.S. Appl. No. 90/019,331 Decision on Petition Under 37 C.F.R. § 1.59, Sep. 16, 2024.
US, Reexamination U.S. Appl. No. 90/019,331 Decision Granting Petition, Aug. 26, 2024.
US, Reexamination U.S. Appl. No. 90/019,331 Petition Under 37 C.F.R. § 1.182 to Seal Document Versions Filed via IDS and Substitute Redacted Document Versions Therfor, Aug. 1, 2024.
US, Reexamination U.S. Appl. No. 90/019,331 Petition Under 37 CFR § 1.59 to Expunge Application Papers, Aug. 1, 2024.
US, Reexamination U.S. Appl. No. 90/019,331 Petition to Withdraw From Issue and Reopen the Proceeding, Jul. 26, 2024.
US, Reexamination U.S. Appl. No. 90/019,331 Decision on Petition Under 37 C.F.R. § 1.59, Jul. 16, 2024.
US, Reexamination U.S. Appl. No. 90/019,331 Notice of Intent to Issue Ex Parte Reexamination Certificate, Jul. 10, 2024.
US, Reexamination No. U.S. Appl. No. 90/019,331 Petition Under 37 CFR § 1.59 to Expunge Application Papers, Jun. 12, 2024.
US, Reexamination U.S. Appl. No. 90/019,330 Notice of Intent to Issue Ex Parte Reexamination Certificate, Oct. 7, 2024.
US, Reexamination U.S. Appl. No. 90/019,330 Decision on Petition Under 37 C.F.R. § 1.59, Sep. 16, 2024.
US, Reexamination U.S. Appl. No. 90/019,330 Decision Granting Petition and Vacating a Reexamination Certificate, Aug. 26, 2024.
US, Ex Parte Reexamination Certificate of U.S. Pat. No. 10,959,654, Aug. 5, 2024.
US, Reexamination U.S. Appl. No. 90/019,330 Petition Under 37 C.F.R. §1.182 to Seal Document Versions Filed via IDS and Substitute Redacted Document Versions Therfor, Aug. 1, 2024.
US, Reexamination U.S. Appl. No. 90/019,330 Petition Under 37 CFR § 1.59 to Expunge Application Papers, Aug. 1, 2024.
US, Reexamination U.S. Appl. No. 90/019,330 Petition to Withdraw From Issue and Reopen the Proceeding, Jul. 26, 2024.
US, Reexamination U.S. Appl. No. 90/019,330 Decision on Petition Under 37 C.F.R. § 1.59, Jul. 16, 2024.
US, Reexamination U.S. Appl. No. 90/019,330 Petition Under 37 CFR § 1.59 to Expunge Application Papers, Jun. 12, 2024.
WO, PCT/US2008/054165 ISR and Written Opinion, Jun. 5, 2008.
WO, PCT/US2008/067791 ISR and Written Opinion, Sep. 30, 2008.
WO, PCT/US24/11756 ISR and Written Opinion, Jun. 28, 2024.
WO, PCT/US24/16127 ISR and Written Opinion, Sep. 11, 2024.
"27 Winners Announced at the 19th Annual Medical Design Excellence Awards (MDEA) Award Ceremony", UBM Americas, 2017, 4 pages.
"55 Chosen as Winners in Annual BIG Innovation Awards", 2018, retrieved from https://www.bintelligence.com/posts/55-chosen-as-winners-in-annual-big-innovation-awards, 2 pages.
2017 Good Design Award, retrieved from https://www.g-mark.org/gallery/winners/9dda01a3-803d-11ed-af7e-0242ac130002, 9 pages.

(56) References Cited

OTHER PUBLICATIONS

"2019 Top 10 Innovations", The Scientist, retrieved from https://www.the-scientist.com/2019-top-10-innovations-66738, 7 pages.
Abbott 2023 Annual Report, retrieved from https://www.abbottinvestor.com/static-files/6cb09c09-2422-40e0-a24b-6545ffcf5267, pp. 1-82.
Abbott Clinical Trials Competitor and Ecosystem Players, 2020, 28 pages.
"Abbott's Freestyle Libre® Is Named Best Medical Technology In Last 50 Years By The Galien Foundation", 2022, PRNewswire, 1 page.
"Abbott's Freestyle® Libre 2 ICGM Cleared in U.S. for Adults and Children With Diabetes, Achieving Highest Level of Accuracy and Performance Standards", retrieved from https://abbott.mediaroom.com/2020-06-15-Abbotts-FreeStyle-R-Libre-2-iCGM-Cleared-in-U-S-for-Adults-and-Children-with-Diabetes-Achieving-Highest-Level-of-Accuracy-and-Performance-tandards#:~:text=FDA%20clears%20Abbott's%20FreeStyle%20Libre,high%20or%20low%20without%20scanning, on Jul. 7, 2024, 3 pages.
"Abbott's Freestyle Libre® 3 Receives U.S. FDA Clearance—Features World's Smallest, Thinnest and Most Accurate 14-Day Glucose Sensor", 2022, PRNewswire, 3 pages.
"Abbott's Freestyle Libre Flash Glucose Monitoring System Wins the IMSTA Most Innovative Product Multi-National Award 2017", retrieved from https://www.ie.abbott/media-center/news/abbotts-freestyle-libre-flash-glucose-monitoring-system-wins-the-imsta-award-2017.html, 2 pages.
"Abbott's Freestyle Libre 14 Day Flash Glucose Monitoring System Now Approved in U.S.", 2018, PRNewswire, 2 pages.
About the Edison Awards retrieved from https://edisonawards.com/about/, 2024, 3 pages.
ACCU-CHEK® Softclix Lancet Device retrieved from file:///C:/Users/afredericks/Downloads/softclix-user-manual.pdf, 2007, 2 pages.
Using your ACCU-CHEK® Multiclix Lancet Device, 2005, retrieved from https://www.northcoastmed.com/wp-content/uploads/2023/03/multiclix_userguide.pdf, 2 pages.
Ahn, D., "Abbott's Euro approved wearable glucose monitor is different than anything on the market", 2014, retrieved from https://www.imedicalapps.com/2014/09/abbotts-wearable-glucose-monitor/, 6 pages.
American National Standard, ANSI/AAMI HE75:2009, Human factors engineering—Design of medical devices, 2010, 465 pages.
Automated Retractable VanishPoint Syringe 510(k) Safety and Effectiveness Summary, 1998, 5 pages.
"BinaxNOW, FreeStyle Libre 2 win BIG innovation honors", 2021, retrieved from https://www.abbott.com/corpnewsroom/strategy-and-strength/binaxnow-freestyle-libre-win-big-innovation-honors.html, 6 pages.
"Bluetooth rival unveiled by Nokia", 2006, retrieved from news.bbc.co.uk/1/hi/technology/5403564.stm, 2 pages.
Blum, A., "Freestyle Libre Glucose Monitoring System", Clinical Pharmacology Update, 2018, vol. 36, No. 2, pp. 203-204.
Breton, M., et al., "Fully Integrated Artificial Pancreas in Type 1 Diabetes: Modular Closed-Loop Glucose Control Maintains Near Normoglycemia", Diabetes, 2012, vol. 61, No. 9, pp. 2230-2237.
Cather, D. E., "Cgm Frustrations Survey", 2020, 36 pages.
Certified Copy of U.S. Appl. No. 61/149,639, filed Feb. 3, 2009.
CES 2022 Innovation Award Honorees, retrieved from https://www.ces.tech/innovation-awards/honorees/2022/best-of/f/freestyle-libre-3-system.aspx, 1 page.
2019 Chicago Innovation Award Winner Abbott Laboratories, retrieved from https://chicagoinnovation.com/winners/abbott-laboratories/, 4 pages.
Design Concepts Project Status Update, Glucose Sensor Applicator Dexcom (project #2554), 2014, 5 pages.
Dexcom G5 Mobile System User Guide, 2015, pp. 1-260.
Dexcom G5 Quick Start Guide, 2020, pp. 1-31.
Dexcom G6 Start Here Set up Guide, 2022, pp. 18 pages.
Dexcom G6 Continuous Glucose Monitoring (CGM) System Section 510(k) Approval, 2022, 7 pages.

"The Dexcom G7. The most accurate CGM system.[1]" retrieved from https://www.dexcom.com/g7-cgm-system on Jun. 27, 2024, 20 pages.
Dexcom G7 Continuous Glucose Monitoring (CGM) System Section 510(k) Approval, 2022, 10 pages.
Dexcom G7 User Guide, 2024, p. i-186.
Edison Awards Announces 2016 Gold, Silver, and Bronze Awards Winners, Edison Awards, 9 pages.
Edison Best New Product Awards™ 2021 Winners retrieved from https://edisonawards.com/2021-winners/, 19 pages.
Edison Best New Product Awards™ 2022 Winners retrieved from https://edisonawards.com/2022-winners/, 52 pages. Email from Christopher M Dougherty dated Dec. 17, 2019, 68 pages.
Email from Christopher M Dougherty dated Dec. 17, 2019, 68 pages.
European Association for the Study of Diabetes, 59th Annual Meeting, Hamburg, Germany, Oct. 2-6, 2023, 326 pages.
File Wrapper of U.S. Appl. No. 61/569,287.
File Wrapper of U.S. Appl. No. 62/524,247.
Freestyle Libre FAQ, 2024, retrieved from https://www.freestyle.abbott/uk-en/support/faq/question-answer.html?q=UKFaqquestion-55#, 2 pages.
"FreeStyle Libre Honored by Prix Galien", 2019, 4 pages.
FreeStyle Libre In-Service Guide, 2021, 28 pages.
FreeStyle Libre 2 Get Started Guide, 2023, pp. 1-28.
Freestyle Libre 2 HCP Pulse Report, 2021, 13 pages.
"FreeStyle Libre 2—Zucker messen ohne stechen per Sensor und App", German Innovation Awards Gold Winner, 2020, retrieved from https://www.german-innovation-award.de/preistraeger/preis/gewinner/freestyle-libre-2-zucker-messen-ohne-stechen-per-sensor-und-app/#:~: text=Beschreibung%20Die%20kontinuierliche%20Glukosemessung%20mit, um%20die%20Glukosewerte%20kontinuierlich%20aufzuzeichnen, 1 page.
FreeStyle Libre 3 Get Started Guide, 2023, pp. 1-20.
FreeStyle Libre 3 User's Manual, 2022-2023, pp. iv-241.
The Galien Foundation is proud to announce the laureates of the best-of-the-best from the half century 1970-2020, The 2022 Galien Golden Jubilee Winners, retrieved from https://www.galienfoundation.org/galien-golden-jubilee, 3 pages.
Gough, D. A., et al., "Development of the Implantable Glucose Sensor: What Are the Prospects and Why Is It Taking So Long?", Diabetes, 1995, vol. 44, pp. 1005-1009.
Hermanides, J., et al., "Current Application of Continuous Glucose Monitoring in the Treatment of Diabetes", Diabetes Care, 2011, vol. 34, Suppl. 2, pp. S197-S201.
"Important Announcement—SIBIONICS is temporarily discontinuing CGM offerings in select European countries.", 2024, retrieved from https://www.sibionicscgm.com/pages/important-announcement-sibionics-is-temporarily-discontinuing-cgm-offerings-in-select-european-countries#:~: text=SIBIONICS%20is%20temporarily%20discontinuing%20CGM, tools%20to% 20transform%20our%20health., 6 pages.
Insert Molding, 1996, retrieved from https://www.mddionline.com/equipment/insert-molding, 4 pages.
International Diabetes Device 2022 Blue Book, Seagrove Partners, 142 pages.
International Standard, IEC 62366, Medical devices—Application of usability engineering to medical devices, 2007, 214 pages.
Joseph, J. I., et al., "Glucose Sensing in the Subcutaneous Tissue: Attempting to Correlate the Immune Response with Continuous Glucose Monitoring Accuracy", Diabetes Technology & Therapeutics, 2018, vol. 20, No. 5, pp. 321-324.
Kaye, R., et al., "Medical Device Use-Safety: Incorporating Human Factors Engineering into Risk Management", 2000, retrieved from https://www.qualysinnova.com/download/files/MD-Use-Safety.pdf, pp. 1-33.
Lomas, P., "Dexcom G7 Release: The Most Exciting New Features", 2024, retrieved from https://notjustapatch.com/dexcom-g7-features/, 13 pages.
Lovett, L., "What's next for Dexcom? CEO, CTO talk G6 for inpatient use, expanding CGMs for patients without diabetes",

(56) References Cited

OTHER PUBLICATIONS 2020, retrieved from https://www.mobihealthnews.com/news/whats-next-dexcom-ceo-cto-talk-g6-inpatient-use-expanding-cgms-patients-without-diabetes, 6 pages.

Medtronic MiniMed One-press Serter User Guide, 2015, 26 pages.

Medtronic MiniMed Paradigm® 512 and 712 Insulin Pumps User Guide, 2005, pp. 1-136.

Microlet® 2 Lancing Device, 2008, retrieved from https://image.tigermedical.com/Manuals/BAY6606-20141216010820833.pdf, 1 page.

Ólafsdóttir, A. F., et al., "A Clinical Trial of the Accuracy and Treatment Experience of the Flash Glucose Monitor FreeStyle Libre in Adults with Type 1 Diabetes", Diabetes Technology & Therapeutics, 2017, vol. 19, No. 3, pp. 164-172.

"Periphery", Cambridge Dictionary of American English, 2000, p. 631.

"Product Review: Abbott FreeStyle Libre Flash Glucose Monitor", DiabetesMine Team, 2021, retrieved from https://www.healthline.com/diabetesmine/abbott-freestyle-libre-review#bottom-line, 6 pages.

"Real-World Data Show Abbott's Freestyle Libre® Systems And GLP-1 Medicines Work Better Together For People With Type 2 Diabetes", 2024, PRNewswire, 2 pages.

Sibionics GS1 Continuous Glucose Monitoring System App User Guide, 2023, 48 pages.

Sibionics GS1 Continuous Glucose Monitoring System User Guide, 2023, 25 pages.

Sibionics GS1 Continuous Glucose Monitoring System Product Insert, 2023, 3 pages.

Sibionics GS1 Quick Start Guide, 2024, 2 pages.

Van Den Boom, L., et al., "Changes in the utilization of blood glucose test strips among patients using intermittent-scanning continuous glucose monitoring in Germany", Diabetes, Obesity and Metabolism, 2020, vol. 22, pp. 922-928.

CA, 3,050,721 Examiner's Report, Nov. 8, 2024.

EP, 20177703.4 Response to Withdrawals, Jan. 7, 2025.

EP, 20177703.4 Withdrawal of Intervention, Dec. 27, 2024.

EP, 20177703.4 Withdrawal of Opposition, Dec. 27, 2024.

EP, 20177703.4 Written Submissions Dexcom, Nov. 22, 2024.

EP, 20195922.8 Withdrawal of Intervention, Dec. 27, 2024.

EP, 20195922.8 Withdrawal of Opposition, Dec. 27, 2024.

EP, 21211041.5 Withdrawal of Opposition, Dec. 27, 2024.

EP, 21211041.5 Notice of Appeal, Dec. 17, 2024.

EP, 21211041.5 Response to Summons to Attend Oral Proceedings Dexcom, Nov. 12, 2024.

EP, 21211041.5 Response to Summons to Attend Oral Proceedings, Nov. 12, 2024.

EP, 24152079.0 Examination Report, Dec. 2, 2024.

EP, 24194029.5 Extended Search Report, Nov. 18, 2024.

EP, 24201435.5 Extended Search Report, Jan. 27, 2025.

JP, 2024-31538 Office Action, Oct. 16, 2024.

MX, MX/a/2021/007294 Office Action, Aug. 20, 2024.

MY, PI2022002786 Examination Report, Jan. 8, 2025.

UP, Oral Hearing—Counterclaim for Revocation in Litigation of EP 3977921, Dec. 19, 2024.

UP, Rejoinder to the Reply to the Defence to the Application to Amend the Patent (EP 3 977 932 B1), Dec. 9, 2024.

UP, Second Expert Opinion of Dr Michael Schoemaker in Litigation of EP 3977921, Nov. 8, 2024.

UP, Rejoinder to the Reply to the Statement of Defence in the Infringement Action Regarding EP 3 977 921 B1, Nov. 8, 2024.

UP, Rejoinder to the Reply to the Defence to the Counterclaim for Revocation and Reply to the Defence to the Conditional Amendment Application in Litigation of EP 3977921, Nov. 8, 2024.

UP, Second Expert Statement of Pantelis Georgiou in Litigation of EP 3977921, Nov. 7, 2024.

UP, Second Expert Statement of Andrew Varde in Litigation of EP 3977921, Nov. 7, 2024.

US, Decision Denying Institution of Inter Partes Review, IPR No. 2024-00860, Nov. 20, 2024.

US, Patent Owner's Response To Petitioner's Explanation Of Parallel Petitions Challenging U.S. Pat. No. 11,510,325, IPR No. 2024-00860, Aug. 23, 2024.

US, Patent Owner Preliminary Response Pursuant to 37 C.F.R. § 42.107, IPR No. 2024-00860, Aug. 23, 2024.

US, Declaration of Julia Castellano, IPR No. 2024-00860, Aug. 21, 2024.

US, Declaration of Scott E. Davis, IPR No. 2024-00860, Jun. 5, 2024.

US, Petitioner's Explanation Of Parallel Petitions Challenging U.S. Pat. No. 11,510,325, IPR No. 2024-00860, May 9, 2024.

US, Termination Due to Settlement After Institution of Trial, IPR No. 2023-01409, Jan. 7, 2025.

US, Joint Motion to Treat Settlement Agreement as Business Confidential Information. IPR No. 2023-01409, Jan. 3, 2025.

US, Joint Motion to Terminate Proceeding Under 35 U.S.C. § 317(a), IPR No. 2023-01409, Jan. 3, 2025.

US, Order Setting Oral Argument, IPR No. 2023-01409, Dec. 11, 2024.

US, Patent Owner's Sur-Reply, IPR No. 2023-01409, Dec. 10, 2024.

US, Deposition of Gary D. Fletcher, Ph.D., IPR No. 2023-01409, Dec. 4, 2024.

US, Patent Owner's Request For Oral Argument, IPR No. 2023-01409, Dec. 3, 2024.

US, Petitioner's Request For Oral Argument, IPR No. 2023-01409, Dec. 3, 2024.

US, Patent Owner's Objections to Petitioner's Exhibits Submitted With Its Reply, IPR No. 2023-01409, Nov. 1, 2024.

US, Petitioner's Updated Exhibit List, IPR No. 2023-01409, Oct. 25, 2024.

US, Second Declaration of Gary Fletcher, Ph.D., IPR No. 2023-01409, Oct. 25, 2024.

US, Petitioner's Reply to Patent Owner's Response, IPR No. 2023-01409, Oct. 25, 2024.

US, Deposition of Karl R. Leinsing, MSME, PE, IPR No. 2023-01409, Oct. 17, 2024.

US, Conference Call Before The Patent Trial And Appeal Board • Before Judge Cynthia Hardman, IPR No. 2023-01409, Oct. 17, 2024.

US, Notice of Joint Stipulation to Modify Schedule, IPR No. 2023-01409, Sep. 26, 2024.

US, Decision Denying Patent Owner's Request on Rehearing of Decision Denying Institution, IPR No. 2023-01396, Aug. 9, 2024.

US, Ex Parte Reexamination Certificate of U.S. Pat. No. 11,000,216, Nov. 14, 2024.

US, Reexamination U.S. Appl. No. 90/019,307 Decision on Petition, Feb. 13, 2025.

US, Ex Parte Reexamination Certificate of U.S. Pat. No. 10,959,654, Nov. 5, 2024.

US, Reexamination U.S. Appl. No. 90/019,330 Notice of Intent to Issue Ex Parte Reexamination Certificate of U.S. Pat. No. 10,959,654, Jul. 1, 2024.

US, Exhibit 591-15 from DexCom, Inc.'s Final Invalidity Contentions, Case No. 23-CV-239 (D. Delaware), Jan. 26, 2024.

US, Exhibit 591-14 from DexCom, Inc.'s Final Invalidity Contentions, Case No. 23-CV-239 (D. Delaware), Jan. 26, 2024.

US, Exhibit 591-13 from DexCom, Inc.'s Final Invalidity Contentions, Case No. 23-CV-239 (D. Delaware), Jan. 26, 2024.

Exhibit 591-12 from DexCom, Inc.'s Final Invalidity Contentions, Case No. 23-CV-239 (D. Delaware), Jan. 26, 2024.

US, Exhibit 591-11 from DexCom, Inc.'s Final Invalidity Contentions, Case No. 23-CV-239 (D. Delaware), Jan. 26, 2024.

US, Exhibit 591-9 from DexCom, Inc.'s Final Invalidity Contentions, Case No. 23-CV-239 (D. Delaware), Jan. 26, 2024.

US, Exhibit 591-8 from DexCom, Inc.'s Final Invalidity Contentions, Case No. 23-CV-239 (D. Delaware), Jan. 26, 2024.

US, Exhibit 591-7 from DexCom, Inc.'s Final Invalidity Contentions, Case No. 23-CV-239 (D. Delaware), Jan. 26, 2024.

US, Exhibit 591-6 from DexCom, Inc.'s Final Invalidity Contentions, Case No. 23-CV-239 (D. Delaware), Jan. 26, 2024.

US, Exhibit 591-4 from DexCom, Inc.'s Final Invalidity Contentions, Case No. 23-CV-239 (D. Delaware), Jan. 26, 2024.

(56) References Cited

OTHER PUBLICATIONS

US, Exhibit 591-3 from DexCom, Inc.'s Final Invalidity Contentions, Case No. 23-CV-239 (D. Delaware), Jan. 26, 2024.
US, Exhibit 591-2 from DexCom, Inc.'s Final Invalidity Contentions, Case No. 23-CV-239 (D. Delaware), Jan. 26, 2024.
US, Exhibit 591-1 from DexCom, Inc.'s Final Invalidity Contentions, Case No. 23-CV-239 (D. Delaware), Jan. 26, 2024.
US, Transcript of Jury Trail. Vol. II, Case No. 21-CV-977-KAJ (D. Delaware), Mar. 12, 2024.
Abbott Patent Marking Diabetes, 2024, retrieved from https://www.abbott.com/patents/diabetes-patents.html, 6 pages.
Burge, M. R., et al., "Continuous Glucose Monitoring: The Future of Diabetes Management", Diabetes Spectrum, 2008, vol. 21, No. 2, pp. 112-119.
Clancy, N. T., et al., "A new device for assessing changes in skin viscoelasticity using indentation and optical measurement", Skin Research and Technology, 2010, vol. 16, pp. 210-228.
Cleo® 90 Infusion Set 510(k) Premarket Notification, 2004, 1 page.
Dexcom STS Continuous Monitors FDA Premarket Approval (PMA), 2006, 2 pages.
Mazze, R. S., et al., "Evaluating the Accuracy, Reliability, and Clinical Applicability of Continuous Glucose Monitoring (CGM): Is CGM Ready for Real Time?", Diabetes Technology & Therapeutics, 2009, vol. 11, No. 1., pp. 11-18.
Piper, H. G., et al., "Real-Time Continuous Glucose Monitoring in Pediatric Patients During and After Cardiac Surgery", Pediatrics, 2006, vol. 118, No. 3, pp. 1176-1184.
Rabiee, A., et al., "Numerical and Clinical Accuracy of a Continuous Glucose Monitoring System during Intravenous Insulin Therapy in the Surgical and Burn Intensive Care Units", Journal of Diabetes Science and Technology, 2009, vol. 3, No. 4, pp. 951-959.
Sacks, A. H., et al., "Skin blood flow changes and tissue deformations produced by cylindrical indentors", Journal of Rehabilitation Research and Development, 1985, vol. 22, No. 3, pp. 1-6.
Schneider, M., et al., "Evaluating the use of the Cleo® 90 infusion set for patients on a palliative care unit", International Journal of Palliative Nursing, 2009, vol. 15,. No. 8, pp. 372-376.
AU, 2019404908 Examiner's Report, Feb. 17, 2025.
CA, 3,228,738 Examiner's Report, May 8, 2025.
CN, 202211091194.1 Notification of Filing Divisional Application, Mar. 27, 2025.
EP, 17182379.2 Reply to Reply to Opposition, May 16, 2025.

EP, 17182379.2 Reply to Opposition, Feb. 27, 2025.
EP, 19900891.3 Examination Report, May 8, 2025.
EP, 21211041.5 Grounds of Appeal, Apr. 23, 2025.
EP, 21211041.5 Minutes of Oral Proceedings, Dec. 13, 2024.
EP, 23190032.5 Examination Report, May 19, 2025.
EP, 24220160.6 Extended Search Report, Jun. 17, 2025.
JP, 2023-516522 Office Action, Mar. 5, 2025.
JP, 2023-514023 Office Action, Apr. 16, 2025.
MX, MX/a/2021/007294 Second Office Action, Feb. 19, 2025.
MY, PI2021003022 Examination Report, Mar. 5, 2025.
US, Reexamination U.S. Appl. No. 90/019,307 Office Action, Mar. 18, 2025.
US, Reexamination U.S. Appl. No. 90/019,329 Decision on Petition Under 37 C.F.R. § 1.181, Mar. 18, 2025.
WO, PCT/US25/13698 ISR and Written Opinion, Jun. 5, 2025.
WO, PCT/US25/13698 Invitation to Pay Additional Fees, Apr. 15, 2025.
CN, 202180063087.5 First Office Action, Aug. 14, 2025.
EP, 17182379.2 Written Submissions, Aug. 6, 2025.
EP, 17182379.2 Summons to Attend Oral Proceedings, Jul. 4, 2025.
EP, 19151577.4 Examination Report, Sep. 3, 2025.
EP, 20177712.5 Written Submissions Gulde, Aug. 21, 2025.
EP, 20177712.5 Response to Summons to Attend Oral Proceedings, Aug. 21, 2025.
EP, 21192910.4 Notice of Opposition Stolmar, Sep. 10, 2025
EP, 21192910.4 Notice of Opposition Strawman, Sep. 10, 2025.
EP, 24218309.3 Extended Search Report, Jul. 9, 2025.
EP, 24194029.5 Examination Report, Aug. 26, 2025.
JP, 2023-514023 Final Office Action, Aug. 20, 2025.
JP, 2023-514024 Office Action, Apr. 30, 2025.
JP, 2023-532327 Office Action, Jul. 23, 2025.
JP, 2025-026588 Office Action, Aug. 27, 2025.
US, Reexamination U.S. Appl. No. 90/019,307 Final Office Action, Jul. 8, 2025.
WO, PCT/US25/27260 Invitation to Pay Additional Fees, Jul. 24, 2025.
EP, 24201435.5 Examination Report, Oct. 28, 2025.
EP, 21192910.4 Notice of Intervenrtion SenEaron, Nov. 14, 2025.
UP, Reply to Objection for Provisional Measures in the Litigation of EP 3960072, Dec. 5, 2025.
UP, Objection to the Application for provisional measures in the Litigation of EP 3960072, Nov. 17, 2025.

* cited by examiner

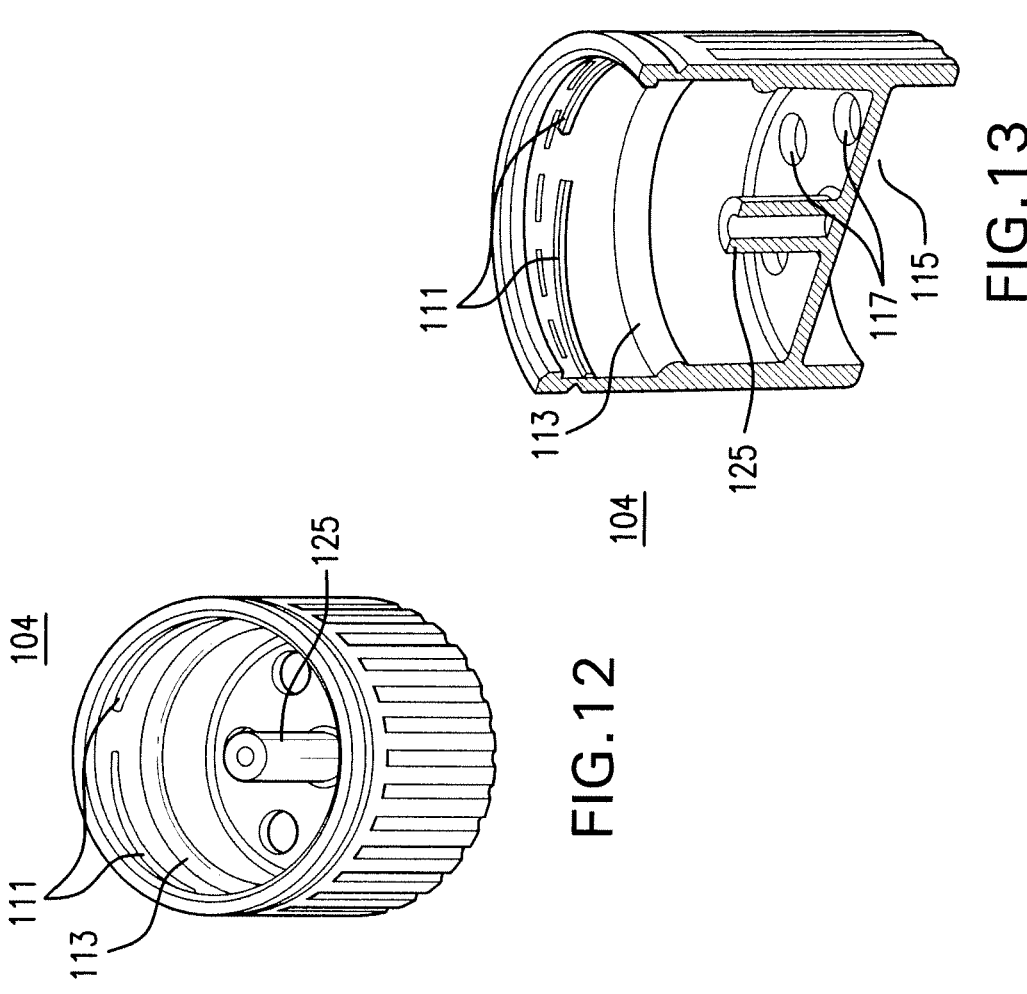
FIG.13
FIG.12
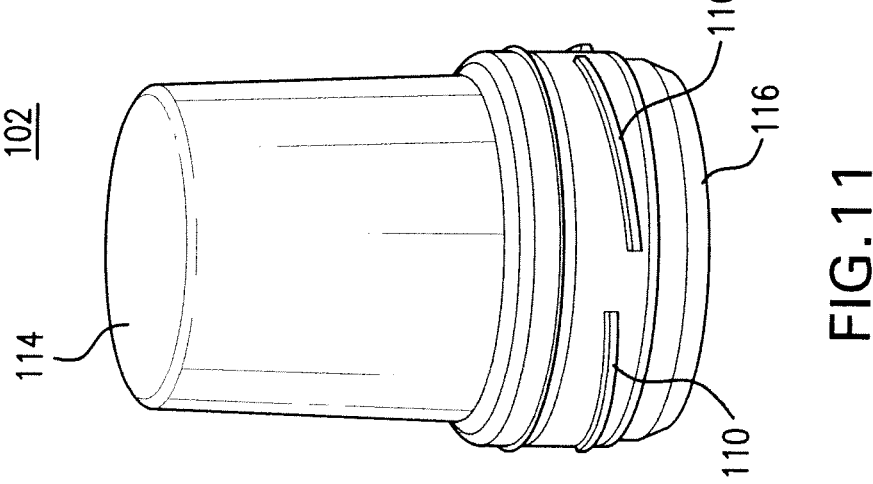
FIG.11

774

774

122

ANALYTE SENSOR AND APPARATUS FOR INSERTION OF THE SENSOR

CROSS-REFERENCE TO RELATED APPLICATIONS

The present application is a continuation of U.S. patent application Ser. No. 17/221,169, filed Apr. 2, 2021, which is a continuation of U.S. patent application Ser. No. 17/009, 647, filed Sep. 1, 2020, now U.S. Pat. No. 11,006,870, which is a continuation of U.S. patent application Ser. No. 16/736, 728, filed Jan. 7, 2020, now U.S. Pat. No. 10,786,190, which is a continuation of U.S. patent application Ser. No. 15/994, 129, filed May 31, 2018, now abandoned, which is a continuation of U.S. patent application Ser. No. 15/475,647, filed Mar. 31, 2017, now U.S. Pat. No. 9,993,188, which is a continuation of U.S. patent application Ser. No. 15/192, 531, filed Jun. 24, 2016, now U.S. Pat. No. 9,636,068, which is a continuation of U.S. patent application Ser. No. 12/698, 129, filed Feb. 1, 2010, now U.S. Pat. No. 9,402,544, which claims priority to U.S. Provisional Application No. 61/149, 639, filed Feb. 3, 2009, all of which are incorporated herein by reference in their entireties for all purposes. This application is further related to U.S. patent application Ser. No. 12/698,124, filed Feb. 1, 2010, the disclosure of which is incorporated by reference in its entirety herein for all purposes.

FIELD OF THE INVENTION

The present invention relates generally to an inserter device, for example, to insert an analyte sensor and/or an infusion set in an animal such as a human.

BACKGROUND OF THE INVENTION

Diabetes Mellitus is an incurable chronic disease in which the body does not produce or properly utilize insulin. Insulin is a hormone produced by the pancreas that regulates blood sugar (glucose). In particular, when blood sugar levels rise, e.g., after a meal, insulin lowers the blood sugar levels by facilitating blood glucose to move from the blood into the body cells. Thus, when the pancreas does not produce sufficient insulin (a condition known as Type 1 Diabetes) or does not properly utilize insulin (a condition known as Type II Diabetes), the blood glucose remains in the blood resulting in hyperglycemia or abnormally high blood sugar levels.

The vast and uncontrolled fluctuations in blood glucose levels in people suffering from diabetes cause long-term, serious complications. Some of these complications include blindness, kidney failure, and nerve damage. Additionally, it is known that diabetes is a factor in accelerating cardiovascular diseases such as atherosclerosis (hardening of the arteries), leading to stroke, coronary heart disease, and other diseases. Accordingly, one important and universal strategy in managing diabetes is to control blood glucose levels.

One way to manage blood glucose levels is testing and monitoring blood glucose levels by using conventional in vitro techniques, such as drawing blood samples, applying the blood to a test strip, and determining the blood glucose level using colorimetric, electrochemical, or photometric test meters. Another more recent technique for monitoring blood glucose levels is by using an in vivo glucose monitoring system, that continuously or automatically tests glucose, such as for example, the FreeStyle Navigator® Continuous Glucose Monitoring System, manufactured by Abbott Diabetes Care Inc. Unlike conventional blood glucose meters, continuous analyte monitoring systems employ an insertable or implantable sensor, which detects and monitors blood glucose levels. Prior to each use of a new sensor, the user self-implants at least a portion of the sensor under his skin. Typically, an inserter assembly is employed to insert the sensor in the body of the user. In this manner, an introducer sharp, while engaged to the sensor, pierces an opening into the skin of the user, releases the sensor and is removed from the body of the user. Accordingly, there exists a need for an easy-to-use, simple, insertion assembly which is reliable, minimizes pain, and is easy to use.

SUMMARY

Sensor assemblies that include a medical device, such as an analyte sensor (e.g., a glucose sensor) and/or an infusion device, and a device to position at least a portion of the medical device beneath a skin surface of a user are provided, as well as methods of positioning at least a portion of a medical device such as an analyte sensor (e.g., a glucose sensor) and/or an infusion device beneath a skin surface of a user, and methods of analyte testing.

Sensor assembly embodiments include a mount adapted to adhere to a skin of a subject; an analyte sensor coupled to the mount, and an insertion sharp having a longitudinal body including a longitudinal opening to receive at least a portion of the sensor body.

In certain embodiments, the sensor includes a body having a proximal section and a distal section, and the distal section may be longitudinally (or otherwise) aligned with the proximal section. Some sensor embodiments may include an intermediate section. An intermediate section, if present, may be laterally displaced from at least the distal member (or distal section), and a gap may be defined between the laterally displaced intermediate section and a portion of the distal section. In some embodiments, the sensor is integrated with the mount to define an on-body device such as a single unit on-body device. A second gap may be defined in the sensor between the proximal section and the laterally displaced intermediate section. The proximal section of the sensor may have a substantially curved profile.

In some embodiments, the distal section of the sensor body is received in the longitudinally defined opening of the insertion sharp. A gap may be defined between the distal section and the laterally displaced intermediate section, which allows the distal section, in some embodiments a substantial portion—including the entirety of the distal section, to be received in the longitudinal opening of the insertion needle. The intermediate section and the proximal section may be proximate the distal section received in the insertion needle.

In some embodiments, the proximal section of the sensor body is in communication with conductive material disposed on the mount. The conductive material disposed on the mount may define a printed circuit board. The proximal section of the sensor may be disposed in a horizontal plane, and the distal section of the sensor body may be disposed in a vertical plane. In some embodiments, the sensor is a transcutaneous sensor. In some embodiments, the sensor is configured for implantation in a soft tissue of a user. In some embodiments, the sensor is a glucose sensor.

Embodiments include sensor assemblies which include a sensor comprising a portion for operative contact with a fluid of the subject; a mount defining a distal surface adapted for attachment to the skin of a subject and housing a circuit coupled to sensor for performing a function with the sensor;

and a switch at least partially disposed in the mount comprising a member having a first position which protrudes from the distal surface of the mount and a second position which is recessed in the mount, the member configured to activate the circuit when in the second position.

In some embodiments, the member is biased in the first position. The member may comprise an elongated member disposed in an opening in the mount. In some embodiments, the member is moved from the first position to the second position when the mount contacts the skin of the subject. In some embodiments, an adhesive layer is disposed on the skin of the subject, and wherein the member is moved from the first position to the second position when the mount contacts the adhesive layer.

In some embodiments, the switch activates the circuit upon the member reaching the second position. In some embodiments, the switch activates the circuit as long as the member is maintained in the second position. In some embodiments, the sensor is a glucose sensor.

In some embodiments, the circuit applies a potential to the sensor. In some embodiments, the circuit applies a current to the sensor.

In some embodiments, a monitor unit is provided to receive information from the sensor/on-body unit. For example, the system is configured for communication (wired or wirelessly) between the on-body unit and a monitor unit, e.g., using radio frequency communication or other protocol. The communication between the two units may be active or passive. In certain embodiments, the on-body unit circuit includes communication components for wired or wireless transmission of signal relating to analyte level monitored by the sensor to the monitor unit. In certain embodiments, RFID components may be included in the on-body unit and monitor unit to enable RFID communication, in which the on-body unit provides data communication to the monitor unit in response to one or more commands or data communication received from the monitor unit. In some embodiments, the transmitter transmits a signal to the receiver automatically, e.g., continuously or in certain embodiments only periodically, such as according to a predetermined schedule. In some embodiments, in addition to or instead of automatic data communication, the on-body unit may transmit signal to the receiver only in response to a request for the data, e.g., received from the monitor unit or otherwise initiated by the user (e.g., activation of a switch on the receiver or on-body unit to initiate data transfer). In some embodiments, a memory is provided, and the circuit stores a signal relating an analyte level provided by the sensor to the memory. In some embodiments, the sensor is a glucose sensor.

Embodiments include apparatuses for inserting medical devices through the skin of a subject. An insertion apparatus may include a sheath defining a distal surface for placement on the skin of the subject; a handle movable between a proximal position and distal position relative to the sheath; a device support for supporting the medical device and defining an aperture therethrough; a sharp support for supporting a sharp extending through said aperture and coupled to the handle; and driver for biasing the handle and the sharp support towards the proximal position.

In some embodiments, the driver comprises a compression member such as a compression spring. In some embodiments, the handle is at least partially disposed within the sheath. In some embodiments, the handle is at least partially disposed surrounding the sheath. In some embodiments, a bellows portion is provided which is disposed between the handle and the sheath.

In some embodiments, the sharp support is permanently fixed to the handle. In some embodiments, the device support is permanently affixed to the handle.

In some embodiments, a stop portion for retaining the device support in the distal position is included. In some embodiments, the device support is coupled to the sharp support until the device support reaches a distal position.

In some embodiments, the device support is uncoupled from the sharp support when the device support reaches the distal position. In some embodiments, a retention member is provided to couple the sharp support to the sheath when the sharp support is disposed in the proximal position.

In some embodiments, the medical device is an analyte sensor. In some embodiments, the medical device is a glucose sensor. In some embodiments, the medical device is an infusion set.

In certain embodiments, apparatuses for inserting a medical device through the skin of a subject, are provided which include a sheath defining a distal surface for placement on the skin of the subject; a handle movable between a proximal position and distal position; a device support for supporting the medical device and defining an aperture therethrough, the device support coupled to the handle; a sharp support for supporting a sharp extending through said aperture and coupled to the device support; and driver for biasing the sharp support towards the proximal position.

In some embodiments, the driver comprises a compression spring. In some embodiments, the handle is at least partially disposed surrounding the sheath.

In some embodiments, a stop portion for retaining the device support in the distal position is included. In some embodiments, the device support is coupled to the sharp support until the device support reaches a distal position. In some embodiments, the device support is uncoupled from the sharp support when the device support reaches the distal position.

Embodiments of analyte sensors are provided which include a body having a proximal section and a distal section. The distal section may be longitudinally aligned with the proximal section. An intermediate section may be included between the proximal and distal sections, and in some embodiments the intermediate section is laterally displaced from at least the distal member. A gap may be defined between the laterally displaced intermediate section and a portion of the distal section.

In some embodiments, the intermediate section is laterally displaced from at least a portion of the proximal section of the sensor body. A second gap may be defined between the laterally displaced intermediate section and the proximal section of the sensor body. The intermediate section may have a distal end and a proximal end, and further the proximal section may be coupled to the proximal section and the distal section may be coupled to the distal section of the sensor body. In some embodiments, the intermediate section is a longitudinal member. The proximal end may be proximate to the gap defined between the distal member and the intermediate member.

In some embodiments, the proximal end is received within a needle seat to create an anchor region to allow the sensor body to slide into an opening defined in the insertion sharp but prevent the sensor body from inadvertently slipping out of the insertion needle. In some embodiments, a width of the distal section of the sensor body is sized to fit within the opening of the insertion sharp having a diameter less than about 22 to about 24 gauge.

In some embodiments, the intermediate member includes a plane-altering portion. The plane-altering portion allows the proximal section of the sensor body to be in a plane different than the distal section of the sensor body. In some embodiments, the proximal section and the distal section are in planes substantially perpendicular to each other, e.g., the area may define an angle of about 120° to about 60°, e.g., about 90 degrees.

In some embodiments, the proximal section has a curved portion.

In some embodiments, the sensor body includes conductive material disposed in or on a surface thereto to define one or more electrodes. The sensor body may include conductive material defining traces disposed in or on a surface of the sensor body. The traces are in communication with the one or more electrodes. The traces may be disposed in or on at least surface of the proximal section of the sensor body. The one or more electrodes may be disposed on the distal section of the sensor body. At least one of the traces or electrodes may include a metal or carbon material such as gold, platinum, titanium, carbon. At least one of the traces or electrodes may be formed by ablation of material. The ablation may include laser ablation.

In some embodiments, the sensor comprises a sensing layer. The sensing layer may comprise an enzyme. The sensing layer may comprise an electron transfer agent. The electron transfer agent may be a redox mediator. In some embodiments, the electron transfer agent includes osmium transition metal complexes and one or more ligands. The electron transfer agent may be configured to transfer electrons directly between the analyte and the working electrode. The electron transfer agent may be configured to transfer electrons indirectly between the analyte and the working electrode.

In some embodiments, the sensing layer comprises a redox polymer. The redox polymer may include osmium. The sensing layer may include a catalyst. The catalyst may include an enzyme. The catalyst may act as an electron transfer agent. In some embodiments, the enzyme includes glucose oxidase. In some embodiments, the enzyme includes glucose dehydrogenase.

In some embodiments, the sensing layer is configured such that the reaction of glucose in the presence of an enzyme forms hydrogen peroxide, and glucose level may be correlated to the level of hydrogen peroxide. In some embodiments, the sensor is a subcutaneous sensor.

These and other features, objects and advantages of the disclosed subject matter will become apparent to those persons skilled in the art upon reading the detailed description as more fully described below.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

FIGS. 11-12 are perspective views of components of the inserter of FIG. 10 in accordance with the disclosed subject matter;

FIG. 13 is a sectional view of a component of the inserter of FIG. 10 in accordance with the disclosed subject matter;

FIGS. 34A-36B illustrate a power supply switch mechanism including conductive pads on the on-body integrated sensor and sensor electronics assembly in accordance with embodiments of the disclosed subject matter;

DETAILED DESCRIPTION OF THE EMBODIMENTS

Figure 1:
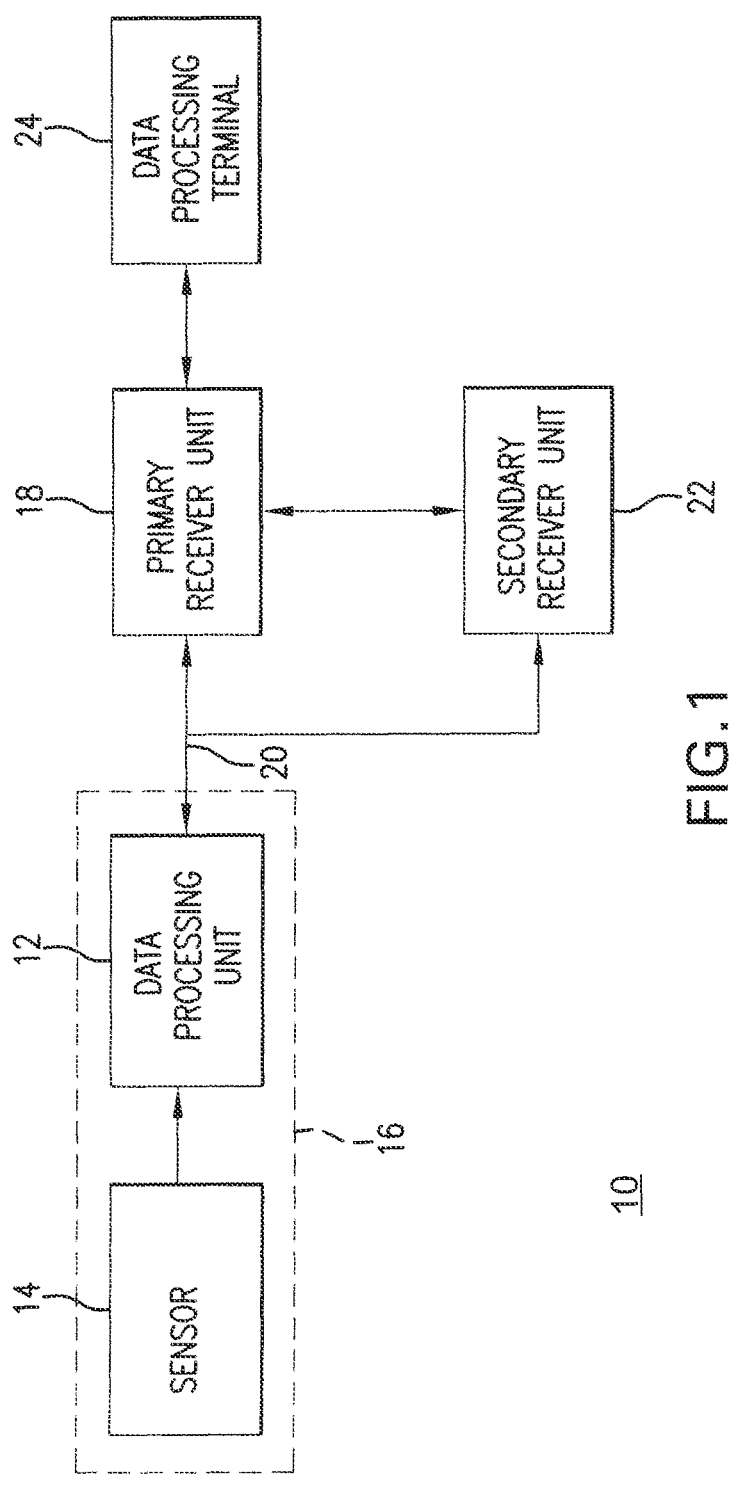
FIG. 1 is a schematic view of the system in accordance with one embodiment of the disclosed subject matter.

A detailed description of the disclosure is provided herein. It should be understood, in connection with the following description, that the subject matter is not limited to particular embodiments described, as the particular embodiments of the subject matter may of course vary. It is also to be understood that the terminology used herein is for the purpose of describing particular embodiments only, and is not intended to be limiting, since the scope of the disclosed subject matter will be limited only by the appended claims.

Where a range of values is provided, it is understood that each intervening value between the upper and lower limit of that range and any other stated or intervening value in that stated range, is encompassed within the disclosed subject matter. Every range stated is also intended to specifically disclose each and every "subrange" of the stated range. That is, each and every range smaller than the outside range specified by the outside upper and outside lower limits given for a range, whose upper and lower limits are within the range from said outside lower limit to said outside upper limit (unless the context clearly dictates otherwise), is also to be understood as encompassed within the disclosed subject matter, subject to any specifically excluded range or limit within the stated range. Where a range is stated by specifying one or both of an upper and lower limit, ranges excluding either or both of those stated limits, or including one or both of them, are also encompassed within the disclosed subject matter, regardless of whether or not words such as "from", "to", "through", or "including" are or are not used in describing the range.

Unless defined otherwise, all technical and scientific terms used herein have the same meaning as commonly understood by one of ordinary skill in the art to which this disclosed subject matter belongs. Although any methods and materials similar or equivalent to those described herein can also be used in the practice or testing of the present disclosed subject matter, this disclosure may specifically mention certain exemplary methods and materials.

All publications mentioned in this disclosure are, unless otherwise specified, incorporated herein by reference for all purposes, including without limitation to disclose and describe the methods and/or materials in connection with which the publications are cited.

The publications discussed herein are provided solely for their disclosure prior to the filing date of the present application. Nothing herein is to be construed as an admission that the present disclosed subject matter is not entitled to antedate such publication by virtue of prior invention. Further, the dates of publication provided may be different from the actual publication dates, which may need to be independently confirmed.

As used herein and in the appended claims, the singular forms "a", "an", and "the" include plural referents unless the context clearly dictates otherwise.

Nothing contained in the Abstract or the Summary should be understood as limiting the scope of the disclosure. The Abstract and the Summary are provided for bibliographic and convenience purposes and due to their formats and purposes should not be considered comprehensive.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosed subject matter. Any recited method can be carried out in the order of events recited, or in any other order which is logically possible. Reference to a singular item, includes the possibility that there are plural of the same item present. When two or more items (for example, elements or processes) are referenced by an alternative "or", this indicates that either could be present separately or any combination of them could be present together except where the presence of one necessarily excludes the other or others.

System Overview

Certain classes of analyte monitors are provided in small, lightweight, battery-powered and electronically-controlled systems. Such a system may be configured to detect signals indicative of in vivo analyte levels using an electrochemical sensor, and collect such signals, with or without processing the signal. In some embodiments, the portion of the system that performs this initial processing may be configured to provide the raw or initially processed data to another unit for further collection and/or processing. Such provision of data may be effected, for example, via a wired connection, such as an electrical, or via a wireless connection, such as an IR or RF connection.

Certain analyte monitoring systems for in vivo measurement employ a sensor that measures analyte levels in interstitial fluids under the surface of the subject's skin. These may be inserted partially through the skin ("transcutaneous") or entirely under the skin ("subcutaneous"). A sensor in such a system may operate as an electrochemical cell. Such a sensor may use any of a variety of electrode configurations, such as a three-electrode configuration (e.g., with "working", "reference" and "counter" electrodes), driven by a controlled potential (potentiostat) analog circuit, a two-electrode system configuration (e.g., with only working and counter electrodes), which may be self-biasing and/or self-powered, and/or other configurations. In some embodiments, the sensor may be positioned within a blood vessel.

In certain systems, the analyte sensor is in communication with a sensor control unit. As used in this disclosure, an on-body unit sometimes refers to such a combination of an analyte sensor with such a sensor control unit.

Certain embodiments are modular. The on-body unit may be separately provided as a physically distinct assembly, and configured to provide the analyte levels detected by the sensor over a communication link to a monitor unit, referred to in this disclosure as a "receiver unit" or "receiver device", or in some contexts, depending on the usage, as a "display unit," "handheld unit," or "meter". The monitor unit, in some embodiments, may include, e.g., a mobile telephone device, a personal digital assistant, other consumer electronic device such as MP3 device, camera, radio, etc., or other communication-enabled data processing device.

The monitor unit may perform data processing and/or analysis, etc. on the received analyte data to generate information pertaining to the monitored analyte levels. The monitor unit may incorporate a display screen, which can be used, for example, to display measured analyte levels, and/or audio component such as a speaker to audibly provide information to a user, and/or a vibration device to provide tactile feedback to a user. It is also useful for a user of an analyte monitor to be able to see trend indications (including the magnitude and direction of any ongoing trend), and such data may be displayed as well, either numerically, or by a visual indicator, such as an arrow that may vary in visual attributes, such as size, shape, color, animation, or direction. The receiver device may further incorporate an in vitro analyte test strip port and related electronics in order to be able to make discrete (e.g., blood glucose) measurements.

The modularity of these systems may vary. In some embodiments the sensor is attachable and detachable from the sensor control unit (and the on-body unit may be reusable), while in other embodiments, the sensor and sensor control unit may be provided as an integrated, un-detachable package, which may be disposable after use.

FIG. 1 shows one embodiment of an analyte measurement system 10. In such a system, a data processing unit or sensor control unit 12 may interact with an analyte sensor 14 to obtain signals representative of analyte levels. Sensor control unit 12 may further include communications circuit with associated electronics (not shown). In some embodiments, the sensor control unit 12 and sensor are constructed to be maintained "on the body" of the subject for a period of time that may include hours, days, weeks, or a month or more. Accordingly, the sensor control unit 12 and sensor 14 may be referred to collectively herein as an on-body unit 16. A receiver unit or monitor unit 18 may also be provided. In the embodiment shown, sensor control unit 12 and monitor unit 18 communicate via connection 20 (in this embodiment, a wireless RF connection). Communication may occur, e.g., via RF communication, infrared communication, Bluetooth® communication, Zigbee® communication, 802.1x communication, or WiFi communication, etc. In some embodiments, the communication may include an RF frequency of 433 MHz, 13.56 MHz, or the like. In some embodiments, a secondary monitor unit 22 may be provided. A data processing terminal 24 is useful for providing further processing or review of analyte data.

In certain embodiments, system 10 may be a continuous analyte monitor (e.g., a continuous glucose monitoring system or CGM), and accordingly operate in a mode in which the communications via connection 20 has sufficient range to support a flow of data from on-body unit 16 to monitor unit 18. In some embodiments, the data flow in a CGM system is automatically provided by the on-body unit 16 to the monitor unit 18. For example, no user intervention may be required for the on-body unit 16 to send the data to the monitor unit 18. In some embodiments, the on-body unit 16 provides the signal relating to analyte level to the receiving unit 18 on a periodic basis. For example, the signal may be provided, e.g., automatically sent, on a fixed schedule, e.g., once every 250 ms, once a second, once a minute, etc. In some embodiments, the signal is provided to the monitor unit 18 upon the occurrence of an event, e.g., a hyperglycemic event or a hypoglycemic event, etc. In some embodiments, data processing unit 12 may further include local memory in which it may record, "logged data" or buffered data collected over a period of time and provide the some or all of the accumulated data to monitor unit 18 from time-to-time. Or, a separate data logging unit may be provided to acquire periodically transmitted data from a transmitter device. Data transmission in a CGM system may be one-way communication, e.g., the on-body unit 16 provides data to the monitor unit 18 without receiving signals from the monitor unit 18. In some embodiments, two-way communication is provided between the on-body unit 16 and the monitor unit 18.

In some embodiments, a signal is provided to the monitor unit 18 "on demand." According to such embodiments, the monitor unit 18 requests a signal from the on-body unit 16, or the on-body unit 16 may be activated to send signal upon activation to do so. Accordingly, one or both of the on-body unit 16 and monitor unit 18 may include a switch activatable by a user or activated upon some other action or event, the activation of which causes analyte-related signal to be transferred from the on-body unit 16 to the monitor unit 18. For example, the monitor unit 18 is placed in close proximity with a transmitter device and initiates a data transfer, either over a wired connection, or wirelessly by various means, including, for example various RF-carried encodings and protocols and IR links.

In some embodiments, the signal relating to analyte level is instantaneously generated by the analyte sensor 14 upon receipt of the request, and transmitted to the monitor unit 18 as requested, and/or the signal relating to analyte level is periodically obtained, e.g., once every 250 ms, once a second, once a minute, etc. Upon receipt of the "on demand" request at the on-body unit 16, an analyte signal is provided to the monitor unit. In some cases, the signal provided to the monitor unit 18 is or at least includes the most recent analyte signal(s).

In further embodiments, additional data is provided to the monitor unit 18 "on demand." For example, analyte trend data may be provided. Such trend data may include two or more analyte data points to indicate that analyte levels are rising, falling, or stable. Analyte trend data may include data from longer periods of time, such as, e.g., several minutes, several hours, several days, or several weeks.

Further details regarding on demand systems are disclosed in U.S. Pat. No. 7,620,438, U.S. Patent Publication Nos. 2009/0054749 A1, published Feb. 26, 2009; 2007/0149873 A1, published Jun. 28, 2007, now U.S. Pat. No. 9,014,773; 2008/0064937 A1, published Mar. 13, 2008; 2008/0071157 A1, published Mar. 20, 2008; 2008/0071158 A1, published Mar. 20, 2008; 2009/0281406 A1, published Nov. 12, 2009; 2008/0058625 A1, published Mar. 6, 2008, now U.S. Pat. No. 7,920,907; 2009/0294277 A1, published Dec. 3, 2009; 2008/0319295 A1, published Dec. 25, 2008, now U.S. Pat. No. 8,597,188; 2008/0319296 A1, published Dec. 25, 2008, now U.S. Pat. No. 8,617,069; 2009/0257911 A1, published Oct. 15, 2009, now U.S. Pat. No. 8,252,229; 2008/0179187 A1, published Jul. 31, 2008, now U.S. Pat. No. 8,808,515; 2007/0149875 A1, published Jun. 28, 2007, now U.S. Pat. No. 8,515,518; 2009/0018425 A1, published Jan. 15, 2009, now U.S. Pat. No. 8,160,670; and U.S. patent application Ser. No. 12/625,524, filed Nov. 24, 2009, now U.S. Pat. No. 8,390,455; Ser. No. 12/625,525, filed Nov. 24, 2009, now U.S. Pat. No. 8,358,210; Ser. No. 12/625,528, filed Nov. 24, 2009, now U.S. Pat. No. 8,115,635; Ser. No.

12/628,201, filed Nov. 30, 2009, now U.S. Patent Publication No. 2010/0076280; Ser. No. 12/628,177, filed Nov. 30, 2009, now U.S. Patent Publication No. 2010/0076289; Ser. No. 12/628,198, filed Nov. 30, 2009, now U.S. Patent Publication No. 2010/0076291; Ser. No. 12/628,203, filed Nov. 30, 2009, now U.S. Patent Publication No. 2010/0076292; Ser. No. 12/628,210, filed Nov. 30, 2009, now U.S. Patent Publication No. 2010/0076293; Ser. No. 12/393, 921, filed Feb. 26, 2009, now U.S. Patent Publication No. 2010/0213057; 61/149,639, filed Feb. 3, 2009; Ser. No. 12/495,709, filed Jun. 30, 2009, now U.S. Patent Publication No. 2010/0326842; 61/155,889, filed Feb. 26, 2009; 61/155, 891, filed Feb. 26, 2009; 61/155,893, filed Feb. 26, 2009; 61/165,499, filed Mar. 31, 2009; 61/227,967, filed Jul. 23, 2009; 61/163,006, filed Mar. 23, 2009; Ser. No. 12/495,730, filed Jun. 30, 2009, now U.S. Patent Publication No. 2010/ 0331643; Ser. No. 12/495,712, filed Jun. 30, 2009, now U.S. Pat. No. 8,437,827; 61/238,461, filed Aug. 31, 2009; 61/256, 925, filed Oct. 30, 2009; 61/238,494, filed Aug. 31, 2009; 61/238,159, filed Aug. 29, 2009; 61/238,483, filed Aug. 31, 2009; 61/238,581, filed Aug. 31, 2009; 61/247,508, filed Sep. 30, 2009; 61/247,516, filed Sep. 30, 2009; 61/247,514, filed Sep. 30, 2009; 61/247,519, filed Sep. 30, 2009; 61/249, 535, filed Oct. 7, 2009; Ser. No. 12/544,061, filed Aug. 19, 2009, now U.S. Patent Publication No. 2011/0046466; Ser. No. 12/625,185, filed Nov. 24, 2009, now U.S. Pat. No. 8,354,013; Ser. No. 12/625,208, filed Nov. 24, 2009, now U.S. Pat. No. 9,042,954; Ser. No. 12/624,767, filed Nov. 24, 2009, now U.S. Patent Publication No. 2011/0124993; Ser. No. 12/242,780, filed Sep. 30, 2008, now U.S. Pat. No. 8,983,568; Ser. No. 12/183,602, filed Jul. 31, 2008, now U.S. Patent Publication No. 2010/0030052; Ser. No. 12/211, 014, filed Sep. 15, 2008, now U.S. Pat. No. 8,636,884; and Ser. No. 12/114,359, filed May 2, 2008, now U.S. Pat. No. 8,080,385, each of which is incorporated by reference in its entirety herein.

The Sensor

The analyte sensor 14 of the analyte measurement system 10 may be used to monitor levels of a wide variety of analytes. Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. One or more analyte may be monitored by a given sensor.

In one embodiment of the present disclosure, sensor 14 is physically positioned in or on the body of a user whose analyte level is being monitored. Sensor 14 may be configured to continuously sample the analyte level of the user and convert the sampled analyte level, e.g., glucose concentration into a corresponding data signal, e.g., a current or voltage, for input into sensor control unit electronics. Alternatively, sensor 14 may be configured to sample analyte levels on demand. The sensor control unit electronics may amplify, filter, or otherwise process the signal provided by the sensor.

The sensor may take on a number of forms. For example, the sensor may include a flexible or rigid substrate. In some embodiments, the sensor may be a wire. In some embodiments, the sensor may include two or three or more electrodes.

Figure 2:
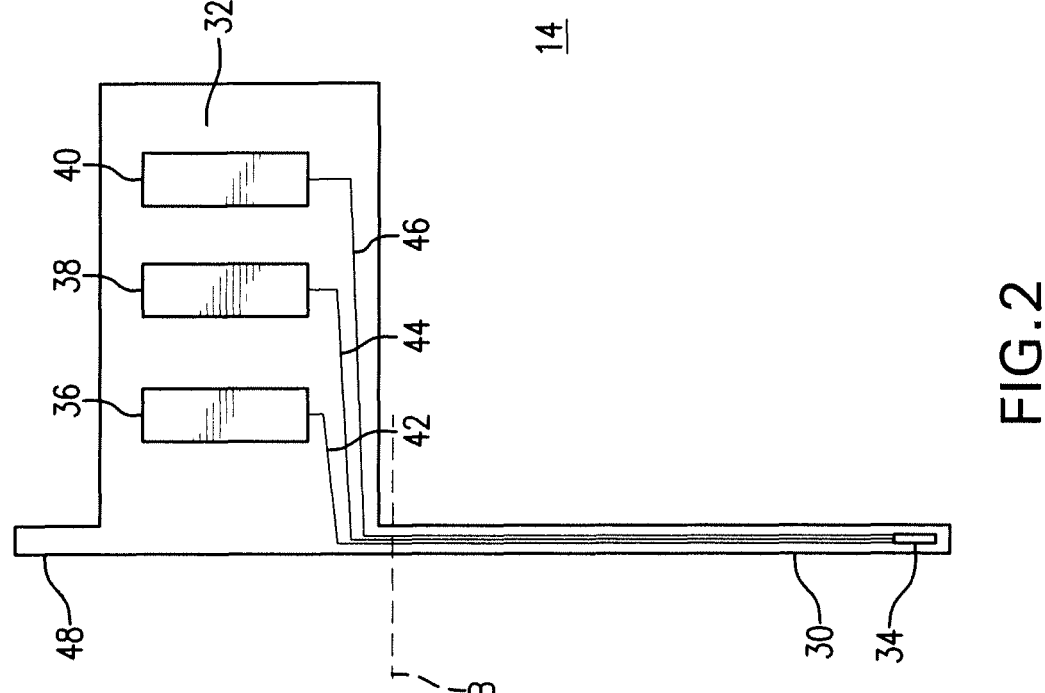
FIG. 2 is a view, in partial cross section, of an electro-chemical sensor in accordance with one embodiment of the disclosed subject matter.

An embodiment of the sensor 14 is illustrated in FIG. 2. In some embodiments, sensor 14 includes a substrate which is a dielectric, e.g., a polymer or plastic material, such as polyester or polyamide. In this embodiment, the sensor is constructed so that a portion is positionable beneath skin and a portion is above skin. Accordingly, sensor 14 includes an insertion portion 30 and a contact portion 32. The contact portion 32 typically includes several conductive contacts 36, 38, and 40 (herein shown as 3 contacts) for connection to other electronics, e.g., at the data processing unit 12. The contacts provided in this embodiment are for a working electrode 36, a reference electrode 38, and a counter electrode 40. In some embodiments, two or more working electrodes are provided. The operative portions of these electrodes, that is, working electrode, reference electrode, and counter electrode (not individually shown), are provided at the distal end of insertion portion 30. The contact and operative portions of the electrodes are connected by circuit traces 42, 44, and 46 running on the surface of substrate. In some embodiments, the traces are provided in channels, or may be embedded within the substrate, or may traverse different sides of the substrate. The conductive contacts, conductive traces, and electrodes are fabricated from a conductive material, such as platinum, palladium, gold, or conductive carbon. Further details of sensors are described, e.g., in U.S. Pat. Nos. 6,175,572; 6,103,033, which are incorporated by reference herein.

Sensor 14 may include a proximal retention portion 48. In some embodiments, the insertion portion 30 and the proximal retention portion 48 are substantially longitudinally aligned. The insertion portion 30 and the proximal retention portion 48 are sized and configured to be positioned with a sharp for installation into the skin of a subject, as described herein. In use, the sensor 14 may be configured to bend (e.g., along the line B) and therefore be positioned in two substantially perpendicular, intersecting planes.

Figure 3:
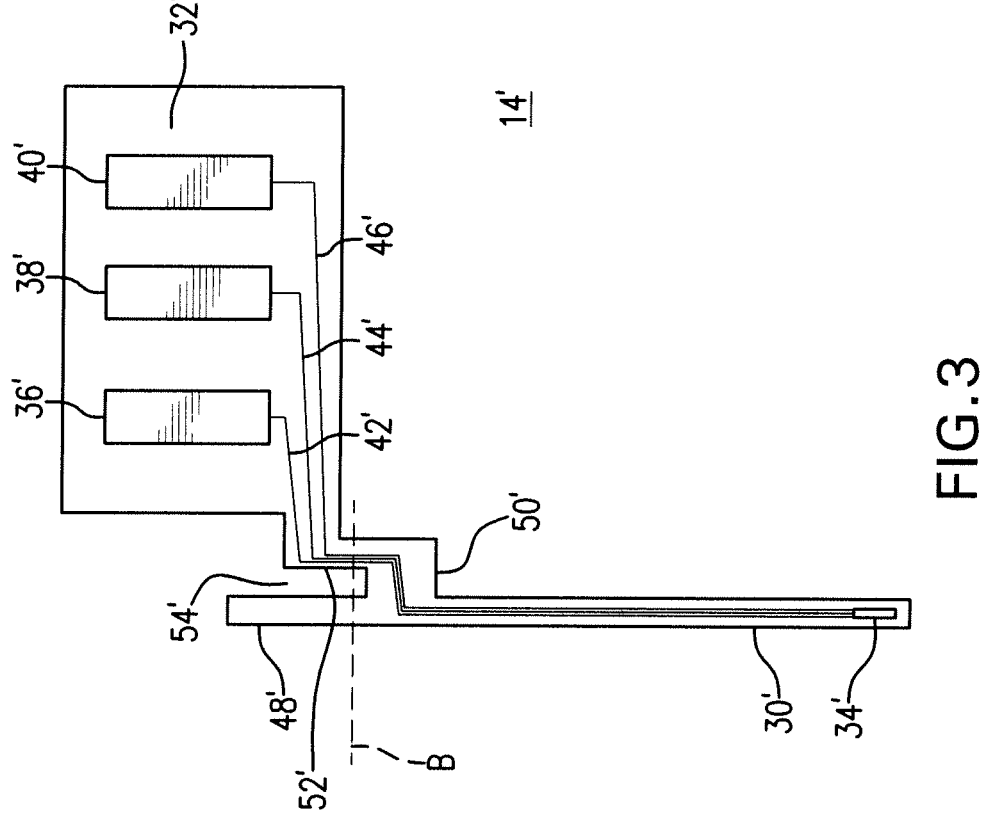
FIG. 3 is a view of an electrochemical sensor in accordance with another embodiment of the disclosed subject matter.
Figure 4:
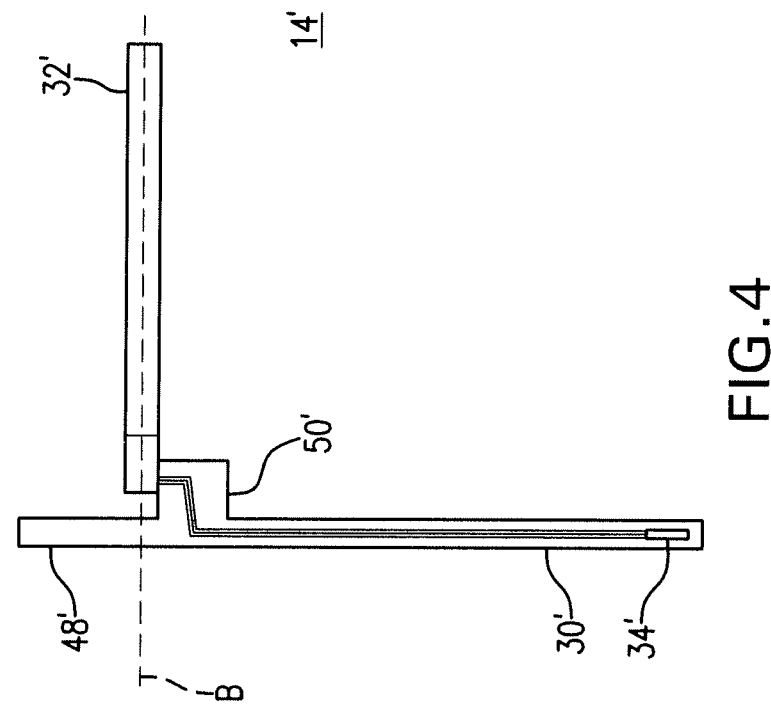
FIG. 4 is a view of the electrochemical sensor of FIG. 3 in a folded configuration in accordance with the disclosed subject matter.

As illustrated in FIG. 3, sensor 14' is substantially identical to sensor 14, with many of the differences illustrated in FIG. 3 and noted herein. Sensor 14' further includes additional features useful for connecting to, e.g., mounting to or in or on, a housing associated with the sensor control unit 12. For example, sensor 14' includes a laterally displaced portion (or sensor tab) 50' and a longitudinal displaced portion 52' which provide a path for electrical connections, e.g., the conductive traces. Sensor 14' is further provided with a notch 54' between the proximal retention portion 48' and the longitudinal displaced portion 52'. Such configuration permits the sensor 14' to bend (e.g., along the line are indicated by line B) and therefore be positioned in two substantially perpendicular, intersecting planes, as illustrated in FIG. 4. As will be described below, the sensor tab 50' can be encased in a portion of the body of the data processing unit 12 to aid in securing and positioning the sensor 14'. Proximal retention portion 48' maintains its longitudinal alignment with insertion portion 30' for positioning within an insertion sharp.

Figure 5:
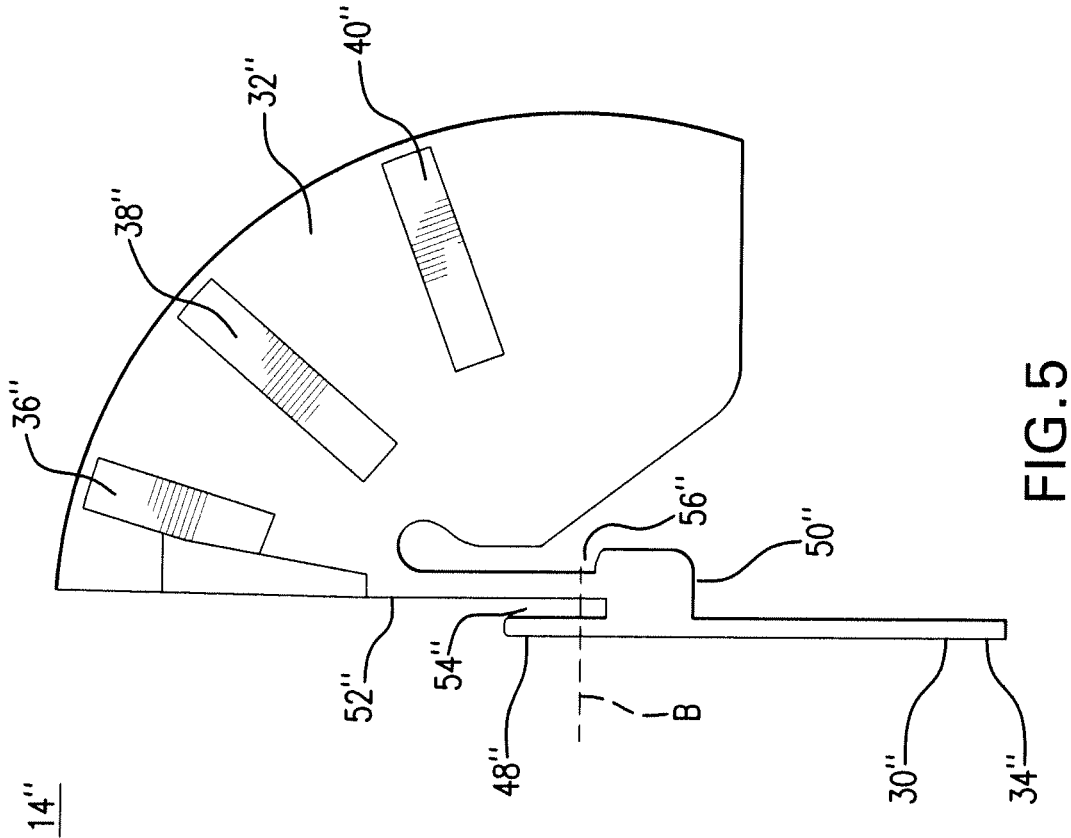
FIG. 5 is a view of an electrochemical sensor in accordance with a further embodiment of the disclosed subject matter.
Figure 6:
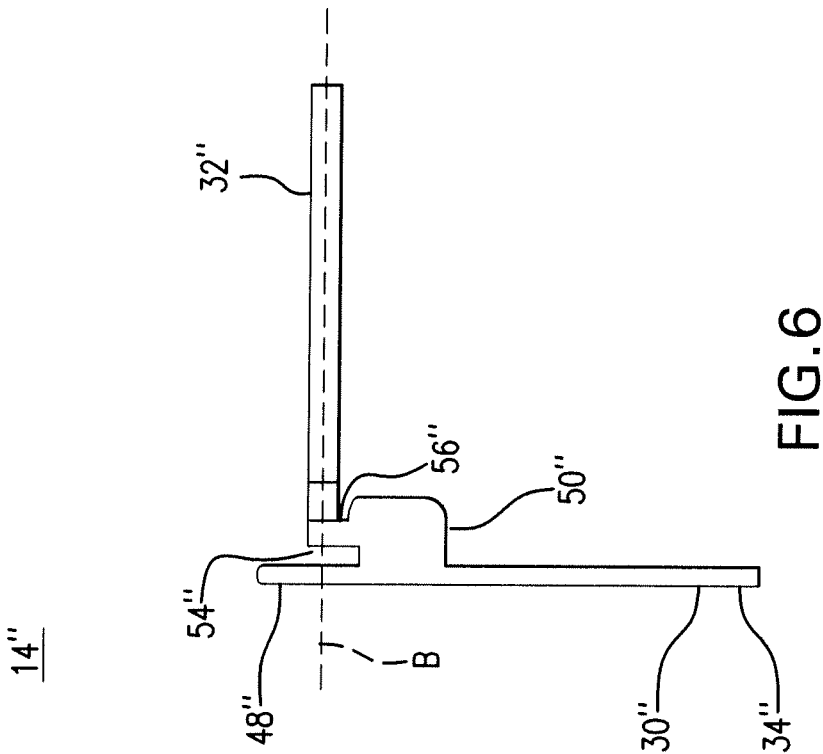
FIG. 6 is a view of the electrochemical sensor of FIG. 5 in a folded configuration in accordance with the disclosed subject matter.

FIG. 5 illustrates a further embodiment of a sensor 14" in accordance with the disclosure. Sensor 14" is substantially identical to sensor 14 and 14', with certain exemplary differences illustrated in FIG. 5 and noted herein. For example, sensor 14" includes a contact portion 32" which defines a fan-like configuration having a curved edge. Sensor 14" defines a sensor flag indentation 56" which also serves to assist in retaining the sensor 14" in vertical direction, as will be described below, and provides a discrete location for mating with a feature of the data processing unit 12, e.g., the bottom surface of a printed circuit board. Sensor 14" is likewise capable of bending along axis B, as illustrated in FIG. 6. In any of the embodiments of the sensor described herein, the distance between insertion portion 30 to retention portion 48 may be, e.g., about 5 mm, or about 10 mm, or about 15 mm, or about 20 mm.

In general, sensors in accordance with the present disclosure operate electrochemically, through an arrangement of electrodes having chemical sensing layers applied thereto, by generating an electrical current proportional to the volume of a redox reaction of the analyte (and indicative of an analyte concentration), catalyzed by an analyte-specific oxidizing enzyme. Embodiments exist in which the number of electrodes provided to bring about and detect the level of these reactions is two, three or a greater number.

A portion of sensor 14 (which collectively refers to sensors 14' and 14" herein) may be situated above the surface of the skin, with a distal portion 30 penetrating through the skin and into the subcutaneous space in contact with the user's biofluid, such as interstitial fluid. The disposition of the sensor in the illustrated embodiment is referred to as "transcutaneous". In general, the term "transcutaneous" as used herein refers to a sensor that is only partially inserted under one or more layers of the skin of the user, whereas the term "subcutaneous" refers to a sensor that is completely inserted under one or more layers of the skin of the user. It is understood that many features described herein would be applicable to both transcutaneous and subcutaneous sensors. Further details regarding the electrochemistry of sensor 14 is provided in U.S. Pat. Nos. 5,264, 104; 5,356,786; 5,262,035, 5,320,725, 6,990,366, each of which is incorporated herein by reference In some embodiments, the sensor is implantable into a subject's body for a period of time (e.g., three to seven days, or in some embodiments, longer periods of up to several weeks) to contact and monitor an analyte present in a biological fluid. In this regard, the sensor can be disposed in a subject at a variety of sites (e.g., abdomen, upper arm, thigh, etc.), including intramuscularly, transcutaneously, intravascularly, or in a body cavity. In one embodiment, the sensor can be a transcutaneous glucose sensor. Alternatively, the sensor can be a subcutaneous glucose sensor.

In some embodiments, sensor 14 is employed by insertion and/or implantation into a user's body for some usage period. In such embodiments, substrate may be formed from a relatively flexible material to improve comfort for the user and reduce damage to the surrounding tissue of the insertion site, e.g., by reducing relative movement of the sensor with respect to the surrounding tissue.

While the embodiments illustrated in FIGS. 2-6 have three electrodes, other embodiments can include a fewer or greater number of electrodes. For example, a two electrode sensor can be utilized. The sensor may be externally-powered and allow a current to pass proportional to the amount of analyte present. Alternatively, the sensor itself may act as a current source in some embodiments. In some two-electrode embodiments, the sensor may be self-biasing and there may be no need for a reference electrode. An exemplary self-powered, two-electrode sensor is described in U.S. patent application Ser. No. 12/393,921, filed Feb. 26, 2009, and entitled "Self-Powered Analyte Sensor," which is hereby incorporated by reference in its entirety herein for all purposes. The level of current provided by a self-powered sensor may be low, for example, on the order of nanoamperes.

On-Body Unit

Figure 7:
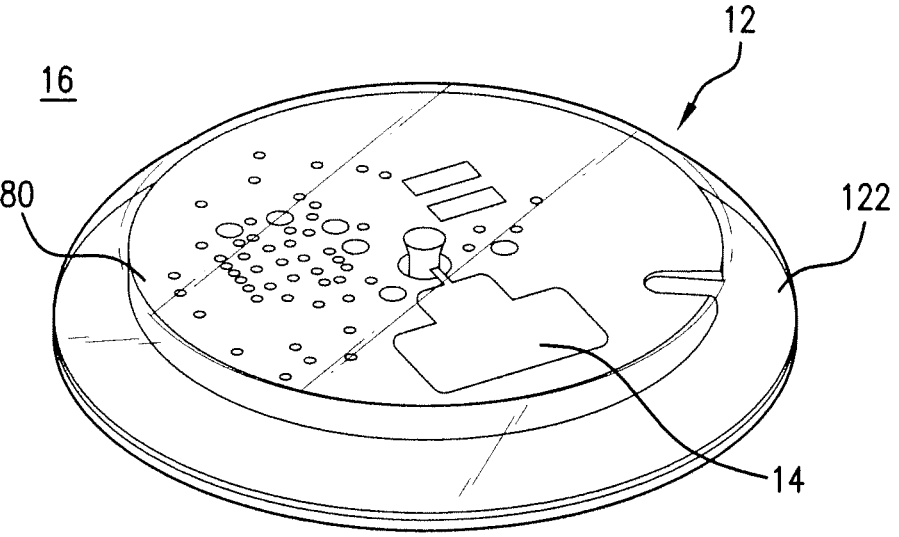
FIG. 7 is a perspective view of an on-body unit in accordance with one embodiment of the disclosed subject matter.
Figure 8:
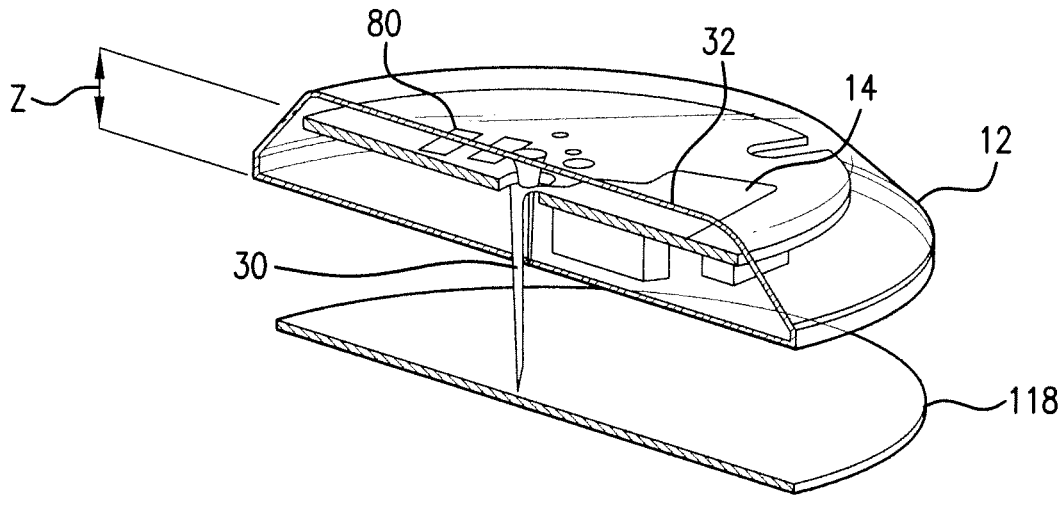
FIG. 8 is a perspective view in partial cross-section of an on-body unit of FIG. 7 in accordance with the disclosed subject matter.

An exemplary configuration for sensor 14 (and sensors 14' and 14") and sensor control unit 12 (e.g., collectively on-body unit 16) is illustrated in FIGS. 7-8. Data processing unit 12, may be provided with a substantially circular configuration having a reduced height (i.e., "Z"-dimension) to provide a low-profile when sitting on the skin of the subject. In some embodiments, the height is about 3 mm to about 25 mm, e.g., may be about 4 mm, about 5 mm, about 10 mm, or about 15 mm. In certain embodiments, the unit 12 may have a variable height. Data processing unit 12, including its associated electronics 80, are housed in a sensor housing 122. For example, electronics may include, e.g., an analog interface for connecting to the sensor 14, a processor, and a power supply. A serial communication section may be provided. A temperature sensor, such as a thermistor, which detects skin and or ambient temperature may be included to provide compensation to the analyte signal. A RF communication circuit is provided to communicate with the monitor unit 18. A data storage unit may be provided to store analyte data points over a short term, e.g., several hours or minutes, or over a long term, e.g., several days or weeks. Additional optional electronics include a serial communication section, a leakage detection circuit, or user input, e.g., a switch to activate/deactivate some or all of the device. Many of the components may be combined together and/or their function provided by common components. Furthermore, certain components may be eliminated entirely. For example, a power supply may be omitted if power is provided by inductive coupling.

In some embodiments, sensor 14 is disposed within the data transmitting unit 12, e.g., in a bent configuration, as illustrated in certain embodiments herein, e.g., in FIGS. 4 and 6. The contact portion 32 of sensor 14 may be oriented in a substantially horizontal configuration, and secured to a printed circuit board of the transmitter unit 12. The insertion portion 30 of the sensor 14 extends in a substantially downwardly vertical orientation for placement in the skin of the subject. It is understood that sensor 14 may be disposed in other configurations, e.g., in an entirely substantially vertical configuration, etc. As a further example, the insertion portion 30 may be disposed at an oblique angle, e.g., between about 0° and about 90° with respect to the skin surface.

Figure 9:
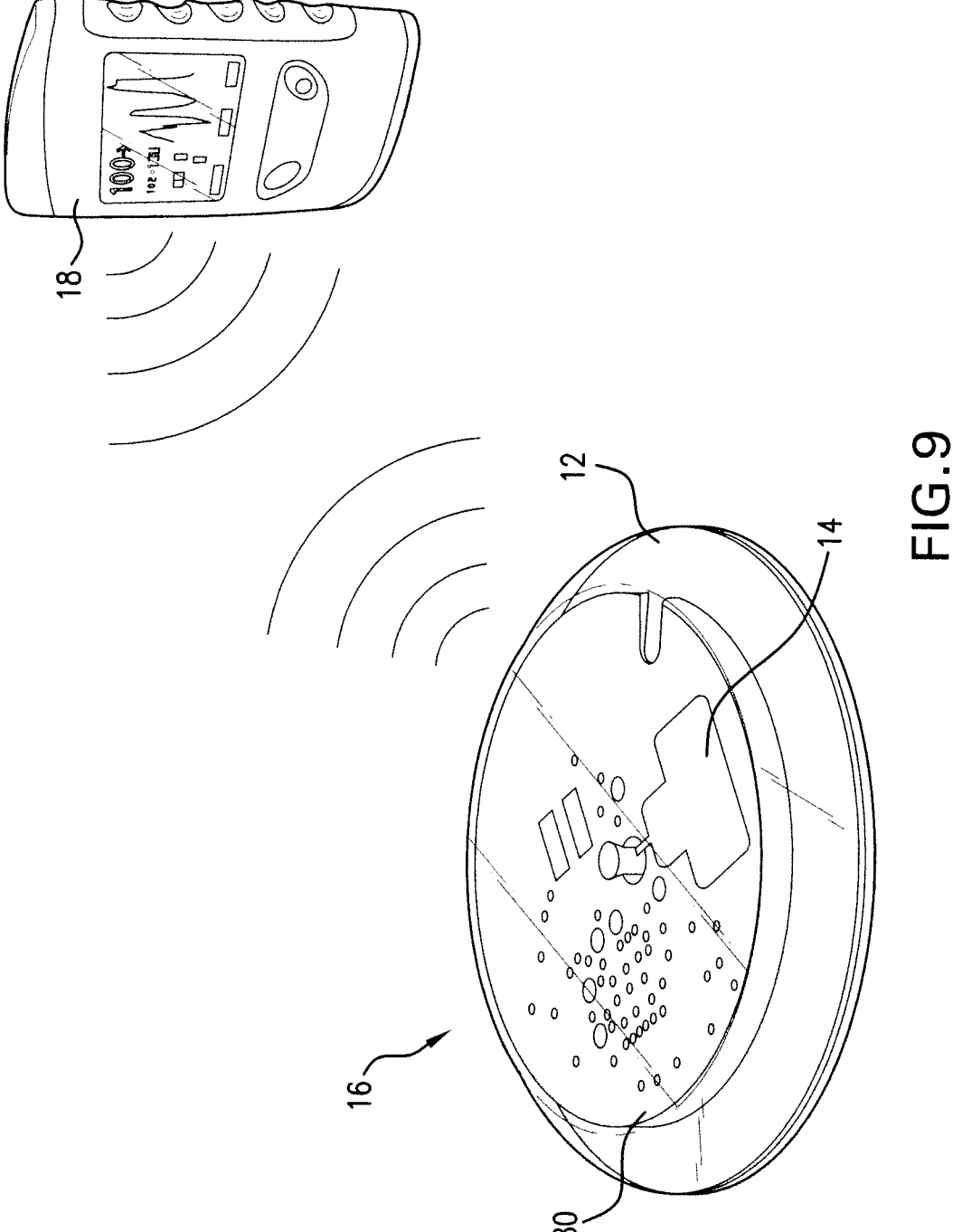
FIG. 9 is a schematic view of the system in accordance with one embodiment of the disclosed subject matter.

As illustrated in FIG. 9, the on-body unit 16 communicates with the monitor unit 18. Such communication may be one-way communication, e.g., from the on-body unit 16 to the monitor unit 18. In some embodiments, the communication may be two-way, e.g., both from the on-body unit 16 to the receiving unit 18 and from the receiving unit 18 to the on-body unit 16. In such cases, the receiving unit 18 may also be referred to herein as a display unit, transceiver or handheld unit. Communication between the on-body unit 16 and monitor unit 18 may occur via RF communication, inductive coupling, direct wired connection, etc.

Insertion Assembly

An insertion assembly is provided, which is used to install a medical device to the subject. In some embodiments, the insertion assembly includes an inserter and the medical device itself. The inserter can be configured to insert various medical devices to the subject, such as for example, an analyte sensor, an infusion set, a cannula, or a lancet. In some embodiments, the inserter can be configured to install a combination of such devices, e.g., a combined sensor/infusion set, etc. In certain embodiments, a given inserter can be configured to install a first device and a second device at different times. For example, an inserter may be modifiable to be used with more than one medical device, include more than one type of medical device, e.g., by attaching an adapter and/or removing detaching a portion of an inserter.

The inserter can install the medical device transcutaneously in, under, or through the skin of the subject; or subcutaneously; or placed on the surface of the skin. The medical device can include features or structures, e.g., barbs, tabs, adhesive, etc., to maintain the device in position with respect to the skin after insertion.

In other embodiments, the insertion assembly includes an inserter, a medical device, such as an analyte sensor, and a mount for supporting the medical device at least partially in or on the skin of the subject. The mount may be inserted simultaneously with the medical device by the inserter. In other embodiments, the mount is installed after or before installation of the medical device. In such case the mount may be applied by the inserter or separately. The mount may include features or structures to maintain the sensor in position with respect to the skin after insertion.

In further embodiments, the insertion assembly includes an inserter, an analyte sensor, a mount, and a power supply. The mount and power supply may be inserted simultaneously with the analyte sensor by the inserter. In other embodiments, the mount and battery are installed after or before installation of the analyte sensor. In such case the mount and/or power supply may be applied by the inserter or separately.

In still further embodiments, the insertion assembly includes an inserter, a medical device such as an analyte sensor, a mount, and electronics. The mount and electronics may be inserted simultaneously with the analyte sensor by the inserter. In other embodiments, the mount and electronics are installed after or before installation of the analyte sensor. For example, the mount and the analyte sensor may be installed by the inserter, and the electronics may be subsequently installed. In other embodiments, the mount is installed, followed by insertion of the analyte sensor by the inserter, and further followed by installation of the electronics. In other embodiments, the mount and electronics are installed first, and the analyte sensor is subsequently installed.

In some embodiments, the electronics provide a voltage or current to the analyte sensor. In some embodiments, the electronics processes signals provided by the analyte sensor. In further embodiments, the electronics may include communication functionality for providing a signal relating to the signal provided by the analyte sensor to a further component, such as, e.g., a monitor unit, a handheld unit, a meter, a display unit, a computer, or other component. In some embodiments, communications circuitry, such as RFID antenna or communications circuitry is provided.

The inserter can include a plurality of different components. For example, the inserter may include one or more components for advancing a sharp towards the skin of the subject. The sensor and associated electronics and/or mounting structure may be supported by a support structure, such as a carriage. An actuator may be provided for advancing the sharp and/or the analyte sensor/support structure. In some embodiments, the actuator is coupled to the sharp and/or support structure, such that manual force and speed applied by the user to the actuator is transferred to the sharp and/or support structure.

The inserter can also include one or more components for retracting the sharp, while allowing the analyte sensor and optional mount and/or electronics to remain to the subject. The components for retracting the sharp can include a retractor. It is understood that the retractor and the actuator may be the same structure or include some common components. In some embodiments, the retractor is directly or indirectly coupled to the sharp such that the manual force applied by the user is transferred from the retractor to the sharp to retract the sharp from the skin. In other embodiments, a drive assembly may be provided to retract the sharp. For example, the drive assembly may include a spring, motor, hydraulic piston, etc., to retract the sharp away from the skin of the subject. The drive assembly may also include a linear drive component.

In some embodiments, the retractor withdraws the sharp upon actuation by the user. In such cases, the user actuates the retractor when it is desired to withdraw the sharp. For example, the retractor may include a release switch. Upon activation of the release switch, the drive assembly, e.g., the spring or other driver, retracts the sharp from the skin. In other embodiments, the retractor and the actuator comprise common components. After activating the actuator to advance the sharp and the analyte sensor, the user releases the actuator, which allows the drive assembly to withdraw the sharp from the skin.

In some embodiments, the retractor withdraws the sharp without further user interaction after actuation of insertion. For example, the inserter may include features or components which automatically retract the sharp upon advancement of the sharp and support structure by a predetermined amount. Inserter devices, in which no further action by the user is required to initiate withdrawal of the sharp after insertion, are referred to herein as having "automatic" withdrawal of the sharp.

Inserter Devices

Figure 10:
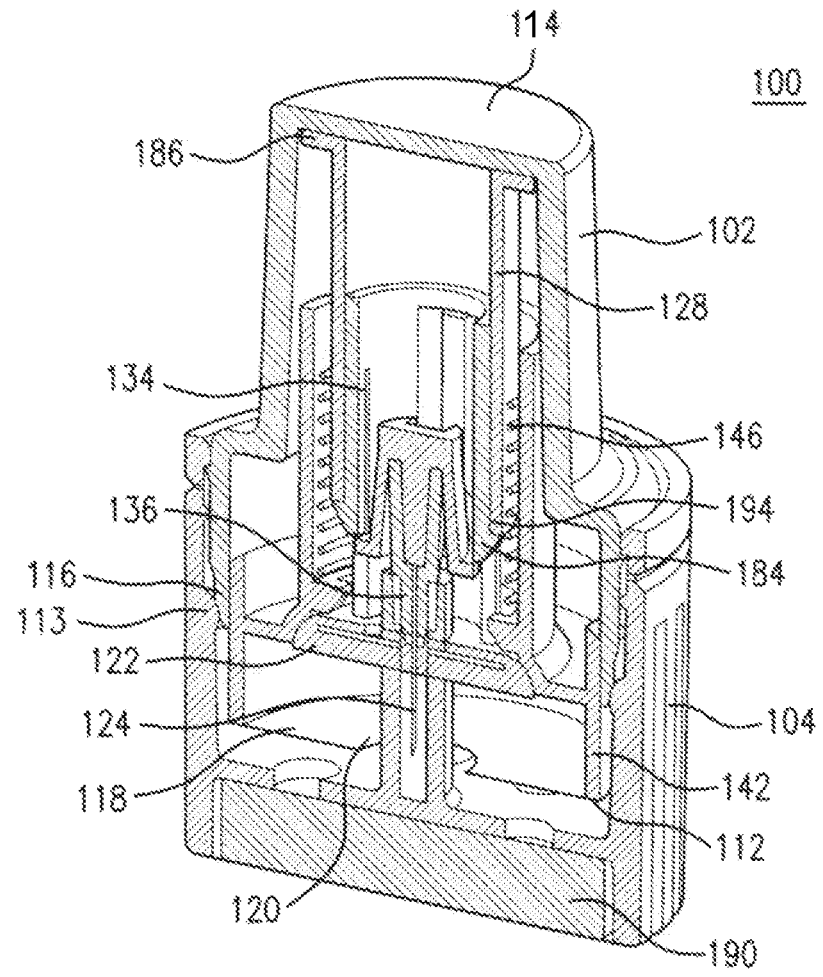
FIG. 10 is a sectional, perspective view of another embodiment of an inserter in accordance with the disclosed subject matter.

An inserter 100 in accordance with an exemplary embodiment is illustrated in FIG. 10. Inserter 100 includes a handle 102 and a removable distal cap 104. The cap 104 may maintain a sterile, contaminant-free environment for the medical device and sharp housed therein. As illustrated in FIGS. 10-16, distal cap 104 is secured to handle 102, e.g., by use of one or more mating members, e.g., threads 110 and 111, or hooks, tape, and the like. Inserter 100 includes a base 142 which defines a distal, substantially planar surface 112 for placement on the skin S of a subject, and in other embodiments may be a curved or inclined surface, e.g., a concave or convex surface. Inserter 100 may be utilized to advance a medical device into the skin of the subject, e.g., an analyte sensor, and infusion set, etc. In some embodiments, handle 102 is advanced relative to base 142 in order to advance the medical device into the skin of the patient, as will be described in greater detail herein.

The components of inserter 100 are illustrated in FIGS. 11-27. As illustrated in FIG. 11, handle 102 includes a contact surface 114 for contact by a user to insert and install the sensor housing 122 and sensor 14. Threads 110 are provided on handle 102 for attachment to cap 104 via threads 111 (as illustrated in FIGS. 12-13). Cap 104 can include an upwardly extending boss 125 to assist positioning of the sharp 124. The distal portion of cap 104 includes a recess 115 for retaining a desiccant 190 therein. In some embodiments, a silica gel or molecular sieves may be used. Such material can be in either in granular form (pellets) or pressed into tablets. In some embodiments, silica gel tablets are used.

Cap 104 is provided with one or more apertures 117, which allows for passage of air to the desiccant 190 to remove moisture from the interior of the inserter 100. Cap 104 includes an annular ridge 113 which engages the distal edge portion 116 of handle 102. In some embodiments, annular ridge 113 prevents distal movement of handle 102 (as well as sharp 124) when cap 104 is attached to handle 102.

Figures 14, 15, 16:
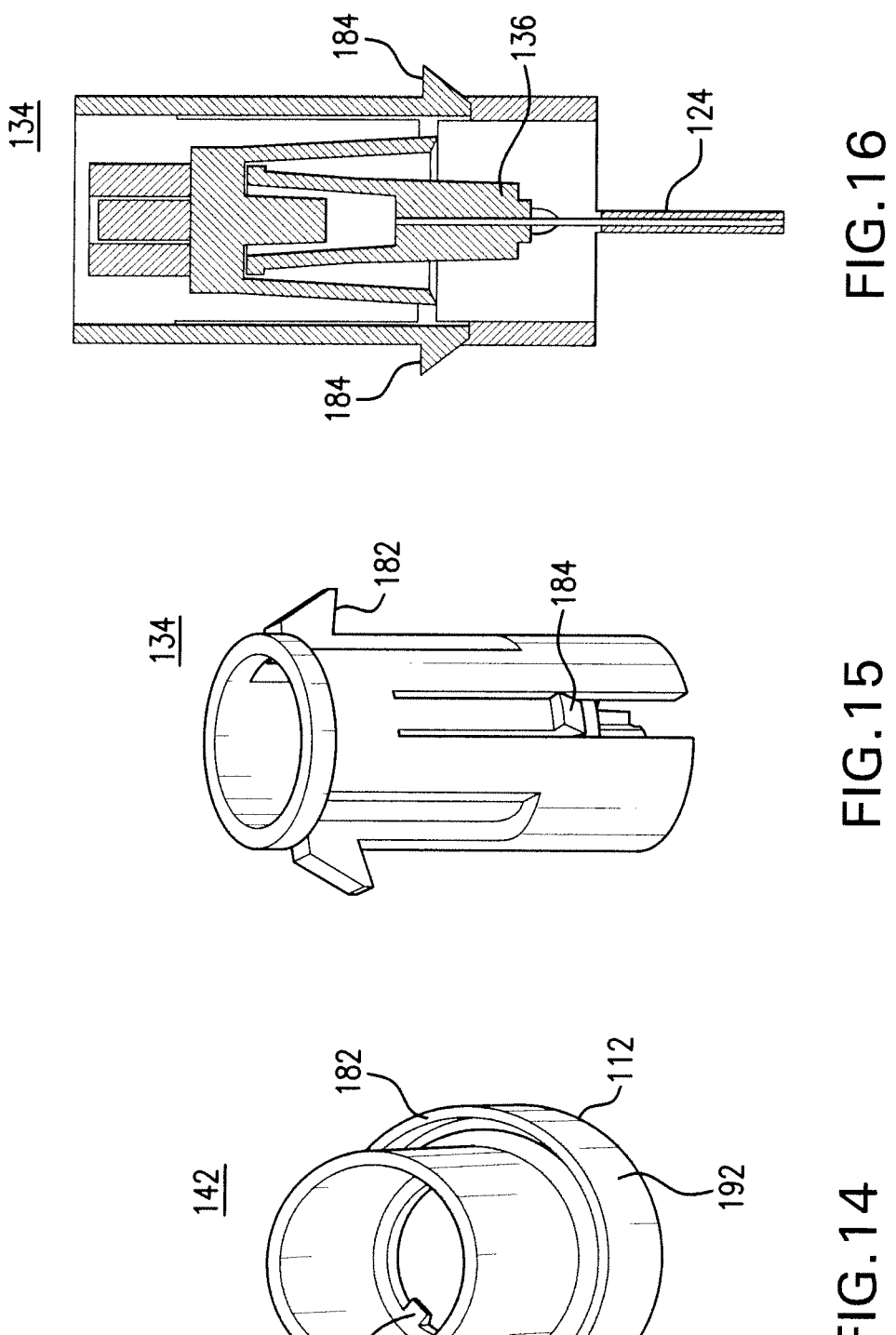
FIGS. 14-15 are a perspective views of components of the inserter of FIG. 10 in accordance with the disclosed subject matter.
FIG. 16 is a sectional view of the component of FIG. 14 in accordance with the disclosed subject matter.
Figure 29:
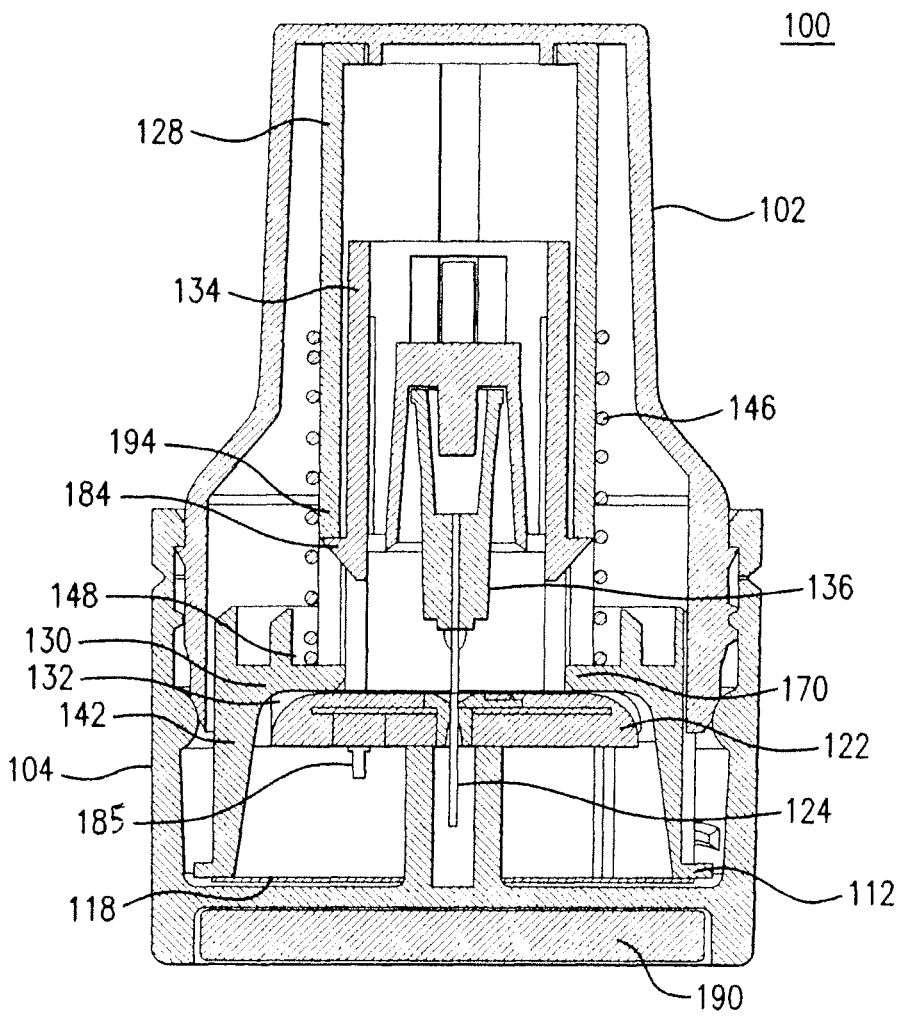

Base 142, as illustrated in FIGS. 10 and 14, includes a distal sheath portion 192, which shields sharp 124 prior to deployment and a distal rim 112 having a substantially planar surface configuration to rest on the subject's skin. Base 142 also includes side walls 191, which along with inner rail 128 defines a recess for retraction spring 146. Base 142 provides a spring floor 148, as illustrated in FIG. 29.

Support member or shuttle 134, as illustrated in FIGS. 15-16, supports needle hub 136, from which sharp 124 extends longitudinally within the inserter 100. In some embodiments, the sharp is supported at an oblique angle, e.g., between about 0° and about 90° with respect to the skin surface. Needle hub 136 can be secured to shuttle 134 via an interlocking O-ring configuration, adhesive, or other techniques known in the art. In some embodiments, sharp 124 is a solid needle. In some embodiments, sharp 124 is provided with a substantially cylindrical configuration defining an interior bore, e.g., a rigid cannula or a hypodermic-style needle.

Figures 17, 18:
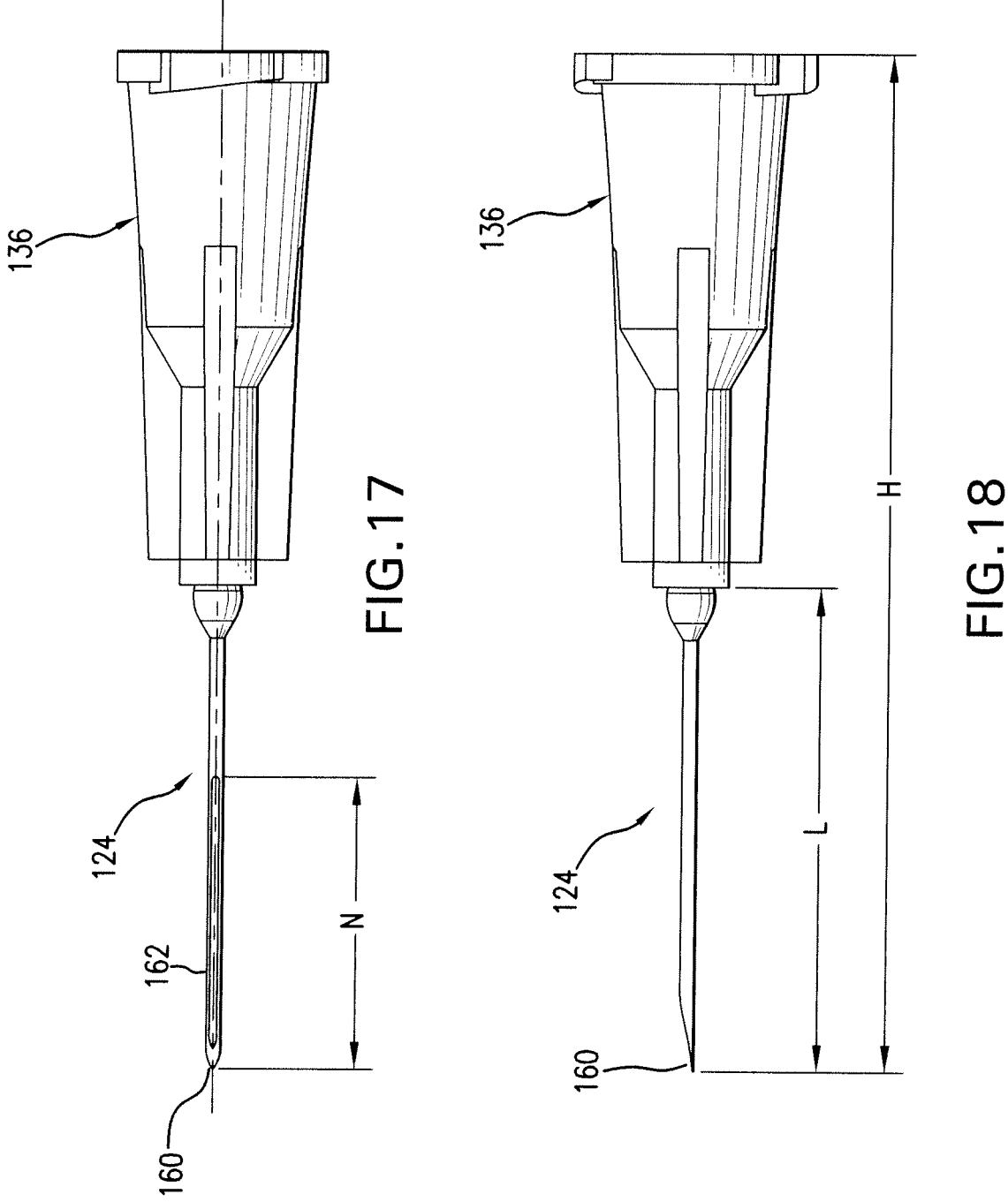
FIGS. 17-18 are schematic views of a needle hub in accordance with one embodiment of the disclosed subject matter.

Needle hub 136 is further illustrated in FIGS. 17-18. Needle hub 136 supports sharp 124, having a sharpened distal portion 160. In some embodiments, as discussed herein, a longitudinal wall opening or gap 162 is provided in at least a portion of the wall of the sharp 124. The length N of the gap 162 is selected to be commensurate with the length of the insertion portion 30 through to the proximal retention portion 48 of the sensor, or about 5 mm, or about 10 mm, or about 15 mm, or about 20 mm. The length L of the sharp 124 may be about 5 mm, or about 10 mm, or about 20 mm, about 30 mm, or about 50 mm, and is selected based upon the desired depth of the insertion portion 30 of the sensor 14.

Figures 19, 20, 21:
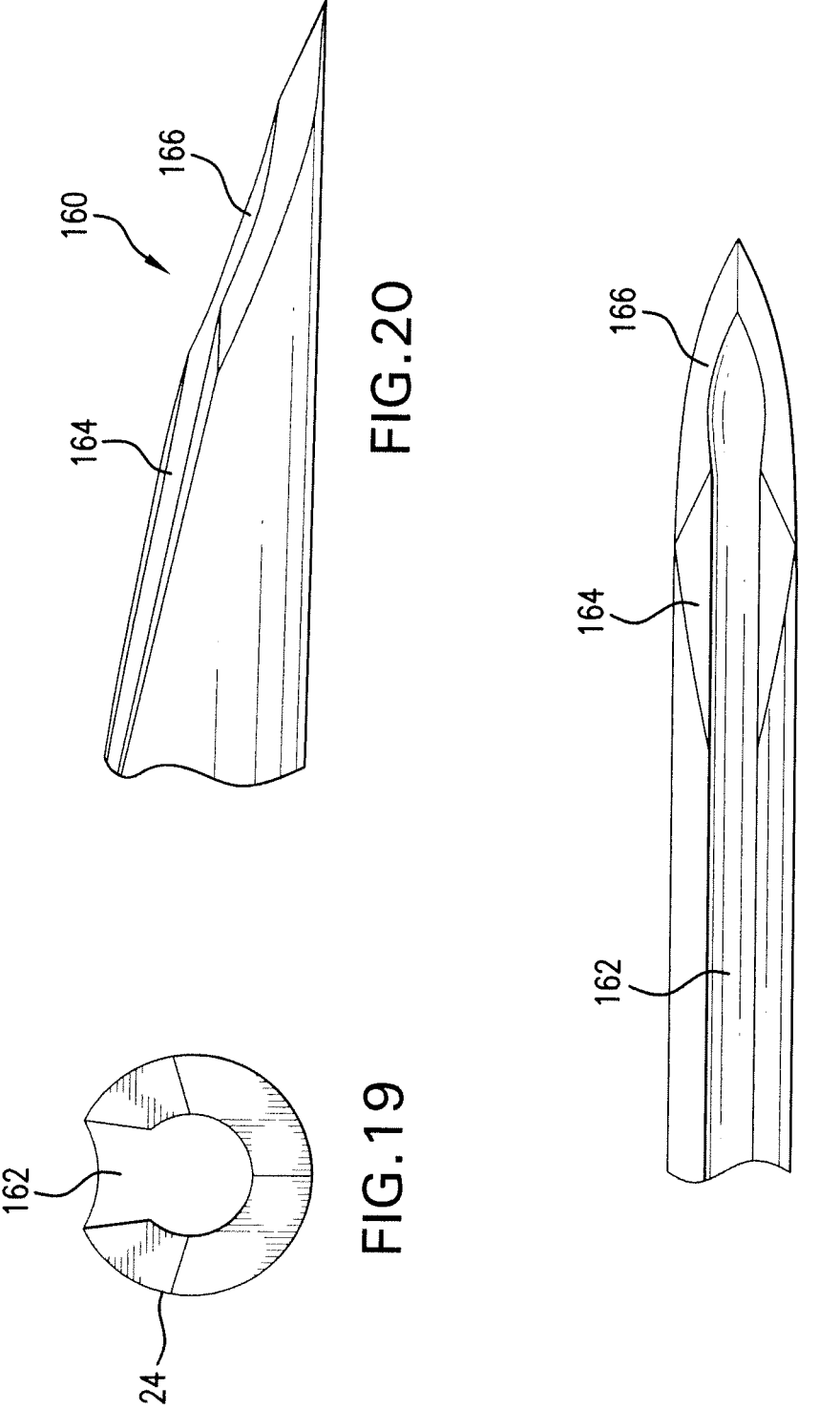
FIG. 19 is a distal end view of a sharp in accordance with one embodiment of the disclosed subject matter.
FIG. 20 is a side view of a sharp in accordance with one embodiment of the disclosed subject matter.
FIG. 21 is a side view of a sharp in accordance with one embodiment of the disclosed subject matter.

The distal portion 160 of sharp 124 is illustrated in greater detail in FIGS. 19-21. As illustrated in FIG. 19, sharp 124 has a substantially "C"- or "U"-shaped profile in this embodiment, but may have other configurations, e.g., substantially "V"-shaped. A longitudinal gap 162 is provided in the wall of the sharp 124. FIG. 20 illustrates distal portion 160 is provided with an angled tip. In some embodiments, the angled tip may be provided with a first angled tip portion 164 and a second steep-angled tip portion 166. The exemplary configuration, which includes multiple edges and faces, provides a sharp point to reduce penetration force, trauma, and bleeding for the subject. The distal section of the sensor body has a width sized to fit within the notch 162 of the insertion sharp 124 having a diameter less than about 22 to about 24 gauge, in certain embodiments the sharp is 25 gauge. In some embodiments, sharp 124 is a fabricated from a sheet of metal, and folded into a substantially "V" or "U" or "C" configuration in cross-section. In some embodiments, a laser is used to form the wall opening or gap 162.

Figure 22:
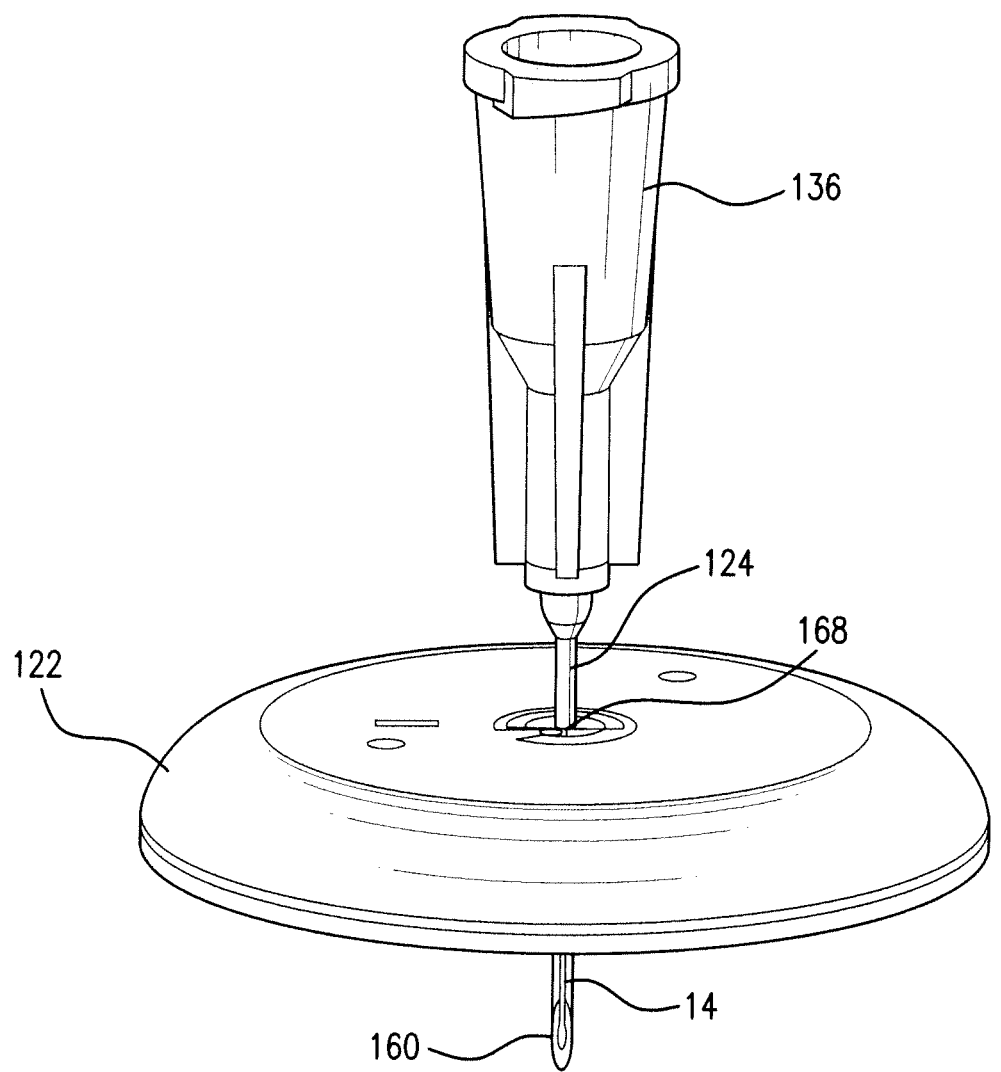
FIG. 22 is a perspective view with parts of an inserter in accordance with one embodiment of the disclosed subject matter.
Figure 23:
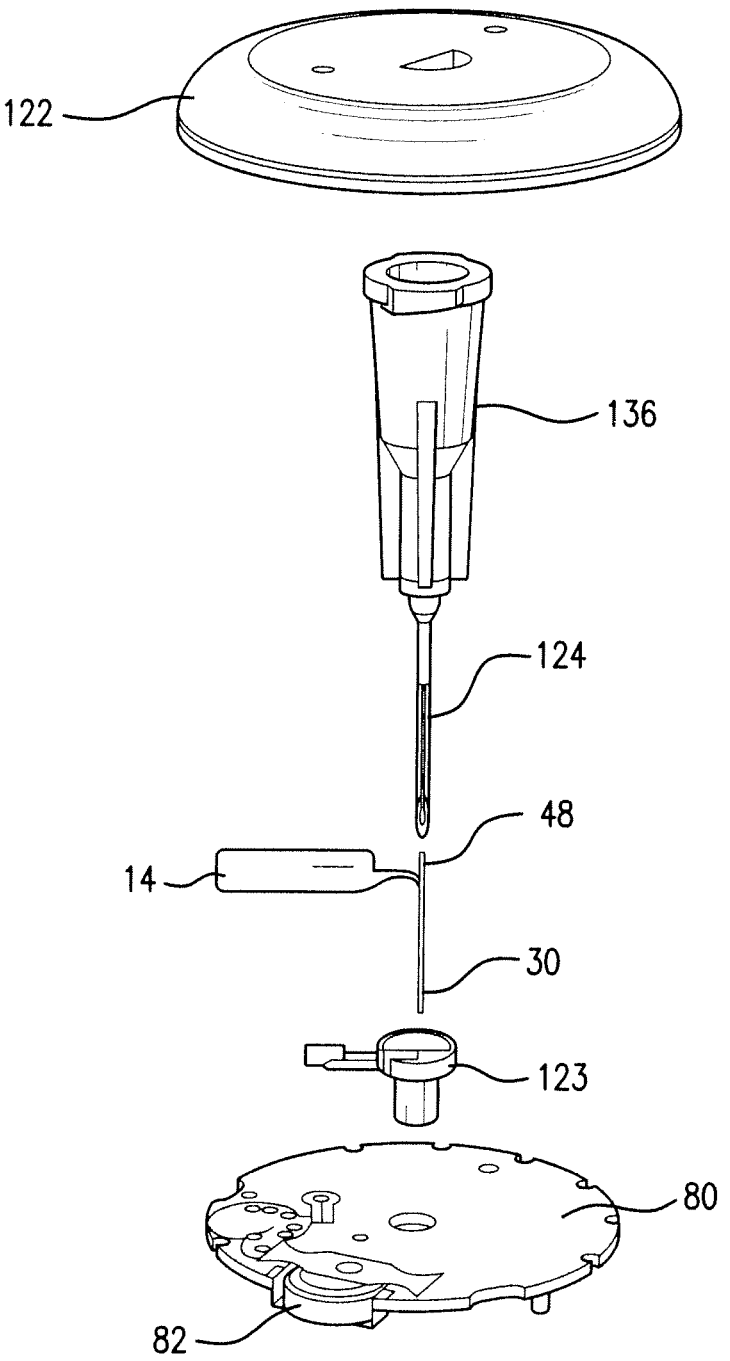
FIG. 23 is a perspective view with parts separated of an inserter in accordance with one embodiment of the disclosed subject matter.

FIGS. 22-23 illustrate the position of sensor housing 122 with respect to the needle hub 136 and sharp 124. As illustrated in FIG. 22, the sharp 124 extends through an aperture 168 in the sensor housing 122. The distal portion of sensor 14 is positioned with the sharp 124. As further illustrated in FIG. 23, electronics 80 (e.g., a printed circuit board containing ASIC electronics) and sensor hub 123 are positioned within sensor housing 122. A power supply 82, such as a battery, e.g., a single use disposable battery, or rechargeable battery, is provided. In some embodiments, the active operational life of the battery may exceed the active operational life of the sensor 14.

Figure 24:
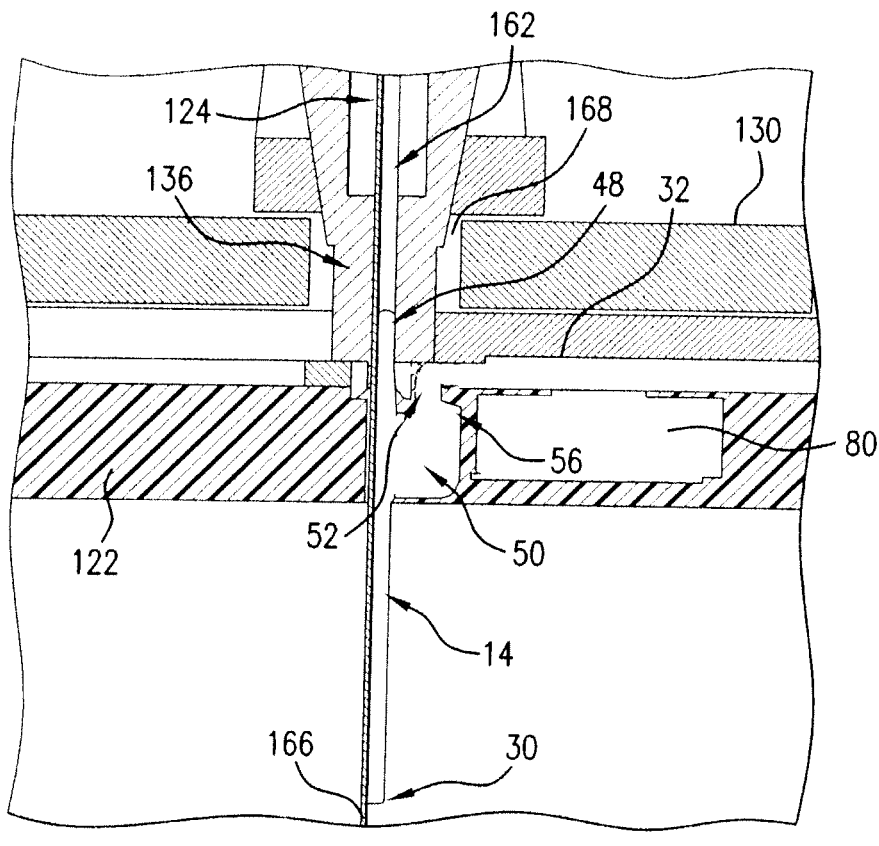
FIG. 24 is an enlarged sectional view with parts separated of an inserter in accordance with one embodiment of the disclosed subject matter.

FIG. 24 illustrates in cross-section the orientation of the sensor housing 122 with respect to the sharp 124 of inserter 100. As discussed herein, sensor 14 is disposed in a substantially bent configuration, such that a portion of the sensor, e.g., the insertion portion 30 and the proximal retention portion 48 are substantially vertical (e.g., substantially aligned with the longitudinal axis of the inserter 100 and substantially perpendicular to the skin surface) and the contact portion 32 (shown in profile) is oriented in a substantially horizontal configuration, and in electrical contact with the data processing unit electronics, such as circuit 80. The sensor tab 50 can be encased in the plastic of the sensor housing 122 (e.g., "overmolded") and secured in place. The notch 56 provides further stability to the sensor 14, e.g., by allowing the sensor tab 50 to be encased by the material of the sensor housing 122, and further provides a means for vertically orienting the sensor 14 during mounting, e.g., by allowing vertical positioning of the notch 56 with respect to a vertical landmark of the housing 122.

The sensor 14, mounted with the sensor housing 122, is disposed within the concave recess in the carriage 130. In the initial configuration of the inserter 100 (see, e.g., FIGS. 10 and 28-29) the sharp 124 extends through a longitudinal aperture 168 formed in a carriage 130. In some embodiments, the aperture 168 is appropriately sized, such that neither the sharp 124 nor needle hub 136 is in contact with the carriage 130. Accordingly, the needle hub 136 (and sharp 124) on the one hand, and the carriage 130 and the sensor housing 122, on the other hand, move simultaneously but independently from one another. In other embodiments, a friction fit may be provided between the aperture and the sharp.

The insertion portion 30 and proximal retention portion 48 of the sensor 14 are disposed within a longitudinal bore 162 within the sharp 124. (See, e.g., FIG. 19) The proximal retention portion 48 is disposed within the longitudinal bore of the sharp and provides additional stability to the mounting of the sensor 14 within the sharp 124. The longitudinal wall gap or opening 162 of sharp 124 is aligned with the sensor 14, such that the tab 50 and the contact portion 32 extend laterally outward from the sharp 124.

Figure 26:
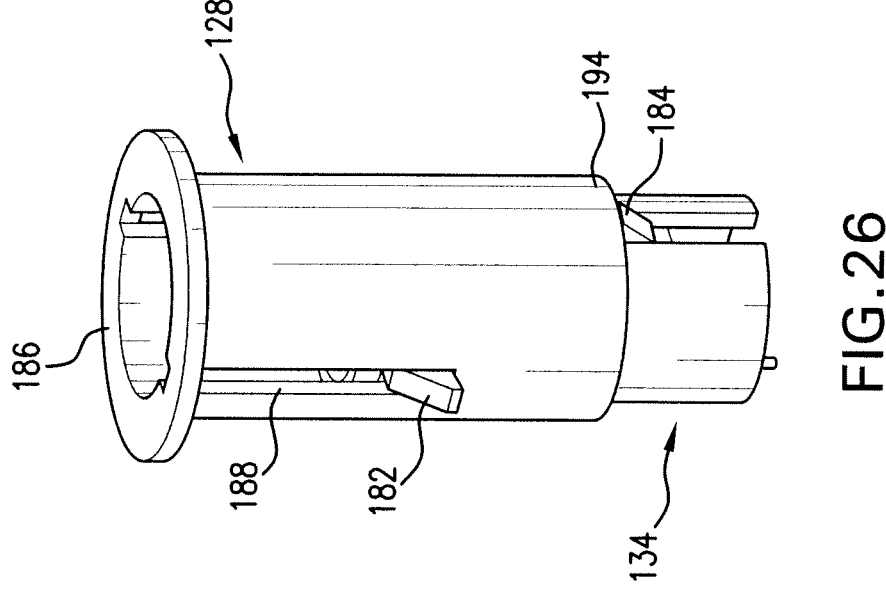
FIGS. 25-27 are perspective views of components of the inserter of FIG. 10 in accordance with the disclosed subject matter.
Figure 25:
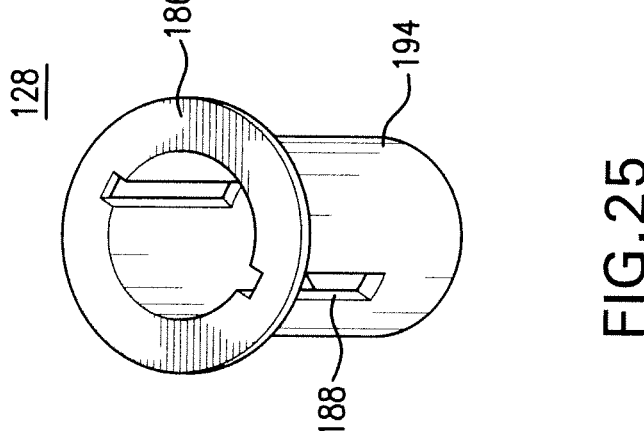

With continued reference to FIGS. 15 and 16, shuttle 134 includes wings 182 and resilient distally-extending fingers 184. Inner rail 128 is illustrated in FIG. 25. As illustrated in FIG. 26, shuttle 134 is sized and configured for slidable movement within inner rail 128. Wings 182 of shuttle 134 are configured for slidable movement within axial notches 188 of inner rail 128. When fingers 184 of shuttle 134 are disposed in their normally biased outward position, fingers 184 engage the lower surface 194 of inner rail 128. In the configuration illustrated in FIG. 26, shuttle 134 is locked with respect to inner rail 128. As will be discussed herein, fingers 184 may be biased radially inward to allow upward movement of shuttle 134 relative to inner rail 128.

As illustrated in FIG. 10, inner rail includes an upper surface 186 for engagement with handle 102. In some embodiments, surface 186 is adhered or otherwise fixed to handle 102.

Figure 27:
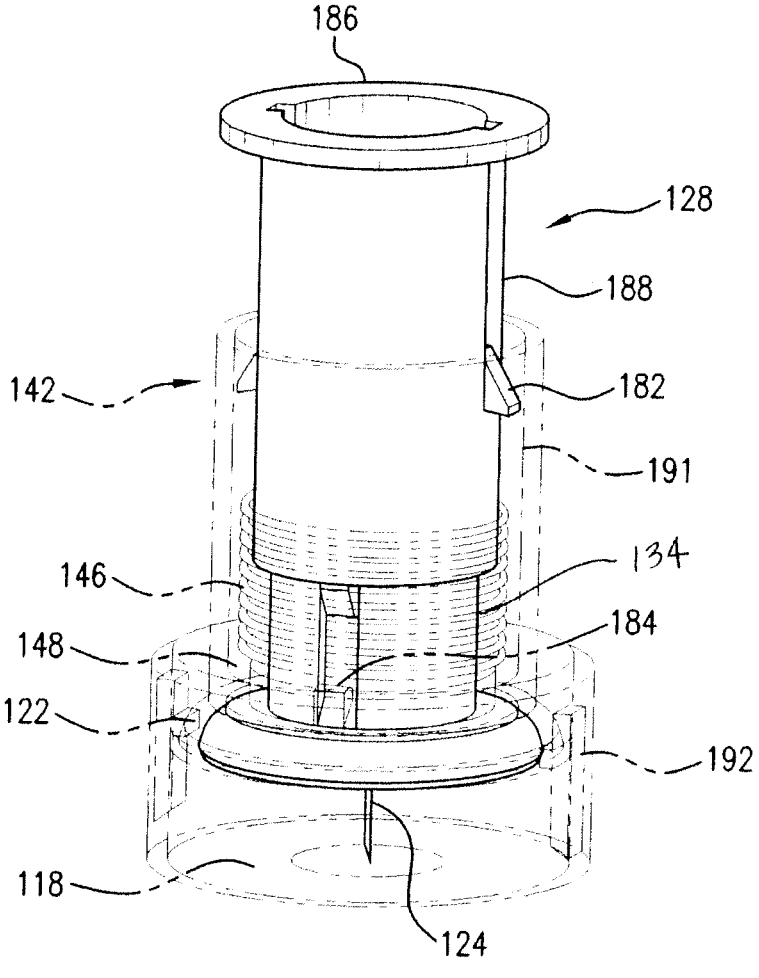

The relationship of inner rail 128, shuttle 134 and base 142 is illustrated in FIG. 27. In an initial configuration, inner rail 128 and shuttle 134 are in a locked relationship by engagement of wings 182 and fingers 184. Inner rail 128 and shuttle 134 are axially movable within base 142. Spring 146, which is secured between spring floor 148 of base 142 and wings 182 of shuttle 134 biases the inner rail 128 and shuttle 134 in a proximal (upward) direction.

Figure 28:
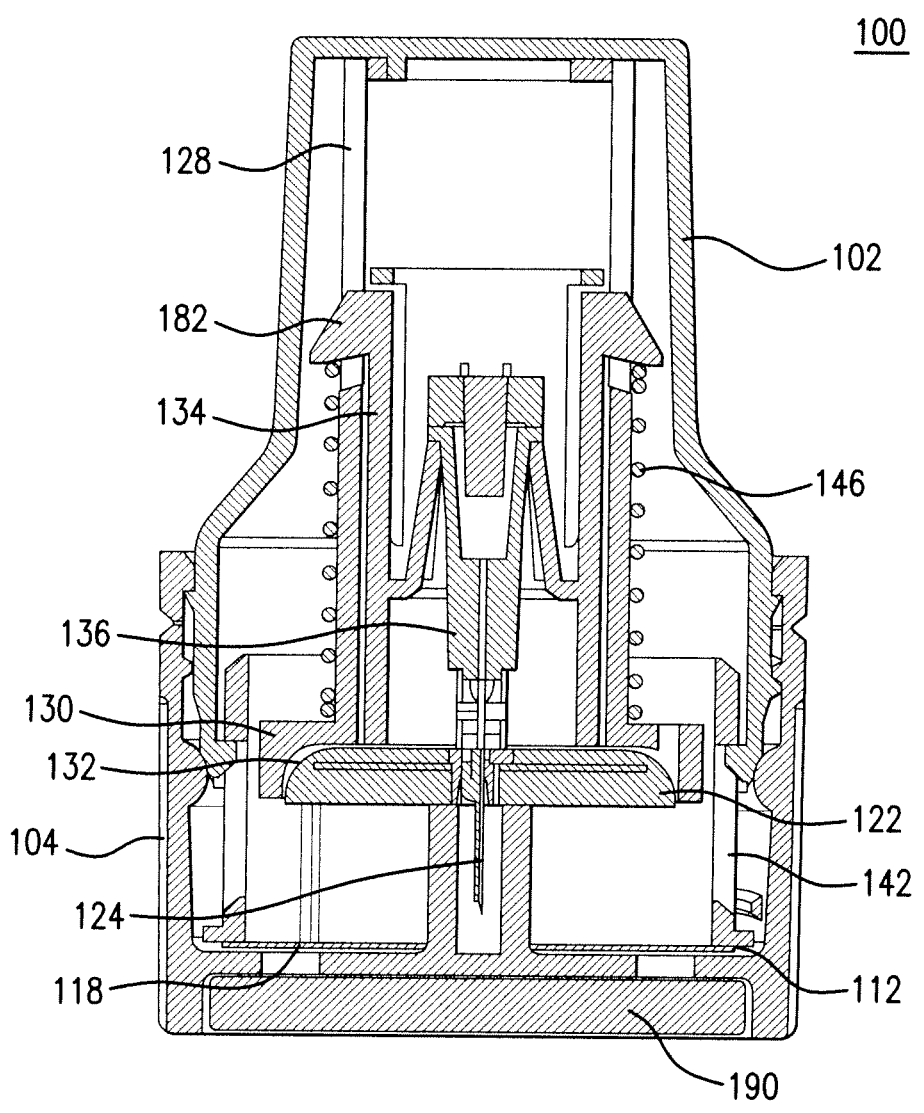
FIGS. 28-31 are sectional views of the inserter of FIG. 10 in accordance with the disclosed subject matter.

Inserter 100 is illustrated in section in FIGS. 28-29 prior to use in a sensor pre-deployment position. Cap 104 is attached to the distal portion of inserter 100, via inter-engagement of threads 110 and 111.

As illustrated in FIG. 28, the inserter 100 includes an initial configuration in which the handle 102 is disposed in a proximal position with respect to the base 142. In such configuration, the sharp 124 is disposed in a configuration spaced apart from an aperture of the adhesive layer 118.

Figure 30:
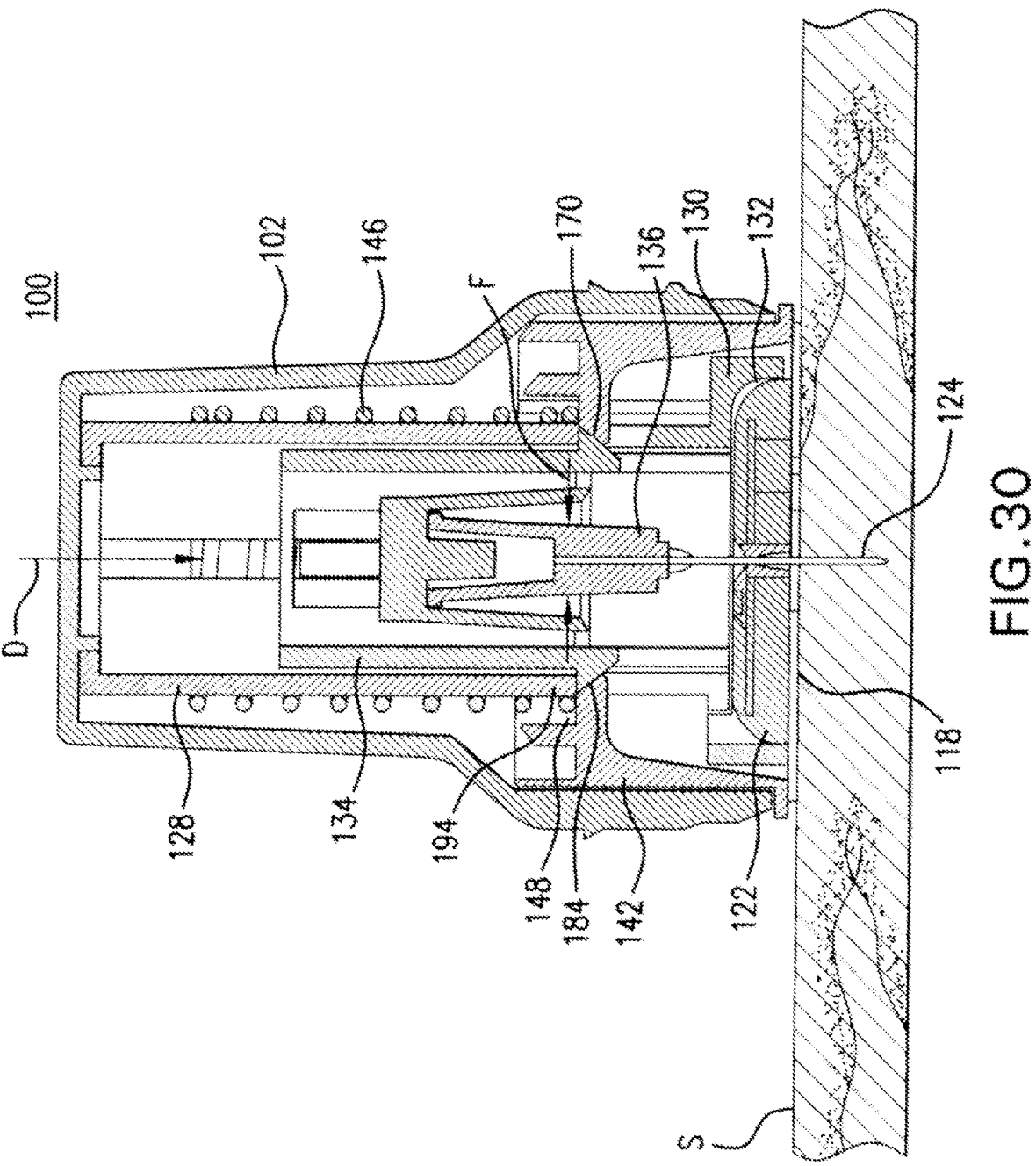

As illustrated in FIG. 30, inner rail 128 includes a carriage 130. In a sensor insertion position, the handle 102 is depressed downward (arrow D) against the bias of spring 146, the inner rail 128 moves downwardly with the carriage 130 and the sensor housing 122. Shuttle 134 supports needle hub 136, from which sharp 124 extends longitudinally within the inserter 100. Initially shuttle 134 is coupled to inner rail 128 via inter-engagement of fingers 184 of shuttle 134 with distal surface 194 of inner rail 128, and both shuttle 134 and inner rail 128 move distally together as a unit.

As the sharp 124 is urged distally (FIG. 30), it carries the sensor insertion portion 30 of sensor 14 into the subcutaneous portion of the subject's skin S and into contact with the interstitial fluid. As carriage 130 reaches a distal position, the distal surface of the sensor housing 122 engages the upper surface of adhesive pad 118, thereby becoming adhered to the skin surface S of the subject.

Flanges 170 on base 142 engage fingers 184 of shuttle 134. Fingers 184 are pivoted or bend inwards by contact with flanges 170 (as indicated by arrows F).

Figure 31:
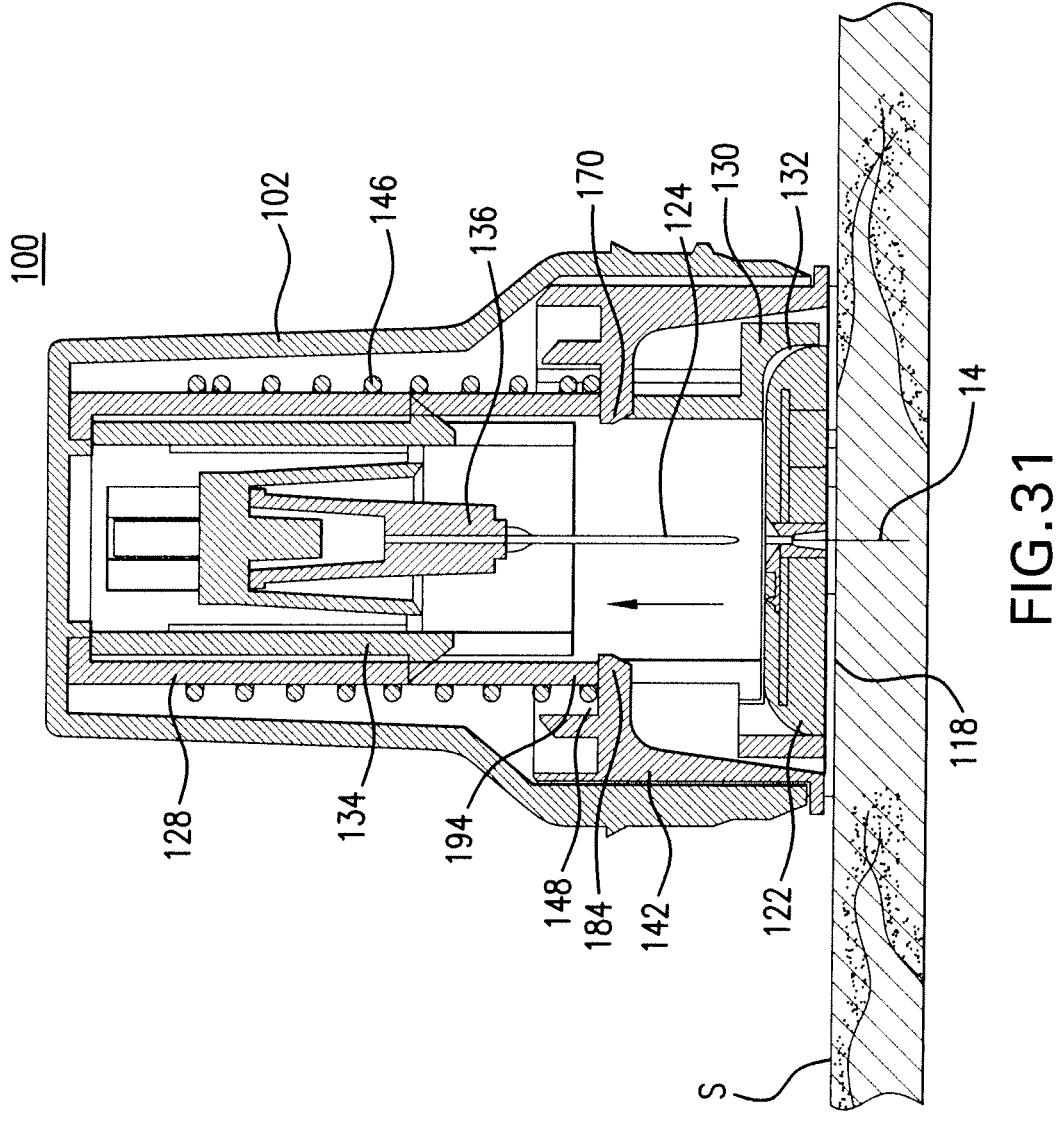

As illustrated in FIG. 31, such pivoting of fingers 184 causes fingers 184 to become disengaged from distal edge 194 of inner rail 128. Shuttle 134 is thereby disengaged from inner rail 128. Disengagement of the shuttle 134 from the inner rail 128 permits the spring 146 to expand, thereby advancing the shuttle 134 to a proximal position, and withdrawing the sharp 124 from the sensor 14 and the skin S of the subject, while leaving the sensor 14 in the skin. Once the sharp has been withdrawn from the subject, it is no longer accessible from the distal portion of the inserter 100, which prevents accidental needle sticks. When the carriage 130 reaches the distal position in which flanges 170 engage fingers 184 of needle shuttle 134, needle shuttle 134 withdraws needle 124 automatically without further input from the user.

Prior to activation of the integrated sensor 14 and sensor electronics assembly 16 for use, there may be a period of time from the manufacturing that the assembly 16 may be in a "sleep" or "idle" mode. With a power supply such as a battery integrated within the assembly, for reasons including cost optimization and prolonging shelf life, embodiments of the present disclosure include systems that are activated merely by positioning the sensor 14 and electronics unit 16 on a skin surface as described above, i.e., no additional action may be required of the user other than applying a force to housing 122. As such, insertion of the sensor 14 and/or mounting of the housing 122 causes activation of the electronics 80. In certain embodiments, activation switch configurations are included which may be configured to be triggered, for example, by the insertion device activation, thereby turning on the integrated sensor and sensor electronics assembly into an active mode.

As illustrated in FIG. 29, inserter 100 is also provided with a plunger switch 185, which provides automatic activation of the electronics 80 of the data processing unit 12. In some embodiments, the plunger switch 185 is a longitudinally slidable member disposed on the distal surface of the sensor housing 122. When the sensor housing is advanced proximally, it engages the adhesive pad 118, or alternatively the skin surface of the subject. Upon such engagement, the plunger switch 185 is moved axially (proximally) with respect to the housing 122. The plunger switch in the proximal position is shown in FIG. 30, for example. Such axial movement is used to activate the sensor electronics 80. In some embodiments, the plunger switch is spring biased. Accordingly, as long as the sensor housing is maintained in a fixed relationship with the adhesive pad 118 against the bias, electronic activation is maintained. If the sensor housing is removed from the adhesive or the skin, the plunger switch moves with the bias, and the electronics are deactivated. In other embodiments, the plunger switch provides a one-time activation of the electronics. In such cases, once the electronics are activated, the sensor housing is not required to remain in contact with the adhesive or the skin in order to maintain activation.

Figure 32:
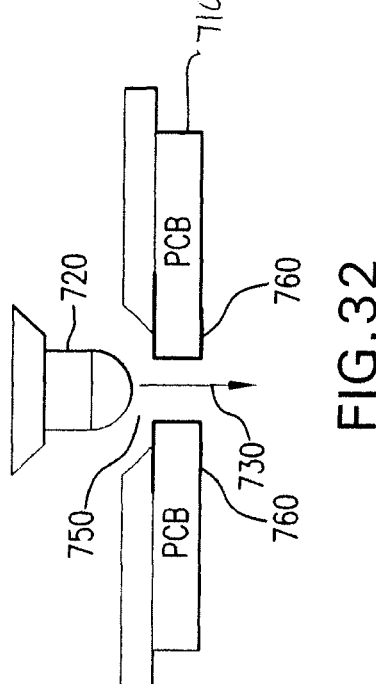
FIGS. 32-33 illustrate a power supply switch mechanism including conductive plug of the on-body integrated sensor and sensor electronics assembly in accordance with embodiments of the disclosed subject matter.
Figure 33:
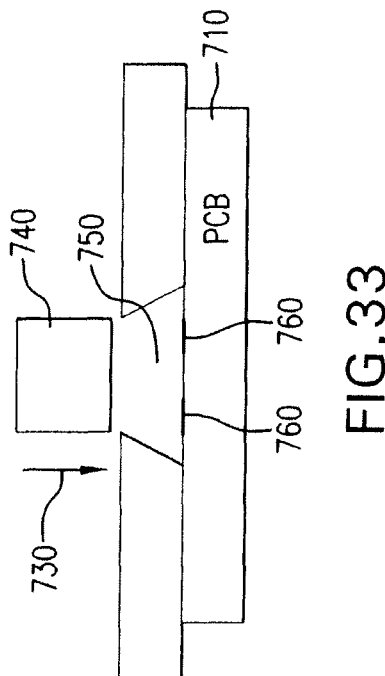

As illustrated in FIGS. 32-33, embodiments of a power supply switch mechanism include conductive plugs of the on-body integrated sensor and sensor electronics assembly 16 in accordance with the present disclosure. FIGS. 32-33 illustrate enlarged sectional views of sensor housing 122. As shown, the sensor electronics assembly circuit board 710 may be provided with a physical gap 750 that breaks the electrical circuit between the power supply (e.g., battery) and the other circuitry of the sensor electronics assembly.

In one embodiment, when the predetermined force is applied on the insertion device 100 as discussed above, a conductive portion 720 provided within the housing 122 of the sensor electronics may be moved in a direction as shown by arrow 730 such that electrical contact is established in the physical gap 750 on the circuit board, by for example, the conductive portion 720 coming into physical contact with the conductive portions 760 of the circuit board 710. In this manner, in one embodiment, the electrical path from the power supply and the remaining circuitry on the circuit board of the sensor electronics is completed, thereby powering the sensor electronics.

By way of another example, referring to FIG. 33, the conductive portions 760 of the circuit board are provided on the board itself, and the conductive plug 740, for example, when pushed into the cavity 750, establishes electrical contact between the conductive portions 760 of the circuit board.

In one embodiment, as discussed above, the actuation of the insertion device 100 to position the sensor and sensor electronics assembly triggers the switch mechanism shown in FIGS. 32-33 by also moving the conductive portion 720 or the conductive plug 760 in the direction complimentary to the direction of the introducer movement, and thereby switching on the sensor electronics. Within the scope of the present disclosure, the activation of the sensor electronics by moving the conductive portion 720 or the conductive plug may include a separate procedure, where after positioning the sensor and the sensor electronics assembly on the skin surface, a predetermined force is applied on the housing of the integrated sensor 14 and sensor electronics assembly such that the desired movement of the conductive portion 720 or the conductive plug 760 may be achieved.

Figures 34A, 34B, 35A, 35B:
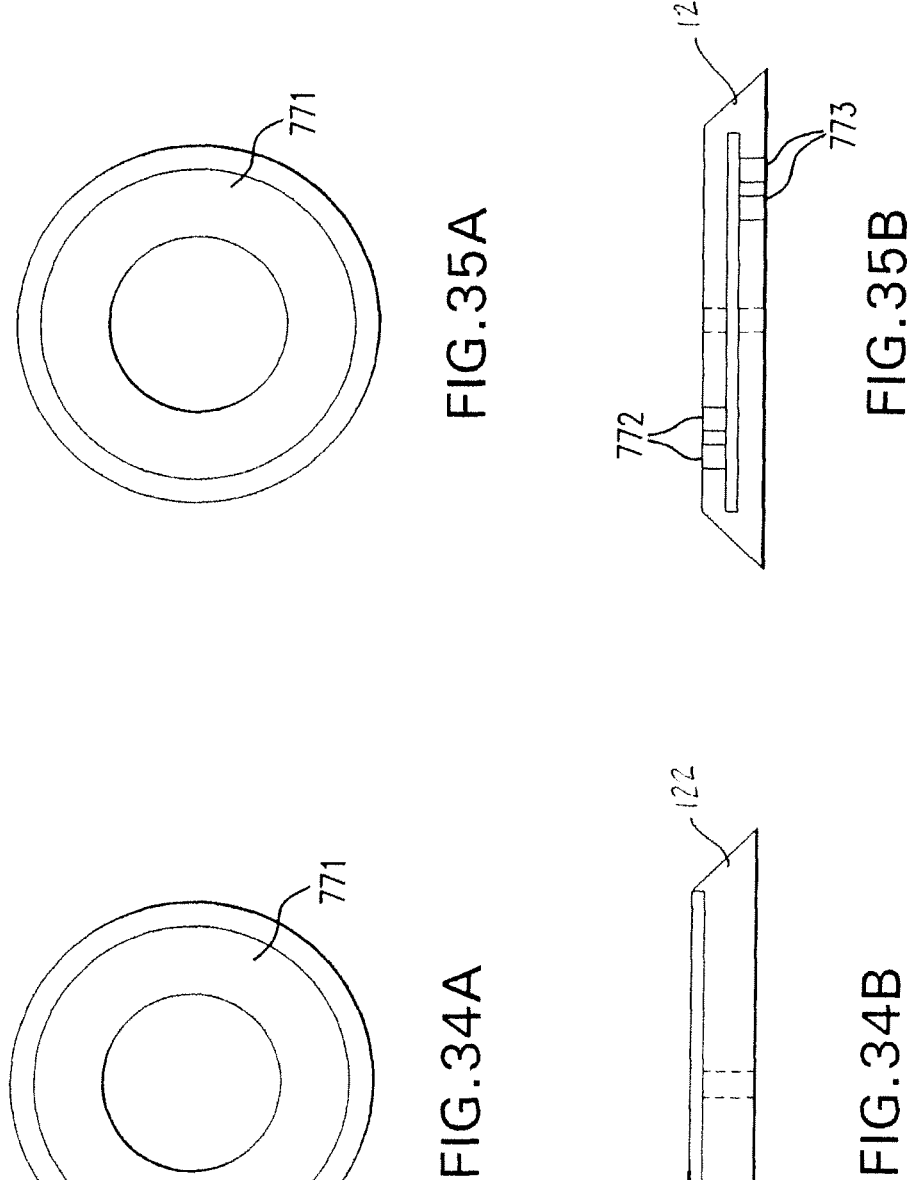

FIGS. 34A-36B illustrate another configuration of the power supply switch mechanism including conductive pads of the on-body integrated sensor and sensor electronics assembly in accordance with embodiments of the present disclosure. Referring to FIG. 34A, an exposed conductive ring 771 may be provided and configured to contact the surface of the circuit board in the sensor housing 122 (shown in cross section in FIG. 34B) such that, the insertion device activation positions the conductive ring 771 on the surface of the circuit board so as to complete the electrical contact of the sensor housing 122 (by for example, manual force applied on the insertion device placing the conductive ring in contact with the circuit board of the sensor electronics).

Figure 36A:
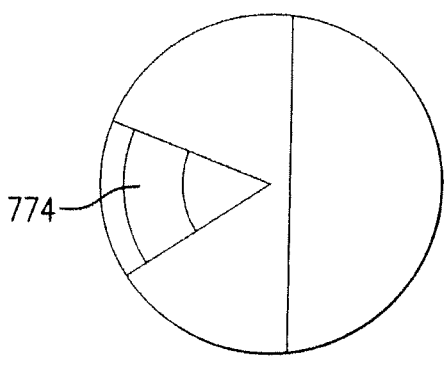
Figure 36B:
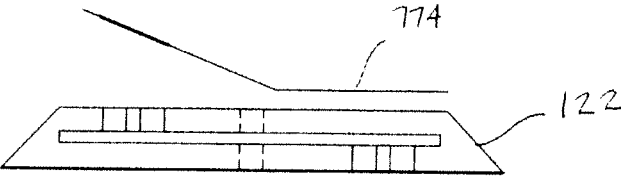

Referring to FIGS. 35A-B, in another aspect, electrical contact pads 772, 773 may be provided to the circuit board in the sensor housing 122 (shown in cross section in FIG. 35B, such that the mating of the contact pads with the conductive ring 771 switches on the sensor electronics device to provide power to the device from its power source. FIGS. 36A-B show yet another configuration of the switch activation mechanism in accordance with the present disclosure, where a portion of the conductive ring 774 is selectively positioned and provided to establish electrical contact in the sensor housing 122 (shown in cross section in FIG. 36B).

As discussed, each of the activation configurations described above includes a break in the circuitry from the power source such that the power supply is not drained when the device is not in use, and upon activation, the break in the electrical contact is completed, thereby powering the device and activating it for operation.

Figures 37, 38:
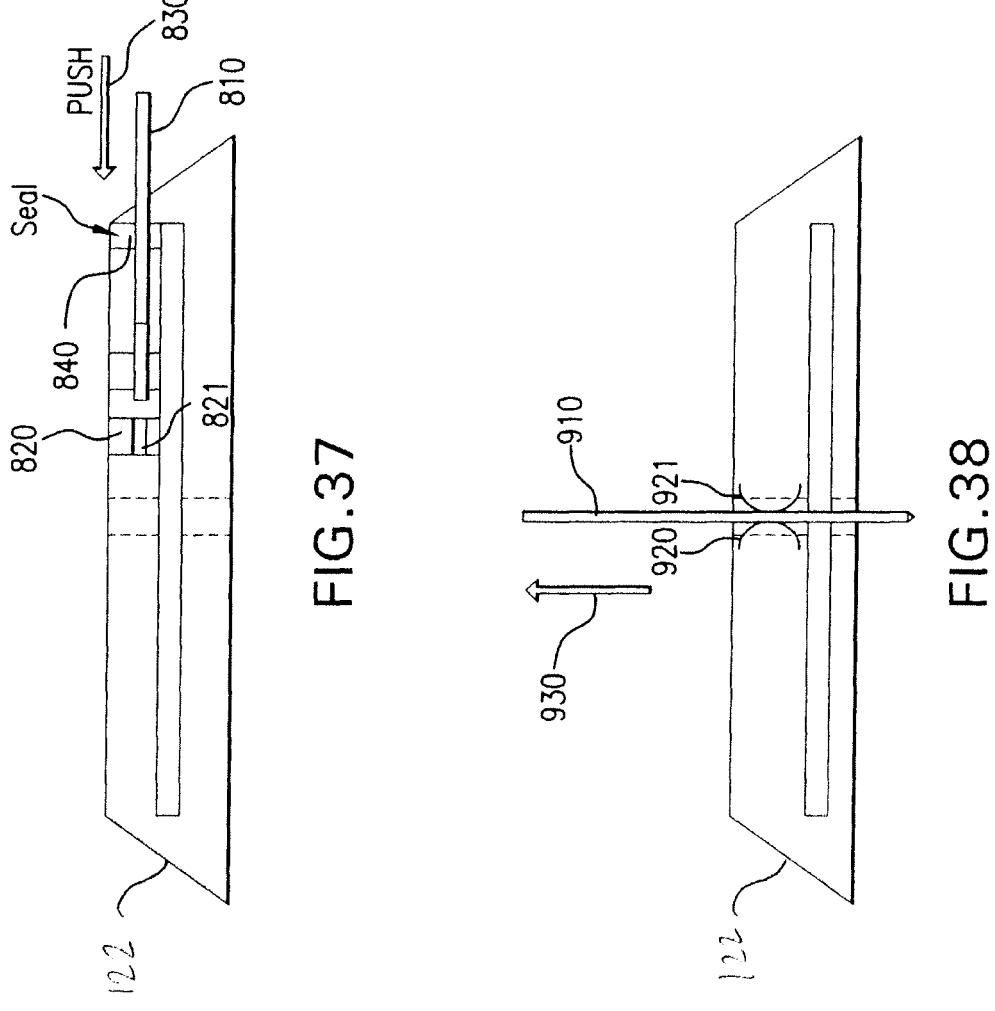
FIG. 37 illustrates a power supply switch mechanism including an internal switch with a push rod activation of the on-body integrated sensor and sensor electronics assembly in accordance with embodiments of the disclosed subject matter.
FIG. 38 illustrates power supply switch mechanism including introducer retraction trigger activation of the on-body integrated sensor and sensor electronics assembly in accordance with embodiments of the disclosed subject matter.

FIG. 37 illustrates a power supply switch mechanism including an internal switch with a push rod activation of the on-body integrated sensor and sensor housing 122 in accordance with embodiments of the present disclosure. As shown, in one embodiment, push rod 810 may be provided and positioned in the sensor electronics such that when a force is applied in the direction as shown by arrow 830, the push rod 810 is displaced in the same direction and completes the electrical contact between the two contacts 820, 821. In one aspect, the push rod 810 may be provided within a seal 840 such as an O-ring or similar components.

FIG. 38 illustrates power supply switch mechanism including introducer retraction trigger activation of the on-body integrated sensor and sensor housing 122 in accordance with embodiments of the present disclosure. As shown, a nonconducting needle or device 910 is provided to physically separate two electrical contacts 920, 921. Each of the electrical contacts 920, 921 is biased or spring loaded to be urged towards each other, physically separated by the nonconducting needle 910. Accordingly, when the nonconducting needle 910 is retracted or pulled away from the sensor electronics assembly in the direction as shown by arrow 930, the electrical contacts 920, 921 are configured to contact each other, thereby completing the break in the circuit and establishing electrical connection to activate the sensor electronics assembly. In one aspect, the nonconducting device or needle 910 may include, for example, but not limited to, glass, plastic or any other material suitable to separate two electrical contacts and provide insulation therebetween.

Figure 39:
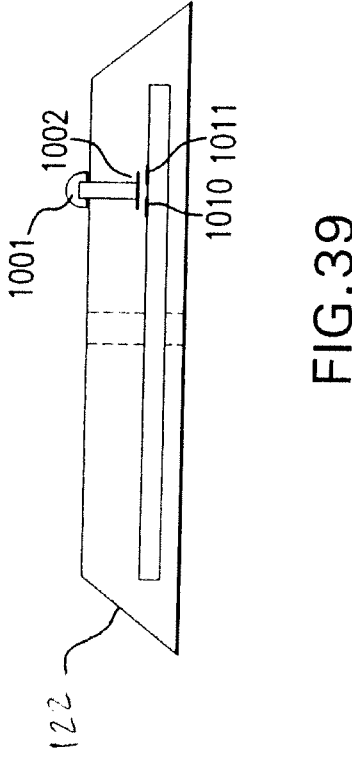
FIG. 39 illustrates a power supply switch mechanism with a contact switch of the on-body integrated sensor and sensor electronics assembly in accordance with embodiments of the disclosed subject matter.

FIG. 39 illustrates power supply switch mechanism with a contact switch of the on-body integrated sensor and sensor electronics assembly in accordance with embodiments of the present disclosure. As shown, in a further aspect, there is provided an electronic switch 1001 (that is configured to draw an insubstantial amount of power from the sensor electronics power supply), and when triggered, completes the break between the contacts 1010, 1011 by physically contacting the two contacts 1010, 1011 with the activation component 1002 that completes the circuit in the sensor electronics from its power supply such as battery to activate the device for operation.

Figures 40, 41:
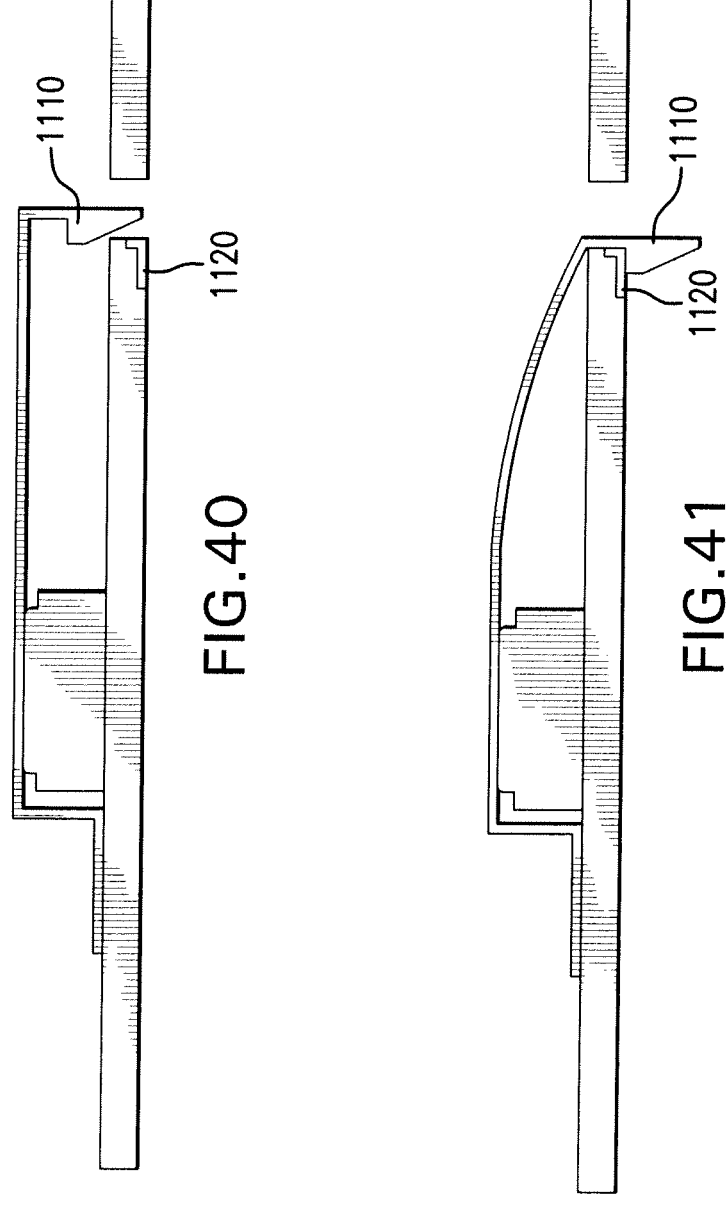
FIGS. 40-41 illustrate a power supply switch mechanism with a battery contact locking mechanism of the on-body integrated sensor and sensor electronics assembly in accordance with embodiments of the disclosed subject matter.

FIGS. 40-41 illustrate a power supply switch mechanism with a battery contact locking mechanism of the on-body integrated sensor and sensor electronics assembly 122 in accordance with the present disclosure. Referring to FIGS. 40-41, in still another aspect, the battery contact of the sensor electronics may be provided with a barbed tab 1110. In post manufacturing shelf mode when the device is non-operational, the tab 1110 is positioned within the sensor electronics housing in the position as shown in FIG. 40 so that it is not in contact with the conductive contact 1120 of the sensor electronics circuit board. When in use as shown in FIG. 41, the tab 1110 may be biased such that it physically contacts the conductive contact 1120 on the circuit board, thereby closing the circuit to/from the battery/power source and thus activating or switching on the sensor electronics. As shown in the Figures, the tab 1110 may be configured that upon biasing to establish contact with the conductive contact 1120, it locks or latches with the conductive contact 1120 and the circuit board so as to maintain the electrical connection.

Figures 42, 43:
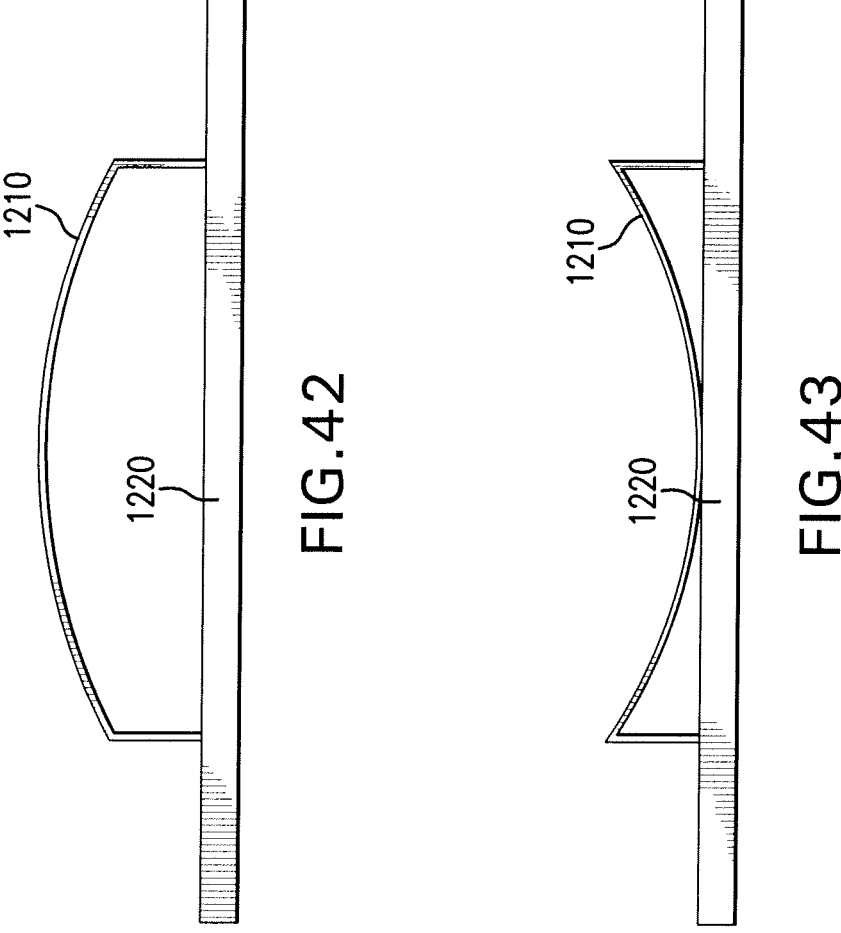
FIGS. 42-43 illustrate a power supply switch mechanism with a bi-modal dome switch of the on-body integrated sensor and sensor electronics assembly in accordance with embodiments of the disclosed subject matter.

FIGS. 42-43 illustrate power supply switch mechanism with a bi-modal dome switch of the on-body integrated sensor and sensor electronics assembly in accordance with embodiments of the present disclosure. Yet in another embodiment, a bi-modal dome shaped switch 1210 is provided on the circuit board of the sensor electronics assembly such that, when pressed down (as shown in FIG. 42), the dome shaped layer 1210 (which may include, for example, a thin sheet metal dome) may be configured to retain the concave shape as shown in FIG. 43 and effectively closing the circuit on the circuit board at the contact point 1220. In one aspect, the dome shaped layer 1210 may be configured to shunt to short two or more electrical contacts at the contact point 1220 of the circuit board. Alternatively, the dome shaped layer 1210 may be connected to the circuit board such that one end of the dome shaped layer 1210 is in contact with one of the two or more open electrical contacts, and the depression of the dome shaped layer 1210 closes the circuit on the circuit board by physically contacting the other one or more of the open electrical contacts.

In the manner described above, in accordance with various embodiments of the present disclosure, sensor electronics activation switch configurations are provided that may be triggered or activated automatically or semi-automatically in response to the activation of the insertion device described above, or alternatively, may be separately activated by the user by, for example, depressing upon a portion of the housing or switch provided on the housing of the sensor electronics. Accordingly, power consumption may be optimized for the sensor electronics assembly while improving post manufacturing shelf life of the device prior to use or activation.

It is understood that the subject matter described herein is not limited to particular embodiments described, as such may, of course, vary. It is also understood that the terminology used herein is for the purpose of describing particular embodiments only, and is not intended to be limiting, since the scope of the present subject matter is limited only by the appended claims.

Additional detailed description of embodiments of the disclosed subject matter are provided in but not limited to: U.S. Pat. Nos. 7,299,082; 7,167,818; 7,041,468; 6,942,518; 6,893,545; 6,881,551; 6,773,671; 6,764,581; 6,749,740; 6,746,582; 6,736,957; 6,730,200; 6,676,816; 6,618,934; 6,616,819; 6,600,997; 6,592,745; 6,591,125; 6,560,471; 6,540,891; 6,514,718; 6,514,460; 6,503,381; 6,461,496; 6,377,894; 6,338,790; 6,299,757; 6,299,757; 6,284,478; 6,270,455; 6,175,752; 6,161,095; 6,144,837; 6,143,164; 6,121,009; 6,120,676; 6,071,391; 5,918,603; 5,899,855; 5,822,715; 5,820,551; 5,628,890; 5,601,435; 5,593,852; 5,509,410; 5,320,715; 5,264,014; 5,262,305; 5,262,035; 4,711,245; 4,545,382; U.S. Patent Publication No. 2004/

0186365, published Sep. 23, 2004, now U.S. Pat. No. 7,811,231; U.S. Patent Application No. 61/238,646, filed Aug. 31, 2009, the disclosures of each of which is incorporated herein by reference.

What is claimed is:

1. An insertion assembly, comprising:
  (a) an on-body unit, comprising:
    a housing comprising a top surface and a bottom surface, wherein the top surface comprises an opening of the top surface, and wherein the bottom surface comprises an opening of the bottom surface;
    a transcutaneous glucose sensor; and
    sensor electronics disposed within the housing and coupled with the transcutaneous glucose sensor; and
  (b) an inserter, comprising:
    a proximal end, a distal end, and an interior;
    a sharp; and
    a driver configured to retract the sharp, wherein the driver comprises a spring,
  wherein the on-body unit, the sharp, and the driver are entirely disposed in the interior of the inserter when the on-body unit is in a first position,
  wherein the sharp extends through the opening of the bottom surface of the housing when the on-body unit is in the first position,
  wherein at least a portion of the transcutaneous glucose sensor is disposed in the sharp when the on-body unit is in the first position,
  wherein the inserter is configured to:
    advance the on-body unit and the sharp in a linear direction from the first position to a second position such that the sharp pierces skin of a user and the housing of the on-body unit is secured to the skin of the user in the second position,
    retract the sharp from within the user and entirely into the interior of the inserter, wherein retraction of the sharp is initiated without requiring user interaction after advancement of the on-body unit and the sharp from the first position, and
    leave a part of the transcutaneous glucose sensor in contact with interstitial fluid of the user, and
  wherein the distal end of the inserter is configured to be positioned on the skin of the user before advancement of the on-body unit and the sharp from the first position.

2. The insertion assembly of claim 1, further comprising an adhesive portion configured to secure the housing to the skin of the user.

3. The insertion assembly of claim 2, wherein the housing is configured to advance a distance when the on-body unit advances from the first position to the second position, and wherein the distance is greater than a maximum height of the housing.

4. The insertion assembly of claim 3, wherein the sensor electronics comprise a processor, a power source, an analog interface, a data storage unit, and wireless communication circuitry.

5. The insertion assembly of claim 3, wherein the on-body unit is configured to transmit data indicative of a glucose level only in response to a request.

6. The insertion assembly of claim 5, wherein the request is received from a handheld display unit.

7. The insertion assembly of claim 3, wherein the sharp is configured to pierce the skin of the user at an angle substantially perpendicular to the skin of the user.

8. The insertion assembly of claim 3, wherein the on-body unit further comprises a side wall of the housing, wherein the side wall is located between the top surface of the housing and the bottom surface of the housing, wherein the side wall comprises a first portion and a second portion, and wherein the second portion of the side wall defines a non-orthogonal angle relative to both the first portion of the side wall and the top surface of the housing.

9. The insertion assembly of claim 3, wherein the sensor electronics are in an inactive mode when the on-body unit is in the first position.

10. The insertion assembly of claim 3, wherein the sensor electronics are configured to be activated when the on-body unit is at or near the second position.

11. The insertion assembly of claim 3, wherein the sharp extends through the opening of the top surface of the housing when the on-body unit is in the first position.

12. The insertion assembly of claim 11, wherein the sensor electronics comprise an opening of the sensor electronics, and wherein the sharp extends through the opening of the sensor electronics when the on-body unit is in the first position.

13. The insertion assembly of claim 3, further comprising a cap removably attached to the inserter by a plurality of threads, wherein the cap is configured to be removed from the inserter before the distal end of the inserter is positioned on the skin of the user.

14. The insertion assembly of claim 3, wherein a height profile of the housing is less than or equal to approximately 10 millimeters.

15. The insertion assembly of claim 3, further comprising a sensor hub,
  wherein the transcutaneous glucose sensor comprises a distal sensor portion and a proximal sensor portion,
  wherein the distal sensor portion is configured to sense a glucose level of the user,
  wherein the proximal sensor portion is engaged with the sensor hub, and
  wherein the distal sensor portion is substantially orthogonal to the proximal sensor portion.

16. The insertion assembly of claim 3, wherein the distal end of the inserter resides in a plane, and wherein the bottom surface of the housing is parallel to the plane when the on-body unit is in the first position.

17. The insertion assembly of claim 3, wherein the opening of the top surface of the housing is a first opening of the top surface, wherein the top surface further comprises a second opening of the top surface, wherein the first opening of the top surface has a first maximum width, and wherein the second opening of the top surface has a second maximum width less than the first maximum width.

18. The insertion assembly of claim 3, wherein the on-body unit is configured to be disposed after a single use.

19. The insertion assembly of claim 3, wherein the adhesive portion is further configured to extend outwardly beyond the bottom surface of the housing along the skin in all directions in a same plane as the bottom surface of the housing when the housing is secured to the skin of the user.

20. The insertion assembly of claim 3, wherein the distal end of the inserter is further configured to be removed from the skin of the user after retraction of the sharp from within the user, and while the housing of the on-body unit remains secured to the skin of the user.

21. An insertion assembly, comprising:
  (a) an on-body unit, comprising:
    a housing comprising a top surface and a bottom surface, wherein the top surface comprises an opening of the top surface, and wherein the bottom surface comprises an opening of the bottom surface;
    a transcutaneous glucose sensor; and sensor electronics disposed within the housing and coupled with the transcutaneous glucose sensor, wherein the sensor electronics comprise a processor, a power source, an analog interface, a data storage unit, and wireless communication circuitry; and (b) an inserter, comprising:

a proximal end, a distal end, and an interior;

a sharp; and a driver configured to retract the sharp, wherein the driver comprises a spring, wherein the on-body unit, the sharp, and the driver are entirely disposed in the interior of the inserter when the on-body unit is in a first position, wherein the sharp extends through the opening of the bottom surface of the housing when the on-body unit is in the first position, wherein at least a portion of the transcutaneous glucose sensor is disposed in the sharp when the on-body unit is in the first position, wherein the inserter is configured to:

advance the on-body unit and the sharp in a linear direction from the first position to a second position such that the sharp pierces skin of a user and the housing of the on-body unit is secured to the skin of the user in the second position, retract the sharp from within the user and entirely into the interior of the inserter, wherein retraction of the sharp is initiated without requiring user interaction after advancement of the on-body unit and the sharp from the first position, and leave a part of the transcutaneous glucose sensor in contact with interstitial fluid of the user, wherein the housing is configured to advance a distance when the on-body unit advances from the first position to the second position, and wherein the distance is greater than a maximum height of the housing, wherein the sharp is configured to pierce the skin of the user at an angle substantially perpendicular to the user, wherein a height profile of the housing is less than or equal to approximately 10 millimeters, and wherein the distal end of the inserter is configured to be positioned on the skin of the user before advancement of the on-body unit and the sharp from the first position.

22. The insertion assembly of claim 21, further comprising an adhesive portion configured to secure the housing to the skin of the user.

23. The insertion assembly of claim 22, wherein the distal end of the inserter resides in a plane, and wherein the bottom surface of the housing is parallel to the plane when the on-body unit is in the first position.

24. The insertion assembly of claim 23, wherein the on-body unit is configured to transmit data indicative of a glucose level only in response to a request, and wherein the request is received from a handheld display unit.

25. The insertion assembly of claim 23, wherein the sharp extends through the opening of the top surface of the housing when the on-body unit is in the first position.

26. The insertion assembly of claim 25, wherein the sensor electronics further comprise an opening of the sensor electronics, and wherein the sharp extends through the opening of the sensor electronics when the on-body unit is in the first position.

27. The insertion assembly of claim 23, wherein the sensor electronics are in an inactive mode when the on-body unit is in the first position, and wherein the sensor electronics are configured to be activated when the on-body unit is at or near the second position.

28. The insertion assembly of claim 23, further comprising a sensor hub, wherein the transcutaneous glucose sensor comprises a distal sensor portion and a proximal sensor portion, wherein the distal sensor portion is configured to sense a glucose level of the user, wherein the proximal sensor portion is engaged with the sensor hub, and wherein the distal sensor portion is substantially orthogonal to the proximal sensor portion.

29. The insertion assembly of claim 23, further comprising a cap removably attached to the inserter by a plurality of threads, wherein the cap is configured to be removed from the inserter before the distal end of the inserter is positioned on the skin of the user.

30. The insertion assembly of claim 23, wherein the distal end of the inserter is further configured to be removed from the skin of the user after retraction of the sharp from within the user, and while the housing of the on-body unit remains secured to the skin of the user.

* * * * *